US010934571B2

(12) United States Patent
Van Berkel et al.

(10) Patent No.: US 10,934,571 B2
(45) Date of Patent: Mar. 2, 2021

(54) RECOMBINANT PRODUCTION OF MIXTURES OF ANTIBODIES

(71) Applicant: Merus N.V., Utrecht (NL)

(72) Inventors: Patricius Hendrikus Van Berkel, Berkel en Rodenrijs (NL); Ronald Hendrik Brus, Voorschoten (NL); Abraham Bout, Leiden (NL); Ton Logtenberg, Utrecht (NL)

(73) Assignee: Merus N.V., Utrecht (NL)

( * ) Notice: Subject to any disclaimer, the term of this patent is extended or adjusted under 35 U.S.C. 154(b) by 59 days.

(21) Appl. No.: 15/090,505

(22) Filed: Apr. 4, 2016

(65) Prior Publication Data

US 2016/0319320 A1    Nov. 3, 2016

Related U.S. Application Data

(60) Continuation of application No. 12/932,719, filed on Mar. 4, 2011, now Pat. No. 9,303,081, which is a continuation of application No. 12/221,021, filed on Jul. 29, 2008, now Pat. No. 7,927,834, which is a division of application No. 11/593,279, filed on Nov. 6, 2006, now Pat. No. 7,429,486, which is a division of application No. 11/039,767, filed on Jan. 18, 2005, now Pat. No. 7,262,028, which is a continuation of application No. PCT/EP03/07690, filed on Jul. 15, 2003, which is a continuation of application No. PCT/EP03/50201, filed on May 27, 2003.

(60) Provisional application No. 60/397,066, filed on Jul. 18, 2002.

(30) Foreign Application Priority Data

Jul. 18, 2002    (EP) .................................... 02077953

(51) Int. Cl.
| C07K 16/00 | (2006.01) |
| C12P 21/00 | (2006.01) |
| C07K 16/10 | (2006.01) |
| C07K 16/28 | (2006.01) |
| C07K 16/30 | (2006.01) |
| C07K 16/32 | (2006.01) |
| A61K 39/395 | (2006.01) |

(52) U.S. Cl.
CPC ...... *C12P 21/005* (2013.01); *A61K 39/39558* (2013.01); *C07K 16/00* (2013.01); *C07K 16/10* (2013.01); *C07K 16/2803* (2013.01); *C07K 16/2833* (2013.01); *C07K 16/2851* (2013.01); *C07K 16/2896* (2013.01); *C07K 16/30* (2013.01); *C07K 16/32* (2013.01); *C07K 2317/12* (2013.01); *C07K 2317/21* (2013.01); *C07K 2317/31* (2013.01); *C07K 2317/50* (2013.01); *C07K 2317/51* (2013.01); *C07K 2317/56* (2013.01); *C07K 2317/622* (2013.01); *C07K 2317/626* (2013.01); *C07K 2317/73* (2013.01); *C07K 2317/732* (2013.01); *C07K 2317/734* (2013.01); *C07K 2319/30* (2013.01); *Y02P 20/582* (2015.11)

(58) Field of Classification Search
CPC .. C07K 16/00; C07K 16/005; C07K 2317/30; C07K 2317/50; C07K 2317/52; C07K 2317/56; C07K 2317/60; C12N 15/09; C12N 15/10; C12N 15/1034; C12N 15/62; C12N 15/63; C12N 15/79; C12N 15/85

See application file for complete search history.

(56) References Cited

U.S. PATENT DOCUMENTS

| 4,399,216 A | 8/1983 | Axel et al. |
| 4,599,311 A | 7/1986 | Kawasaki |
| 4,634,665 A | 1/1987 | Axel et al. |
| 4,801,687 A | 1/1989 | Ngo |
| 4,816,567 A | 3/1989 | Cabilly et al. |
| 4,868,103 A | 9/1989 | Stavrianopoulos et al. |
| 4,937,190 A | 6/1990 | Pahnenberg et al. |
| 5,030,002 A | 7/1991 | North |
| 5,137,809 A | 8/1992 | Loken et al. |
| 5,151,504 A | 9/1992 | Croze |
| 5,179,017 A | 1/1993 | Axel et al. |
| 5,223,409 A | 6/1993 | Ladner et al. |

(Continued)

FOREIGN PATENT DOCUMENTS

| AU | 2003250074 A1 | 2/2004 |
| CA | 2 405 961 | 11/2001 |

(Continued)

OTHER PUBLICATIONS

Carter, J Immunol, 248:7-15, section 3.2, 3.3 p. 10, 2001.*

(Continued)

*Primary Examiner* — Mark Halvorson
(74) *Attorney, Agent, or Firm* — Sterne, Kessler, Goldstein & Fox P.L.L.C.

(57) ABSTRACT

Provided is methods for producing mixtures of antibodies from a single host cell clone, wherein, a nucleic acid sequence encoding a light chain and nucleic acid sequences encoding different heavy chains are expressed in a recombinant host cell. The recombinantly produced antibodies in the mixtures according to the invention suitably comprise identical light chains paired to different heavy chains capable of pairing to the light chain, thereby forming functional antigen-binding domains. Mixtures of the recombinantly produced antibodies are also provided by the invention. Such mixtures can be used in a variety of fields.

20 Claims, 31 Drawing Sheets
Specification includes a Sequence Listing.

(56) References Cited

U.S. PATENT DOCUMENTS

| | | | |
|---|---|---|---|
| 5,385,839 A | 1/1995 | Stinski | |
| 5,627,037 A | 5/1997 | Ward et al. | |
| 5,631,169 A | 5/1997 | Lakowicz et al. | |
| 5,641,640 A | 6/1997 | Hanning | |
| 5,667,988 A | 9/1997 | Barbas et al. | |
| 5,667,998 A | 9/1997 | Dougherty et al. | |
| 5,733,779 A | 3/1998 | Reff | |
| 5,770,429 A | 6/1998 | Lonberg et al. | |
| 5,772,997 A | 6/1998 | Hudziak et al. | |
| 5,783,186 A | 7/1998 | Arakawa et al. | |
| 5,789,208 A | 8/1998 | Sharon | |
| 5,789,215 A | 8/1998 | Berns et al. | |
| 5,827,690 A * | 10/1998 | Meade | A01K 67/0278 800/7 |
| 5,830,698 A * | 11/1998 | Reff | A61K 48/0008 435/69.1 |
| 5,834,237 A | 11/1998 | Jacobs et al. | |
| 5,849,500 A | 12/1998 | Breitling et al. | |
| 5,885,827 A | 3/1999 | Wabl et al. | |
| 5,888,789 A | 3/1999 | Rodriquez | |
| 5,939,598 A | 8/1999 | Kucherlapati et al. | |
| 5,965,371 A | 10/1999 | Marasco et al. | |
| 6,004,940 A | 12/1999 | Marasco et al. | |
| 6,054,297 A | 4/2000 | Carter et al. | |
| 6,080,560 A | 6/2000 | Russell et al. | |
| 6,114,598 A | 9/2000 | Kucherlapati et al. | |
| 6,180,357 B1 | 1/2001 | Young et al. | |
| 6,207,446 B1 | 3/2001 | Szostak et al. | |
| 6,265,150 B1 | 7/2001 | Terstappan et al. | |
| 6,291,740 B1 | 9/2001 | Bremel et al. | |
| 6,303,341 B1 | 10/2001 | Hiatt et al. | |
| 6,335,163 B1 | 1/2002 | Sharon | |
| 6,570,061 B1 | 5/2003 | Rajewsky et al. | |
| 6,586,251 B2 | 7/2003 | Economides et al. | |
| 6,596,541 B2 | 7/2003 | Murphy et al. | |
| 7,067,284 B1 | 6/2006 | Barbas et al. | |
| 7,105,348 B2 | 9/2006 | Murphy et al. | |
| 7,183,076 B2 | 2/2007 | Arathoon et al. | |
| 7,262,028 B2 | 8/2007 | Van Berkel et al. | |
| 7,329,530 B2 | 2/2008 | Houtzager et al. | |
| 7,429,486 B2 | 9/2008 | Van Berkel et al. | |
| 7,491,516 B2 | 2/2009 | Collinson et al. | |
| 7,579,446 B2 | 8/2009 | Bakker et al. | |
| 7,642,228 B2 | 1/2010 | Carter et al. | |
| 7,696,330 B2 | 4/2010 | Meulen et al. | |
| 7,740,852 B2 | 6/2010 | Bakker et al. | |
| 7,777,010 B2 | 8/2010 | Logtenberg | |
| 7,858,086 B2 | 12/2010 | Geuijen et al. | |
| 7,901,919 B2 | 3/2011 | Houtzager et al. | |
| 7,919,257 B2 | 4/2011 | Hoogenboom et al. | |
| 7,927,834 B2 | 4/2011 | Van Berkel et al. | |
| 7,932,360 B2 | 4/2011 | Van Berkel et al. | |
| 7,960,518 B2 | 6/2011 | Throsby et al. | |
| 7,968,092 B2 | 6/2011 | Throsby et al. | |
| 8,052,974 B2 | 11/2011 | Throsby et al. | |
| 8,106,170 B2 | 1/2012 | Ter Meulen et al. | |
| 8,148,497 B2 | 4/2012 | Bakker et al. | |
| 8,192,927 B2 | 6/2012 | Van Den Brink et al. | |
| 8,211,431 B2 | 7/2012 | Throsby et al. | |
| 8,241,631 B2 | 8/2012 | Throsby et al. | |
| 8,268,756 B2 | 9/2012 | Logtenberg et al. | |
| 8,470,327 B2 | 6/2013 | Throsby et al. | |
| 8,592,562 B2 | 11/2013 | Kannan et al. | |
| 8,911,738 B2 | 12/2014 | Throsby et al. | |
| 9,012,371 B2 | 4/2015 | Logtenberg et al. | |
| 9,248,181 B2 | 2/2016 | De Kruif et al. | |
| 9,248,182 B2 † | 2/2016 | De Kruif | |
| 9,303,081 B2 | 4/2016 | Van Berkel et al. | |
| 9,358,286 B2 | 6/2016 | De Kruif et al. | |
| 9,738,701 B2 | 8/2017 | Hoogenboom et al. | |
| RE47,770 E | 12/2019 | Van Berkel et al. | |
| 2002/0088016 A1 | 7/2002 | Bruggeman | |
| 2002/0138857 A1 | 9/2002 | Ghayur | |
| 2003/0039958 A1 | 2/2003 | Holt et al. | |
| 2003/0077739 A1 | 4/2003 | Simmons et al. | |
| 2003/0091561 A1 | 5/2003 | Van De Winkel et al. | |
| 2003/0093820 A1 | 5/2003 | Green et al. | |
| 2003/0096225 A1 | 5/2003 | Logtenberg | |
| 2003/0194403 A1 | 10/2003 | van de Winkel et al. | |
| 2003/0207346 A1 | 11/2003 | Arathoon et al. | |
| 2003/0215914 A1 | 11/2003 | Houtzager et al. | |
| 2003/0219829 A1 | 11/2003 | Logtenberg et al. | |
| 2003/0224408 A1 | 12/2003 | Hoogenboom et al. | |
| 2005/0014261 A1 | 1/2005 | Houtzager et al. | |
| 2005/0037001 A1 | 2/2005 | Germeraad et al. | |
| 2005/0037427 A1 | 2/2005 | Houtzager et al. | |
| 2005/0170398 A1 | 8/2005 | Van Berkel et al. | |
| 2006/0015949 A1 | 1/2006 | Lonberg | |
| 2006/0015957 A1 | 1/2006 | Lonberg | |
| 2006/0088520 A1 | 4/2006 | Germeraad et al. | |
| 2006/0117699 A1 | 6/2006 | Di Trapani | |
| 2006/0160184 A1 | 7/2006 | Hoogenboom et al. | |
| 2006/0177437 A1 | 8/2006 | Houtzager et al. | |
| 2006/0205077 A1 | 9/2006 | Schwenk et al. | |
| 2006/0257397 A1 | 11/2006 | Throsby et al. | |
| 2006/0292634 A1 | 12/2006 | Houtzager et al. | |
| 2007/0054362 A1 | 3/2007 | Van Berkel | |
| 2007/0059766 A1 | 3/2007 | Logtenberg | |
| 2007/0178552 A1 | 8/2007 | Arathoon et al. | |
| 2007/0280945 A1 | 12/2007 | Stevens et al. | |
| 2008/0070799 A1 | 3/2008 | Bakker et al. | |
| 2008/0241166 A1 | 10/2008 | Tomlinson et al. | |
| 2009/0017521 A1 | 1/2009 | Houtzager et al. | |
| 2009/0054254 A1 | 2/2009 | Throsby et al. | |
| 2009/0130652 A1 | 5/2009 | Throsby et al. | |
| 2009/0181855 A1 | 7/2009 | Vasquez et al. | |
| 2009/0182127 A1 | 7/2009 | Kjaergaard et al. | |
| 2009/0263864 A1 | 10/2009 | Van Berkel et al. | |
| 2010/0015133 A1 | 1/2010 | Igawa et al. | |
| 2010/0069614 A1 | 3/2010 | Houtzager et al. | |
| 2010/0146647 A1 | 6/2010 | Logtenberg et al. | |
| 2010/0172917 A1 | 7/2010 | Ter Meulen et al. | |
| 2010/0286374 A1 | 11/2010 | Kannan et al. | |
| 2010/0297153 A1 | 11/2010 | Geuijen et al. | |
| 2010/0310572 A1 | 12/2010 | Bakker et al. | |
| 2010/0310586 A1 | 12/2010 | Dolcetti et al. | |
| 2010/0331527 A1 | 12/2010 | Davis et al. | |
| 2011/0177073 A1 | 7/2011 | Van Berkel et al. | |
| 2011/0195454 A1 | 8/2011 | McWhirter et al. | |
| 2011/0268739 A1 | 11/2011 | Throsby et al. | |
| 2012/0021409 A1 | 1/2012 | McWhirter et al. | |
| 2012/0039898 A1 | 2/2012 | Throsby et al. | |
| 2012/0058907 A1 | 3/2012 | Logtenberg et al. | |
| 2012/0076794 A1 | 3/2012 | Throsby et al. | |
| 2012/0093823 A1 | 4/2012 | Van Den Brink et al. | |
| 2012/0141493 A1 | 6/2012 | Throsby et al. | |
| 2012/0177637 A1 | 7/2012 | Hoogenboom et al. | |
| 2012/0192300 A1 | 7/2012 | Babb et al. | |
| 2012/0276115 A1 | 11/2012 | Van Den Brink et al. | |
| 2012/0315278 A1 | 12/2012 | Throsby et al. | |
| 2013/0115208 A1 | 5/2013 | Ho et al. | |
| 2013/0145484 A1 | 6/2013 | Logtenberg et al. | |
| 2013/0336981 A1 | 12/2013 | De Kruif et al. | |
| 2014/0072579 A1 | 3/2014 | De Kruif et al. | |
| 2014/0120096 A1 | 5/2014 | Bakker et al. | |
| 2014/0140999 A1 | 5/2014 | De Kruif et al. | |
| 2014/0314755 A1 | 10/2014 | Logtenberg et al. | |
| 2014/0317766 A1 | 11/2014 | Logtenberg et al. | |
| 2015/0139996 A1 | 5/2015 | De Kruif et al. | |
| 2015/0196637 A1 | 7/2015 | De Kruif et al. | |
| 2016/0238600 A1 | 8/2016 | Hoogenboom et al. | |
| 2016/0319320 A1 | 11/2016 | Van Berkel et al. | |
| 2018/0094289 A1 | 4/2018 | Van Berkel et al. | |
| 2018/0112247 A1 | 4/2018 | Van Berkel et al. | |

FOREIGN PATENT DOCUMENTS

| | | |
|---|---|---|
| CA | 1 341 364 | 6/2002 |
| CA | 2 445 255 | 10/2002 |
| CA | 2 114 353 | 1/2006 |
| EP | 0 120 694 | 10/1984 |
| EP | 0 314 161 | 5/1989 |
| EP | 0 402 029 | 12/1990 |
| EP | 0 445 625 | 9/1991 |

(56) References Cited

FOREIGN PATENT DOCUMENTS

| | | |
|---|---|---|
| EP | 0 469 897 A2 | 2/1992 |
| EP | 0469025 A1 | 2/1992 |
| EP | 0 481 790 | 4/1992 |
| EP | 171142 A1 | 7/1992 |
| EP | 0 523 949 | 1/1993 |
| EP | 469025 A1 | 8/1995 |
| EP | 0814159 | 12/1997 |
| EP | 0 724 639 | 1/2001 |
| EP | 666868 | 4/2002 |
| EP | 1349234 A2 | 10/2003 |
| EP | 1399575 A2 | 3/2004 |
| EP | 1439234 | 11/2004 |
| EP | 1 325 932 B1 | 4/2005 |
| EP | 1870459 A1 | 12/2007 |
| EP | 2147594 | 1/2010 |
| FR | 2817875 | 6/2002 |
| JP | 5-68599 | 3/1993 |
| JP | 8116978 A | 5/1996 |
| JP | 2001523971 A | 11/2001 |
| JP | 2004008214 | 8/2003 |
| JP | 20048218 | 1/2004 |
| JP | 2004-524841 | 8/2004 |
| JP | 2006-109711 | 4/2006 |
| JP | 2006-515503 | 6/2006 |
| JP | 2008-538912 | 11/2008 |
| JP | 2010-505418 | 2/2010 |
| JP | 2010-512749 | 4/2010 |
| JP | 2011508604 A | 3/2011 |
| JP | 2011-525808 | 9/2011 |
| JP | 2013004215 A | 1/2013 |
| JP | 5749161 | 5/2015 |
| RU | 2236127 C2 | 9/2004 |
| WO | WO 90/02809 | 3/1990 |
| WO | 9004036 A1 | 4/1990 |
| WO | 9012878 A1 | 11/1990 |
| WO | 9100906 | 1/1991 |
| WO | 9100906 A1 | 1/1991 |
| WO | WO 91/08216 | 6/1991 |
| WO | WO 91/17271 | 11/1991 |
| WO | WO 92/01047 | 1/1992 |
| WO | 9203918 A1 | 3/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | 9312227 A1 | 6/1993 |
| WO | 9402602 | 2/1994 |
| WO | WO 94/02610 | 2/1994 |
| WO | 9404667 A1 | 3/1994 |
| WO | 9423046 A1 | 10/1994 |
| WO | WO 94/25591 | 11/1994 |
| WO | WO 95/17085 | 6/1995 |
| WO | WO 95/17500 | 6/1995 |
| WO | WO 95/20401 | 8/1995 |
| WO | WO 96/27011 | 9/1996 |
| WO | 9630498 A1 | 10/1996 |
| WO | WO 97/42313 | 11/1997 |
| WO | WO 97/47739 | 12/1997 |
| WO | WO 98/15627 | 4/1998 |
| WO | WO 98/15833 | 4/1998 |
| WO | 9824893 A2 | 6/1998 |
| WO | 9824923 A1 | 6/1998 |
| WO | WO 98/39416 | 9/1998 |
| WO | WO 98/41645 | 9/1998 |
| WO | 98/50431 A2 † | 11/1998 |
| WO | 9852976 | 11/1998 |
| WO | WO 98/50431 | 11/1998 |
| WO | 9915684 A2 | 4/1999 |
| WO | WO 99/20749 | 4/1999 |
| WO | WO 99/23221 | 5/1999 |
| WO | 9926569 A1 | 6/1999 |
| WO | WO 99/26569 | 7/1999 |
| WO | WO 99/36569 | 7/1999 |
| WO | 9945962 | 9/1999 |
| WO | 1999050657 | 10/1999 |
| WO | WO 99/64582 | 12/1999 |
| WO | 44777 A1 | 8/2000 |
| WO | WO 00/63403 | 10/2000 |
| WO | WO 00/70023 | 11/2000 |
| WO | WO 00/71694 A1 | 11/2000 |
| WO | WO 00/76310 A1 | 12/2000 |
| WO | 0100245 | 1/2001 |
| WO | WO 01/19394 | 3/2001 |
| WO | WO 01/27279 | 4/2001 |
| WO | WO 01/32901 | 5/2001 |
| WO | WO 01/48485 | 7/2001 |
| WO | WO 01/64929 | 9/2001 |
| WO | 188132 A2 | 11/2001 |
| WO | WO 01/88132 A2 | 11/2001 |
| WO | WO 02/18948 | 3/2002 |
| WO | 236789 A2 | 5/2002 |
| WO | WO 02/43478 A2 | 6/2002 |
| WO | WO 02/46233 A1 | 6/2002 |
| WO | 2059297 A2 | 8/2002 |
| WO | 02066630 | 8/2002 |
| WO | WO 02/074969 A2 | 9/2002 |
| WO | WO 02/096948 A2 | 12/2002 |
| WO | WO 03/002609 A2 | 1/2003 |
| WO | WO 03/004704 | 1/2003 |
| WO | WO 03/016501 A2 | 2/2003 |
| WO | 3033670 A2 | 4/2003 |
| WO | WO 03/046560 A2 | 6/2003 |
| WO | WO 03/048306 A2 | 6/2003 |
| WO | 3106674 A2 | 12/2003 |
| WO | WO 03/102157 A2 | 12/2003 |
| WO | WO 03/106684 A2 | 12/2003 |
| WO | WO 2004/009618 | 1/2004 |
| WO | 2004061104 A2 | 7/2004 |
| WO | 2004003211 | 8/2004 |
| WO | 2004106375 A1 | 12/2004 |
| WO | WO 2004/106375 A1 | 12/2004 |
| WO | WO 2005/068622 A2 | 7/2005 |
| WO | 2005118635 A2 | 12/2005 |
| WO | 2006028936 A2 | 3/2006 |
| WO | 2006106905 A1 | 10/2006 |
| WO | 2006117699 | 11/2006 |
| WO | 2006117699 A2 | 11/2006 |
| WO | 2007110205 A2 | 10/2007 |
| WO | 2007117410 | 10/2007 |
| WO | 2007147901 A1 | 12/2007 |
| WO | 2008054606 | 5/2008 |
| WO | 2008076379 | 6/2008 |
| WO | 2008119353 A1 | 10/2008 |
| WO | 2009051974 A1 | 4/2009 |
| WO | 2009080251 A1 | 7/2009 |
| WO | 2009080252 A1 | 7/2009 |
| WO | 2009080253 A1 | 7/2009 |
| WO | 2009089004 A1 | 7/2009 |
| WO | 2009098596 A2 | 8/2009 |
| WO | 2009157771 | 12/2009 |
| WO | 2010084197 A1 | 7/2010 |
| WO | 2010129304 A2 | 11/2010 |
| WO | 2011028952 A1 | 3/2011 |
| WO | 2011028953 A1 | 3/2011 |
| WO | 2011097603 | 8/2011 |
| WO | 2011143545 A1 | 11/2011 |
| WO | 2012020096 A1 | 2/2012 |
| WO | 2012023053 A2 | 2/2012 |
| WO | 2012058768 A1 | 5/2012 |
| WO | 2012131555 A2 | 10/2012 |
| WO | 2012141798 | 10/2012 |

OTHER PUBLICATIONS

Lucas, BK. et al, High-level production of recombinant proteins in CHO cells using a dicistronic DHFR intron expression vector, Nucleic Acids Res., 1996, 24(9), 1774-1779.

Macatonia, SE. et al., Primary stimulation by dendritic cells induces antiviral proliferative and cytotoxic T cell responses in vitro, J Exp Med., 1989,169(4), 1255-1264.

(56) References Cited

OTHER PUBLICATIONS

Macatonia, SE. et al., Dendritic cells produce IL-12 and direct the development of Th1 cells from naive CD4+ T cells, J Immunol., 1995, 154(10), 5071-5079.
Macejak, DG., Sarnow, P., Internal initiation of translation mediated by the 5' leader of a cellular mRNA, Nature, 1991, 353(6339), 90-94.
Manen, D. et al., A sensitive reporter gene system using bacterial luciferase based on a series of plasmid cloning vectors compatible with derivatives of pBR322, Gene, 1997, 186(2), 197-200.
Marasco, WA., Intrabodies as antiviral agents, Curr Top Microbiol Immunol., 2001, 260, 247-270.
Marks, JD., Deciphering antibody properties that lead to potent botulinum neurotoxin neutralization, Mov Disord., 2004, 19 Suppl 8, S101-108.
Massengale, WT et al., CD20-negative relapse of cutaneous B-cell lymphoma after anti-CD20 monoclonal antibody therapy, J Am Acad Dermatol., 2002, 46(3), 441-443.
Mattheakis, LC. et al., An in vitro polysome display system for identifying ligands from very large peptide libraries, Proc Natl Acad Sci U S A, 1994, 91(19), 9022-9026.
Mayer, MP., A new set of useful cloning and expression vectors derived from pBlueScript, Gene, 1995, 163(1), 41-46.
McBurney, MW. et al., Evidence for repeat-induced gene silencing in cultured Mammalian cells: inactivation of tandem repeats of transfected genes, Exp Cell Res., 2002, 274(1), 1-8.
McClanahan, T. et al., Hematopoietic growth factor receptor genes as markers of lineage commitment during in vitro development of hematopoietic cells, Blood, 1993, 81(11), 2903-2915.
McConnell, S.J., Hoess, Rh., Tendamistat as a scaffold for conformationally constrained phage peptide libraries, J Mol Biol., 1995, 250(4), 460-470.
Muyldermans, S., Single domain camel antibodies: current status, J Biotechnol., 2001, 74(4), 277-302.
Nair, S. et al., Induction of primary, antiviral cytotoxic, and proliferative responses with antigens administered via dendritic cells, J Virol., 1993, 67(7), 4062-4069.
Nanbru, C. et al., Alternative translation of the proto-oncogene c-myc by an internal ribosome entry site, J Biol Chem., 1997, 272(51), 32061-32066.
Neumann, E., Gene transfer into mouse lyoma cells by electroporation in high electric fields, EMBO J.,1982, 1(7), 841-845.
Nord, K. et al., A combinatorial library of an alpha-helical bacterial receptor domain, Protein Eng., 1995, 8(6), 601-608.
Nord, K. et al., Recombinant human factor VIII-specific affinity ligands selected from phage-displayed combinatorial libraries of protein A, Eur J Biochem., 2001, 268(15), 4269-4277.
Office Action Response in U.S. Appl. No. 12/932,719 (dated Oct. 8, 2013) filed in protest against U.S. Appl. No. 15/158,543.
Office Action Response in U.S. Appl. No. 12/932,719 (dated Feb. 27, 2012) filed in protest against U.S. Appl. No. 15/158,543.
Office Action Response in U.S. Appl. No. 12/932,719 (dated Jun. 11, 2014) filed in protest against U.S. Appl. No. 15/158,543.
Oh, SK., et al., Homeotic gene Antennapedia mRNA contains 5'-noncoding sequences that confer translational initiation by ribosome binding, Genes Dev., 1992, 6(9), 1643-1653.
Patel AK, Boyd, PN., An improved assay for antibody dependent cellular cytotoxicity based on time resolved fluorometry, J Immunol Methods, 1995, 184(1), 29-38.
Pl?ckthun, A. et al, In vitro selection and evolution of proteins. In: Adv. Prot. Chem., F.M. Richards et al, Eds, Academic Press, San Diego, 2001, vol. 55, 367-403.
Porgador, A. et al., Bone marrow-generated dendritic cells pulsed with a class I-restricted peptide are potent inducers of cytotoxic T lymphocytes, J Exp Med., 1995, 182(1), 255-260.
Rebar, EJ. et al., Phage display methods for selecting zinc finger proteins with novel DNA-binding specificities, Methods Enzymol., 1996, 267, 129-149.

Rees, S. et al, Bicistronic vector for the creation of stable mammalian cell lines that predisposes all antibiotic-resistant cells to express recombinant protein, Biotechniques, 1996, 20(1), 102-4, 106, 108-10.
Reiter, Y. et al., An antibody single-domain phage display library of a native heavy chain variable region: isolation of functional single-domain VH molecules with a unique interface, J Mol Biol., 1999, 290(3), 685-698.
Repp, R. et al., Phase I clinical trial of the bispecific antibody MDX-H210 (anti-FcgammaRI x anti-HER-2/neu) in combination with Filgrastim (G-CSF) for treatment of advanced breast cancer, Br J Cancer, 2003,89(12), 2234-2243.
Riechmann, L., Winter, G., Novel folded protein domains generated by combinatorial shuffling of polypeptide segments, Proc Natl Acad Sci U S A, 2000, 97(18), 10068-10073.
Roitt, I.M. et al., Anti-idiotypes as surrogate antigens: structural considerations, Immunol Today, 1985, 6(9), 265-267.
Rosenberg A., et al., T7Select Phage Display System: A Powerful New Protein Display System Based on Bacteriophage T7, 1996, Innovations 6, 1-6.
Röttgen, P., Collins, J. et al., A human pancreatic secretory trypsin inhibitor presenting a hypervariable highly contrained epitope via monovalent phagemid display, Gene, 1995, 164(2), 243-250.
Sambrook, Fritsch and Maniatis, Molecular Cloning: A Laboratory Manual, 2nd edition, 1989.
Santini, C. et al., Efficient display of an HCV cDNA expression library as C-terminal fusion to the capsid protein D of bacteriophage lambda, J Mol Biol., 1998, 282(1), 125-135.
Schaffitzel, C. et al., Ribosome display: an in vitro method for selection and evolution of antibodies from libraries, J Immunol Methods, 1999, 231(1-2), 119-135.
Schaffitzel,C. et al., In vitro selection and evolution of protein-ligand interactions by ribosome display. In: Protein-Protein Interactions. A Molecular Cloning Manual, E. Golemis, Ed., Cold Spring Harbor Laboratory Press, New York, 2001, pp. 535-567.
Schlehuber et al., Tuning ligand affinity, specificity, and folding stability of an engineered lipocalin variant—a so-called "anticalin"—using a molecular random approach, Biophysical Chemistry 96 (2002) 213-228.
Schoonjans et al., A new model for intermediate molecular weight recombinant bispecific and trispecific antibodies by efficient heterodimerization of single chain variable domains through fusion to a Fab-chain, Biomolecular Engineering 17 (2001) 193-202.
Shields, RL., et al., High resolution mapping of the binding site on human IgGl for FcgRI, FcgRII, FcgRIII and FcRn and design of IgGl variants with improved binding to the FcgR, J Biol Chem., 2001, 276(9), 6591-6604.
Smith, CA., Rennick, DM., Characterization of a murine lymphokine distinct from interleukin 2 and interleukin 3 (IL-3) possessing a T-cell growth factor activity and a mast-cell growth factor activity that synergizes with IL-3, Proc Natl Acad Sci U S A, 1986, 83(6), 1857-1861.
Smith, GP. et al., Small binding proteins selected from a combinatorial repertoire of knottins displayed on phage, J Mol Biol., 1998, 27, 277(2), 317-332.
Spiridon CI, et al., Tartgeting multiple Her-2 epitopes with monoclonal antibodies results in improved antigrowth activity of a human breast cancer cell line in vitro and in vivo, Clin Cancer Res., 2002, 8(6), 1720-1730.
Stein, I., et al., Translation of vascular endothelial growth factor mRNA by internal ribosome entry: implications for translation under hypoxia, Mol Cell Biol., 1998, 18(6), 3112-3119.
Stijlemans, B. et al., Efficient targeting of conserved cryptic epitopes of infectious agents by single domain antibodies. African trypanosomes as paradigm, J Biol Chem., 2004, 279(2), 1256-1261.
Stoneley, M., et al., C-Myc 5' untranslated region contains an internal ribosome entry segment, Oncogene, 1998 , 16(3), 423-428.
Strelkauskas, AJ. Et al., Human monoclonal antibody: 2. Simultaneous expression of IgG and IgM with similar binding specificities by a human hybrid clone, Hybridoma, 1987, 6(5), 479-487.
Struhl, K. et al., High-frequency transformation of yeast: autonomous replication of hybrid DNA molecules, Proc Natl Acad Sci U S A, 1979, 76(3), 1035-1039.

(56) References Cited

OTHER PUBLICATIONS

Takai, Y. et al., Requirement for three distinct lymphokines for the induction of cytotoxic T lymphocytes from thymocytes, J Immunol., 1986,137(11), 3494-3500.
Takai, Y. et al., B cell stimulatory factor-2 is involved in the differentiation of cytotoxic T lymphocytes, J Immunol., 1988, 140(2), 508-512.
Tanha, J. et al.,Selection by phage display of llama conventional V(H) fragments with heavy chain antibody V(H)H properties, J Immunol Methods, 2002, 263(1-2), 97-109.
Teaching of U.S. Appl. No. 12/589,181 (MeMo), submitted in U.S. Appl. No. 12/589,181 (Jun. 20, 2012).
Thomassen ,Y. et al, Large-scale production of VHH antibody fragments by *Saccharomyces cerevisiae*, 2002, Enzyme Microb. Technol., 30, 273-278.
Thotakura, NR., Blithe, DL., Glycoprotein hormones: glycobiology of gonadotrophins, thyrotrophin and free alpha subunit, Glycobiology, 1995, 5(1), 3-10.
Toki, J. et al., Analyses of T-cell differentiation from hemopoietic stem cells in the G0 phase by an in vitro method, Proc Natl Acad Sci U S A, 1991, 88(17), 7548-7551.
Transue, TR. et al., Camel single-domain antibody inhibits enzyme by mimicking carbohydrate substrate, Proteins, 1998, 32(4), 515-522.
Urlaub, G. et al., Isolation of Chinese hamster cell mutants deficient in dihydrofolate reductase activity, Proc Natl Acad Sci U S A, 1980, 77(7), 4216-4220.
Vagner, S. et al, Alternative translation of human fibroblast growth factor 2 mRNA occurs by internal entry of ribosomes, Mol Cell Biol., 1995, 15(1), 35-44.
Valenzuela, DM., High-throughput engineering of the mouse genome coupled with high-resolution expression analysis, Nat Biotechnol, 2003, 21(6), 652-659.
Van der Vuurst de Vries A, Logtenberg T, Dissecting the human peripheral B-cell compartment with phage display-derived antibodies, Immunology, 1999, 98(1), 55-62.
Wang, G. et al, A T cell-independent antitumor response in mice with bone marrow cells retrovirally transduced with an antibody/Fc-gamma chanin chimeric receptor gene recognizing a human ovarian cancer antigen, Nat Med., 1998, 4(2), 168-172.
Weinberger, O. et al., Cellular interactions in the generation of cytolytic T lymphocyte responses: role of la-positive splenic adherent cells in presentation in H-2 antigen, Proc Natl Acad Sci U S A, 1980,77(10), 6091-6095.
Weinberger, O. et al, Cellular interactions in the generation of cytolytic T lymphocyte responses. Analysis of the helper T cell pathway, Eur J Immunol., 1981, 11(5), 405-411.
WHO Technical Series Report, 1994, vol. 848, p. 8.
Wigler, M. et al.,Biochemical transfer of single-copy eucaryotic genes using total cellular DNA as donor, Cell, 1978, 14(3), 725-731.
Wilson TJ, Kola I., The LoxP/CRE system and genome modification, Methods Mol Biol., 2001, 158, 83-94.
Wright A, Morrison SL., Effect of glycosylation on antibody function: implications for genetic engineering, Trends Biotechnol., Jan. 1997;15(1):26-32.
Ye, X., et al., Ultrabithorax and Antennapedia 5' untranslated regions promote developmentally regulated internal translation initiation, Mol. Cell Biol., 1997, 17(3), 1714-17121.
Yelverton E, et al., Rabies virus glycoprotein analogs: biosynthesis in *Escherichia coli*, Science, 1983, 219(4585), 614-620.
Yoo EM et al., Structural requirements for polymeric immunoglobulin assembly and association with J chain, J Biol Chem., 1999, 274(47), 33771-33777.
Zacharchuk, CM. Et al., Programmed T lymphocyte death. Cell activation- and steroid-induced pathways are mutually antagonistic, J Immunol., 1990, 145(12), 4037-4045.
Zamai et al., Optimal detection of apoptosis by flow cytometry depends on cell morphology, Cytometry, 1993, 14(8), 891-897.
Zou, YR. et al, Cre-loxP-mediated gene replacement: a mouse strain producing humanized antibodies, Curr Biol, 1994; 4(12), 1099-1103.
Arnold, LW., et al., Development of B-1 cells: segregation of phosphatidyl choline-specific B cells to the B-1 population occurs after immunoglobulin gene expression, J Exp Med., 1994;179(5),1585-1595.
Attaelmannan, M., Understanding and identifying monoclonal gammopathies, Clin Chem., 2000, 46(8 Pt 2), 1230-1238.
Aucouturier et al., Monocloanl Ig L Chain and L Chain V Domain Fragment Crystallization in Myelloma-Associated Fanconi's Syndrome, and Aucouturier et al. Sequence alignment, The Journal of Immunology, 1993, 3561-3568.
Betz, AG. Elements regulating somatic hypermutation of an immunoglobulin kappa gene: critical role for the intron enhancer/matrix attachment region, Cell, 1994, 77(2), 239-248.
Cheong et al., Affinity Enhancement of Bispecific Antibody Against Two Different Epitopes in the Same Antigen, Biochemical and Biophysical Research Communications, vol. 173, No. 3, 1990, pp. 795-800.
Conrath K.E. et al., Emergence and evolution of functional heavy-chain antibodies in Camelidae.Development & Comparative Immunology., 2003, 27(2), 87-103.
Davies, J. Riechmann, L., Antibody VH domains as small recognition units, Biotechnology (N Y), 1995, 13(5), 475-479.
De Chiara 2009, Chapter 16 of Gene Knockout Protocols: 2nd Ed, vol. 530, Humana Press, 311-324.
Decision of UK High Court of Justice (REGN against Kymab Limited; Novo Nordisk) dated Feb. 2, 2016.
Decision of US District Court about U.S. Pat. No. 8,502,018, *REGN vs. Menus B.V.*, dated Nov. 2, 2015.
Decl. Robert Brink (1st) Apr. 2015.
Decl. Robert Brink (2nd) Jun. 2015.
Decl. Robert Brink (4th), Oct. 19, 2016 (-AU10).
Decl. Anthony De Franco (1st) Dec. 2014.
Decl. Anthony De Franco (2nd) Oct. 2015.
Decl. Anthony De Franco (3rd) Oct. 4, 2016 (against -AU10).
Decl. Anthony De Franco (4th) Oct. 18, 2016 (against -AU10).
Decl. Anthony De Franco filed in Aug. 2016 (-EP).
Decl. Christopher Carl Goodnow (1st) Oct. 2015.
Decl. Christopher Carl Goodnow (2nd), Oct. 4, 2016 against -AU10.
Decl. Peter Hudson (1st) May 2015.
Decl. Peter Hudson (2nd) Jun. 2015.
Declaration of Prof. Ton Logtenberg dated Sep. 15, 2015 filed in U.S. Appl. No. 13/750,753, four pages.
Decl. John McWhirter incl. Sequence Alignment filed on Feb. 8, 2016.
Decl. David Tarlinton (2nd) Oct. 2015.
Desmet et al., Fast and accurate side-chain topology and energy refinement (FASTER) as a new method for protein structure optimization, Proteins, Jul. 1, 2002, pp. 31-43, vol. 48, Issue 1.
Desmet et al., Anchor profiles of HLA-specific peptides: Analysis by a novel affinity scoring method and experimental validation, Proteins, Jan. 1, 2005, pp. 53-69, vol. 58.
Fecteau, JF. et al., A new memory CD27-IgG+ B cell population in peripheral blood expressing VH genes with low frequency of somatic mutation, J Immunol., 2006, 177(6), 3728-3736.
Gen Bank Acc. No. DQ187586-1 2005.
Gen Bank Acc. No. X59315 (human Ig kappa LC variable region).
Matsuda, F. et al, The complete nucleotide sequence of the human immunoglobulin heavy chain variable region locus, J. Exp. Med., 1998, 188 (11), 2151-2162.
Green et al., Antigen-specific human monoclonal antibodies from mice engineered with human Ig heavy and light chain YACs, Nat. Genet., 1994, pp. 13-21, vol. 7.
Hardy, R., Hayakawa, K., B cell development pathways, Annu Rev Immunol., 2001, 19, 595-621.
Hengstschläger, M. et al, A lambda 1 transgene under the control of a heavy chain promoter and enhancer does not undergo somatic hypermutation., Eur J Immunol., 1994, 24(7), 1649-1656.
Hoogenboom et al., Selecting and screening recombinant antibody libraries, Nat. Biotechnol., Sep. 7, 2005, pp. 1105-1116, vol. 23.

(56) References Cited

OTHER PUBLICATIONS

Jakobovits A., The long-awaited magic bullets: therapeutic human monoclonal antibodies from transgenic mice, Expert Opinion Investigating Drugs, 1998, 7(4), 607-614.
McCafferty; Hoogenboom; Chiswell: Antibody engineering : a practical approach, 1996, Oxford University press.
Jones et al., Replacing the complementarity-determining regions in a human antibody with those from a mouse, Nature, May 29, 1986, pp. 522-525, vol. 321.
Kim, MS. et al., Comparative analyses of complex formation and binding sites between human tumor necrosis factor-alpha and its three antagonists elucidate their different neutralizing mechanisms, J Mol Biol., 2007, 374(5), 1374-1388.
Kitamura D., A B cell-deficient mouse by targeted disruption of the membrane exon of the immunoglobulin mu chain gene, Nature, 1991, 350(6317), 423-426.
Klotz, EL. Storb, U, Somatic hypermutation of a lambda 2 transgene under the control of the lambda enhancer or the heavy chain intron enhancer, J Immunol, 1996, 157(10), 4458-4463.
Kontermann,RE, Dual targeting strategies with bispecific antibodies, 2012, mAbs 4(2), pp. 182-197.
Kroesen et al., Bispecific antibodies for treatment of cancer in experimental animal models and man, Department of Clinical Immunology, 1998 pp. 105-129.
Little, M., Recombinant antibodies for immunotherapy, chapter 7; 8; 2009, Cambridge Univ. Press.
Lonberg, N., Human antibodies from transgenic animals, Nat Biotechnol., 2005, 23(9), 1117-1125.
Lonberg, N., Fully human antibodies from transgenic mouse and phage display platforms, Curr Opin Immunol, 2008, 20(4), pp. 450-459.
Macdonald, LE. et al, Precise and in situ genetic humanization of 6 Mb of mouse immunoglobulin genes, Proc Natl Acad Sci USA, 2014, 111(14):5147-5152.
Mao, X. et al., Activation of EGFP expression by Cre-mediated excision in a new ROSA26 reporter mouse strain, Blood, 2001, 97(1), 324-6.
Translation of pertinent portions of the Action.
Japan, Argument, Jun. 21, 2016, 15 pages.
Japan, Notice of Reasons for Revocation, Mar. 17, 2016, 8 pages.
Japan, Declaration of Peter Hudson, Jun. 17, 2016, 15 pages.
Japan, Third Party Observation 2011-516168, 14 pages.
Japan, declaration of Ton Logtenberg, Sep. 15, 2015, 5 pages.
Japan, English translation and Opponents counter arguments, 25 pages.
Japan, IMGT/LIGM-DB sequence, Jul. 26, 2016, 13 pages.
Japan, Information Sheet for Submitted Publications, 3 pages.
Japan, Notification 084747, 1 page.
Japan, Opponents Counterargument 2016-700031, 19 pages.
(Page 1) EPO Form 2906 regarding Patent Application No. 10 186 063.3 dated Jul. 27, 2016, indicating the description needs to be brought in conformity with the claims, 1 page.
(Pages 2-3) EPO Document regarding Patent Application No. 10 186 063.3 dated Jul. 27, 2016, Communication pursuant to Article 101(1) and Rule 81(2) to (3) EPC 2 pages.
(Page 4) The communication was printed for and notified to each of the representatives/parties, regarding EP Application 10186063.3, at least as early as Jul. 27, 2016, 1 page.
(Page 5-6) Letter from Isenbruck to the European Patent Office dated Jun. 20, 2016, indicating Ton Logtenberg will not be in attendance at the oral proceedings, 2 pages.
(Page 7) EPO Brief Communication regarding the Opposition against EP Application 10186063.3, dated Jun. 13, 2016, 1 page.
(Page 8) EPO Brief Communication regarding the Opposition against EP Application 10186063.3, dated Jun. 10, 2016, 1 page.
(Pages 9-61) Deed of Conversion and Amendment of the Articles of Association for Merus B.V. (new name: Merus N.V.), first in Dutch and then in English (Dutch version previously submitted without English translation).

(Page 62) EPO Payment of fees and expenses for EP Application 10186063.3 dated May 27, 2016, 1 page.
(Page 63-64) Letter dated May 27, 2016, accompanying the Deed of Conversion and Amendment, and Form 1010, 2 pages.
(Page 65) EPO Brief Communication regarding the Opposition against EP Application 10186063.3, dated May 26, 2016, 1 page.
(Page 66-70) Main Request with annotations, EP Patent No. 2314629B1, Reference No. M70120EPEIN FLZ, May 20, 2016, five pages (previously submitted); (pp. 71-75) Auxiliary Request 1 with annotations, EP Patent No. 2314629B1, Reference No. M70120EPEIN FLZ, May 20, 2016, five pages (previously submitted); (pp. 76-80) Auxiliary Request 2, EP Patent No. 2314629B1, Reference No. M70120EPEIN FLZ, May 20, 2016, five pages (previously submitted).
(Pages 81-85) Auxiliary Request 3 with annotations, EP Patent No. 2314629B1, Reference No. M70120EPEIN FLZ, May 20, 2016, five pages (previously submitted); (pp. 86-90) Auxiliary Request 4 with annotations, EP Patent No. 2314629B1, Reference No. M70120EPEIN FLZ, May 20, 2016, five pages (previously submitted); (pp. 91-95) Auxiliary Request 5 with annotations, EP Patent No. 2314629B1, Reference No. M70120EPEIN FLZ, May 20, 2016, five pages (previously submitted).
(Pages 96-100) Auxiliary Request 6 with annotations, EP Patent No. 2314629B1, Reference No. M70120EPEIN FLZ, May 20, 2016, five pages (previously submitted); (pp. 101-107) Auxiliary Request 7 with annotations, EP Patent No. 2314629B1, Reference No. M70120EPEIN FLZ, May 20, 2016, seven pages (previously submitted); (pp. 108-114) Auxiliary Request 8 with annotations, EP Patent No. 2314629B1, Reference No. M70120EPEIN FLZ, May 20, 2016, seven pages (previously submitted).
(Pages 115-123) Auxiliary Request 9 with annotations, EP Patent No. 2314629B1, Reference No. M70120EPEIN FLZ, May 20, 2016, nine pages (previously submitted); (pp. 124-132) Auxiliary Request 10 with annotations, EP Patent No. 2314629B1, Reference No. M70120EPEIN FLZ, May 20, 2016, nine pages (previously submitted); (pp. 133-137) Auxiliary Request 11 with annotations, EP Patent No. 2314629B1, Reference No. M70120EPEIN FLZ, May 20, 2016, five pages.
(Pages 138-142) Auxiliary Request 12 with annotations, EP Patent No. 2314629B1, Reference No. M70120EPEIN FLZ, May 20, 2016, five pages (previously submitted); (pp. 143-147) Auxiliary Request 13 with annotations, EP Patent No. 2314629B1, Reference No. M70120EPEIN FLZ, May 20, 2016, five pages; (Pages 148-152) Auxiliary Request 14 with annotations, EP Patent No. 2314629B1, Reference No. M70120EPEIN FLZ, May 20, 2016, five pages.
(Pages 153-157) Auxiliary Request 1, EP Patent No. 2314629B1, Reference No. M70120EPEIN FLZ, May 20, 2016, five pages.
(Pages 158-162) Auxiliary Request 2, EP Patent No. 2314629B1, Reference No. M70120EPEIN FLZ, May 20, 2016, five pages; (previously submitted); (pp. 163-167) Auxiliary Request 4, EP Patent No. 2314629B1, Reference No. M70120EPEIN FLZ, May 20, 2016, five pages (previously submitted); (pp. 173-177) Auxiliary Request 5, EP Patent No. 2314629B1, Reference No. M70120EPEIN FLZ, May 20, 2016, five pages (previously submitted).
(Pages 178-182) Auxiliary Request 6, EP Patent No. 2314629B1, Reference No. M70120EPEIN FLZ, May 20, 2016, five pages (previously submitted); (pp. 183-197) Auxiliary Request 7, EP Patent No. 2314629B1, Reference No. M70120EPEIN FLZ, May 20, 2016, five pages (previously submitted); (pp. 188-192); Auxiliary Request 8, EP Patent No. 2314629B1, Reference No. M70120EPEIN FLZ, May 20, 2016, five pages (previously submitted).
(Pages 193-197) Auxiliary Request 9, EP Patent No. 2314629B1, Reference No. M70120EPEIN FLZ, May 20, 2016, five pages (previously submitted); (pp. 198-202) Auxiliary Request 10, EP Patent No. 2314629B1, Reference No. M70120EPEIN FLZ, May 20, 2016, five pages (previously submitted); (pp. 203-205) Auxiliary Request 11, EP Patent No. 2314629B1, Reference No. M70120EPEIN FLZ, May 20, 2016, three pages (previously submitted).
(Pages 206-208); Auxiliary Request 12, EP Patent No. 2314629B1, Reference No. M70120EPEIN FLZ, May 20, 2016, three pages

(56) References Cited

OTHER PUBLICATIONS (previously submitted); (pp. 209-213); Auxiliary Request 13, EP Patent No. 2314629B1, Reference No. M70120EPEIN FLZ, May 20, 2016, five pages (previously submitted); (pp. 214-218) Auxiliary Request 14, EP Patent No. 2314629B1, Reference No. M70120EPEIN FLZ, May 20, 2016, five pages.
(Pages 219-225) Logtenberg, Prof. Ton Declaration of, CEO, Merus B.V., dated May 4, 2016, 7 pages (previously submitted); (pp. 226-251) Appeal Brief under 37 C.F.R. § 41.37 filed by Brenda Herschbach Jarrell, U.S. Appl. No. 13/948,818, Jul. 20, 2015, 26 pages with Claims Appendix (previously submitted).
(Pages 252-267) Response to the Summons to attend Oral Proceedings dated Nov. 29, 2015 and in preparation of the Hearing of Jun. 22, 2016, from Isenbruck Bösl Förschler LLP to European Patent Office dated May 20, 2016.
(Pages 268-272) Main Request with annotations, EP Patent No. 2314629B1, Reference No. M70120EPEIN FLZ, May 20, 2016, five pages (previously submitted); (pp. 273-279) EPO communication to Fritz Lahrtz of Isenbruck Bösl Höschler LLP, Brief Communication regarding Oral proceedings on Jun. 22, 2016 at 10:00 in S2.1, EP Application No. 10186063.3 and EP Patent No. 2314629, Apr. 26, 2016, (previously submitted).
(Page 280) Correspondence from Dr. Fritz Lahrtz of Isenbruck Bösl Föschler LLP to the European Patent Office regarding the Oral Proceedings on Jun. 22, 2016, EP Patent No. 10186063.3 and EP Patent No. 2314629, Feb. 16, 2016, one page (previously submitted); (p. 281) EPO communication to Fritz Lahrtz of Isenbruck Bösl Höschler LLP, Communication of amended entries concerning the representative (R. 143(1)(h) EPC), EP Application No. 10186063.3 and EP Patent No. 2314629, Jan. 12, 2016, EPO Form 2548 08.13, one page (previously submitted).
(Page 282) Correspondence from Dr. Fritz Lahrtz of Isenbruck Bösl Förschler LLP to the European Patent Office regarding change of correspondence, EP Patent No. 10186063.3 and EP Patent No. 2314629, Jan. 8, 2016, one page (previously submitted); (p. 283) EPO Acknowledgement of receipt, Application No. 10186063.3, Dec. 17, 2015, one page; (previously submitted).
(Page 284-285) EPO Letter accompanying subsequently filed items, Document concerning representation filed by C. M. Jansen of V.O., EP Application No. 10186063.3, Dec. 17, 2015, two pages (previously submitted); (pp. 286-287) EPO Communication to J A Kemp, Acknowledgement of receipt of EPO Forms 2310 and 2043, EP Application No. 10186063.3 and EP Patent No. 2314629, Nov. 19, 2015, EPO Form 2936 08.10, one page; (previously submitted).
(Pages 288-298) EPO Communication regarding opposition, EP Application No. 10186063.3, Nov. 19, 2015, EPO Form 2906 01.91TRI with Consolidated list of documents, 11 pages (previously submitted).
(Pages 299-301) EPO Communication regarding important information concerning oral proceedings, requesting information by Apr. 20, 2016, EPO Form 2043 02.09, three pages (previously submitted).
(Page 302-303) EPO Communication in preparation for oral proceedings dated Jun. 22, 2016, EP Application No. 10186063.3, EPO Form 2040, two pages.
(Page 304-305) Summons to Attend Oral Proceedings, EP Application No. 10186063.3, dated Nov. 19, 2015, two pages.
(Page 306) EPO Communication of amended entries concerning the representative (R. 143(1)(h) EPC), EP Application No. 10186063.3 and EP Patent No. 2314629, Oct. 8, 2015, EPO Form 2548, 08.13, one page (previously submitted); (p. 307) Correspondence from C.M. Jansen of V.O. to European Patent Office regarding the Registration of the Association and change of address, reference No. RvE/E100EPEP, Sep. 29, 2015, one page (previously submitted).
(Page 308) EPO Acknowledgement of Receipt of the submission by the proprietor, EP Application No. 10186063.3 and EP Patent No. 2314629, date of receipt Feb. 24, 2015, one page (previously submitted).
(Pages 309-310) EPO Communication regarding Submission in opposition proceedings, Reply of the patent proprietor to the notice(s) of opposition, EP Application No. 10186063.3 and Patent No. 2314629, Oct. 16, 2013, two pages.
(Pages 311-330) Reply to Communication under Rule 79(1) EPC, EP Application No. 10186063.3 and EP Patent No. 2314629, dated Feb. 24, 2015, 20 pages (previously submitted).
(Page 331) EPO Extension of time limit pursuant to Rule 132 EPC, EP Application No. 10186063.3 and EP Patent No. 2314629, Oct. 24, 2014, EPO Form 2944C, 06.12, one page.
(Page 332-335) EPO Communication regarding Submission in opposition proceedings, Request for extension of time, EP Application No. 10186063.3 and Patent No. 2314629, Oct. 16, 2014, four pages.
(Page 336) EPO Communication of a notice of opposition (R. 79(1) EPC), EP Application No. 10186063.3 and EP Patent No. 2314629, Aug. 22, 2014, EPO Form 2317A, 12.07, one page (previously submitted).
(Page 337) EPO Communication of a notice of opposition EP Application No. 10186063.3 and EP Patent No. 2314629, Jul. 21, 2014, EPO Form 2316, one page.
Aug. 8, 2016 Invitation to confirm maintenance of the application and to correct deficiencies in the Written Opinion/amend application, 2 pages.
Jul. 13, 2016 Refund of fees, 1 page.
Jun. 30, 2016 Communication regarding the transmission of the European search report, 1 page.
Jun. 30, 2016 European search opinion, 6 pages.
Jun. 30, 2016 European search report, 9 pages.
Jun. 30, 2016 Information on Search Strategy, 1 page.
Jun. 20, 2016 Communication of the registration of a transfer or change of name and/or address, 2 pages.
Jun. 16, 2016 General enquiry, 1 page.
Jun. 15, 2016 Search started, 1 page.
May 30, 2016 Annexes in respect of a request for a change, 53 pages.
May 30, 2016 Payment of fees and costs, 1 page.
May 30, 2016 Request for change of name—applicant, 1 page.
Dec. 23, 2015 Communication of amended entries concerning the representative, 1 page.
Dec. 22, 2015 Request for change of applicant's representative, 2 pages.
Dec. 17, 2015 (Electronic) Receipt, 1 page.
Dec. 17, 2015 Letter accompanying subsequently filed items, 1 page.
Dec. 17, 2015 Request for change of applicant's representative, 1 page.
Oct. 8, 2015 Communication of amended entries concerning the representative, 1 page.
Sep. 29, 2015 Request for change of applicant's representative, 1 page.
Apr. 23, 2013 CDS Clean up—amended data concerning the representative for the applicant, 1 page.
Apr. 2, 2013 Document concerning representation, 3 pages.
Jan. 6, 2013 Notification of forthcoming publication, 2 pages.
Oct. 29, 2012 Non-scannable object, 1 page.
Oct. 29, 2012 Reply to the invitation to remedy deficiencies, 2 pages.
Oct. 29, 2012 Sequence listing, 76 pages.
Aug. 31, 2012 Deficiencies in sequence listing, 2 pages.
Aug. 20, 2012 (Electronic) Receipt, 1 page.
Aug. 20, 2012 (Partial) description filed in response to formal objections, 8 pages.
Aug. 20, 2012 Drawings, 79 pages.
Aug. 20, 2012 Letter accompanying subsequently filed items, 1 page.
Jul. 20, 2012 Deficiencies in application documents—annex B and C, 4 pages.
Jul. 9, 2012 Abstract, 1 page.
Jul. 9, 2012 Acknowledgement of receipt of electronic submission of the request for grant of a European patent, 2 pages.
Jul. 9, 2012 Claims, 6 pages.
Jul. 9, 2012 Description, 87 pages.
Jul. 9, 2012 Designation of inventor Daniel, 1 page.
Jul. 9, 2012 Designation of inventor Erwin, 1 page.

(56) References Cited

OTHER PUBLICATIONS

Jul. 9, 2012 Designation of inventor Ton, 1 page.
Jul. 9, 2012 Designation of inventor Mark, 1 page.
Jul. 9, 2012 Drawings, 72 pages.
Jul. 9, 2012 Request for grant of a European patent (divisional application), 6 pages.
Oct. 27, 2009 Priority document, 72 pages.
Notice of Third Party Submission filed with the U.S. Patent Office on Aug. 29, 2016 in U.S. Appl. No. 15/140,321, 2 pages.
Concise Description of Relevance in Third Party Submission filed with the U.S. Patent Office on Aug. 29, 2016 in U.S. Appl. No. 15/140,321, 46 pages.
Concise Description of Relevance in Third Party Submission filed with the U.S. Patent Office on Aug. 29, 2016 in U.S. Appl. No. 15/140,321, 6 pages.
Third-Party Submission filed with the U.S. Patent Office on Aug. 29, 2016 in U.S. Appl. No. 15/140,321, 4 pages.
Documents listed in the Third-Party Submission include the following: U.S. Pat. No. 7,262,028 (previously submitted); Merchant et al., 1998 (previously submitted); Declaration of Dr. Joel Martin executed May 18, 2016 (previously submitted); U.S. Pat. No. 9,248,182 (previously submitted); WO 1998/050431 (previously submitted); Carter, 2001; WO 1999/045962 (previously submitted); Ritchie et al., 1984 (previously submitted); WO 02/066630 (previously submitted).
Canadian Intellectual Property Office—office action for Application No. 2,729,095 held by Merus B.V. dated Nov. 10, 2015 listing references considered: D8—Sirac et al., 2006 (previously submitted); D10—WO 2006/117699 (previously submitted); D12—WO 2004/106375 (previously submitted); D13—WO 02/066630 (previously submitted); D14—US 2007/0280945 (previously submitted).
D15—WO 2008/076379 (previously submitted); D16—WO 2008/054606 (previously submitted); D17—DeFrancesco et al., 2007 (listed separately below); D18—Scott, et al., 2007 (previously submitted); D19—Nagle, 2007 (previously submitted); Examination Search Report lists Family Members EP2147594B1 and AU2009263082B9.
Defrancesco et al., Big Pharma vies for mice, Nature Biotechnology, 25/6, pp. 613-614, Jun. 2007.
Response to office action for Canadian Application No. 2,729,095 dated May 10, 2016, 12 pages.
Third-Party Opposition dated Sep. 16, 2015, for Canadian Application No. 2,729,095, and Protest and Submission of Prior Art, which lists the following documents D8, D9, D10, D11, D12, D13, D14, D15, D16, D17, D18, D19, D20.
The Third-Party Opposition of Sep. 16, 2015, indicates the following attachments: 1) Second Protest (13 pages); 2) D8—Sirac et al., 2006, 9 pages (previously submitted); 3) D9—US20060015957 (299 pages); 4) D10—WO 2006117699 (79 pages) (previously submitted); 5) D11—WO 2004009618 (186 pages); 6) D12—WO 2004106375 (189 pages) (previously submitted); 7) D13—WO 20066630 (74 pages) (previously submitted).
8) D14—US 20070280945 (71 pages) (previously submitted); 9) D15—WO2008076379 (37 pages) (previously submitted); 10) D16—WO 2008054606 (30 pages) (previously submitted); 11) D17—New in Brief 2007 (2 pages) (previously submitted); 12) D18—Scott et al., 2007 (3 pages) (previously submitted); 13) D19—Nagle et al., 2007 (2 pages) (previously submitted) and 14) D20—Sirac et al., 2011 (15 pages) (previously submitted).
Voluntary Amendment filed by Borden Ladner Gervais LLP dated May 12, 2016 in Canadian Application No. 2,729,095, 2 pages.
Correspondence from the Canadian Intellectual Property Office in Canadian Application No. 2,729,095 to Borden Ladner Gervais LLP dated Apr. 16, 2014, advising that a protest has been filed by Blake Cassels & Graydon LLP, 1 page.
Correspondence from the Canadian Intellectual Property Office in Canadian Application No. 2,729,095 to Blake, Cassels & Graydon LLP dated Apr. 16, 2014, regarding filed protest, 1 page.

Protest and Submission of Prior Art submitted by Blake, Cassels & Graydon LLP dated Apr. 8, 2014, indicates the following attachments: 1) Protest and Submission of Prior Art (13 pages); 2) D8—Sirac et al., 2006, 9 pages (previously submitted); 3) D9—Aucouturier et al. (8 pages) (previously submitted); D10—GenBank M87478 (1 page) (previously submitted); D11—Sequence Alignment of GenBank (7 pages) (previously submitted); D12—de Wildt (7 pages) (previously submitted); D13—US 20060015957 (299 pages) (previously submitted); D14—WO 2004106375.
D17—WO 9850431 (70 pages) (previously submitted); D18—WO 02066630 (74 pages) (previously submitted); D19—US 20070280945 (71 pages) (previously submitted); D20—WO 2008076379 (37 pages) (previously submitted); D21—WO 2008054606 (30 pages) (previously submitted); D22—NIB 2007 (2 pages) (previously submitted); 23—Scott et al., 2007 (3 pages) (previously submitted); and D24—Nagle et al., 2007 (2 pages) (previously submitted).
Protest and Submission of Prior Art submitted by Blake, Cassels & Graydon LLP dated Sep. 16, 2015, indicates the following attachments: D8—Sirac et al., 2006, 9 pages (previously submitted); D9—US 20060015957 (299 pages) (previously submitted); D10—WO 2006117699 (previously submitted); D11—WO 2004009618 (previously submitted); D12—WO 2004106375 (previously submitted).
D13—WO 02066630 (previously submitted); D14—US 20070280945 (previously submitted); D15—WO 2008076379 (previously submitted); D16—WO 2008054606 (previously submitted); D17—News in Brief Article (previously submitted); D18—Scott, 2007 (previously submitted); D19, Nagle, 2007 (previously submitted); D20, Sirac et al., 2011.
EPO Letter accompanying subsequently filed items dated Aug. 20, 2012, EP12175544.1.
EPO Partial description filed in response to formal objections dated Aug. 20, 2012, EP12175544.1.
Drawings dated Aug. 20, 2012, EP12175544.1.
EPO Request for recording a change in name of representative dated Apr. 2, 2013, EP12175544.1.
EPO Client Database System—clean up dated Apr. 23, 2013, EP12175544.1.
EPO Letter accompanying subsequently filed items dated Dec. 17, 2015, EP12175544.1.
Almagro et al., Humanization of antibodies, Frontiers in Bioscience, Jan. 1, 2008, pp. 1619-1633, vol. 13.
Koochekpour et. al., Met and Hepatocyte Growth Factor/Scatter Factor Expression in Human Gliomas, Cancer Res., Dec. 1, 1997, pp. 5391-5398, vol. 57.
Zhu et al., Inhibition of vascular endothelial growth factor-induced receptor activation with anti-kinase insert domain-containing receptor single-chain antibodies from a phage display library, Cancer Res., Aug. 1998, pp. 3209-3214, vol. 58, No. 15.
Lu et al., Complete Inhibition of Vascular Endothelial Growth Factor (VEGF) Activities with a Bifunctional Diabody Directed against Both VEGF Kinase Receptors, fms-like Tyrosine Kinase Receptor and Kinase Insert Domain-containing Receptor, Cancer Res., Oct. 1, 2001, pp. 7002-7008, vol. 61.
Nahta et al.,The HER-2-Targeting Antibodies Trastuzumab and Pertuzumab Synergistically Inhibit the Survival of Breast Cancer Cells, Cancer Research, Apr. 1, 2004, pp. 2343-2346, vol. 64.
Mendel et al., The Angiogenesis Inhibitor SU5416 Has Long-lasting Effects on Vascular Endothelial Growth Factor Receptor Phosphorylation and Function, Clin. Cancer Res., Dec. 2000, pp. 4848-4858, vol. 6.
EPO Acknowledgement of receipt dated Aug. 20, 2012, EP12175544.1.
EPO Invitation to remedy deficiencies dated Aug. 31, 2012, EP12175544.1.
EPO Payment of fees and expenses dated Oct. 29, 2012, EP12175544.1.
EPO Reply to the invitation to remedy deficiencies dated Oct. 29, 2012, EP12175544.1.
EPO Model-Sheet dated Oct. 29, 2012, EP12175544.1.
EPO Sequence Listing dated Oct. 29, 2012, EP12175544.1.
EPO Notification of European publication number dated Jan. 16, 2013, EP12175544.1.

(56) References Cited

OTHER PUBLICATIONS

Auerbach et al., Angiogenesis Assays: A Critical Overview, Clin. Chemistry, Jan. 2003, pp. 32 40, vol. 49, No. 1.
Fendly et al., Characterization of Murine Monoclonal Antibodies Reactive to Either the Human Epidermal Growth Factor Receptor or HER2/neu Gene Product, Cancer Research, Mar. 1, 1990, pp. 1550-1558, vol. 50.
Kasprzyk et al., Therapy of an Animal Model of Human Gastric Cancer Using a Combination of Anti-erbB-2 Monoclonal Antibodies, Cancer Research, May 15, 1992, pp. 2271-2776, vol. 52.
Dammacco et al., Immunoglobulin secretion by peripheral blood and bone marrow B cells in patients with multiple myeloma. Studies by the reverse haemolytic plaque assay, Clin. Exp. Immunol., Sep. 1984, pp. 743-751, vol. 57, No. 3.
Desmet et al., The dead-end elimination theorem and its use in protein side-chain positioning, Nature, Apr. 9, 1992, pp. 539-542, vol. 356.
Desmet et al., Computation of the binding of fully flexible peptides to proteins with flexible side chains, FASEB J., Feb. 1997, pp. 164-172, vol. 11, No. 2.
Franklin et al., Insights into ErbB signaling from the structure of the ErbB2-pertuzumab complex, Cancer Cell, Apr. 2004, pp. 317-328, vol. 5, issue 4.
F.T. Wunderlich (2004), "Generation of inducible Cre systems for conditional gene inactivation in mice," Inauguraldissertation zur Erlangung des Doktorgrades der Mathematisch Naturwissenschaftlichen Fakultät der Universität zu Köln; on the World Wide Web at deposit.ddb.de/cgi binldokserv?idn=97557230x&dok_var=d1&dok_ext=pdf&filename= 97557230x.pd.
Galun et al., Clinical evaluation (Phase I) of a combination of two human monoclonal antibodies to HBV: Safety and antiviral properties., Hepatology, Mar. 2002, pp. 673-679, vol. 35, Issue 3.
Griffiths, et al., Human anti-self antibodies with high specificity from phage display libraries, EMBO J., Feb. 1993, pp. 725-734, vol. 12, No. 2.
Griffiths et al., Isolation of high affinity human antibodies directly from large synthetic repertoires, EMBO J., Jul. 15, 1994, pp. 3245-3260, vol. 13, No. 14.
Meyer et al., The Igk 3'-enhancer triggers gene expression in early B lymphocytes but its activity in enhanced on B cell activation, Int. Immunol., 1996, pp. 1561-1568, vol. 8, No. 10.
Gascan et al., Human B cell clones can be induced to proliferate and to switch to IgE and IgG4 synthesis by interleukin-4 and a signal provided by activated CD4C T cell clones. J Exp Med. 1991;173:747-750.
Nicholson et al., Antibody Repertoires of Four- and Five-Feature Translocus Mice Carrying Human Immunoglobulin Heavy Chain and kappa and lambda Light Chain Yeast Artificial Chromosomes, The Journal of Immunology, 1999, pp. 6898-6906, vol. 163.
Castelli et al., HLA-DP4, The Most Frequent HLA II Molecule, Defines a New Supertype of Peptide-Binding Specificity, J. Immunol., Dec. 15, 2002, pp. 6928-6934, vol. 169, No. 12.
Middendorp et al., Impaired Precursor B Cell Differentiation in Bruton's Tyrosine Kinase-Deficient Mice, J. Immunol., Mar. 15, 2002, pp. 2695-2703, vol. 168 No. 6.
Tan et al., "Superhumanized" Antibodies: Reduction of Immunogenic Potential by Complementarity-Determining Region Grafting with Human Germline Sequences: Application to an Anti-CD281, J. Immunol., Jul. 15, 2002, pp. 1119-1125, vol. 169, No. 2.
Middendorp et al., Cellular Maturation Defects in Bruton's Tyrosine Kinase-Deficient Immature B Cells Are Amplified by Premature B Cell Receptor Expression and Reduced by Receptor Editing, J. Immunol., Feb. 1, 2004, pp. 1371-1379, vol. 172, No. 3.
Gerbert et al., Vascular endothelial growth factor regulates endothelial cell survival through the phosphatidylinositol 3'-kinase/Akt signal transduction pathway. Requirement for Flk-1/KDR activation, J Biol. Chem., Nov. 13, 1998, pp. 30336-30343, vol. 273.
Lu et al., Identification of the Residues in the Extracellular Region of KDR Important for Interaction with Vascular Endothelial Growth Factor and Neutralizing Anti-KDR Antibodies, J. Biol. Chem., May 12, 2000, pp. 14321-14330, vol. 275.
Burger et al., An integrated strategy for the process development of a recombinant antibody-cytokine fusion protein expressed in BHK cells, Appl. Microbiol. Biotechnol., Sep. 1999, pp. 345-353, vol. 52, Issue 3, Abstract only.
Cherrington et al., New paradigms for the treatment of cancer: The role of anti-angiogenesis agents, Adv. Cancer. Res., 2000, pp. 1-38, vol. 79, Abstract only.
Cho et al., Structure of the extracellular region of HER2 alone and in complex with the Herceptin Fab, Nature, Feb. 13, 2003, pp. 756-760, vol. 421, Abstract only.
Desmet et al., Fast and accurate side-chain topology and energy refinement (FASTER) as a new method for protein structure optimization, Proteins, Jul. 1, 2002, pp. 31-43, vol. 48, Issue 1, Abstract only.
Cheung et al., A recombinant human Fab expressed in *Escherichia coli* neutralizes rabies virus, J. Virol., Nov. 1992, pp. 6714-6720, vol. 66, No. 11.
Throsby, Isolation and Characterization of Human Monoclonal Antibodies from Individuals Infected with West Nile Virus, J. Virol., Jul. 2006, pp. 6982-6992, vol. 80, No. 14.
Kunkel et al., Rapid and efficient site-specific mutagenesis without phenotypic selection, Methods in Enzymol., 1987, pp. 367-382, vol. 154.
Allen, Ligand-targeted therapeutics in anticancer therapy, Nat. Rev. Cancer, 2002, 2:750-783, Abstract only.
Atwell et al., Stable heterodimers from remodeling the domain interface of a homodimer using a phage display library1, J. Mol. Biol., Jul. 4, 1997, pp. 26-35, vol. 270, Issue 1, Abstract only.
Birchmeier et. al., Met, metastasis, motility and more, Nat. Rev. Mol. Cell Biol., Dec. 2003, pp. 915-925, vol. 4, Abstract only.
EPO Request for change of applicant's representation dated Dec. 22, 2015, EP12175544.1.
EPO Communication of amended entries concerning the representation dated Dec. 23, 2015, EP12175544.1.
EPO Annexes in respect of a request for a change dated May 30, 2016, EP12175544.1.
EPO Request for recordation of a transfer dated May 30, 2016, EP12175544.1.
EPO Payment of fees and expenses dated May 30, 2016, EP12175544.1.
EPO Search has started dated Jun. 15, 2016, EP12175544.1.
EPO General enquiry dated Jun. 16, 2016, EP12175544.1.
EPO Communication concerning the registration of amendments relating to entries pertaining to the applicant/the proprietor dated Jun. 20, 2016, EP12175544.1.
EPO Information on Search Strategy dated Jun. 30, 2016, EP12175544.1.
Letter accompanying subsequently filed items regarding examination, EP Application No. 09075279.1, Jun. 13, 2013, one page.
EPO Communication, Provision of the minutes in accordance with Rule 124(4) EPC, EP Application No. 09075279.1, Aug. 8, 2013, EPO Form 2042 12.07TRI, one page.
EPO Communication, Minutes, EP Application No. 09075279.1, Aug. 8, 2013, EPO Form 2906 01.91TRI, 25 pages.
Letter accompanying subsequently filed items regarding German and French translation of the claims, EP Application No. 09075279.1, Sep. 2, 2013, two pages.
EPO Communication under Rule 71(3) EPC, EP Application No. 09075279.1, dated Sep. 2, 2013, EPO Form 2004C 06.13TRI, five pages.
EPO Communication, Annex to EPO Form 2004, Communication pursuant to Rule 71(3) EPC, EP Application No. 09075279.1, dated Sep. 2, 2013, EPO Form 2056, two pages.
German Translation of claims for EP Application No. 09075279.1, at least as early as Sep. 2, 2013, four pages.
French Translation of claims for EP Application No. 09075279.1, at least as early as Sep. 2, 2013, three pages.
EP Application No. 09075279.1 with annotations, Aug. 3, 2010, 170 pages.

(56) References Cited

OTHER PUBLICATIONS

EPO Acknowledgement of receipt of letter regarding French and German translated claims, EP Application No. 09075279.1, date of receipt Sep. 2, 2013, one page.
Letter accompanying subsequently filed items regarding documents filed during examination procedure, EP Application No. 09075279.1, Sep. 3, 2013, one page.
Correspondence from S.T. van Doorn of V.O. to European Patent Office regarding in vivo data, EP Application No. 09075279.1, Jun. 13, 2013, two pages.
Correspondence from S. van Doorn to European Patent Office regarding request to hold application, EP Application No. 09075279.1, Sep. 3, 2013, one page.
EPO Acknowledgement of receipt of letter regarding request to hold application, EP Application No. 09075279.1, date of receipt Sep. 3, 2013, one page.
Third Party Observations Against European Parent Application No. 09075279.1 in the name of Merus BV, at least as early as Sep. 5, 2013, four pages.
Third Party Observation for application No. EP20090075279, Anonymous, at least as early as Sep. 5, 2013, seven pages.
Dietzschold et al., Delineation of putative mechanisms involved in antibody-mediated clearance of rabies virus from the central nervous system, PNAS, 1992, pp. 7252-7256, vol. 89, No. 15.
Jakobovits et al., Analysis of homozygous mutant chimeric mice: deletion of the immunoglobulin heavy-chain joining region blocks B-cell development and antibody production, Proc. Natl. Acad. Sci. U.S.A., Mar. 1993, pp. 2551-2555, vol. 90.
Cao et al., Neutralizing monoclonal antibodies to hepatocyte growth factor/scatter factor (HGF/SF) display antitumor activity in animal models, Proc. Natl. Acad. Sci. U.S.A., Jun. 19, 2001, pp. 7443-7448, vol. 98, No. 13.
Eggan et al., Hybrid vigor, fetal overgrowth, and viability of mice derived by nuclear cloning and tetraploid embryo complementation, PNAS, May 22, 2001, pp. 6209-6214, vol. 98, No. 11.
Schnieke et al., Human Factor IX Transgenic Sheep Produced by Transfer of Nuclei from Transfected Fetal Fibroblasts, Science, Dec. 19, 1997, pp. 2130-2133, vol. 278, Issue 5346.
Campbell et al., Sheep cloned by nuclear transfer from a cultured cell line, Nature, Mar. 7, 1996, pp. 64-66, vol. 380, Nature Publishing Group.
Wilmut et al., Viable offspring derived from fetal and adult mammalian cells, Nature, Feb. 27, 1997, pp. 810-813, vol. 385, Issue 6619.
Peeters et al., Production of antibodies and antibody fragments in plants, Vaccine, Mar. 21, 2001, pp. 2756-2761, vol. 19, Issues 17-19, Elsevier.
EPO Request for change of applicant's representation dated Dec. 17, 2015, EP12175544.1.
EPO Acknowledgement of receipt dated Dec. 17, 2015, EP12175544.1.
Segal et al., Introduction: bispecific antibodies, Journal of Immunological Methods, 2001, pp. 1-6, vol. 248, Elsevier.
David Nemazee, Receptor Editing in B Cells, Advances in Immunology, 2000, pp. 89-126, vol. 74, Academic Press.
Casellas et al., Contribution of Receptor Editing to the Antibody Repertoire, Science, Feb. 23, 2001, pp. 1541-1544, vol. 291, Issue 5508.
Radic et al., Ig H and L chain contributions to autoimmune specificities, The Journal of Immunology, Jan. 1, 1991, pp. 176-182, vol. 146, No. 1, The American Association of Immunologists.
Larrick et al., Producing proteins in transgenic plants and animals, Current Opinion in Biotechnology, Aug. 1, 2001, pp. 411-418, vol. 12, Issue 4.
Rajewsky et al., Conditional gene targeting, J Clin Invest, Aug. 1, 1996, pp. 600-603, vol. 98, No. 3.
Seibler et al., Rapid generation of inducible mouse mutants, Nucleic Acids Res., Feb. 15, 2003, e12, vol. 31, No. 4.
Srinivas et al., Cre reporter strains produced by targeted insertion of EYFP and ECFP into the ROSA26 locus, BMC Dev. Bioi., Mar. 27, 2001, vol. 1 :4.
Thiebe et al., The variable genes and gene families of the mouse immunoglobulin Kappa locus, European Journal of Immunology, Jul. 1999, pp. 2072-2081, vol. 29, Issue 7.
Van der Heijden et al., Structural and functional studies on a unique linear neutralizing antigenic site (G5) of the rabies virus glycoprotein, J. Gen. Virol., Aug. 1993, pp. 1539-1545, vol. 74, Issue 8.
Wen et al., Tricistronic viral vectors co-expressing interleukin-12 (1L-12) and CD80 (B7-1) for the immunotherapy of cancer: Preclinical studies in myeloma, Cancer Gene Therapy, 2001, pp. 361-370, vol. 8 No. 5.
Wilmut et al., Basic techniques for transgenesis, Journals of Reproduction and Fertility, 1991, pp. 265-275, vol. 43, Journals of Reproduction & Fertility LTD.
Xu et al., "Deletion of the Ig kappa light chain intronic enhancer/matrix attachment region impairs but does not abolish V kappa J kappa rearrangement," Immunity (1996) 4:377-385.
Zhu et al., Remodeling domain interfaces to enhance heterodimer formation, Protein Science, Apr. 1997, pp. 781-788, vol. 6, Issue 4.
Giddings et al., Transgenic plants as factories for biopharmaceuticals, Nature Biotechnology, 2000, pp. 1151-1155, vol. 18, Nature America Inc.
Brief Communication from European Patent Office to Isenbruck Bösl Förschler LLP regarding EP 10186063.3 dated Jun. 13, 2016.
Brief Communication from European Patent Office to JA Kemp regarding EP 10186063.3 dated Jun. 13, 2016.
Letter regarding the opposition procedure (no time limit) dated Jun. 20, 2016 from Isenbruck Bösl Förschler LLP to European Patent Office, 1 page.
Brief communication from European Patent Office to JA Kemp about Opposition—Oral proceedings on Jun. 22, 2016.
Response to the Summons to attend Oral Proceedings dated Nov. 29, 2015 and in preparation of the Hearing of Jun. 22, 2016, from Isenbruck Bösl Förschler LLP to European Patent Office dated May 20, 2016.
Acknowledgement of receipt from European Patent Office for EP 10186063.3 dated May 20, 2016.
Brief communication in Opposition proceedings in EP 10186063.3 dated May 26, 2016.
Request for recordal of change of Proprietor from Merus B.V. to Merus N.V. filed by Isenbruck Bösl Förschler LLP with European Patent Office dated May 27, 2016, 2 pages.
Annexes in respect of a request for a change from Merus B.V. to Merus N.V. dated May 27, 2016 (Dutch version).
Annexes in respect of a request for a change from Merus B.V. to Merus N.V. dated May 19, 2016 (English version).
Payment of fees and expenses for EP Application No. 10186063.3 dated May 27, 2016, one page.
Desmet et al., Anchor profiles of HLA-specific peptides: Analysis by a novel affinity scoring method and experimental validation, Proteins, Jan. 1, 2005, pp. 53-69, vol. 58, Abstract only.
Eigenbrot et al., X-ray Structures of the Antigen-binding Domains from Three Variants of Humanized anti-p185HER2 Antibody 4D5 and Comparison with Molecular Modeling, J. Mol. Biol., Feb. 20, 1993, pp. 969-995, vol. 229, Issue 4, Elsevier, Abstract only.
Ewert et al., Biophysical properties of human antibody variable domains, J. Mol. Biol., Jan. 17, 2003, pp. 531-553, vol. 325, Iss. 3.
Folkman, Angiogenesis in cancer, vascular, rheumatoid and other disease, J. Nat. Med., 1995, pp. 27-31, vol. 1, Abstract only.
Gerstner et al., Sequence Plasticity in the Antigen-binding Site of a Therapeutic Anti-HER2 Antibody, J. Mol. Biol., Aug. 30, 2002, pp. 851-862, vol. 321, issue 5, Elsevier, Abstract only.
Gluzman, SV40-transformed simian cells support the replication of early SV40 mutants, Cell, Jan. 1981, pp. 175-182, vol. 23, Issue 1, Abstract only.
Green et al., Antigen-specific human monoclonal antibodies from mice engineered with human Ig heavy and light chain YACs, Nat. Genet., 1994, pp. 13-21, vol. 7, Abstract only.

(56) References Cited

OTHER PUBLICATIONS

Hoogenboom et al., By-passing immunisation. Human antibodies from synthetic repertoires of germline VH gene segments rearranged in vitro, J Mol Biol., Sep. 20, 1992, pp. 381-388, vol. 227, Issue 2, Abstract only.
Hoogenboom, Designing and optimizing library selection strategies for generating high-affinity antibodies, Trends Biotechnol., 1997, pp. 62-70, vol. 15, Issue 2, Abstract only.
Hoogenboom, et al., Natural and designer binding sites made by phage display technology, Immunol. Today, Aug. 1, 2000, pp. 371-378, vol. 21, Issue 8, Abstract only.
Hoogenboom et al., Selecting and screening recombinant antibody libraries, Nat. Biotechnol., Sep. 7, 2005, pp. 1105-1116, vol. 23, Abstract only.
Ignatovich et al., Dominance of intrinsic genetic factors in shaping the human immunoglobulin Vlambda repertoire, J. Mol. Biol., Nov. 26, 1999, pp. 457-465, vol. 294, Issue 2.
Inlay et al., Essential roles of the kappa light chain intronic enhancer and 3' enhancer in kappa rearrangement and demethylation, Nat Immunol., Apr. 22, 2002, pp. 463-468, vol. 3, Abstract only.
Jain et al., Engineering antibodies for clinical applications, Trends in Biotechnol., Jul. 2007, pp. 307-316, vol. 25, Issue 7.
Jakobovits et al., Germ-line transmission and expression of a human-derived yeast artificial chromosome, Nature, Mar. 18, 1993, pp. 255-258, vol. 362, Abstract only.
Jones et al., Replacing the complementarity-determining regions in a human antibody with those from a mouse, Nature, May 29, 1986, pp. 522-525, vol. 321, Abstract only.
Kaufman et al., Amplification and expression of sequences cotransfected with a modular dihydrofolate reductase complementary DNA gene, J. Mol. Biol., Aug. 25, 1982, pp. 601-621, vol. 159, Issue 4, Abstract only.
Szabo et al., Surface plasmon resonance and its use in biomolecular interaction analysis (BIA), Curr. Opin. Struct. Biol., Oct. 1995, pp. 699-705, vol. 5, Issue 5, Abstract only.
Van den Beucken et al., Building novel binding ligands to B7.1 and B7.2 based on human antibody single variable light chain domains, J. Mol. Biol., Jul. 13, 2001, pp. 591-601, vol. 310, Issue 3, Abstract only.
Winter et al., Making antibodies by phage display technology, Annu. Rev. Immunol., Apr. 1994, pp. 433-455, vol. 12, Abstract only.
Zahn Zabel et al., Development of stable cell lines for production or regulated expression using matrix attachment regions, J. Biotechnology, Apr. 27, 2001, pp. 29-42, vol. 87, Issue 1.
Zhu et. al., Inhibition of Tumor Growth and Metastasis by Targeting Tumor-Associated Angiogenesis with Antagonists to the Receptors of Vascular Endothelial Growth Factor, Invest. New Drugs, Aug. 1999, pp. 195-212, vol. 17, Issue 3, Abstract only.
Hudziak et al., p185HER2 monoclonal antibody has antiproliferative effects in vitro and sensitizes human breast tumor cells to tumor necrosis factor, Mol. Cell. Biol., Mar. 1989, pp. 1165-1172, vol. 9. No. 3.
Rong et al., Tumorigenicity of the met proto-oncogene and the gene for hepatocyte growth factor, Mol. Cell Biol., Nov. 1992, pp. 5152-5158, vol. 12, No. 11.
Klagsbrun et al., Vascular endothelial growth factor and its receptors, Cytokine Rev., Oct. 1996, pp. 259-270, vol. 7, Issue 3, Abstract only.
Klitz et al., New HLA haplotype frequency reference standards: High-resolution and large sample typing of HLA DR-DQ haplotypes in a sample of European Americans, Tissue Antigens, pp. 296-307, vol. 62, Issue 4, Abstract only.
Lazar et al., A molecular immunology approach to antibody humanization and functional optimization, Mol Immunol., Mar. 2007, pp. 1986-1998, vol. 44, Issue 8.
Li et al., Stable expression of three genes from a tricistronic retroviral vector containing a picornavirus and 9-nt cellular internal ribosome entry site elements, J. Virol. Methods, Feb. 2004, pp. 137-144, vol. 115, Issue 2.
Lu et al., Acquired antagonistic activity of a bispecific diabody directed against two different epitopes on vascular endothelial growth factor receptor 2, J. Immunol. Methods, Nov. 19, 1999, pp. 159-171, vol. 230.
Marks et al., By-passing immunization: Human antibodies from V-gene libraries displayed on phage, J. Mol. Biol., Dec. 5, 1991, pp. 581-597, vol. 222, Issue 3, Abstract only.
Min Soo Kim et al., Comparative Analyses of Complex Formation and Binding Sites between Human Tumor Necrosis Factor-alpha and its Three Antagonists Elucidate their Different Neutralizing Mechanisms, JMB, Dec. 14, 2007, pp. 1374-1388, vol. 374, Issue 5.
Mostoslavsky et al., "Asynchronous replication and allelic exclusion in the immune system," Nature (2001) 414:221-225, Abstract only.
Padlan et al., A possible procedure for reducing the immunogenicity of antibody variable domains while preserving their ligand-binding properties, Mol. Immunol., 1991, pp. 489-498, vol. 28, Abstract only.
Persic, L. et al. An integrated vector system for the eukaryotic expression of antibodies or their fragments after selection from phage display libraries, Gene, Mar. 10, 1997, pp. 9-18, vol. 187, Issue 1.
Sidhu et al., Phage display for selection of novel binding peptides, Methods Enzymol., 2000 328:333 363.
Simmons et al., Expression of full-length immunoglobulins in *Escherichia coli*: rapid and efficient production of aglycosylated antibodies, J. Immunol. Methods, May 1, 2002, pp. 133-147, vol. 263.
Sjolander and Urbaniczky, Integrated fluid handling system for biomolecular interaction analysis, Anal. Chem., 1991, pp. 2338-2345, vol. 63, No. 20, Abstract only.
Smith, G.P., Filamentous fusion phage: Novel expression vectors that display cloned antigens on the virion surface. Science, Jun. 14, 1985, pp. 1315-1317, vol. 228, Issue 4705, Abstract only.
Jeffers et al., Enhanced tumorigenicity and invasion-metastasis by hepatocyte growth factor/scatter factor-met signalling in human cells concomitant with induction of the urokinase proteolysis network, Mol. Cell. Biol., Mar. 1996, pp. 1115-1125, vol. 16, No. 3.
G. Neufeld et al., Vascular endothelial growth factor (VEGF) and its receptors, FASEB J., Jan. 1999, pp. 9-22, vol. 13, No. 1.
Hoogenboom et al., Multi-subunit proteins on the surface of filamentous phage: methodologies for displaying antibody (Fab) heavy and light chains, Nucl. Acids Res., 1991, pp. 4133-4137, vol. 19, Issue 15.
Kramer et al., A novel helper phage that improves phage display selection efficiency by preventing the amplification of phages without recombinant protein, Nucleic Acids Res., 2003, e59, vol. 31, No. 11.
Kakitani et al., "A novel transgenic chimaeric mouse system for the rapid functional evaluation of genes encoding secreted proteins," Nucleic Acids Research (2005) 33(9):e85.
Statement of Fact and Arguments in Support of Opposition dated Jul. 15, 2014 for EP 2 314 629 B1.
Banger et al., DNA sequencing with chain-terminating inhibitors, PNAS, Dec. 1, 1997, pp. 5463-5467, vol. 74, No. 12.
Urlaub et al., Isolation of Chinese hamster cell mutants deficient in dihydrofolate reductase activity, PNAS, Jul. 1, 1980, pp. 4216-4220, vol. 77, No. 7.
Morrison et al., Chimeric human antibody molecules: mouse antigen-binding domains with human constant region domains, Proc. Natl. Acad. Sci. USA, Nov. 1, 1984, pp. 6851-6855, vol. 81, No. 21.
Queen et al., A humanized antibody that binds to the interleukin 2 receptor, Proc. Natl. Acad. Sci. U.S.A., Dec. 1, 1989, pp. 10029-10033, vol. 86, No. 24.
Conn et al., Purification of a glycoprotein vascular endothelial cell mitogen from a rat glioma-derived cell line, Proc. Natl. Acad. Sci. U.S.A., Feb. 1, 1990, pp. 1323-1327, vol. 87, No. 4.
Carter et al.,Humanization of anti-p185her2 antibody for human cancer therapy, PNAS, 1992, pp. 4285-4289, vol. 89.
EPO Brief Communication regarding the Opposition against EP Application No. 10186063.3 and EP Patent No. 2314629, Feb. 27, 2015, EPO Form 2911O 01.12, one page.

(56) References Cited

OTHER PUBLICATIONS

Letter from Mr. C.M. Jansen of V.O. Patents & Trademarks to European Patent Office, Regarding Registration of the Association and change of address, Sep. 29, 2015, one page.
EPO Communication of amended entries concerning the representative (R. 143(1)(h) EPC), EP Application No. 10186063.3 and EP Patent No. 2314629, Oct. 8, 2015, EPO Form 2548, 08.13, one page.
EPO Communication regarding the oral proceedings dated Jun. 22, 2016, EP Application No. 10186063.3, EPO Form 2341 09.14, one page.
EPO Communication regarding the preparation for oral proceedings—Instructions to Support Service dated Nov. 11, 2015, EP Application No. 10186063.3 and EP Patent No. 2314629, EPO Form 2040 12.01TRI, two pages.
EPO Communication regarding important information concerning oral proceedings, at least as early as Nov. 19, 2015, EPO Form 2043 02.09, three pages.
EPO Communication, Summons to V.O. to attend oral proceedings pursant to Rule 115(1) EPC, EP Application No. 10186063.3 and EP Patent No. 2314629, Nov. 19, 2015, EPO Form 2310 12.14, one page.
EPO Communication, Summons to J A Kemp to attend oral proceedings pursuant to Rule 115(1) EPC, EP Application No. 10186063.3 and EP Patent No. 2314629, Nov. 19, 2015, EPO Form 2310 12.14, one page.
EPO Communication regarding opposition, EP Application No. 10186063.3, Nov. 19, 2015, EPO Form 2906 01.91TRI, 11 pages.
EPO Communication to V.O., Acknowledgement of receipt of EPO Forms 2310 and 2043, EP Application No. 10186063.3 and EP Patent No. 2314629, Nov. 19, 2015, EPO Form 2936 08.10, one page.
EPO Communication to J A Kemp, Acknowledgement of receipt of EPO Forms 2310 and 2043, EP Application No. 10186063.3 and EP Patent No. 2314629, Nov. 19, 2015, EPO Form 2936 08.10, one page.
V.O. communication to EPO, Executed Acknowledgement of receipt of EPO Form 2310 and 2043, EP Application No. 10186063.3 and EP Patent No. 2314629, Nov. 20, 2015, EPO Form 2936 08.10, one page.
EPO Submission in opposition proceedings, Request for extension of time, EP Application No. 10186063.3 and EP Patent No. 2314629, Oct. 16, 2014, two pages.
EPO Acknowledgement of Receipt of the submission by the proprietor, EP Application No. 10186063.3 and EP Patent No. 2314629, date of receipt Oct. 16, 2014, one page.
EPO Brief Communication regarding the Opposition againts EP Application No. 10186063.3 and EP Patent No. 2314629, Oct. 24, 2014, EPO Form 2911O 01.12, one page.
EPO Extension of time limit pursuant to Rule 132 EPC, EP Application No. 10186063.3 and EP Patent No. 2314629, Oct. 24, 2014, EPO Form 2944C, 06.12, one page.
EPO Submission in opposition proceedings, Reply of the patent proprietor to the notice(s) of opposition, EP Application No. 10186063.3 and EP Patent No. 2314629, Feb. 24, 2015, two pages.
Reply to Communication under Rule 79(1) EPC, EP Application No. 10186063.3 and EP Patent No. 2314629, Feb. 24, 2015, 20 pages.
EPO Acknowledgement of Receipt of the submission by the proprietor, EP Application No. 10186063.3 and EP Patent No. 2314629, date of receipt Feb. 24, 2015, one page.
Letter from Mr. T.J. Elmore of V.O. Patents & Trademarks to European Patent Office, at least as early as Oct. 16, 2014, accompanying subsequently filed items, one page.
Letter from Mr. Andrew Bentham of JA Kemp to European Patent Office dated Jul. 15, 2014, accompanying subsequently filed items, one page.
Statement of Fact and Argument in Support of Opposition filed against EP Patent No. 2314629, at least as early as Jul. 15, 2014, 30 pages.

EPO Acknowledgement of Receipt of the Notice of Opposition against EP Application No. 10186063.3 and EP Patent No. 2314629, date of receipt Jul. 15, 2014, three pages.
EPO Communication of a notice of opposition for EP Application No. 10186063.3 and EP Patent No. 2314629, Jul. 21, 2014, EPO Form 2316, 01.12, one page.
EPO Communication of a notice of opposition (R. 79(1) EPC), EP Application No. 10186063.3 and EP Patent No. 2314629, Aug. 22, 2014, EPO Form 2317A, 12.07, one page.
EPO Communication of further notices of opposition pursuant to Rule 79(2) EPC, EP Application No. 10186063.3 and EP Patent No. 2314629, Aug. 22, 2014, EPO Form 2318, 01.12, one page.
EPO Submission in opposition proceedings, Acknowledgement of Receipt filed by David Power of J A Kemp, EP Application No. 10186063.3 and EP Patent No. 2314629, Nov. 20, 2015, two pages.
EPO Acknowledgement of receipt, Acknowledgement of Receipt, Application No. 10186063.3 and EP Patent No. 2314629, Nov. 27, 2015, one page.
J A Kemp communication to EPO, Executed Acknowledgement of receipt of EPO Form 2310 and 2043, EP Application No. 10186063.3 and EP Patent No. 2314629, Nov. 25, 2015, EPO Form 2936 08.10, one page.
EPO Letter accompanying subsequently filed items, Document concerning representation filed by C.M. Jansen of V.O., EP Application No. 10186063.3, Dec. 17, 2015, one page.
Correspondence from C.M. Jansen of V.O. to the European Patent Office regarding change of correspondence, EP Application No. 10186063.3 and EP Patent No. 2314629, Dec. 17, 2015, one page.
EPO Acknowledgement of receipt, request, Application No. 10186063.3, Dec. 17, 2015, one page.
Correspondence from Dr. Fritz Lahrtz of Isenbruck Bösl Förschler LLP to the European Patent Office regarding change of correspondence, EP Application No. 10186063.3 and EP Patent No. 2314629, Jan. 8, 2016, one page.
Opposition Filed Against European Patent No. EP 2 314 629 B1 (European Patent Application No. 10186063.3) in the Name of Merus B.V., Declaration of Dr. Joel Martin, May 18, 2016, 13 pages.
Declaration of Prof. Ton Logtenberg, CEO, Merus B.V., European Patent No. EP 2 314 629 B1, May 4, 2016, seven pages.
Appeal Brief under 37 C.F.R. § 41.37 filed by Brenda Herschbach Jarrell, U.S. Appl. No. 13/948,818, Jul. 20, 2015, 26 pages.
Jones et al., "High-Level Expression of Recombinant IgG in the Human Cell Line PER.C6", Biotechnology Progress, vol. 19, 2003, pp. 163-168.
Brief communication in opposition proceedings for EP application 10186063.3 dated May 31, 2016, one page.
Letter from European Patent Office to Mr. Andrew Bentham of JA Kemp dated Jun. 6, 2016, accompanying subsequently filed items, one page.
Verma et al., Antibody engineering: Comparison of bacterial, yeast, insect and mammalian expression systems, Journal of Immunological Methods, 1998, pp. 165-181, vol. 216.
Tada et al., Expression and characterization of a chimeric bispecific antibody against fibrin and against urokinase-type plasminogen activator, Journal of Biotechnology, 1994, pp. 157-174, vol. 33.
Fussenegger et al., Genetic optimization of recombinant glycoprotein production by mammalian cells, Reviews, Tibtech, Jan. 1999, pp. 35-42, vol. 17.
Phelps et al., Expression and Characterization of a Chimeric Bifunctional Antibody with Therapeutic Applications, The Journal of Immunology, Aug. 15, 1990, pp. 1200-1204, vol. 145, No. 4.
List of references in Opposition to Merus B.V.'s EP 2 314 29 B1, Consolidated List of Documents, undated, one page.
Acknowledgement of receipt of European Patent Office regarding EP 10186063.3 dated Jun. 6, 2016, 2 pages.
Communication from the European Patent Office to Isenbruck Bösl Förschler LLP regarding change to Merus N.V. dated Jun. 7, 2016.
Letter from JA Kemp to the European Patent Office regarding Oral Proceedings scheduled for Jun. 22, 2016.
JA Kemp to the European Patent Office of Final Written Submissions for Oral Proceedings scheduled for Jun. 22, 2016 in Opposition to Merus B.V.'s EP 2 314 629 B1 dated May 20, 2016.

(56) References Cited

OTHER PUBLICATIONS

Brief Communication from European Patent Office to JA Kemp regarding EP 10186063.3 dated Jun. 7, 2016.
Brief Communication from European Patent Office to Isenbruck Bösl Förschler LLP regarding EP 10186063.3 dated Jun. 10, 2016 about Oral proceedings on Jun. 22, 2016.
Gonzales-Fernandez et al., Analysis of somatic hypennutation in mouse Peyer's patches using immunoglobulin K lightchain transgenes, Proc. Natl. Acad. Sci., Nov. 1993, pp. 9862-9866, vol. 90.
Goyenechea et al., Modifying the sequence of an immunoglobulin V-gene alters the resulting pattern of hypermutation, Proc. Natl. Acad. Sci. 1996, pp. 13979-13984, vol. 93.
Goyenechea, Beatriz et al., "Cells strongly expressing Igk transgenes show clonal recruitment of hypermutation: a role for both MAR and the enhancers," The EMBO Journal, vol. 16(13):3987-3994 (1997).
Hardy et al., B Cell Development Pathways, Annu. Rev. Immunol., 2001, pp. 595-621, vol. 19.
Hengstschlager et al., A lambda 1 trans gene under the control of a heavy chain promoter and enhancer does not undergo somatic hypennutation, Eur. J. Immunol. 1994, pp. 1649-1656, vol. 24.
Hochedlinger, Konrad et al., "Monoclonal mice generated by nuclear transfer from mature B and T donor cells," Nature, vol. 415:1 035-1 038 (2002).
Homig-Holzel et al., Constitutive CD40 signaling in B cells selectively activates the noncanonical NF-kappaB pathway and promotes lymphomagenesis, J. Exp. Med., 2008, pp. 1317-1329, vol. 205, No. 6.
ImMunoGeneTics Information System, for analysed sequence CHEB VK, http://www.imgt.org/IMGT vguesVvguest, at least as early as Apr. 25, 2012.
PCT International Search Report, PCT/NL2009/050381 dated Dec. 7, 2009.
EPO Communication pursuant to Article 94(3) EPC, EP Application No. 09075279.1, dated Jun. 29, 2012, EPO Form 2001 12.10CSX, six pages.
Response to communication pursuant Article 94(3) EPC, EP Application No. 09075279.1, dated Sep. 11, 2012, Reference No. P85231EP00, eleven pages.
EPO Communication pursuant to Rule 114(2) EPC, EP Application No. 09075279.1 and Patent No. 2147594, dated Nov. 5, 2012, EPO Form 2022 12.07, one page.
Correspondence from S. van Doom of Vereenigde to the European Patent Office in response to the communication pursuant to Article 94(3) EPC, European Patent Application No. 09075279.1, dated Dec. 22, 2011, five pages.
EPO Communication regarding Preparation for oral Proceedings—Instructions to Support Service, EP Application No. 09075279.1, Feb. 5, 2013, EPO Form 2040 12.07TRI, two pages.
EPO Communication to Martin Hatzmann of Vereenigde, Summons to attend oral proceedings pursuant to Rule 115(1) EPC, EP Application No. 09075279.1, Mar. 6, 2013, EPO form 2008 12.12, one page.
EPO Communication, Annex to Summons to attend oral proceedings pursuant to Rule 115(1) EPC, EP Application No. 09075279.1, Mar. 6, 2013, EPO form 2906 01.91TRI, six pages.
EPO Communication to Martin Hatzmann of Vereenigde, Acknowledgement of receipt of the document specified above, EP Application No. 09075279.1, Mar. 6, 2013, EPO Form 2936 08.10, one page.
Executed Acknowledgement of receipt of the document specified above, EP Application No. 09075279.1, Mar. 7, 2013, EPO Form 2936 08.10, one page.
Letter accompanying subsequently filed items regarding amended claims with clean and annotated copies, EP Application No. 09075279.1, Apr. 23, 2013, 2 pages.
EPO communication, Client Database System (CDS)—clean up, EP Application No. 19075279.1, Apr. 23, 2013, EPO Form 2596C, 04.08, 1 page.
Auxiliary request 1, EP Application No. 09075279.1, Reference No. P85261EP00, Apr. 23, 2013, three pages.
Auxiliary request 2, EP Application No. 09075279.1, Reference No. P85261EP00, Apr. 23, 2013, three pages.
Auxiliary request 3, EP Application No. 09075279.1, Reference No. P85261EP00, Apr. 23, 2013, three pages.
Auxiliary request 5 (amendments indicated), EP Application No. 09075279.1, Reference No. P85261EP00, Apr. 23, 2013, three pages.
Auxiliary request 6 (amendments indicated), EP Application No. 09075279.1, Reference No. P85261EP00, Apr. 23, 2013, three pages.
Auxiliary request 4 (amendments indicated), EP Application No. 09075279.1, Reference No. P85261EP00, Apr. 23, 2013, three pages.
Correspondence from S.T. van Doorn to European Patent Office regarding written submissions in response to the summons to attend oral proceedings dated Mar. 6, 2013, EP Application No. 09075279.1, Apr. 23, 2013, 15 pages.
EPO Acknowledgement of receipt of claim requests, EP Application No. 09075279.1, date of receipt Apr. 23, 2013, two pages.
Auxiliary request 5, EP Application No. 09075279.1, Reference No. P85261EP00, Apr. 23, 2013, three pages.
Auxiliary request 6, EP Application No. 09075279.1, Reference No. P85261EP00, Apr. 23, 2013, three pages.
Main request, EP Application No. 09075279.1, Reference No. P85261EP00, Apr. 23, 2013, three pages.
Auxiliary request 4, EP Application No. 09075279.1, Reference No. P85261EP00, Apr. 23, 2013, three pages.
Auxiliary request 1 (amendments indicated), EP Application No. 09075279.1, Reference No. P85261EP00, Apr. 23, 2013, three pages.
Auxiliary request 2 (amendments indicated), EP Application No. 09075279.1, Reference No. P85261EP00, Apr. 23, 2013, three pages.
Auxiliary request 3 (amendments indicated), EP Application No. 09075279.1, Reference No. P85261EP00, Apr. 23, 2013, three pages.
Letter accompanying subsequently filed items regarding oral proceedings, EP Application No. 09075279.1, Apr. 24, 2013, one page.
GenBank Accession No. ABA26122.1, Immunoglobulin light chain variable region, partial [Homo sapiens], 2005, 1 page.
GenBank Accession No. M87478, "Human rearranged IgK mRNA VJC region," 1 page (1994).
Correspondence from S.T. van Doorn to European Patent Office regarding written submissions filed Apr. 23, 2013, EP Application No. 09075279.1, Apr. 24, 2013, one page.
Second Declaration by David Tarlington dated Oct. 15, 2015, Australian patent application No. 2009263082, 24 pages.
Fecteau, Jessie F. et al., "A New Memory CD27 IgG+ B Cell Population in Peripheral Blood Expressing VH Genes with Low Frequency of Somatic Mutation," The Journal of Immunology, vol. 177:3728-3736 (2006).
Ferrara, N., Vascular endothelial growth factor: molecular and biological aspects., Curr Top. Microbiol. Immunol., 1999, 237:1-30.
EPO Acknowledgement of receipt of written submissions, EP Application No. 09075279.1, date of receipt Apr. 24, 2013, one page.
EPO communication, Maintenance / Change of date / Cancellation of oral proceedings arranged for: May 23, 2013 at 10.00 hrs, EP Application No. 19075279.1, Apr. 25, 2013, EPO Form 2088 04.10, two pages.
EPO communication, Executed Maintenance / Change of date / Cancellation of oral proceedings arranged for: May 23, 2013 at 10.00 hrs, EP Application No. 190752791, May 14, 2013, EPO Form 2088 0410, two pages.
EPO communication to Martin Hatzmann of V.O., Brief Communication regarding the letter of Apr. 23, 2013, EP Application No. 09075279.1 and EP Patent No. 2147594, May 22, 2013, EPO Form 2008A 12.07, one page.
EPO communication, EP Application No. 19075279.1, at least as early as May 22, 2013, EPO Form 2906 01.91TRI, one page.
European Patent Office Communication for Application No. 09075279.1 dated Nov. 5, 2012.

(56) References Cited

OTHER PUBLICATIONS

Letter submitting declarations of Peter Hudson and Robert Brink dated Jun. 2, 2015, Australian Application No. 2009263082, 1 page.
Second Declaration of Anthony L. DeFranco dated Oct. 18, 2015, Australian application No. 2009263082, 31 pages.
EPO communication, Client Database System (CDS)—clean up, EP Application No. 10186063.3, Apr. 23, 2013, EPO Form 2596C, 04.08, 1 page.
EPO Communication, Annex to EPO Form 2004, Communication pursuant to Rule 71(3) EPC, Bibliographical data of EP Application No. 10186063.3, Jun. 5, 2013, EPO Form 2056, 11.08, 1 page.
EPO Communication pursuant to the Decision of the President of the European Patent Office on the filing of priority document, EP Application No. 10186063.3, Oct. 21, 2010, EPO Form 1195, 04.09 PRIO, 1 page.
Refund of Fees, EP Application No. 10186063.3, Nov. 17, 2010, EPO Form 2907, 12.07, 1 page.
EPO Invitation to remedy deficiencies pursuant to Rule 30(3) EPC / Rule 163(3) EPC, EP Application No. 10186063.3, Nov. 23, 2010, EPO Form 1128, 05.10, 3 pages.
EPO Communication pursuant to Rule 55 EPC, EP Application No. 10186063.3, dated Nov. 25, 2010, EPO Form 1047A, 11.09, 1 page.
Response to Invitation to remedy deficiencies pursuant to Rule 30(3) EPC / Rule 163(3) EPC, EP Application No. 10186063.3, Jan. 27, 2011, 2 pages.
Xiang, Yougui et al., "The Downstream Transcriptional Enhancer, Ed, Positively Regulates Mouse Igk Gene Expression and Somatic Hypermutation," J. Immunol., vol. 180(10):6725-6732 (2008).
Yang, X.W. et al., "Homologous recombination based modification in *Escherichia coli* and germline transmission in transgenic mice of a bacterial artificial chromosome," Nat. Biotechnol., vol. 15(9):859-865 (1997).
Zou et al., Cre-loxP-mediated gene replacement: a mouse strain producing humanized antibodies, Current Biology, 1994, pp. 1099-1103, vol. 4.
EP Priority Document of EP Application No. 02077953.4, "Recombinant Production of Mixtures of Antibodies", submitted in International Application No. PCT/EP03/07690, Sep. 5, 2003, 140 pages.
Abstract, "Recombinant Production of Mixtures of Antibodies", Reference No. P61090EP20, at least as early as Oct. 1, 2010, 1 page.
Claims, Replacement pp. 125-129, Reference No. P61090EP20, at least as early as Oct. 1, 2010, 5 pages.
U.S. Priority Document of U.S. Appl. No. 60/397,066, "Recombinant Production of Mixtures of Antibodies", submitted in International Application No. PCT/EP03/07690, Sep. 1, 2003, 140 pages.
EP Priority Document of International Application No. PCT/EP03/50201, "Recombinant Production of Mixtures of Antibodies", submitted in International Application No. PCT/EP03/07690, Sep. 1, 2003, 168 pages.
EP Acknowledgement of Receipt for Request for Grant of EP Application No. 10186063.3, Oct. 1, 2010, 2 pages.
Request for Grant of a European Patent for EP Application No. 10186063.3, Oct. 1, 2010, 6 pages.
Designation of Inventor Van Berkel Patricius Hendrikus, User Reference No. P61090EP20, at least as early as Oct. 1, 2010, 1 page.
Designation of Inventor Logtenberg Ton, User Reference No. P61090EP20, at least as early as Oct. 1, 2010, 1 page.
Designation of Inventor Bout Abraham, User Reference No. P61090EP20, at least as early as Oct. 1, 2010, 1 page.
Designation of Inventor Brus Ronald Hendrik Peter, User Reference No. P61090EP20, at least as early as Oct. 1, 2010, 1 page.
Specification of International Application No. PCT/EP03107690, "Recombinant Production of Mixtures of Antibodies", at least as early as Oct. 1, 2010, 122 pages.
Drawings, at least as early as Oct. 1, 2010, 33 pages.
EP Priority Document of International Application No. PCT/EP2003/07690, "Recombianant Production of Mixtures of Antibodies", Oct. 25, 2010, 186 pages.
Sequence Listing, at least as early as Oct. 1, 2010, 18 pages.
Spillner et al., Paratope-based protein identification by antibody and peptide phage display, Analytical Biochemistry, 2003, pp. 96-104, vol. 321, Academic Press.
Stevens, Sean, "Human Antibody Discovery, VelocImmune—A novel platform," Pharma Focus Asia, Issue 8, pp. 72-74 (2008).
Strelkauskas et al., Human Monoclonal Antibody: 2. Simultaneous Expression of IgG and IgM with Similar Binding Specificities by a Human Hybrid Clone, Hybridoma, 1987, pp. 479-487, vol. 6, No. 5, Mary Ann Liebert, Inc., Publishers.
Opposition Summary, Australian Application No. 2009263082, May 18, 2015, 11 pages.
Taylor, Lisa D. et al., "Human immunoglobulin transgenes undergo rearrangement, somatic mutation and class switching in mice that lack endogenous IgM," International Immunology, vol. 6(4):579-591 (1994).
Third Party Observations Under Article 115 EPC Against European Parent Application No. 09075279.1 in the name of Merus B.V., dated Oct. 25, 2012. 6 pages.
Thomas et al., Site-Directed Mutagenesis by Gene Targeting in Mouse Embryo-Derived Stem Cells, Cells, Nov. 5, 1987, pp. 503-512, vol. 51.
Approved Judgement in *Regeneron Pharmaceuticals Inc.vs Kymab Limited and Novo Nordisk A/S*, Case No. HP-2013-000001/HP-2014-000001 for Hearing dates: Nov. 18-20, 23-27,30 and Dec. 7 & 8, 2015.
Weiner, et al., Abstract, Fully human therapeutic monoclonal antibodies, Journal of Immunotherapy, Jan. 1, 2006, pp. 1-9, vol. 29, No. 1, Lippincott Williams & Wilkins, Hagerstown, MD, US.
Winter et al., Insertion of 2 kb of bacteriophage DNA between an immunoglobulin promoter and leader exon stops somatic hypermutation in a kappa trans gene, Molecular Immunology, Apr. 1997, pp. 359-366, vol. 34, No.5.
Sequence Listing, Reference No. P61909EP20, Jan. 27, 2011, 12 pages.
EPO Communication pursuant to Article 94(3) EPC, Application No. 10186063.3, dated Dec. 12, 2011, EPO Form 2001, 12.10CSX, 5 pages.
Response to Communication pursuant to Article 94(3) EPC, EP Application No. 10186063.3, dated Dec. 21, 2011, 13 pages.
Notification to EPO regarding Applicant Address Change, EP Application No. 10186063.3, Jan. 4, 2012, 1 page.
EPO Communication regarding Applicant Address Change, EP Application No. 10186063.3, Jan. 26, 2012, EPO FOrm 2544, 04.10, 1 page.
EPO Communication pursuant to Article 94(3) EPC, Application No. 10186063.3, dated Jun. 11, 2012, EPO Form 2001, 12.10CSX, 3 pages.
European Search Report for EP Application No. 10186063, dated Mar. 16, 2011, EPO Form 1503, 03.82 (P04C01), 2 pages.
Response to Communication pursuant to Article 94(3) EPC, EP Application No. 10186063.3, dated Jul. 19, 2012, 45 pages.
Notification to EPO regarding Request for recording a change in name of representative, EP Application No. 10186063.3, Mar. 23, 2013, 3 pages.
EPO Communication, EP Application No. 10186063.3, dated Mar. 3, 2011, EPO Form 1507N, 08.10, 1 page.
European Search Opinion, EP Application No. 10186063.3, at least as early as Mar. 24, 2011, EPO Form 1703, 01,91TRI, 3 pages.
EPO Notification of European Publication Number and Information on the application of Article 67(3) EPC, EP Application No. 10186063.3, Mar. 3, 2011, EPO Form 1133, 05.10, 1 page.
Refund of Fees, EP Application No. 10186063.3, Jun. 4, 2011, EPO Form 2907, 12.07, 1 page.
EPO Communication pursuant to Rules 70(2) and 70a(2) EPC and reference to Rule 39(1) EPC, EP Application No. 10186063.3, dated May 2, 2011, EPO Form 1082, 04.10, 2 pages.
Response to Communication pursuant to Rules 70(2) and 70a(2) EPC and reference to Rule 39(1) EPC, EP Application No. 10186063. 3, dated Oct. 17, 2011, 16 pages.
Gorczyca, W. et al., DNA strand breaks occurring during apoptosis—their early insitu detection by the terminal deoxynucleotidyl transferase and nick translation assays and prevention by serine protease inhibitors, Int J Oncol., 1992, 1(6), 639-648.

(56) References Cited

OTHER PUBLICATIONS

Gorczyca, W. et al., Detection of DNA strand breaks in individual apoptotic cells by the in situ terminal deoxynucleotidyl transferase and nick translation assays, Cancer Res., 1993, 53(8), 1945-1951.
Gorczyca, W. et al., Induction of DNA strand breaks associated with apoptosis during treatment of leukemias, Leukemia, 1993, 7(5), 659-670.
Gorman, C., Bullock, C., Site-specific gene targeting for gene expression in eukaryotes, Curr Opin Biotechnol., 2000, 11(5), 455-460.
Graham, FL., van der Eb,AJ., A new technique for the assay of infectivity of human adenovirus 5 DNA, Virology, 1973, 52(2), 456-467.
Gram, H. et al., In vitro selection and affinity maturation of antibodies from a naive combinatorial immunoglobulin library, Proc Natl Acad Sci U S A, 1992, 89(8), 3576-3580.
Gräslund, T. et al., Integrated strategy for selective expanded bed ion-exchange adsorption and site-specific protein processing using gene fusion technology, J Biotechnol., 2002, 96(1), 93-102.
Gray, F. et al., Secretion capture and report web: use of affinity derivatized agarose microdroplets for the selection of hybridoma cells, J Immunol Methods, 1995, 182(2), 155-163.
Greenberger, JS. et al., Demonstration of permanent factor-dependent multipotential (erythroid/neutrophil/basophil) hematopoietic progenitor cell lines, Proc Natl Acad Sci U S A, 1983, 80(10), 2931-2935.
Groeneveld EH., Burger EH., Bone morphogenetic proteins in human bone regeneration, Eur J Endocrinol., 2000, 142(1), 9-21.
Grosveld, F., Activation by locus control regions?, Curr Opin Genet Dev., 1999, 9(2),152-157.
Guéry, JC, Adorini, L., Dendritic cells are the most efficient in presenting endogenous naturally processed self-epitopes to class II-restricted T cells, J Immunol., 1995, 154(2), 536-544.
Hamers-Casterman, C. et al., Naturally occurring antibodies devoid of light chains, Nature, 1993, 363(6428), 446-448.
Hanes, J. et al., Picomolar affinity antibodies from a fully synthetic naive library selected and evolved by ribosome display, Nat Biotechnol., 2000, 18(12), 1287-1292.
Hanes, J. et al., Selecting and evolving functional proteins in vitro by ribosome display, Methods Enzymol., 2000, 328, 404-430.
Harjunpää, A., et al, Rituximab (anti-CD20) therapy of B-cell lymphomas: direct complement killing is superior to cellular effector mechanisms, Scand J Immunol., 2000, 51(6), 634-641.
Hawkins, RE. et al., Selection of phage antibodies by binding affinity. Mimicking affinity maturation, J Mol Biol., 1992, 226(3), 889-896.
Hay, BN. et al., Bacteriophage cloning and *Escherichia coli* expression of a human IgM Fab, Hum Antibodies Hybridomas, 1992, 3(2), 81-85.
Hiatt A, et al., Production of antibodies in transgenic plants, Nature, 1989, 342(6245), 76-78.
Hitzeman, RA. et al., Isolation and characterization of the yeast 3-phosphoglycerokinase gene (PGK) by an immunological screening technique, J Biol Chem., 1980, 255(24), 12073-12080.
Holmes, P., Al-Rubeai, M., Improved cell line development by a high throughput affinity capture surface display technique to select for high secretors, J Immunol Methods, 1999, 230(1-2), 141-147.
Holt, L.J. et al., Domain antibodies: proteins for therapy, Trends Biotechnol., 2003, 21(11), 484-490.
Hooper, D., "Rabies Virus," In: Manual of Clinical Laboratory Immunology, Part II, 5 ed., N.R. Rose (Ed.), ASM Press, Wash. D.C., pp. 755-760, (1997).
Houshmand, H. et al., Use of bacteriophage T7 displayed peptides for determination of monoclonal antibody specificity and biosensor analysis of the binding reaction, Anal Biochem., 1999, 268(2), 363-370.
Houston, M.E., Jr. et al., Use of a conformationally restricted secondary structural element to display peptide libraries: a two-stranded alpha-helical coiled-coil stabilized by lactam bridges, J Mol Biol., 1996, 262(2), 270-282.

Huang, AY. et al., Role of bone marrow-derived cells in presenting MHC class I-restricted tumor antigens, Science, 1994, 264(5161), 961-965.
Huls, G. A., et al., A recombinant, fully human monoclonal antibody with antitumor activity constructed from phage-displayed antibody fragments, Nat Biotechnol., 1999, 17(3), 276-281.
Huse, WD. et al., Generation of a large combinatorial library of the immunoglobulin repertoire in phage lambda, Science, 1989, 246(4935), 1275-1281.
Hynes, RO., Cell adhesion: old and new questions, Trends Cell Biol., 1999, 9(12), M33-37.
Inaba, K. et al., Dendritic cells pulsed with protein antigens in vitro can prime antigen-specific, MHC-restricted T cells in situ, J Exp Med., 1990, 172(2), 631-640.
Inaba, M. et al., Distinct mechanisms of neonatal tolerance induced by dendritic cells and thymic B cells, J Exp Med., 1991, 173(3), 549-559.
Itoh, N. et al., The polypeptide encoded by the cDNA for human cell surface antigen Fas can mediate apoptosis, Cell, 1991, 66(2), 233-243.
Jespers LS, et al., Guiding the selection of human antibodies from phage display repertoires to a single epitope of an antigen, Biotechnology (N Y), 1994, 12(9), 899-903.
Johansson, BM. et al., Evidence for involvement of activin A and bone morphogenetic protein 4 in mammalian mesoderm and hematopoietic development, Mol Cell Biol., 1995, 15(1), 141-151.
Jonasson, P. et al., Genetic design for facilitated production and recovery of recombinant proteins in *Escherichia coli*, Biotechnol Appl Biochem., 2002, 35(Pt 2), 91-105.
Jones, D., et al., High-level expression of recombinant IgG in the human cell line PER.CX , Biotechnol Prog, 2003, 19(1), 163-168.
Keller, G. et al., Hematopoietic commitment during embryonic stem cell differentiation in culture, Mol Cell Biol., 1993, 13(1), 473-486.
Kelley et al, Antigen Binding Thermodynamics and Antiproliferative Effects of Chimeric and Humanized anti-p185HER2 Anitbody Fab Fragments, 1992 Biochemistry 31:5435-5441.
Kim SJ, et al., Characterization of chimeric antibody producing CHO cells in the course of dihydrofolate reductase-mediated gene amplification and their stability in the absence of selective pressure, Biotechnol Bioeng., 1998, 58(1), 73-84.
Klagsbrun, M., D'Amore PA.,Vascular endothelial growth factor and its receptors, Cytokine Growth Factor Rev., 1996, 7(3), 259 270.
Köhler, G., Milstein, C., Continuous cultures of fused cells secreting antibody of predefined specificity, Nature, 1975, 256(5517), 495-497.
Koide, A. et al., The fibronectin type III domain as a scaffold for novel binding proteins, J Mol Biol., 1998, 284(4), 1141-1151.
Koopman G, et al., Annexin V for Flow Cytometric Detection of Phosphatidylserine Expression on B Cells Undergoing Apoptosis, The Blood Journal, 1994, pp. 1415-1420.
Korndörfer, IP. et al., Crystallographic analysis of an "anticalin" with tailored specificity for fluorescein reveals high structural plasticity of the lipocalin loop region, Proteins, 2003, 53(1), 121-129.
Korndörfer, IP. et al., Structural mechanism of specific ligand recognition by a lipocalin tailored for the complexation of digoxigenin, J Mol Biol., 2003, 330(2), 385-396.
Kruse PF and Patterson MK (eds) Tissue Culture. Methods and Applications, 1973, Academic Press, New York, no pages provided.
Ku, J. et al., Alternate protein frameworks for molecular recognition, Proc Natl Acad Sci U S A, 1995, 92(14), 6552-6556.
Kuhlman, B. et al, Design of a novel globular protein fold with atomic-level accuracy, Science, 2003, 302(5649), 1364-1368.
Letter of Protest filed by Regeneron against U.S. Appl. No. 15/158,543 on Oct. 14, 2016.
Lobato MN., Rabbitts, TH., Intracellular antibodies and challenges facing their use as therapeutic agents, Trends Mol Med., 2003, 9(9), 390-396.
McGinnes, K., B-lineage colonies from normal, human bone marrow are initiated by B cells and their progenitors, Blood, 1991, 77(5), 961-970.

(56) References Cited

OTHER PUBLICATIONS

Mostoslavsky et al., "Asynchronous replication and allelic exclusion in the immune system," Nature (2001) 414:221-225.
Murakami, T. et al, Splenic CD19-CD35+B220+ cells function as an inducer of follicular dendritic cell network formation, Blood, 2007,110(4), 1215-1224.
Murphy, Chapter 6: Antigen Presentation to T Lymphocytes, Janeway's Immunobiology, Eighth Edition, 2012, 31 pages.
Nelson, AL. et al., Development trends for human monoclonal antibody therapeutics, Nat Rev Drug Discov, 2010, 9(10), pp. 767-774.
Nikolic, T. et al, A subfraction of B220(+) cells in murine bone marrow and spleen does not belong to the B cell lineage but has dendritic cell characteristics, Eur J Immunol., 2002, 32(3), 686-692.
O'Brien, RL., Somatic hypermutation of an immunoglobulin transgene in kappa transgenic mice, Nature, 1987, 326(6111), 405-409.
Opponent's submissions filed on Jan. 15, 2016 (oppo JP5749161).
Opponent's (REGN) submissions filed on Oct. 19, 2016 in -AU10.
Orban, PC. et al, Tissue- and site-specific DNA recombination in transgenic mice, Proc Natl Acad Sci U S A, 1992, 89(15), 6861-6865.
Padlan et al., A possible procedure for reducing the immunogenicity of antibody variable domains while preserving their ligand-binding properties, Mol. Immunol., 1991, pp. 489-498, vol. 28.
Phan, TG., High affinity germinal center B cells are actively selected into the plasma cell compartment, J Exp Med., 2006; 203(11); 2419-2424.
Retter, MW., Nemazee, D., Receptor editing: genetic reprogramming of autoreactive lymphocytes, Cell Biochem Biophys., 1999, 31(1), 81-88.
Roitt, Immunology, Moscow, 2000.
Shaffer, AL. Et al., In vivo occupancy of the kappa light chain enhancers in primary pro- and pre-B cells: a model for kappa locus activation, Immunity, 1997, 6(2), 131-143.
Singer et al., Genes & Genomes A Changing Perspective, University Science Books, Mill Valley, California, 1991, 134-145.
Smith, EJ. et al., A novel, native-format bispecific antibody triggering T-cell killing of B-cells is robustly active in mouse tumor models and cynomolgus monkeysSci Rep., 2015, 5: 17943.
Soriano, P., Generalized lacZ expression with the ROSA26 Cre reporter strain, Nat Genet. 1999;21(1), 70-71.
Submissions filed by applicant on Oct. 19, 2016 in -AU10.
Submissions filed by applicant on Sep. 6, 2016 in -AU10.
Weiner, et al., Fully human therapeutic monoclonal antibodies, Journal of Immunotherapy, Jan. 1, 2006, pp. 1-9, vol. 29, No. 1, Lippincott Williams & Wilkins.
Yang, SY. Et al, Control of gene conversion and somatic hypermutation by immunoglobulin promoter and enhancer sequences, J Exp Med., 2006, 203(13), 2919-2928.
Yarilin, Fundamentals of Immunology, Moscow, 1999.
Yoshio-Hoshino, N. et al., Establishment of a new interleukin-6 (IL-6) receptor inhibitor applicable to the gene therapy for IL-6-dependent tumor, Cancer Res., 2007, 67(3), 871-875.
Zou, YR. et al, Generation of a mouse strain that produces immunoglobulin kappa chains with human constant regions, Science, 1993, 262(5137), 1271-1274.
Inlay et al., Essential roles of the kappa light chain intronic enhancer and 3' enhancer in kappa rearrangement and demethylation, Nat Immunol., Apr. 22, 2002, pp. 463-468, vol. 3.
Section 27 Notice, Australia, Oct. 31, 2013.
Section 27 Notice, Australia, Mar. 18, 2014.
Applicant request for extension of time, Australia, May 18, 2015, 6 pages.
CD Marker Handbook, Australia.
Lai et al., (1998), Mouse Cell Surface Antigens: Nomenclature and Immunophenotyping, The American Association of Immunologists. 3861-3868.
Opponent Objects to the Allowability of the Ext, Australia, May 4, 2015.
Applicant Written Submission, Australia, Sep. 6, 2016, 49 pages.
Opponents Initial Supplementary Submissions, Australia 10/5/1.
Letter with Fee, Australia, May 18, 2015, 1 page.
Acknowledgment of Receipt of Notice of Opposition from the APO, Jun. 23, 2014, 1 page.
Annexure PH-4 referred to in Peter Hudson Jun. 2, 2015 Declaration, 37 pages—Part 1.
Annexure PH-4 referred to in Peter Hudson Jun. 2, 2015 Declaration, 37 pages—Part 2.
Mead G.P. et al., Poster, Detection of Bence Jones myeloma and monitoring of myeloma chemotherapy using immunoassays specific for free immunoglobulin light chains, Clinical Laboratory, 2003, vol. 49, No. 1-2, 2003, p. 25-27.
Roebroek, Anton J. et al., Mutant Lrp1 Knock-In mice generated by recombinase-mediated cassette exchange reveal differential importance of the NPXY motifs in the intracellular domain on LRP1 for normal fetal development, Molecular and Cellular Biology, 2006, vol. 26, No. 2, p. 605-616.
Shmerling, D. et al., Strong and ubiquitous expression of transgenes targeted into the beta-actin locus by Cre/lox cassette replacement, Genesis: The Journal of Genetics and Development, 2005, vol. 42, No. 4, p. 229-235.
Toledo, F, et al., RMCE-ASAP: a gene targeting method for ES and somatic cells to accelerate phenotype analyses, Nucleic Acids Research, 2006, vol. 34 No. 13, pp. e92-1.
Boel et al., Functional human monoclonal antibodies of all isotypes constructed from phage display library-derived single-chain Fv antibody fragments, Journal of Immunological Methods, 2000, pp. 153-166, vol. 239.
Burioni et al., Nonneutralizing Human Antibody Fragments against Hepatitis C Virus E2 Glycoprotein Modulate Neutralization of Binding Activity of Human Recombinant Fabs, Abstract, Virology, Sep. 2001, pp. 29-35, vol. 288, No. 1.
Champion et al., Abstract, The development of monoclonal human rabies virus-neutralizing antibodies as a substitute for pooled human immune globulin in the prophylactic treatment of rabies virus exposure, Abstract, Journal of Immunological Methods, Feb. 2000, pp. 81-90, vol. 235, No. 1-2, Elsevier Science Publishers B.V., Amsterdam, NL.
Chen et al., Abstract, Selection and analysis of an optimized anti-VEGF antibody: crystal structure of an affinity-matured Fab in complex with antigen, Journal of Molecular Biology, Nov. 5, 1999, pp. 865-881, vol. 293, No. 4.
De Kruif et al., Rapid selection of cell subpopulation-specific human monoclonal antibodies from a synthetic phage antibody library, Proc. Natl. Acad. Sci., USA, Apr. 1995, pp. 3938-3942, vol. 92.
De Kruif et al., Selection and Application of Human Single Chain Fv Antibody Fragments from a Semi-synthetic Phage Antibody Display Library with Designed CDR3 Regions, Journal of Molecular Biology, 1995, pp. 97-105, vol. 248.
ECACC deposit, Deposit Ref. 96022940.
ECACC deposit, Deposit Reference 03041601.
Figini et al., In Vitro Assembly of Repertoires of Antibody Chains on the Surface of Phage by Renaturation, Journal of Molecular Biology, 1994, pp. 68-78, vol. 239.
Franconi et al., Functional expression in bacteria and plants of an scFv antibody fragment against tospoviruses, Immunotechnology, 1999, pp. 189-201, vol. 4.
French, et al., Cancer Research, 1991, pp. 2353-2361, vol. 51.
Friedenson et al., Immunoglobulin G Antibodies from an Individual Rabbit in Which Several Heavy Chain Variants Are Paired with One Light Chain Sequence, The Journal of Biological Chemistry, 1973, pp. 7073-7079, vol. 248, No. 20.
Heintges et al., Cloning, Bacterial Expression and Sequencing of Human Antibody Fragments Against Hepatitis C Virus NS3 by Phage Display of a Combinatorial Phagemid Library, Hepatology, p. 497, vol. 28, No. 4.
Holliger et al., "Diabodies": Small bivalent and bispecific antibody fragments, Proc. Natl. Acad. Sci., Jul. 1993, pp. 6444-6448, vol. 90.
Hoogenboom et al., Antibody phage display technology and its applications, Immunotechnolgy, 1998, pp. 1-20, vol. 4.

(56) References Cited

OTHER PUBLICATIONS

Huse et al., Purification of antibodies by affinity chromatography, Journal of Biochemical and Biophysical Methods, 2002, pp. 217-231, vol. 51.
Kang et al., Linkage of recognition and replication functions by assembling combinatorial antibody Fab libraries along phage surfaces, Proc. Natl. Acad. Sci., May 1991, pp. 4363-4366, vol. 88.
Kortt et al., Dimeric and trimeric antibodies: high avidity scFvs for cancer targeting, Biomol. Eng., Oct. 15, 2001, pp. 95-108, vol. 18, No. 3.
Krebs et al., High-throughput generation and engineering of recombinant human antibodies, Journal of Immunological Methods, 2001, pp. 67-84, vol. 254.
Kwaks et al., Identification of anti-repressor elements that confer high and stable protein production in mammalian cells, Nature Biotechnology, 2003, pp. 553-558, vol. 21.
Lekkerkerker, Phage antibodies against human dendritic cell subpopulations obtained by flow cytometry-based selection on freshly isolated cells, Journal of Immunological Methods, 1999, pp. 53-63, vol. 231.
Lindhofer et al., Preferential Species-Restricted Heavy/Light Chain Pairing in Rat/Mouse Quadromas, 1995, pp. 219-225, vol. 155.
Lu et al., Selection of high affinity human neutralizing antibodies to VEGFR2 from a large antibody phage display library for antiangiogenesis therapy, Abstract, International Journal of Cancer, Jan. 20, 2002, pp. 393-399, vol. 97, No. 3.
Ma et al., Assembly of monoclonal antibodies with IgG1 and IgA heavy chain domains in transgenic tabacco plants, Eur. J. Immunol., 1994, p. 131-138, vol. 24.
Merchant et al., An efficient route to human bispecific IgG, Nature Biotechnology, Jul. 1998, pp. 677-681, vol. 16.
Morrison, Sherie L., Transfectomas Provide Novel Chimeric Antibodies, Science, Sep. 20, 1985, pp. 1202-1207, vol. 229.
Norderhaug et al., Balanced expression of single subunits in a multisubunit proteins, achieved by cell fusion of individual transfectants, European Journal of Biochemistry, 2002, pp. 3205-3210, vol. 269.
Pau et al, The human cell line PER.C6 provides a new manufacturing system for the production of influenza vaccines, Vaccine, 2001, pp. 2716-2712, vol. 19.
PCT International Preliminary Examination Report, PCT/EP03/07690, dated Nov. 11, 2004.
PCT International Search Report, PCT/EP03/07690, dated Apr. 16, 2004.
PCT International Search Report, PCT/NL2004/000386 dated Nov. 23, 2004.
PCT International Search Report, PCT/NL2005/000036, dated Jan. 19, 2005.
Sidhu et al., Phage-displayed antibody libraries of synthetic heavy chain complementarity determining regions, Abstract, Journal of Molecular Biology, Apr. 23, 2004, pp. 299-310, vol. 338, No. 2.
Sugita, et al., Int. J. Cancer, 1986, pp. 351-357, vol. 37.
Vaughan et al., Human Antibodies with Sub-nanomolar Affinities Isolated from a Large Non-immunized Phage Display Library, Nature Biotechnology, Mar. 1996, pp. 309-314, vol. 14.
Ward et al., Nature, 1989, pp. 544-546, vol. 341.
Warnaar et al., Hybridoma, 1994, pp. 519-526, vol. 13, No. 6.
Marvin, J.S., et al., Acta Parmacologica Sinica, 16(6): 649-58, 2005.
Ngo, T.H., et al., FEBS Letters, 416: 373-76, 1997.
Lang A.B., et al., Journal of Immunology, 151(13): 466-72, 1993.
Huls, G., et al. Cancer Research, 59: 5778-84, 1999.
Tanaka et al., De novo production of diverse intracellular antibody libraries, Nucleic Acids Research, 2003, e23, pp. 1-10, vol. 31, No. 5.
Nguyen et al., Heavy-chain only antibodies derived from dromedary are secreted and displayed by mouse B cells, Immunology, 2003, pp. 93-101, vol. 109.
Conrath et al., Camel Single-domain Antibodies as Modular Building Units in Bispecific and Bivalent Antibody Constructs, The Journal of Biological Chemistry, 2001, pp. 7346-7350, vol. 276, No. 10.
Friedenson, Bernard et al., "Immunoglobulin G Antibodies from an Individual Rabbit in Which Several Heavy Chain Variants are Paired with One Light Chain Sequence," The Journal of Biological Chemistry, Oct. 25, 1973, pp. 7073-7079, vol. 248, No. 20.
Schmitz et al., Phage Display: A Molecular Tool for the Generation of Antibodies—A Review, Placenta, 2000, pp. S106-S112, Supplement A, Trophoblast Research, vol. 14.
Muyldermans, Reviews in Molecular Biotechnology, 2001, pp. 277-302, vol. 72.
Roholt et al., Antibodies of Limited Heterogeneity: L. Chains of a Single Mobility, Immunochemistry, Pergamon Press, 1970, vol. 7, pp. 329-340.
Carmack et al, Influence of a Vκ8 L Chain Transgene on Endogenous Rearrangements and the Immune Response to the HA(SB) Determinant on Influenza Virus The Journal of Immunology, 1991, vol. 147, No. 6, pp. 2024-2033.
Morimoto et al., Abstract, High level expression of a human rabies virus-neutralizing monoclonal antibody by a rhabdovirus-based vector, J. Immunol. Methods, Jun. 2001, pp. 199-206, vol. 1, No. 252(1-2).
Arai et al., Abstract, Antibody responses induced by immunization with a Japanese rabies vaccine determined by neutralization test and enzyme-linked immunosorbent assay, Vaccine, Jun. 2002, pp. 2448-2453, vol. 7, No. 20(19-20).
Perrin et al., Abstract, In vitro rabies vaccine potency appraisal by ELISA: advant of the immunocapture method with a neutralizing anti-glycoprotein monoclonal antibody, Biologicals, Oct. 1990, pp. 321-330, vol. 18(4).
Rojas et al. Phage antibody fragments library combining a single human light chain variable region with immune mouse heavy chain variable regions, Journal of Biotechnology, 2002, pp. 287-298, vol. 94.
European Search Report for European patent application No. 10189886.4 dated Nov. 20, 2012.
Logtenberg, Ton, Antibody cocktails: Next-Generation Biopharmaceuticals with Improved Potency, Trends in Biotechnology, 2007, pp. 390-394, vol. 25, No. 9, Science Direct.
Skerra, Arne, 'Anticalins': A New Class of Engineered Ligand-Binding Proteins with Antibody-Like Properties, 2001, Reviews in Molecular Biotechnology, pp. 257-275, vol. 74, Elsevier.
Communication from copending European patent application No. 05704566.8 dated Jun. 6, 2013.
Flavell et al., Systemic Therapy with 3BIT, a Triple Combination Cocktail of Anti-CD19, -CD22, and -CD38-Saporin Immunotoxins, Is Curative of Human B-Cell Lymphoma in Severe Combined Immunodeficient Mice, Cancer Research, Nov. 1997, pp. 4824-4829, vol. 57.
Esposito. Gloria et al.. "Phage display of a human antibody against Clostridium tetani toxin," Gene, vol. 148:167-168 (1994).
Christophe Sirac; Sirac et al. (2006) Role of the monoclonal kappa chain V domain and reversibility of renal damage in a transgenic model of acquired Fanconi syndrome, Blood 108:536-543.
Drew Murphy Statement dated Sep. 8, 2015, (5 pages).
A.L. Joyner, Gene Targeting: A Practical Approach, The Practical Approach Series, 2005, (196 pages), Second Edition, Oxford University Press.
Aya Jakobovits, The long-awaited magic bullets: therapeutic human monoclonal antibodies from transgenic mice, Exp. Opin. Invest. Drugs, 1998, pp. 607-614, vol. 7, No. 4, Ashley Publications Ltd.
Application for U.S. Appl. No. 11/645,238, sharing common inventors, available on the U.S. Patent Office website.
Application for U.S. Appl. No. 15/090,505, sharing common inventors, available on the U.S. Patent Office website.
Cvetkovic et al., Appropriate Tissue- and Cell-specific Expression of a Single Copy Human Angiotensinogen Transgene Specifically Targeted Upstream of the HPRT Locus by Homologous Recombination, The Journal of Biological Chemistry, Jan. 14, 2000, pp. 1073-1078, vol. 275, No. 2, The American Society for Biochemistry and Molecular Biology, Inc.
Davies, Nicholas P. et al., "Creation of Mice Expressing Human Antibody Light Chains by Introduction of a Yeast Artificial Chromosome Containing the Core Region of the Human Immunoglobulin kappa Locus," Bio/Technology, vol. 11:911-914 (1993).

(56) References Cited

OTHER PUBLICATIONS

De Kruif et al., Human Immunoglobulin Repertoires against Tetanus Toxoid Contain a Large and Diverse Fraction of High-Affinity Promiscuous VH Genes, J. Mol. Biol., 2009, pp. 548-558, vol. 387.
U.S. Appl. No. 15/140,321, Method for Selecting a Single Cell Expressing a heterogeneous combination of antibodies, filed Apr. 27, 2016.
Carter, Paul, "Bispecific human IgG by design," Journal of Immunological Methods, vol. 248:7-15 (2001).
Third Party Observations Against European Parent Application No. 09075279.1 in the Name of Merus BV, 3 pages, dated Jul. 1, 2013.
Third Party Observations for Application No. EP09075279.1, 6 pages, dated Oct. 25, 2012.
Brady et al., Rapid specific amplification of rat antibody cDNA from nine hybridomas in the presence of myeloma light chains, Journal of Immunological Methods, Aug. 31, 2006, pp. 61-67, vol. 315.
Chothia, et al., Canonical Structures for the Hypervariable Regions of Immunoglobulins, J. Mol. Biol., Aug. 20, 1987, pp. 901-917, vol. 196, Issue 4.
De Haard, et al., A large non-immunized human Fab fragment phage library that permits rapid isolation and kinetic analysis of high affinity antibodies,J. Biol. Chem., 1999, pp. 18218-18230, vol. 274.
Hwang et al., Immunogenicity of engineered antibodies, Methods, May 2005, pp. 3-10, vol. 36, Issue 1.
Inlay et al., Roles of the Ig kappa light chain intronic and 3' enhancers in Igk somatic hypermutation, J. Immunol., 2006, pp. 1146-1151, vol. 177(2).
International Search Report for Application No. PCT/NL2009/050381, 5 pages, dated Dec. 7, 2009.
International Preliminary Report on Patentability and Written Opinion for Application No. PCT/NL2009/050381, 11 pages, dated Jan. 5, 2011.
Kohler and Milstein, Continuous cultures of fused cells secreting antibody of predefined specificity, Nature, Aug. 7, 1975, pp. 495-497, vol. 256.
Lofgren et al., Comparing ELISA and Surface Plasmon Resonance for Assessing Clinical Immunogenicity of Panitumumab, .J Immunol., 2007, pp. 7467-7472, vol. 178.
Mirick et al., A review of human anti-globulin antibody (HAGA, HAMA, HACA, HAHA) responses to monoclonal antibodies: not four letter words, Q. Nucl. Med. Mol. Imaging, Dec. 2004, pp. 251-257, vol. 48, No. 4.
Novobrantseva et al., Rearrangement and expression of immunoglobulin light chain genes can precede heavy chain expression during normal B cell development in mice, J. Exp. Med., Jan. 4, 1999, pp. 75-88, vol. 189, No. 1.
Nowakowski et al., Potent neutralization of botulinum neurotoxin by recombinant oligoclonal antibody, PNAS, Aug. 20, 2002, pp. 11346-11350, vol. 99, No. 17.
Pasqualucci et al., BCL-6 mutations in normal germinal center B cells: evidence of somatic hypermutation acting outside Ig loci, Proc. Natl. Acad. Sci. USA, Sep. 1998, pp. 11816-11821, vol. 95.
Roberts and Szostak, RNA-peptide fusions for the in vitro selection of peptides and proteins, Proc. Natl. Acad. Sci. U.S.A., Nov. 1997, pp. 12297-12302, vol. 94.
Rong et al., Tumorigenesis induced by coexpression of human hepatocyte growth factor and the human met protooncogene leads to high levels of expression of the ligand and receptor, Cell Growth Differ., Jul. 1993, pp. 563-569, vol. 4, No. 7.
Shvarts et al., A senescence rescue screen identifies BCL6 as an inhibitor of anti-proliferative p19(ARF)-p53 signaling, Genes Dev., Mar. 15, 2002, pp. 681-686, vol. 16(6).
Statement of Grounds and Particulars submitted in opposition to Australian Patent Application 2009263082, filed Sep. 22, 2014, 35 pages.
Storb et al., Immunoglobulin transgenes as targets for somatic hypermutation, Int. J. Dev. Biol., 1998, pp. 977-982, vol. 42(7).

Vajdos et al., Comprehensive Functional Maps of the Antigen-binding Site of an Anti-ErbB2 Antibody Obtained with Shotgun Scanning Mutagenesis, J. Mol. Biol., Jul. 5, 2002, pp. 415-428, vol. 320, issue 2, Elsevier.
Priority Document dated Oct. 27, 2009, EP12175544.
EPO Acknowledgement of receipt dated Jul. 9, 2012, Application No. EP12175544.1.
EPO Request for grant of a European patent dated Jul. 9, 2012, Application No. EP12175544.1.
Designation of inventor Pinto Rui Daniel dated Jul. 9, 2012, User Reference P85261EP10, EP12175544.
Designation of inventor Ton Logtenberg dated Jul. 9, 2012, User Reference: P85261EP10, EP12175544.
Designation of inventor Mark Throsby dated Jul. 9, 2012, User Reference: P85261EP10, EP12175544.
Designation of inventor Erwin Houtzager dated Jul. 9, 2012, EP12175544.
Abstract dated Jul. 9, 2012, EP12175544.
Claims dated Jul. 9, 2012, EP12175544.
Description dated Jul. 9, 2012, EP12175544.
Drawings continued dated Jul. 9, 2012, EP12175544.
Drawings dated Jul. 9, 2012, EP12175544.
Deficiencies in application documents dated Jul. 20, 2012, EP12175544.1.
Bruggemann et al., A Repertoire of Monoclonal Antibodies with Human Heavy Chains from Transgenic Mice, Proc. Natl. Acad. Sci., Sep. 1989, pp. 6709-6713, vol. 86, USA.
Attaelmannan, Mohammed et al., "Understanding and Identifying Monoclonal Gammopathies," Clinical Chemistry, vol. 46(88):1230-1238 (2000).
Aucouturier et al., Monoclonal Ig L Chain and L Chain V Domain Fragment Crystallization in Myeloma-Associated Fanconi's Syndrome, The Journal of Immunology, Apr. 15, 1993, pp. 3561-3568, vol. 150, No. 8.
Bogen, Bjarne et al., "A rearranged lambda 2 light gene chain retards but does not exclude kappa and lambda 1 expression," Eur. J. Immunol., vol. 21:2391-2395 (1991).
Correspondence from A. Bentham of J A Kemp to the European Patent Office regarding request to change date of Oral Proceedings, EP Patent No. 2147594, Jan. 29, 2016, two pages.
EPO Acknowledgement of receipt of letter regarding request for extension of time, EP Application No. 09075279.1, date of receipt Oct. 16, 2014, one page.
EPO Authorization of Johan Renew regarding Oral Proceedings, EP Application No. 09075279.1, Dec. 2, 2015, one page.
Summons to Attend Oral Proceedings, EP Patent No. 2147594, at least as early as Feb. 1, 2016, five pages.
Judgement in Preliminary Relief Proceedings of Aug. 14, 2015 with English translation, Case No. C/09/480452/KG ZA 15-9, 33 pages.
Correspondence from Fritz Lahrtz of Isenbruck Bösl Höschler LLP to European Patent Office regarding request for Postponement of Oral Proceedings, EP Application No. 09075279.1 and EP Patent No. 2147594, Feb. 1, 2016, two pages.
EPO communication, Maintenance / Change of date / Cancellation of oral proceedings arranged for: Jun. 22, 2016 at 10.00 hrs, EP Application No. 09075279.1 and EP Patent No. 2147594, Feb. 4, 2016, EPO Form 2088 06.14, two pages.
EPO Brief Communication to Fritz Lahrtz of Isenbruck Bösl Höschler LLP regarding the Opposition and Oral Proceedings, EP Application No. 09075279.1 and Patent No. 2147594, Feb. 9, 2016, EPO Form 2911O 01.12, one page.
EPO Brief Communication to Andrew Bentham of J A Kemp regarding the Opposition and Oral Proceedings, EP Application No. 09075279.1 and Patent No. 2147594, Feb. 9, 2016, EPO Form 2911O 01.12, one page.
Submission in opposition proceedings by Andrew Bentham, Letter providing alternated dates for Oral Proceedings, EP Application No. 09075279.1 and Patent No. 2147594, Feb. 15, 2016, one page.
Correspondence from A. Bentham of J A Kemp to the European Patent Office regarding possible dates for Oral Proceedings, EP Patent No. 2147594, Feb. 15, 2016, one page.

(56) References Cited

OTHER PUBLICATIONS

EPO Acknowledgement of receipt of possible dates for oral proceedings, EP Application No. 09075279.1 and Patent No. 2147594, date of receipt Feb. 15, 2016, one page.
Correspondence from T.J. Elmore of V.O. to European Patent Office regarding request for extension of time, EP Application No. 09075279.1 and Patent No. 2147594, Oct. 16, 2014, one page.
Advice of receipt to Fritz Lahrtz of Isenbruck Bösl Höschler LLP, Registration No. of item RD119029438NL, Mar. 14, 2016, one page.
EPO Brief Communication regarding the Opposition, EP Application No. 09075279.1 and Patent No. 2147594, Oct. 22, 2014, EPO Form 2911O 01.12, one page.
EPO Communication regarding Extension of time limit pursuant to Rule 132 EPC, EP Application No. 09075279.1 and Patent No. 2147594, Oct. 22, 2014, one page.
David Power of J A Kemp communication to EPO, Executed Acknowledgement, EP Application No. 09075279.1 and EP Patent No. 2147594, Mar. 22, 2016, EPO Form 2936 08.10, one page.
Advice of receipt to Fritz Lahrtz of Isenbruck Bösl Höschler LLP, Registration No. of item RD118911257NL, May 25, 2016, one page.
Correspondence from Dr. Fritz Lahrtz of Isenbruck Bösl Förschler LLP to the European Patent Office regarding change of name for Proprietor, EP Application No. 09075279.1 and EP Patent No. 2147594, May 30, 2016, one page.
Deed of Conversion and Amendment of the Articles of Association for Merus BV (new name: Merus N.V.), May 19, 2016, 27 pages.
English translation of Deed of Conversion and Amendment of the Articles of Association for Merus BV (new name: Merus N.V.), May 19, 2016, 26 pages.
EPO Communication, Payment of fees and expenses, EP Application No. 09075279.1, May 30, 2016, EPO Form 1010 03.15, one page.
EPO Brief Communication to Andrew Bentham of J A Kemp regarding the telephone conversation on the Opposition, EP Application No. 09075279.1 and Patent No. 2147594, Mar. 16, 2016, EPO Form 2911O 01.12, one page.
EPO Communication regarding the entries pertaining to the applicant / the proprietor (R. 143(1)(f) EPC), EP Application No. 09075279.1 and EP Patent No. 2147594, Jun. 13, 2016, EPO Form 2544 03.14, two pages.
EPO Brief Communication to Andrew Bentham of J A Kemp regarding the Opposition, EP Application No. 09075279.1 and Patent No. 2147594, Jun. 14, 2016, EPO Form 2911O 01.12, one page.
EPO Communication to Fritz Lahrtz of Isenbruck Bösl Förschler LLP, Refund of fees, EP Application No. 09075279.1 and Patent No. 2147594, Jun. 15, 2016, EPO Form 2907 04.14, one page.
EPO Communication regarding the cancelling of the Summons for Oral Proceedings dated Oct. 13, 2016, EP Application No. 09075279.1, Mar. 17, 2016, EPO Form 2088 06.14, one page.
EPO Communication regarding important information concerning oral proceedings, at least as early as Mar. 22, 2016, EPO Form 2043 02.09, three pages.
EPO Brief Communication to Fritz Lahrtz of Isenbruck Bösl Höschler LLP regarding the Oral Proceedings on Oct. 13, 2016, EP Application No. 09075279.1 and Patent No. 2147594, Mar. 22, 2016, EPO Form 2310A 12.07, one page.
EPO Brief Communication to Andrew Bentham of J A Kemp regarding the Oral Proceedings on Oct. 13, 2016, EP Application No. 09075279.1 and Patent No. 2147594, Mar. 22, 2016, EPO Form 2310A 12.07, one page.
EPO Communication, Summons to Fritz Lahrtz of Isenbruck Bösl Höschler LLP to attend oral proceedings pursuant to Rule 115(1) EPC, EP Application No. 09075279.1 and EP Patent No. 2147594, Mar. 22, 2016, EPO Form 2310 12.14, one page.
EPO Communication, Summons to Andrew Bentham of J A Kemp to attend oral proceedings pursuant to Rule 115(1) EPC, EP Application No. 09075279.1 and EP Patent No. 2147594, Mar. 22, 2016, EPO Form 2310 12.14, one page.
EPO Communication to Fritz Lahrtz of Isenbruck Bösl Höschler LLP, Acknowledgement of receipt of EPO Forms 2310 and 2043, EP Application No. 09075279.1 and EP Patent No. 2147594, dated Mar. 22, 2016, EPO Form 2936 08.10, one page.
Letter disclosing in vivo data dated Jun. 13, 2013, European patent application No. 09075279.1, 2 pages.
Arnold et al., Development of B-1 Cells: Segregation of Phosphatidyl Choline-specific B Cells to the B-1 Population Occurs After Immunoglobulin Gene Expression, J. Exp. Med., May 1994, pp. 1585-1595, vol. 179, The Rockfeller University Press.
Bitter et al., Expression and Secretion Vectors for Yeast, in Methods in Enzymology, Ed. Wu & Grossman, Acad. Press, N.Y. 153:516 544 (1987) Abstract only.
Cascalho et al., A Quasi-Monoclonal Mouse, Science, Jun. 14, 1996, pp. 1649-1652, vol. 272.
De Graaf et al., Expression of scFvs and scFv Fusion Proteins in Eukaryotic Cells, Antibody Phage Display Methods and Protocals, Methods in Molecular Biology, 2002, pp. 379-387, vol. 178.
Dechiara et al., "Chapter 16: VelociMouse: Fully ES Cell-Derived FO-Generation Mice Obtained from the Injection of ES Cells into Eight-Cell-Stage Embryos", Gene Knockout Protocols, Second Edition, vol. 530, 2009, pp. 311-324, Humana Press.
De Wildt et al., Analysis of Heavy and Light Chain Pairings Indicates that Receptor Editing Shapes fhe Human Antibody Repertoire, J. Mol. Biol., 1999, pp. 895-901, vol. 285, No. 3.
Claims (amendments indicated), European Patent Application No. 09075279.1, Dec. 22, 2011, Reference No. P85231EP00, five pages.
Third Party Observations Under Article 115 EPC Against European Parent Application No. 09075279.1 in the name of Merus B.V., dated Apr. 25, 2012. 6 pages.
EPO Communication pursuant to Rule 114(2) EPC, EP Application No. 09075279.1 and Patent No. 2147594, dated May 8, 2012, EPO Form 2022 12.07, one page.
EPO Communication regarding Submission in opposition proceedings, Reply of the patent proprietor to the notice(s) of opposition, EP Application No. 09075279.1 and Patent No. 2147594, Apr. 2, 2015, two pages.
Correspondence from S.T. van Doorn of V.O. to European Patent Office in response to Communication under Rule 79(1) EPC, EP Application No. 09075279.1 and U.S. Pat. No. 2147594, dated Apr. 2, 2015, 32 pages.
EPO Brief Communication to Fritz Lahrtz of Isenbruck Bösl Höschler LLP regarding the telephone conversation on the Opposition, EP Application No. 09075279.1 and Patent No. 2147594, Mar. 16, 2016, EPO Form 2911O 01.12, one page.
EPO Communication to Andrew Bentham of J A Kemp, Acknowledgement of receipt of EPO Forms 2310 and 2043, EP Application No. 09075279.1 and EP Patent No. 2147594, Mar. 22, 2016, EPO Form 2936 08.10, one page.
Fritz Lahrtz of Isenbruck Bösl Höschler LLP communication to EPO, Executed Acknowledgement, EP Application No. 09075279.1 and EP Patent No. 2147594, Mar. 29, 2016, EPO Form 2936 08.10, one page.
Letter accompanying subsequently filed items regarding acknowledgement, EP Application No. 09075279.1, Submitted by David Power of J A Kemp, Apr. 12, 2016, one page.
EPO Acknowledgement of receipt of executed acknowledgment, EP Application No. 09075279.1 and Patent No. 2147594, date of receipt Apr. 12, 2016, one page.
Atwell S. et al, Stable heterodimers from remodeling the domain interface of a homodimer using a phage display library, J Mol Biol, 1997, 270(1), 26-35.
Baeuerle, PA., Reinhard, C., Bispecific T-cell engaging antibodies for cancer therapy, Cancer Res., 2009, 69(12), 4941-4944.
Bendig, MM., The production of foreign proteins in mammalian cells, Genet Eng., 1988, (7):91-127.
Bogan, AA., Thorn KS., Anatomy of hot spots in protein interfaces, J Mol Biol., 1998, 280(1), 1-9.
Bostrom, J., et al. Variants of the antibody herceptin that interact with HER2 and VEGF at the antigen binding site, Science, 2009, 323(5921), 1610-1614.

(56) References Cited

OTHER PUBLICATIONS

Capelle, MA et al., Spectroscopic characterization of antibodies adsorbed to aluminium adjuvants: correlation with antibody vaccine immunogenicity, 2005, Vaccine, 23(14), 1686-1694.
Carter, P. et al, Toward the production of bispecific antibody fragments for clinical applications, J Hematother., 1995, 4(5), 463-470.
Coligan JE, Commonly used detergents, Curr protoc Protein sci, 2001, Appendix 1.
Davies, J. et al., Antibody VH domains as small recognition units, Biotechnology, 1995, 13(5), 475-479.
Davis, JH. et al, SEEDbodies: fusion proteins based on strand-exchange engineered domain (SEED) CH3 heterodimers in an Fc analogue platform for asymmetric binders or immunofusions and bispecific antibodies, 2010, Protein Eng Des Sel., 23(4), 195-202.
De Kruif, J. et al, Generation of stable cell clones expressing mixtures of human antibodies, 2010, 106(5), 741-750.
De Vries, SJ. et al, The HADDOCK web server for data-driven biomolecular docking, 2010, 5(5):883-897.
Deisenhofer, Crystallographic refinement and atomic models of a human Fc fragment and its complex with fragment B of protein A from *Staphylococcus aureus* at 2.9- and 2.8-A resolution, 1981, 20(9), 2361-2370.
Demeule, B. Characterization of protein aggregation: the case of a therapeutic immunoglobulin, Biochim Biophys Acta, 2007, 1774(1),146-153.
Demeule, Detection and characterization of protein aggregates by fluorescence microscopy, 2007, Int J Pharm, 329(1-2):37-45.
Ellerson; JR: et al, Structure and function of immunoglobulin domains. III. Isolation and characterization of a fragment corresponding to the Cgamma2 homology region of human immunoglobin G1, J Immunol., 1976, 116(2), 510-517.
Farnan, D, Moreno GT, Multiproduct high-resolution monoclonal antibody charge variant separations by pH gradient ion-exchange chromatography, Anal Chem, 2009, 81(21), 8846-8857.
Gunasekaran, K. et al., Enhancing antibody Fc heterodimer formation through electrostatic steering effects: applications to bispecific molecules and monovalent IgG, JBC, 2010, 285(25), 19637-19646.
Hendsch, ZS. et al., Preferential heterodimer formation via undercompensated electrostatic interactions, J Am Chem Soc, 2001,123(6),1264-1265.
Idusogie, EE. Mapping of the C1q binding site on rituxan, a chimeric antibody with a human IgG1 Fc, 2000, J Immunol., 164(8), 4178-4184.
Ionescu, RM. et al, Contribution of variable domains to the stability of humanized IgG1 monoclonal antibodies, 2008, J Pharm Sci., 2008, 97(4), 1414-1426.
Kabat, EA., Wu, TT, Identical V region amino acid sequences and segments of sequences in antibodies of different specificities. Relative contributions of VH and VL genes, minigenes, and complementarity-determining regions to binding of antibody-combining sites, J Immunol., 1991,147(5), 1709-1719.
Kumar, R., Shieh, BH, The second PDZ domain of INAD is a type I domain involved in binding to eye protein kinase C. Mutational analysis and naturally occurring variants, J Biol Chem., 2001, 276(27), 24971-24977.
Lakowicz, JR, Principles of fluorescence spectroscopy, 2nd edition, Kluwer Academic/Plenum Publisher, 2006.
Lee, B, Richards,FM: The interpretation of protein structures: estimation of static accessibility., J Mol Biol, 1971, 55(3), 379-400.
Marvin, JS. et al., Redesigning an antibody fragment for faster association with its antigen, Biochemistry, 2003,42(23), 7077-7083.
McPhee, F. et al., Engineering human immunodeficiency virus 1 protease heterodimers as macromolecular inhibitors of viral maturation, PNAS, 1996, 93(21),11477-11481.
Merchant, AM. et al., An efficient route to human bispecific IgG, Nat. Biotechnol, 1998, 16(7), 677-681.
Merus, Press Release (www.merus.nl), Jan. 7, 2013, 2 pages.
Merus, Press Release (www.merus.nl),Jun. 17, 2013, 3 pages.
Miller S., Protein-protein recognition and the association of immunoglobulin constant domains, J Mol Biol, 1990, 216(4), 965-973.
Nieba, L. et al., Disrupting the hydrophobic patches at the antibody variable/constant domain interface: improved in vivo folding and physical characterization of an engineered scFv fragment, Protein Eng., 1997, 10(4), 435-444.
Nohaile; MJ. et al., Altering dimerization specificity by changes in surface electrostatics, Proc Natl Acad Sci USA, 2001, 98(6), 3109-3114.
Padlan, EA, X-ray crystallography of antibodies, Adv Protein Chem, 1996, 49, 57-133.
Papadea, EA. and Check, IJ, Human immunoglobulin G and immunoglobulin G subclasses: biochemical, genetic, and clinical aspects, Crit Rev Clin Lab Sci, 1989, 27(1), 27-58.
Raffen, R. et al., Reengineering immunoglobulin domain interactions by introduction of charged residuesProtein Eng., 1998, 11(4), 303-309.
Ridgway, JB. et al., 'Knobs-into-holes' engineering of antibody CH3 domains for heavy chain heterodimerization, Protein Eng, 1996, 9(7), 617-621.
Sal-Man, N. and Shai, Y., Arginine mutations within a transmembrane domain of Tar, an *Escherichia coli* aspartate receptor, can drive homodimer dissociation and heterodimer association in vivo, Biochem J, 2005, 385(Pt 1):29-36.
Schaefer, G. et al, A two-in-one antibody against HER3 and EGFR has superior inhibitory activity compared with monospecific antibodies, Cancer Cell, 2011, 20(4), 472-486.
Schiffer, M. et al., Analysis of immunoglobulin domain interactions. Evidence for a dominant role of salt bridges, J Mol Biol, 1988, 203(3),799-802.
Selzer, T. et al., Rational design of faster associating and tighter binding protein complexes, Nat Struct Biol, 2000, 7(7), 537-541.
Sheinerman, FB. et al., Electrostatic aspects of protein-protein interactions, Curr Opin Struc Biol, 2000, 10(2),153-159.
Sinha, N. et al., Differences in electrostatic properties at antibody-antigen binding sites: implications for specificity and cross-reactivity, Biophys. J., 2002, 83(6), 2946-2968.
Sinha, N. and Smith-Gill, SJ., Electrostatics in protein binding and function, Curr Protein Pept Sci, 2002, 3(6),601-614.
Tahallah, N. et al, The effect of the source pressure on the abundance of ions of noncovalent protein assemblies in an electrospray ionization orthogonal time-of-flight instrument, Rapid Commun Mass Spectrom., 2001, 15(8):596-601.
Van Rhenen, A. et al., The novel AML stem cell associated antigen CLL-1 aids in discrimination between normal and leukemic stem cells, Blood, 2007, 110(7), 2659-2666.
Zhao, X., et.al., Targeting C-type lectin-like molecule-1 for antibody-mediated immunotherapy in acute myeloid leukemia, Haematologica, 2010, 95(1), 71.
PCT International Preliminary Report on Patentability, PCT/NL2009/050381 dated Jan. 5, 2011.
Jakobovits et al., From XenoMouse technology to panitumumab, the first fully human antibody product from transgenic mice, Nature Biotechnology, Oct. 2007, pp. 1134-1143, vol. 25, No. 10.
Janeway, The Development and Survival of Lymphocytes, Chapter 8, Immunobiology, 1999, pp. 275-290.
Storb, Ursula et al., "Transgenic Mice with mu and kappa Genes Encoding Antiphosphorylcholine Antibodies," J. Exp. Med., vol. 164:627-641 (1986).
Popov, Andrei V. et al., "A Human Immunoglobulin lambda Locus Is Similarly Well Expressed in Mice and Humans," J. Exp. Med., vol. 189(10):1611-1619 (1999).
Jolly et al. Rapid methods for the analysis of immunoglobulin gene hypennutation: application to transgenic and gene targeted mice, Nucleic Acids Research, 1997, pp. 1913-1919, vol. 25, No. 10.
Kabat, et al. (1991) Sequences of Proteins of Immunological Interest, Fifth Edition, U.S. Department of Health and Human Services, NIH Publication No. 91 3242 Abstract only.
Kling, Jim, Big Pharma vies for mice, Nature Biotechnology, Jun. 1, 2007, pp. 613-614, vol. 25.

(56) References Cited

OTHER PUBLICATIONS

Klohn, Peter-Christian et al., "IBC's 23rd Annual Antibody Engineering, 10th Annual Antibody Therapeutics International Conferences and the 2012 Annual Meeting of the Antibody Society," mAbs, vol. 5(2):178-201 (2013).
Klotz et al., Somatic Hypermutation of a lambda, Transgene Under the Control of the lambda, Enhancer or the Heavy Chain Intron Enhancer, The Journal of Immunology, 1996. pp. 4458-4463. vol. 157.
Kong et al., A lambda 3' Enhancer Drives Active and Untemplated Somatic Hypermutation of a lambda1 Trans gene, The Journal ofImmunology, 1998, pp. 294-301, vol. 161.
Kwaks et al., Employing epigenetics to augment the expression of therapeutic proteins in mammalian cells, Trends in Biotechnology, Mar. 1, 2006, pp. 137-142, vol. 24, No. 3, Elsevier Publications, Cambridge, GB.
Lenz, et al.; Expression of heterobispecific antibodies by genes transfected into producer hybridoma cells, Gene; 87 Mar. 15, 1990, No. 2; pp. 213-218.
Lie, Y.S. et al., "Advances in quantitative PCR technology: 5' nuclease assays," Curr. Opin. Biotechnol., vol. 9(1):43-48 (1998).
Melvyn Little, Antibodies for Immunotherapy, Cambridge University Press, 2009. 23 pages.
Little et al., Human antibody libraries in *Escherichia coli*, Journal of Biotechnology, 1995, pp. 187-195, vol. 41, Elsevier.
Lonberg, Nils et al., "Antigen-specific human antibodies from mice comprising four distinct genetic modifications," Nature, vol. 368:856-859 (1994).
Lonberg et al., Human antibodies from transgenic animals, Nature Biotechnology, Sep. 1, 2005, pp. 1117-1125, vol. 23, No. 9, Nature Publishing Group, New York, NY, US.
Meyer, Kerstin B. et al., "The importance of the 3'-enhancer region in immunoglobulin kappa gene expression," Nucleic Acids Research, vol. 18(19):5609-5615 (1990).
Taylor, Lisa D. et al., "A transgenic mouse that expresses a diversity of human sequence heavy and light chain immunoglobulins," Nucleic Acids Research, vol. 20(23):6287-6295 (1992).
Odegard et al., Targeting of somatic hypermutation, Nature Reviews, Immunology, Aug. 2006, pp. 573-583, vol. 6, No. 8.
Sasaki, Yoshiteru et al., "Canonical NF-kB Activity, Dispensable forB Cell Development, Replaces BAFF-Receptor Signals and Promotes B Cell Proliferation upon Activation," Immunity, vol. 24:729-739 (2006).
Scott, Christopher Thomas, "Mice with a human touch," Nature Biotechnology, vol. 25:1075-1077 (2007).
Macdonald et al., Precise and in situ genetic humanization of 6 Mb of mouse immunoglobulin genes, PNAS, 2013, (6 Pages), Early Edition.
Mao, Xiaohong et al., "Activation of EGFP expression by ere-mediated excision in a new ROSA26 reporter mouse strain," Blood, vol. 97(1 ):324-326 (2001).
McCafferty et al., Antibody Engineering, PAS, 2002, 178 Pages, Oxford University Press.
Merus, "MeMo—the ingenious mouse, for improved antibody therapeutics," www.merus.nl, 3 pages (2011).
Mendez et al., Functional transplant of megabase human immunoglobulin loci recapitulates human antibody response in mice, Nature Genetics. 1997. pp. 146-156. vol. 15.
Declaration of Andrew Murphy, Dec. 19, 2014, 18 pages.
Murphy et al., Mice with megabase humanization of their immunoglobulin genes generate antibodies as efficiently as normal mice, PNAS, 2013, 6 pages, Early Edition.
Nagle, "Regeneron helps make Sanofi Velcolmmue to its 'weak' pipline", Outsourcing-Pharma.com, Dec. 3, 2007, two pages, William Reed Business Media SAS.
NCBI, Aucouturier et al., Monoclonal IgL Claim and L chain V domain fragment crystallization in myeloma-associated Fanconi's syndrome, <http://www.ncbi.nlm.nib/gov/nuccore/M87478, at least as early as Apr. 25, 2012.

Nemazee, David, "Receptor editing in lymphocyte development and central tolerance," Nature, vol. 6(10):728-740 (2006).
Neuberger, M.S. et al., "Isotype exclusion and transgene down-regulation in immunoglobulin-lambda transgenic mice," Nature, vol. 338:350-352 (1989).
Second Declaration of Robert Brink, Jun. 2, 2015, 38 pages.
Second Declaration of Peter Hudson, Jun. 2, 2015, 81 pages.
Sharpe et al., Somatic hypermutation of immunoglobulin kappa may depend on sequences 3' of C kappa and occurs on passengertransgenes, The EMBO.Ioumal. 1991. pp. 2139-2145, vol. 10, No. 8.
Nissim et al., Antibody fragments from a 'single pot' phage display library as immunochemical reagents, The EMBO Journal, 1994, pp. 692-698, vol. 13. No. 3.
Notice of Opposition dated Jul. 8, 2016, EP2264163 10010741.6.
Notice of Opposition, Australian application No. 2009263082, Jun. 20, 2014, 1 page.
Third Party Observation for Application No. 2009263082, 25 pages, Oct. 21, 2013.
Rickert, Robert C. et al., "B lymphocyte-specific, Cre-mediated mutagenesis in mice," Nucleic Acids Research, vol. 25(6):1317-1318 (1997).
Pelanda et al., A prematurely expressed Ig(kappa) transgene, but not V(kappa)J(kappa) gene segment targeted into the Ig(kappa) locus, can rescue B cell development in lambdaS-deficient mice, Immunity, Sep. 1996, pp. 229-239, vol. 5, No. 3.
Peled, Jonathan U. et al., "The Biochemistry of Somatic Hypermutation," Annu. Rev. Immunol., vol. 26:481-511 (2008).
Prak, Eline Lunning, Light Chain Replacement: A new model for antibody gene rearrangement, J. Exp. Med., Aug. 1995, pp. 541-548, vol. 182, The Rockefeller University Press.
Presta et al., Engineering of therapeutic antibodies to minimize immunogenicity and optimize function, Advanced Drug Delivery Reviews, Aug. 7, 2006, pp. 640-656, vol. 58, No. 5-6, Elsevier BV, Amsterdam, NL.
Amendment, Australian patent application No. 2009263082, dated Jan. 23, 2014, 22 pages.
Retter, Marc W. et al., "Receptor Editing Occurs Frequently during Normal B Cell Development," J. Exp. Med., vol. 188(7):1231-1238 (1998).
Sirac et al., Role of the monoclonal kappa chain V domain and reversibility of renal damage in a transgenic model of acquired Fanconi syndrome, Blood, Jul. 15, 2006, pp. 536-543, vol. 108, No. 2.
Smith-Gill et al., Contributions of immunoglobulin heavy and light chains to antibody specificity for lysozyme and two haptens, Journal of Immunology, Dec. 15, 1987, pp. 4135-4144, vol. 139, No. 12., Baltimore, MD, US.
Second Declaration of Ton Logtenberg Under 37 C.F.R. 1.132, U.S. Appl. No. 13/750,753 dated Dec. 18, 2015, ten pages.
Janeway et al., Chapter 3: Structure of the Antibody Molecule and the Immunoglobulin Genes, ImmunoBiology The Immune System in Health and Disease, Fourth Edition, 1999, pp. 90-108, Elsevier Science Ltd/Garland Publishing.
Declaration of Professor Anthony DeFranco, European Patent No. 2147594 B1, European Patent Application No. 09075279.1, dated Aug. 24, 2016, 23 pages.
Sequence Alignment and Declaration of Dr. John McWhirter, European Patent Application No. 09075289.1, European Patent No. 2147594 B1, dated Aug. 2, 2016, four pages.
Lefranc, Marie-Paule, Nomenclature of the Human Immunoglobulin Kappa (IGK) Genes, Exp Clin Immunogenet, 2001, pp. 161-174, vol. 18, Karger.
J A Kemp to European Patent Office, Final Written Submissions Oral Proceedings Scheduled for Oct. 28, 2016, Opposition to Merus N.V.'s EP2147594 dated Aug. 26, 2016, 40 pages.
EPO Acknowledgement of receipt—Opposition proceedings in relation to EP09075279.1 dated Aug. 26, 2016, two pages.
Canadian Intellectual Property Office, Office Action, Application No. 2729095, dated Nov. 10, 2015, eight pages.
Borden Ladner Gervais LLP to Canadian Patent Office, Response to Official Action dated Nov. 10, 2015, Application No. 2729095, dated May 10, 2016, 12 pages.

(56) References Cited

OTHER PUBLICATIONS

Third Party Opposition filed in Canadian Intellectual Property Office, Application No. 2729095, dated Sep. 16, 2015, 15 pages.
Borden Ladner Gervais LLP in the Canadian Patent Office, Voluntary Amendment, Application No. 2729095, dated May 12, 2016, two pages.
Japan Patent Office, Notification of Third Party Observation, Japanese Patent Application No. 2011-516168, May 20, 2014, one page.
Japan Patent Office, Certificate of Patent, Japanese Patent No. 5749161, Japanese Application No. 2011-516168, May 22, 2015.
Japan Patent Office, As-Filed english language application, Japanese Patent Application No. 2015-097258, May 12, 2015, 218 pages.
Japan Patent Office, Request for Substantive Examination, Japanese Patent Application No. 2015-097258, Jun. 1, 2015, 1 page.
Japan Patent Office, As-Filed Application, Japanese Patent Application No. 2015-097258, May 13, 2015, 270 pages.
Japan Patent Office, Official Action, Japan Patent Application No. 2015-097258, dated Mar. 31, 2016, seven pages.
Canadian Patent Office, Completion Requirement, Submission of Sequence Listing , CA Application No. 2729095, Mar. 9, 2011, one page.
Canadian Intellectual Property Office to Blake Cassels & Graydon LLP, Protest Confirmation, Canadian Patent Application No. 2729095, Apr. 16, 2014, one page.
Canadian Intellectual Property Office, General Correspondence Form, CA Application No. 2729095, PCT Application No. PCT/NL2009/050381, Dec. 22, 2010, three pages.
Canadian Patent Office, Information Letter, Foreign and non-patent references, CA Application No. 2729095, Mar. 9, 2011, two pages.
Japan Patent Office, Acknowledgement of receipt, Japanese Patent Application No. 2015-097258, May 12, 2015, 1 page.
Canadian Intellectual Property Office to Borden Ladner Gervais LLP, Requisition by the Examiner, CA Application No. 2729095, Jun. 11, 2014, three pages.
Canadian Patent Office, Response to the Office Action dated Jun. 11, 2014, CA Application No. 2729095, dated Dec. 10, 2014, 24 pages.
Canadian Intellectual Property Office to Borden Ladner Gervais LLP, Requisition by the Examiner, CA Application No. 2729095, Apr. 16, 2013, seven pages.
Canadian Patent Office, Response to the Examiner's Report dated Apr. 16, 2013, CA Application No. 2729095, Oct. 15, 2013, 20 pages.
Canadian Patent Office, Voluntary Amendment , CA Application No. 2729095, dated Dec. 5, 2011, thirteen pages.
Canadian Intellectual Property Office to Borden Ladner Gervais LLP, Advisement of protest filed, CA Application No. 2729095, Nov. 2, 2015, one page.
Canadian Patent Office, Statement and Declaration Under Rule 37, CA Application No. 2729095, Dec. 22, 2010, one page.
Canadian Patent Office, Statement of Support , CA Application No. 2729095, Mar. 9, 2011, one page.
Ritchie et al., Allelic exclusion of control of endogenous immunoglobin gene rearrangement in kappa transgenic mice, Nature, Dec. 1984, pp. 517-520, vol. 312, Nature Publishing Group.
Third Party Observation for application No. EP20120783456, Anonymous, Jun. 16, 2016, three pages.
Opposition Filed Against European Patent No. 2147594 (European Patent Application No. 09075279.1) in the Name of Merus N.V., Declaration of Professor Anthony DeFranco, dated Aug. 24, 2016, 23 pages.
Japan Patent Office, Notice of Reasons for Rejection, Japanese Patent Application No. 2011-516168, dated Oct. 15, 2013, four pages.
Japan Patent Office, Third Party Observation, Japanese Patent Application No. 2011-516168, May 9, 2014, 14 pages.
Third Party Observation for U.S. Appl. No. 15/140,321, Sep. 2, 2016, two pages.
Japan Patent Office, Opposition against Patent, JP Patent No. 5749161, Jan. 15, 2016, 55 pages.
Third Party citation for application No. 14163642.3, 3 pages, dated Jan. 29, 2016.
SHIGA International Patent Office to Japan Patent Office, Amendments to claims made in response to notice of reasons for rejection, Japanese Patent Application No. 2011-516168, dated Jan. 5, 2015, three pages.
SHIGA International Patent Office to Japan Patent Office, Amendments to claims made in response to notice of reasons for rejection, Japanese Patent Application No. 2011-516168, dated Jan. 14, 2014, three pages.
Japan Patent Office, Registration Fee Payment, Japanese Patent Application No. 2011-516168, May 13, 2015, one page.
SHIGA International Patent Office to Japan Patent Office, Remarks in response to notice of reasons for rejection, Japanese Patent Application No. 2011-516168, dated Jan. 5, 2015, 16 pages.
SHIGA International Patent Office to Japan Patent Office, Remarks in response to notice of reasons for rejection, Japanese Patent Application No. 2011-516168, dated Jan. 14, 2014, six pages.
Japan Patent Office, Final Notice of Reasons for Rejection, Japanese Patent Application No. 2011-516168, dated Jul. 28, 2014, six pages.
Japan Patent Office, Notice of Allowance, Japanese Patent Application No. 2011-516168, dated Apr. 13, 2015, four pages.
Sirac et al., Light chain inclusion permits terminal B cell differentation and does not necessarily result in autoreactivity, PNAS, May 16, 2006, pp. 7747-7752, vol. 103, No. 20.
Isenbruck Bosl Horschler LLP to European Patent Office, Documents filed by Proprietor, Response to the summons to attend oral proceedings scheduled for Oct. 28, 2016 and to the preliminary opinion of the Opposition Division dated Jan. 19, 2016, EP 2147594 / 09075279.1-1405, dated Aug. 26, 2016, 32 pages.
EPO Communication to J A Kemp, Submission in opposition proceedings made following summons to attend oral proceedings, Patent No. EP 2147594, Application No. EP09075279.1, dated Aug. 26, 2016, two pages.
Appeal Briefs filed with the U.S. Patent Office in U.S. Appl. No. 13/948,818 at least as early as Jul. 17, 2015, available on the U.S. Patent Office website.
Houldsworth et al., Comparative Genomic Hybridization: An Overview, American Journal of Pathology, vol. 145, Dec. 1994.
Jessen et al (1998) Modification of bacterial artificial chromosomes through Chi-stimulated homologous recombination and its application in zebrafish transgenesis. Proc. Natl. Acad. Sci. USA 95:5121-5126.
Muyrers et al., Rapid modification of bacterial artificial chromosomes by ET-recombination. Nucleic Acids Research, 1999, 27(6):1555-1557.
Narayanan et al., Efficient and precise engineering of a 200 kb beta-globin human/bacterial artificial chromosome in *E. coli* DH1OB using an inducible homologous recombination system, Gene Therapy, 1999, 6:442-447.
U.S. Appl. No. 60/244,665, filed Oct. 31, 2000, available on the U.S. Patent Office website.
Roitt, et al., Really Essential Medical Immunology, pp. 23-35, 17 pages.
Soukharev et al., Segmental genomic replacement in embryonic stem cells by double lox targeting, Nucleic Acids Research, 1999, pp. e21, vol. 27, No. 18.
Waterhouse et al., Combinatorial infection and in vivo recombination: strategy for making large phage antibody repertoires, Nucleic Acids Research 21(9), 1993, pp. 2265-2266.
Chu, 66 F.3d, 292—Case Summary and Opinion; United States Court of Appeals for the Federal Circuit, Sep. 14, 1995.
Description of relevance of Third Party Submission in U.S. Appl. No. 15/140,321 dated Feb. 10, 2017.
Materials from examination—submission in response to attend oral proceedings of a European Patent Application No. 09075279.1, Apr. 23, 2013.
Abedi, M.R. et al., Green, fluorescent protein as a scaffold for intracellular presentation of peptides, Nucleic Acids Res., 1998, 26(2), 623-630.
Akerström, B. et al., On the interaction between single chain Fv antibodies and bacterial immunoglobulin-binding proteins, J Immunol Methods., 1994, 177(1-2), 151-163.

(56) References Cited

OTHER PUBLICATIONS

Alber, T., Kawasaki, G., Nucleotide sequence of the triose phosphate isomerase gene of *Saccharomyces cerevisiae*, J Mol Appl Genet., 1982, 1(5), 419-434.

Ammerer, G., Expression of genes in yeast using the ADCI promoter, Methods Enzymol., 1983, 101, 192-201.

Antica, M. et al., Thymic stem cells in mouse bone marrow, Blood, 1994, 84(1), 111-117.

Appel RD, et al., A new generation of information retrieval tools for biologists: the example of the ExPASy WWW server, 1994, Trends Biochem. Sci., 19, 258-260.

Aranda, A., Pascual, A., Nuclear hormone receptors and gene expression, Physiol Rev., 2001, 81(3), 1269-1304.

Barbas, CF. et al., Assembly of combinatorial antibody libraries on phage surfaces: the gene III site, Proc Natl Acad Sci U S A, 1991, 88(18), 7978-7982.

Barnes, LM. et al, Characterization of the stability of recombinant protein production in the GS-NS0 expression system, Biotechnol Bioeng., 2001, 73(4), 261-270.

Bebbington, CR. et al, High-level expression of a recombinant antibody from myeloma cells using a glutamine synthetase gene as an amplifiable selectable marker, Biotechnology (N Y), 1992, 10(2), 169-175.

Bell, AC. et al., Insulators and boundaries: versatile regulatory elements in the eukaryotic genome, Science, 2001, 291(5503), 447-450.

Bertagnolli, M., Herrmann, S., IL-7 supports the generation of cytotoxic T lymphocytes from thymocytes. Multiple lymphokines required for proliferation and cytotoxicity, J Immunol., 1990,145(6), 1706-1712.

Bertagnolli, MM. et al., IL-4-supported induction of cytolytic T lymphocytes requires IL-2 and IL-6, Cell Immunol., 1991, 133(2), 327-341.

Bertagnolli, MM. et al., IL-12 augments antigen-dependent proliferation of activated T lymphocytes, J Immunol., 1992, 149(12), 3778-3783.

Bhardwaj, N. et al., Influenza virus-infected dendritic cells stimulate strong proliferative and cytolytic responses from human CD8+ T cells, J Clin Invest., 1994; 94(2), 797-807.

Binz, H.K. et al., Designing repeat proteins: well-expressed, soluble and stable proteins from combinatorial libraries of consensus ankyrin repeat proteins, J Mol Biol., 2003, 332(2), 489-503.

Bode et al. 2001, Int. J. Gene Ther. Mol. Biol. 6:33-46.

Boder, ET., Wittrup, KD., Yeast surface display for screening combinatorial polypeptide libraries, Nat Biotechnol., 1997, 15(6), 553-557.

Bowman, MR. et al., The cloning of CD70 and its identification as the ligand for CD27, J Immunol., 1994, 152(4), 1756-1761.

Brezinsky, SC. Et al., A simple method for enriching populations of transfected CHO cells for cells of higher specific productivity. J Immunol Methods, 2003, 277(1-2),141-155.

Brink MF, et al., Developing efficient strategies for the generation of transgenic cattle which produce biopharmaceuticals in milk, Theriogenology, 2000, 53(1), 139-148.

Broach; JR. et al., Transformation in yeast: development of a hybrid cloning vector and isolation of the CAN1 gene, Gene, 1979, 8(1), 121-133.

Chan, A., Mak, TW., Genomic organization of the T cell receptor, Cancer Detect Prev., 1989,14(2), 261-267.

Chesnut, J. et al., Selective isolation of transiently transfected cells from a mammalian cell population with vectors expressing a membrane anchored single-chain antibody, Journal of Immunological Methods, 1996 pp. 17-27.

Clackson, T. et al., Making antibody fragments using phage display libraries, Nature, 1991, 352(6336), 624-628.

Cockett MI, Bet al., High level expression of tissue inhibitor of metalloproteinases in Chinese hamster ovary cells using glutamate synthetase gene amplification, Biotechnology, 1990, 8(7), 662-667.

Corsaro, CM., Pearson, ML., Enhancing the efficiency of DNA-mediated gene transfer in mammalian cells, Somatic Cell Genet., 1981, 7(5), 603-616.

Darzynkiewicz, Z. et al., Features of apoptotic cells measured by flow cytometry, Cytometry, 1992,13(8), 795-808.

De Vries, P. et al., The effect of recombinant mast cell growth factor on purified murine hematopoietic stem cells, J Exp Med, 1991, 173(5), 1205-1211.

De Jong, G., Mammalian artificial chromosome pilot production facility: large-scale isolation of functional satellite DNA-based artificial chromosomes, Cytometry, 1999, 35(2), 129-133.

Declaration of Joel Martin filed May 18, 2016 in EP2314629B.

Desmyter, A. et al., Crystal structure of a camel single-domain VH antibody fragment in complex with lysozyme, Nat Struct Biol., 1996, 3(9), 803-811.

Dumoulin, M. et al., Single-domain antibody fragments with high conformational stability, Protein Sci., 2002, 11(3), 500-515.

Dumoulin, M. et al., A camelid antibody fragment inhibits the formation of amyloid fibrils by human lysozyme, Nature, 2003, 424(6950), 783-788.

Eren, R. et al., Preclinical evaluation of two human anti-hepatitis B virus (HBV) monoclonal antibodies in the HBV-trimera mouse model and in HBV chronic carrier chimpanzees, Hepatology, 2000, 32(3), 588-596.

Ezzell, C., Magic bullets fly again, Sci Am., 2001, 285(4), 34-41.

Feige, U. et. al., Anti-interleukin-1 and anti-tumor necrosis factor-alpha synergistically inhibit adjuvant arthritis in Lewis rats, Cell Mol Life Sci., 2000, 57(10), 1457-1470.

Fine, JS. et al., Interleukin-10 enhances gamma delta T cell development in the murine fetal thymus, Cell Immunol., 1994, 155(1), 111-122.

Fishwild DM, et al., High-avidity human IgG kappa monoclonal antibodies from a novel strain of minilocus transgenic mice, Nat Biotechnol, 1996, 14(7), 845-851.

Frenken, LG. et al., Isolation of antigen specific llama VHH antibody fragments and their high level secretion by *Saccharomyces cerevisiae*, J Biotechnol., 2000, 78(1), 11-21.

Frykman, S. et al, Quantitating secretion rates of individual cells: design of secretion assays, Biotechnol Bioeng., 1998,59(2), 214-226.

Galy, AH. et al., Delineation of T-progenitor cell activity within the CD34+ compartment of adult bone marrow, Blood, 1995, 85(10), 2770-2778.

Gan, W. et al, Functional characterization of the internal ribosome entry site of eIF4G mRNA, J Biol Chem., 1998, 273(9), 5006-5012.

Garber, K. Biotech industry faces new bottleneck, Nat Biotechnol., 2001, 19(3), 184-185.

Garnick, RL., Peptide mapping for detecting variants in protein products, Dev Biol Stand., 1992, 76, 117-130.

Garrard, LJ. et al., Fab assembly and enrichment in a monovalent phage display system, Biotechnology (N Y), 1991, 9(12), 1373-1377.

Gelpi, E., Biomedical and biochemical applications of liquid chromatography-mass spectrometry, J Chromatogr A, 1995, 703(1-2), 59-80, Abstract Only.

Ghetie, M-A., et al., Homodimerization of tumor-reactive monoclonal antibodies markedly increases their ability to induce growth arrest or apoptosis of tumor cells, Proc Natl Acad Sci U S A, 1997, 94(14), 7509-7514.

EPO communication to Andrew Bentham of J A Kemp, Brief Communication regarding EPO Form 2548 of Jan. 12, 2016, EP Application No. 09075279.1 and EP Patent No. 2147594, dated Jan. 12, 2016, EPO Form 291000 31.12, two pages.

EPO communication, Preparation for oral proceedings—Instruction to Support Service, EP Application No. 09075279.1 and EP Patent No. 2147594, Jan. 14, 2016, EPO Form 2040 12.07TRI, two pages.

EPO Communication regarding Submission in opposition proceedings, Request for extension of time, EP Application No. 09075279.1 and Patent No. 2147594, Oct. 16, 2014, two pages.

EPO Communication regarding important information concerning oral proceedings, at least as early as Jan. 19, 2016, EPO Form 2043 02.09, three pages.

(56) References Cited

OTHER PUBLICATIONS

EPO Acknowledgement of receipt of letter of inquiry, EP Application No. 09075279.1 and Patent No. 2147594, date of receipt Nov. 17, 2015, one page.
EPO Brief Communication regarding the Opposition, EP Application No. 09075279.1 and Patent No. 2147594, Dec. 9, 2015, EPO Form 2911O 01.12, one page.
Letter accompanying subsequently filed items regarding Document concerning representation, EP Application No. 09075279.1, Submitted by C.M. Jansen of V.O., Dec. 17, 2015, one page.
Correspondence from C.M. Jansen of V.O. to European Patent Office regarding change of representation, EP Patent No. 2147594, Dec. 17, 2015, one page.
EPO Acknowledgement of receipt of change of representation, EP Application No. 09075279.1 and Patent No. 2147594, date of receipt Dec. 17, 2015, one page.
Correspondence from Dr. Fritz Lahrtz of Isenbruck Bösl Förschler LLP to the European Patent Office regarding change of representation, EP Application No. 09075279.1 and EP Patent No. 2147594, Jan. 8, 2016, one page.
EPO communication to Fritz Lahrtz of Isenbruck Bösl Höschler LLP, Communication of amended entries concerning the representative (R. 143(1)(h) EPC), EP Application No. 09075279.1 and EP Patent No. 2147594, Jan. 12, 2016, EPO Form 2548 08.13, one page.
EPO Communication, After communication under Rule 71(3) EPC (IGRA) but before decision to grant (EPO Form 2006A), EP Application No. 09075279.1, dated Sep. 5, 2013, EPO Form 2092C 04.12, two pages.
EPO Communication pursuant to Rule 114(2) EPC, EP Application No. 09075279.1, dated Oct. 10, 2013, EPO Form 2022 12.07, one page.
EPO Communication, Consultation by telephone with the applicant / representative, EP Application No. 09075279.1, Oct. 9, 2013, EPO Form 2036 12.07TRI, one page.
EPO Communication, Result of consultation, EP Application No. 09075279.1, Oct. 14, 2013, EPO Form 2049A 12.07TRI, two pages.
EPO Communication, Decision to grant a European patent pursuant to Article 97(1) EPC, EP Application No. 09075279.1, dated Oct. 17, 2013, EPO Form 2006A 12.07, two pages.
EPO Communication, Transmission of the certificate for a European patent pursuant to Rule 74 EPC, EP Application No. 09075279.1, Nov. 13, 2013, EPO Form 2047 12.07, one page.
EPO Acknowledgement of receipt of letter regarding in vivo data, EP Application No. 09075279.1, date of receipt Jun. 13, 2013, one page.
EPO Communication, Notice of Opposition to a European Patent, EP Application No. 09075279.1 and EP Patent No. 2147594, Aug. 11, 2014, EPO Form 2300E, eight pages.
EPO Communication pursuant to Rule 114(2) EPC, EP Application No. 09075279.1 and Patent 2147594, dated Jun. 14, 2013, EPO Form 2022 12.07, one page.
Torres et al., "Chapter 10: LoxP-containing transgenes", Laboratory Protocols for Conditional Gene Targeting, 1997, pp. 42-53, Oxford University Press Inc., New York, USA.
Murphy, "Chapter 8: The Development and Survival of Lymphocytes", Janeway's Immunobiology, Eight Edition, Jul. 24, 2011, pp. 275-290.
Correspondence from A Bentham of J A Kemp to European Patent Office regarding an opposition, EP Patent No. 2147594, Aug. 11, 2014, one page.
Statement of Facts and Arguments in support of Opposition, EP Application No. 09075279.1 and EP Patent No. 2147594, at least as early as Aug. 11, 2014, 46 pages.
EPO Acknowledgement of receipt of Notice of Opposition, EP Application No. 09075279.1 and EP Patent No. 2147594, date of receipt Aug. 11, 2014, two pages.
EPO Communication of a Notice of Opposition, EP Application No. 09075279.1 and EP Patent No. 2147594, Aug. 20, 2014, EPO Form 2316 01.12, one page.

EPO Communication pursuant to Rule 114(2) EPC, EP Application No. 09075279.1 and Patent No. 2147594, dated Jul. 2, 2013, EPO Form 2022 12.07, one page.
EPO Communication, Minutes of the oral proceedings before the Examining Division, EP Application No. 09075279.1 and Patent No. 2147594, May 23, 2013, EPO Form 2009.1 12.07TRI, two pages.
Australian Office Action for Application No. 2009263082, 8 pages, dated Mar. 18, 2014.
EPO Communication of notices of opposition (R. 79(1) EPC), EP Application No. 09075279.1 and Patent No. 2147594, Sep. 25, 2014, EPO Form 2317A 12.07, one page.
EPO Acknowledgement of receipt of letter regarding reply to opposition, EP Application No. 09075279.1 and Patent No. 2147594, date of receipt Apr. 2, 2015, one page.
EPO Brief Communication regarding the Opposition, EP Application No. 09075279.1 and Patent No. 2147594, Apr. 13, 2015, EPO Form 2911O 01.12, one page.
Letter accompanying subsequently filed items regarding revocation procedure, EP Application No. 09075279.1, dated Aug. 20, 2015, one page.
Sirac et al., "Toward Understanding Renal Fanconi Syndrome: Step by Step Advances through Experimental Models", Contributions to Nephrology, Experimental Models of Renal Fanconi Syndrome, vol. 169, 2011, pp. 247-261.
Correspondence from A. Bentham of J A Kemp to the European Patent Office regarding the reply to the Patentees response to Opposition, EP Application No. 09075279.1, Aug. 20, 2015, eight pages.
EPO Acknowledgement of receipt of letter regarding reply patentee's response to opposition, EP Application No. 09075279.1 and Patent No. 2147594, date of receipt Aug. 20, 2015, one page.
EPO Brief Communication regarding the Opposition, EP Application No. 09075279.1 and Patent No. 2147594, Aug. 25, 2015, EPO Form 2911O 01.12, one page.
Correspondence from C.M. Jansen of V.O. to European Patent Office regarding the Registration of the Association and change of address, reference No. RvE/E100EPEP, Sep. 29, 2015, one page.
EPO Communication of amended entries concerning the representative (R. 143(1)(h) EPC), EP Application No. 09075279.1 and Patent No. 2147594, Oct. 8, 2015, EPO Form 2548 08.13, one page.
Submission in opposition proceedings by Andrew Bentham, EP Application No. 09075279.1 and Patent No. 2147594, Nov. 17, 2015, two pages.
EPO Communication of further notices of opposition Rule 79(2) EPC, EP Application No. 09075279.1 and Patent No. 2147594, Sep. 25, 2014, EPO Form 2318 01.12, one page.
Correspondence from A. Bentham of J A Kemp to the European Patent Office regarding inquiry on status of opposition, EP Application No. 09075279.1, Nov. 17, 2015, one page.
EPO Communication, Summons to Fritz Lahrtz of Isenbruck Bösl Höschler LLP to attend oral proceedings pursuant to Rule 115(1) EPC, EP Application No. 09075279.1 and EP Patent No. 2147594, Jan. 19, 2016, EPO Form 2310 12.14, one page.
EPO Communication, Summons to Andrew Bentham of J A Kemp to attend oral proceedings pursuant to Rule 115(1) EPC, EP Application No. 09075279.1 and EP Patent No. 2147594, Jan. 19, 2016, EPO Form 2310 12.14, one page.
EPO Communication regarding Preliminary, Non-binding Opinion of the Opposition Division, EP Application No. 09075279.1, Jan. 19, 2016, EPO Form 2906 01.91TRI, 11 pages.
EPO Communication to Fritz Lahrtz of Isenbruck Bösl Höschler LLP, Acknowledgement of receipt of EPO Forms 2310 and 2043, EP Application No. 09075279.1 and EP Patent No. 2147594, Jan. 19, 2016, EPO Form 2936 08.10, one page.
EPO Communication to Andrew Bentham of J A Kemp, Acknowledgement of receipt of EPO Forms 2310 and 2043, EP Application No. 09075279.1 and EP Patent No. 2147594, Jan. 19, 2016, EPO Form 2936 08.10, one page.
Fritz Lahrtz of Isenbruck Bösl Höschler LLP communication to EPO, Executed Acknowledgement, EP Application No. 09075279.1 and EP Patent No. 2147594, Jan. 25, 2016, EPO Form 2936 08.10, one page.

(56) References Cited

OTHER PUBLICATIONS

Submission in opposition proceedings by Andrew Bentham, EP Application No. 09075279.1 and Patent No. 2147594, Jan. 29, 2016, two pages.
EPO Acknowledgement of receipt of request to change date of oral proceedings, EP Application No. 09075279.1 and Patent No. 2147594, date of receipt Jan. 29, 2016, one page.
EPO Communication under rule 71(3) EPC, EP Application No. 10186063.3, dated Jun. 17, 2013, EPO Form 2004C, 04.12TRI, 196 pages.
Flavell et al., "Therapy of human T-cell acute lymphoblastic leukaemia with a combination of anti-CD7 and anti-CD38-SAPORIN immunotoxins is significantly better than therapy with each individual immunotoxin", British Journal of Cancer, vol. 84, No. 4, 2001, pp. 571-578.
Dinnyes et al., "Somatic Cell Nuclear Transfer: Recent Progress and Challenges", Cloning and Stem Cells, vol. 4, No. 1, 2002, pp. 81-90.
Hiatt et al., "Production of antibodies in transgenic plants", Department of Molecular Biology, Letters to Nature, vol. 342, Nov. 2, 1989, pp. 76-78.
Paul Carter, "Bispecific human IgG by design", Elsevier, Journal of Immunological Methods, vol. 248, 2001, pp. 7-15.
Letter accompanying subsequently filed items regarding translations of claims, EP Application No. 10186063.3, Sep. 6, 2013, 13 pages.
EP Acknowledgement of Receipt for EP Application No. 10186063.3, Sep. 6, 2013, 1 page.
EPO Decision to grant a European patent pursuant to Article 97(1) EPC, EP Application No. 10186063.3, dated Sep. 19, 2013, EPO Form 2006A, 12.07, 2 pages.
EPO Transmission of the certificate for a European patent pursuant to Rule 74 EPC, EP Application No. 10186063.3, Oct. 18, 2013, EPO Form 2047, 12.07, 1 page.
Notice of Opposition to a European patent, EP Patent No. 2314629, EP Application No. 10186063.3, Jul. 14, 2014, EPO Form 2300E, Q40114EP, 8 pages.
Pollock et al., "Transgenic milk as a method for the production of recombinant antibodies", Elsevier, Journal of Immunological Methods, 231 (1999), pp. 147-157.
EPO communication to Fritz Lahrtz of Isenbruck Bösl Höschler LLP, Communication of amended entries concerning the representative (R. 143(1)(h) EPC), EP Application No. 10186063.3 and EP Patent No. 2314629, Jan. 12, 2016, EPO Form 2548 08.13, one page.
Auxiliary Request 1, EP Patent No. 2314629B1, Reference No. M70120EPEIN FLZ, May 20, 2016, five pages.
Auxiliary Request 2, EP Patent No. 2314629B1, Reference No. M70120EPEIN FLZ, May 20, 2016, five pages.
Auxiliary Request 3, EP Patent No. 2314629B1, Reference No. M70120EPEIN FLZ, May 20, 2016, five pages.
Auxiliary Request 4, EP Patent No. 2314629B1, Reference No. M70120EPEIN FLZ, May 20, 2016, five pages.
Auxiliary Request 5, EP Patent No. 2314629B1, Reference No. M70120EPEIN FLZ, May 20, 2016, five pages.
Auxiliary Request 6, EP Patent No. 2314629B1, Reference No. M70120EPEIN FLZ, May 20, 2016, five pages.
Auxiliary Request 7, EP Patent No. 2314629B1, Reference No. M70120EPEIN FLZ, May 20, 2016, five pages.
Auxiliary Request 8, EP Patent No. 2314629B1, Reference No. M70120EPEIN FLZ, May 20, 2016, five pages.
Auxiliary Request 9, EP Patent No. 2314629B1, Reference No. M70120EPEIN FLZ, May 20, 2016, five pages.
Auxiliary Request 10, EP Patent No. 2314629B1, Reference No. M70120EPEIN FLZ, May 20, 2016, five pages.
EPO communication to Andrew Bentham of J A Kemp, Brief Communication regarding EPO Form 2548 of Jan. 12, 2016, EP Application No. 10186063.3 and EP Patent No. 2314629, dated Jan. 12, 2016, EPO Form 2910O 01.12, two pages.
Auxiliary Request 11, EP Patent No. 2314629B1, Reference No. M70120EPEIN FLZ, May 20, 2016, three pages.
Auxiliary Request 12, EP Patent No. 2314629B1, Reference No. M70120EPEIN FLZ, May 20, 2016, three pages.
Auxiliary Request 13, EP Patent No. 2314629B1, Reference No. M70120EPEIN FLZ, May 20, 2016, five pages.
Auxiliary Request 14, EP Patent No. 2314629B1, Reference No. M70120EPEIN FLZ, May 20, 2016, five pages.
Main Request with annotations, EP Patent No. 2314629B1, Reference No. M70120EPEIN FLZ, May 20, 2016, five pages.
Auxiliary Request 1 with annotations, EP Patent No. 2314629B1, Reference No. M70120EPEIN FLZ, May 20, 2016, five pages.
Auxiliary Request 2 with annotations, EP Patent No. 2314629B1, Reference No. M70120EPEIN FLZ, May 20, 2016, five pages.
Auxiliary Request 3 with annotations, EP Patent No. 2314629B1, Reference No. M70120EPEIN FLZ, May 20, 2016, five pages.
Auxiliary Request 4 with annotations, EP Patent No. 2314629B1, Reference No. M70120EPEIN FLZ, May 20, 2016, five pages.
Auxiliary Request 5 with annotations, EP Patent No. 2314629B1, Reference No. M70120EPEIN FLZ, May 20, 2016, five pages.
Correspondence from Dr. Fritz Lahrtz of Isenbruck Bösl Förschler LLP to the European Patent Office regarding the Oral Proceedings on Jun. 22, 2016, EP Application No. 10186063.3 and EP Patent No. 2314629, Feb. 16, 2016, one page.
Auxiliary Request 6 with annotations, EP Patent No. 2314629B1, Reference No. M70120EPEIN FLZ, May 20, 2016, five pages.
Auxiliary Request 7 with annotations, EP Patent No. 2314629B1, Reference No. M70120EPEIN FLZ, May 20, 2016, seven pages.
Auxiliary Request 8 with annotations, EP Patent No. 2314629B1, Reference No. M70120EPEIN FLZ, May 20, 2016, seven pages.
Auxiliary Request 9 with annotations, EP Patent No. 2314629B1, Reference No. M70120EPEIN FLZ, May 20, 2016, nine pages.
Auxiliary Request 10 with annotations, EP Patent No. 2314629B1, Reference No. M70120EPEIN FLZ, May 20, 2016, nine pages.
Auxiliary Request 11 with annotations, EP Patent No. 2314629B1, Reference No. M70120EPEIN FLZ, May 20, 2016, five pages.
Auxiliary Request 12 with annotations, EP Patent No. 2314629B1, Reference No. M70120EPEIN FLZ, May 20, 2016, five pages.
Auxiliary Request 13 with annotations, EP Patent No. 2314629B1, Reference No. M70120EPEIN FLZ, May 20, 2016, five pages.
Auxiliary Request 14 with annotations, EP Patent No. 2314629B1, Reference No. M70120EPEIN FLZ, May 20, 2016, five pages.
Main Request, EP Patent No. 2314629B1, Reference No. M70120EPEIN FLZ, May 20, 2016, five pages.
EPO communication, Maintenance / Change of date / Cancellation of oral proceedings arranged for: Jun. 22, 2016 at 10.00 hrs, EP Application No. 10186063.3 and EP Patent No. 2314629, Feb. 22, 2016, EPO Form 2088 06.14, two pages.
EPO communication to Andrew Bentham of J A Kemp, Brief Communication regarding Oral Proceedings on Jun. 22, 2016 at 10:00 in S2.1., EP Application No. 10186063.3 and EP Patent No. 2314629, Feb. 25, 2016, EPO Form 2910O 01.12, one page.
EPO communication to Fritz Lahrtz of Isenbruck Bösl Höschler LLP, Brief Communication regarding letter dated Feb. 16, 2016, EP Application No. 10186063.3 and EP Patent No. 2314629, Mar. 7, 2016, EPO Form 2310A 12.07, one page.
EPO communication to Andrew Bentham of J A Kemp, Brief Communication regarding Oral Proceedings on Jun. 22, 2016 and the Letter from the proprietor of the patent of Feb. 16, 2016, EP Application No. 10186063.3 and EP Patent No. 2314629, Mar. 7, 2016, EPO Form 2310A 12.07, two pages.
EPO communication to Fritz Lahrtz of Isenbruck Bösl Höschler LLP, Brief Communication regarding Oral proceedings on Jun. 22, 2016 at 10:00 in S2.1, EP Application No. 10186063.3 and EP Patent No. 2314629, Apr. 26, 2016, EPO Form 2911O 01.12, one page.
EPO Letter accompanying subsequently filed items, Documents filed during examination procedure and Letter dealing with Oral proceedings filed by David Power of J A Kemp, EP Application No. 10186063.3, May 20, 2016, one page.
Abuin, A. and Bradley, A., "Recycling Selectable Markers in Mouse Embryonic Stem Cells," Molecular and Cellular Biology 16(4):1851-1856, American Society for Microbiology, United States (Apr. 1996).
Acknowledgement of receipt, Jul. 13, 2016.

(56) References Cited

OTHER PUBLICATIONS

Askew, G.R., et al., "Site-directed Point Mutations in Embryonic Stem Cells: A Gene-targeting Tag-and-exchange Strategy," Molecular and Cellular Biology 13(7):4115-4124, American Society for Microbiology, United States (Jul. 1993).
Bagchi, A., et al., "CHD5 is a Tumor Suppressor at Human 1p36," Cell 128(3):459-475, Cell Press, United States (Feb. 2007).
Blair, K., et al., "The Liberation of Embryonic Stem Cells," PLoS Genetics 7(4):1-6, Public Library of Science, United States (Apr. 2011).
Bolland, D.J., et al., "Antisense Intergenic Transcription in V(D)J Recombination," Nature Immunology 5(6):630-637, Nature America Inc., United States (Jun. 2004).
Bradley, A., "Embryonic Stem Cells: Proliferation and Differentiation," Current Opinion in Cell Biology 2(6):1013-1017, Current Science, England (Dec. 1990).
Brief Communication regarding EP Application 10186063.3, dated Oct. 24, 2014, 1 page.
Bruggemann, Transgenic Animals: Generation and Use, pp. 397-402, 1997.
Chevillard, C., et al., "A Three-megabase Yeast Artificial Chromosome Contig Spanning the C57BL Mouse Igh Locus," The Journal of Immunology 168(11):5659-5666, American Association of Immunologists, United States (Jun. 2002).
Cleary, M.A., et al., "Disruption of an Imprinted Gene Cluster by a Targeted Chromosomal Translocation in Mice," Nature Genetics 29(1):78-82, Nature Pub. Co., United States (Sep. 2001).
Communication of further notices of opposition, Aug. 23, 2016.
Communication of further notices of opposition pursuant to Rule 79(2) EPC, dated Aug. 22, 2014, 1 page.
Corcoran, A.E., et al., "The Interleukin-7 Receptor alpha Chain Transmits Distinct Signals for Proliferation and Differentiation During B Lymphopoiesis," The EMBO Journal 15(8):1924-1932, Wiley Blackwell, England (Apr. 1996).
Davis, A.C., et al. "A Null C-myc Mutation Causes Lethality Before 10.5 Days of Gestation in Homozygotes and Reduced Fertility in Heterozygous Female Mice," Genes & Development 7(4):671-682, Cold Spring Harbor Laboratory Press, United States (Apr. 1993).
De Bono, B., et al., "VH Gene Segments in the Mouse and Human Genomes," Journal of Molecular Biology 342(1):131-143, Academic Press, England (Sep. 2004).
Declaration from Professor Allen Bradley in Respect of the opposition to EP2264163 filed by Kymab Limited, dated Jul. 7, 2016, with curriculum vitae.
Deng, C. and Capecchi, M.R., "Reexamination of Gene Targeting Frequency as a Function of the Extent of Homology Between the Targeting Vector and the Target Locus," Molecular and Cellular Biology 12(8):3365-3371, American Society for Microbiology, United States (Aug. 1992).
Documents titled Opposition to Merus B.V.'s EP 2 314 629 B1 Consolidated List of Documents filed by All Parties, listing of US patents and applications, foreign patents and non-patent literature, at least as early as Jun. 6, 2016, 1 page, (all documents on the Consolidated List have been or are being submitted on Information Disclosure Statements in the currently pending U.S. Patent Application).
Ebert A., et al., "The Distal V(H) Gene Cluster of the Igh Locus Contains Distinct Regulatory Elements With Pax5 Transcription Factor-dependent Activity in Pro-b Cells," Immunity Articles 34(2):175-187, Cell Press, United States (Feb. 2011).
EPO Acknowledgement of receipt for EP Application 10186063.3, dated Jun. 6, 2016, 2 pages.
EPO Acknowledgement of receipt for EP Application 10186063.3, dated May 20, 2016, 2 pages.
EPO Acknowledgement of receipt for EP Application 10186063.3, dated Nov. 27, 2015, 1 page.
EPO Acknowledgement of receipt for EP Application 10186063.3 regarding submission in opposition proceedings, lated Nov. 27, 2015, 2 pages.
EPO Application No. 10186063.3, dated Jun. 6, 2016, Letter accompanying subsequently filed items, including the following: 1) comments on patentees subs., 2) consolidated document list, 3) Phelps, 4) Fussenegger, 5) Tada, and 6) Verma (non-patent literature documents previously submitted individually).
EPO Application No. 10186063.3, dated May 20, 2016, Letter accompanying subsequently filed items, including the following: 1) Final Written Submissions for Oral Proceedings Scheduled for Jun. 22, 2016; 2) Huls; 3) Jones; 3) U.S. Pat. No. 9,248,182; 3) PCT Publication WO 02/18948 A2 ; PCT Publication WO 00/63403 ; (US Patent, PCT Publications and non-patent literature documents previously submitted individually).
EPO Brief Communication regarding EP Application 10186063.3, dated Feb. 27, 2015, 1 page.
EPO Brief Communication regarding EP Application 10186063.3, dated Jan. 12, 2016, 1 page.
EPO Brief Communication regarding EP Application 10186063.3, dated Jun. 7, 2016, 1 page.
EPO Brief Communication regarding the Opposition against EP Application 10186063.3, dated Jun. 13, 2016 regarding Oral proceedings on Jun. 22, 2016, 1 page.
EPO Brief Communication regarding the Opposition against EP Application 10186063.3, dated Jun. 21, 2016 regarding Oral proceedings on Jun. 22, 2016, 1 page.
EPO Brief Communication regarding the Opposition against EP Application 10186063.3, dated May 31, 2016 regarding Oral proceedings on Jun. 22, 2016.
EPO Communication of amended entries concerning the representative, regarding EP Application 10186063.3, dated Jan. 12, 2016, 1 page.
EPO Communication regarding EP Application 10186063.3, dated Jun. 7, 2016, 4 pages.
EPO Request for change of applicants representative dated Sep. 29, 2015, EP12175544.1.
EPO Summons to attend oral proceedings pursuant to Rule 115(1) EPC, dated Nov. 19, 2015.
Fedorov, L.M., et al., "A Comparison of the Germline Potential of Differently Aged ES Cell Lines and Their Transfected Descendants," Transgenic Research 6(3):223-231, Kluwer Academic Publishers, Netherlands (May 1997).
Gu, H., et al., "Independent Control of Immunoglobulin Switch Recombination at Individual Switch Regions Evidenced Through Cre-loxP-mediated Gene Targeting," Cell 73(6):1155-1164, Cell Press, United States (Jun. 1993).
Haines, B.B., et al., "Germline Diversity of the Expressed BALB/c VhJ558 Gene Family," Molecular Immunology 38(1):9-18, Pergamon Press, England (Jan. 2001).
Hansen, G.M., et al., "Large-scale Gene Trapping in C57BL/6N Mouse Embryonic Stem Cells," Genome Research 18(10):1670-1679, Cold Spring Harbor Laboratory Press, United States (Oct. 2008).
Herault, Y., et al., "Engineering Chromosomes in Mice Through Targeted Meiotic Recombination (TAMERE)," Nature Genetics 20(4):381-384, Nature Pub. Co., United States (Dec. 1998).
Huang, J., et al., "Association of Telomere Length With Authentic Pluripotency of ES/iPS Cells," Cell Research 21(5):779-792, Nature Publishing Group, England (Feb. 2011).
In the High Court of Justice, Chancery Division, Patents Court, Case No. HP-2013-000001/HP-2014-000001 dated Jan. 2, 2016, between Regeneron Pharmaceuticals Inc., Claimant and Kymab Limited and Novo Nordisk A/S, Defendants, Mr. Justice Henry Carr, Approved Judgment.
In the High Court of Justice, Chancery Division, Patents Court, Case No. HP-2013-000001/HP-2014-000001 dated Nov. 12, 2015, Third Expert Report of Professor Sir Martin Evans FRS Ph.D., Report relates to patents owned by Regeneron Pharmaceuticals, Inc., EP 1 360 287 and 2 264 163.
In the High Court of Justice, Chancery Division, Patents Court, Case No. HP-2013-000001/HP-2014-000001 dated Nov. 15, 2015, Third Witness Statement of Andrew Joseph Murphy, Report relates to patent owned by Regeneron Pharmaceuticals, Inc., EP 1 360 287.
In the High Court of Justice, Chancery Division, Patents Court, Case No. HP-2013-000001/HP-2014-000001 dated Nov. 17, 2015,

(56) References Cited

OTHER PUBLICATIONS

Third Expert Report of Adrian Francis Stewart, Report relates to a patent owned by Regeneron Pharmaceuticals, Inc., EP 1 360 287. In the High Court of Justice, Chancery Division, Patents Court, Case No. HP-2013-000001/HP-2014-000001 dated Nov. 2, 2015, Second Expert Report of Adrian Francis Stewart, Report relates to a patent owned by Regeneron Pharmaceuticals, Inc., EP 1 360 287. In the High Court of Justice, Chancery Division, Patents Court, Case No. HP-2013-000001/HP-2014-000001 dated Nov. 3, 2015, Second Expert Report of Professor Hiddie L Ploegh, Report relates to patents owned by Regeneron Pharmaceuticals, Inc., EP 1 360 287 and 2 264 163.
In the High Court of Justice, Chancery Division, Patents Court, Case No. HP-2013-000001/HP-2014-000001 dated Nov. 3, 2015, Second Expert Report of Professor Jonathan Charles Howard, Report relates to patents owned by Regeneron Pharmaceuticals, Inc., EP 1 360 287 and 2 264 163.
In the High Court of Justice, Chancery Division, Patents Court, Case No. HP-2013-000001/HP-2014-000001 dated Nov. 3, 2015, Second Expert Report of Professor Sir Martin Evans FRS Ph.D., Report relates to patents owned by Regeneron Pharmaceuticals, Inc., EP 1 360 287 and 2 264 163.
In the High Court of Justice, Chancery Division, Patents Court, Case No. HP-2013-000001/HP-2014-000001 dated Nov. 3, 2015, Second Witness Statement of A. J. Murphy, Report relates to patent owned by Regeneron Pharmaceuticals, Inc., EP 1 360 287.
In the High Court of Justice, Chancery Division, Patents Court, Case No. HP-2013-000001/HP-2014-000001 dated Oct. 6, 2015, Expert Report of Adrian Francis Stewart, Report relates to a patent owned by Regeneron Pharmaceuticals, Inc., EP 1 360 287.
In the High Court of Justice, Chancery Division, Patents Court, Case No. HP-2013-000001/HP-2014-000001 dated Oct. 6, 2015, Expert Report of Professor Jonathan Charles Howard, Report relates to patents owned by Regeneron Pharmaceuticals, Inc., EP 1 360 287 and 2 264 163.
Johnston, C.M., et al., "Complete Sequence Assembly and Characterization of the C57BL/6 Mouse Ig Heavy Chain V Region," The Journal of Immunology 176(7):4221-4234, American Association of Immunologists, United States (Apr. 2006).
Joyner, 2007, previously submitted.
Karu, A.E., et al., "Recombinant Antibody Technology," ILAR Journal 37(3):132-141 (1995).
Keane, et al., "Mouse Genomic Variation and Its Effect on Phenotypes and Gene Regulation," Nature 477:289-294, Nature Publishing Group, England (Sep. 2011).
Kuehn, M.R., et al., "A Potential Animal Model for Lesch-nyhan Syndrome Through Introduction of HPRT Mutations Into Mice," Nature 326(6110):295-298, Nature Publishing Group, England (Mar. 1987).
Kuroiwa, Y., et al., "Sequential Targeting of the Genes Encoding Immunoglobulin-mu and Prion Protein in Cattle," Nature Genetics 36(7):775-780, Nature Pub. Co., United States (Jun. 2004).
Lee, E.C., et al., "Complete Humanization of the Mouse Immunoglobulin Loci Enables Efficient Therapeutic Antibody Discovery," Nature Biotechnology 32(4):356-363, Nature America Publishing, United States (Apr. 2004).
Lewis, J., et al., "A Common Human β Globin Splicing Mutation Modeled in Mice," Blood 91(6):2152-2156 (Mar. 1998).
Liang, Q., et al., "Extensive Genomic Copy Number Variation in Embryonic Stem Cells," Proceedings of the National Academy of Sciences 105(45):17453-17456, National Academy of Sciences, United States (Nov. 2008).
Liu, P., et al., "Embryonic Lethality and Tumorigenesis Caused by Segmental Aneuploidy on Mouse Chromosome 11," Genetics 150(3):1155-1168, Genetics Society of America, United States (Nov. 1998).
Liu, X., et al., "Trisomy Eight in ES Cells Is a Common Potential Problem in Gene Targeting and Interferes With Germ Line Transmission," Development Dynamics 209(1):85-91, Wiley, United States (May 1997).

Lu, Z.H., et al., "Long Targeting Arms Do Not Increase the Efficiency of Homologous Recombination in the beta-globin Locus of Murine Embryonic Stem Cells," Red Cells 102(4):1531-1533 (Aug. 2003).
Matzuk, M.M., et al., "Alpha-inhibin Is a Tumour-suppressor Gene With Gonadal Specificity in Mice," Nature 360(6402):313-319, Nature Publishing Group, England (Nov. 1992).
McMahon, A.P., et al., "The Wnt-1 (Int-1) Proto-oncogene Is Required for Development of a Large Region of the Mouse Brain," Cell 62(6):1073-1085, Cell Press, United States (Sep. 1990).
Muller, U., "Ten Years of Gene Targeting: Targeted Mouse Mutants, From Vector Design to Phenotype Analysis," Mechanisms of Development 82(1-2):3-21, Elsevier, Ireland (Apr. 1999).
Murphy, Statement of, Exhibit Murphy 1, Mar. 18, 2015, Defendant's Exhibit DX145, Case No. 14-CV-1650 (KBF).
Nagy, A., et al., "Derivation of Completely Cell Culture-derived Mice From Early-passage Embryonic Stem Cells," Proceedings of the National Academy of Sciences 90(18):8424-8428, National Academy of Sciences, United States (Sep. 1993).
Nakatani, J., et al., "Abnormal Behavior in a Chromosome-engineered Mouse Model for Human 15q11-13 Duplication Seen in Autism," Cell 137(7):1235-1246, Cell Press, United States (Jun. 2009).
Nobrega, M.A., et al., "Megabase Deletions of Gene Deserts Result in Viable Mice," Nature 431(7011):988-993, Nature Publishing Group, England (Oct. 2004).
Notice of Opposition with statement and facts dated Oct. 14, 2015.
Pawlilzky, I., et al., "Identification of a Candidate Regulatory Element Within the 5' Flanking Region of the Mouse Igh Locus Defined by Pro-b Cell-specific Hypersensitivity Associated With Binding of Pu.1, Pax5, and E2a," Journal of Immunology 176(11):6839-6851, American Association of Immunologists, United States (Jun. 2006).
Perlot, T., et al., "Analysis of Mice Lacking DNasei Hypersensitive Sites at the 5' End of the Igh Locus," PLoS One 5(11):1-10, Public Library of Science, United States (Nov. 2010).
Popov, Dr. Andrei, Statement by with curriculum vitae, undated.
Prosser, H.M., et al., "A Resource of Vectors and ES Cells for Targeted Deletion of Micrornas in Mice," Nature Biotechnology 29(9):840-845, Nature America Publishing, United States (Aug. 2011).
Ramirez-Solis, R., et al., "Chromosome Engineering in Mice," Nature 378(6558):720-724, Nature Publishing Group, England (Dec. 1995).
Reh, et al., "Gene Targeting by Homologous Recombination," Els 10(2):1-10 (Apr. 2014).
Retter, I., et al., "Sequence and Characterization of the Ig Heavy Chain Constant and Partial Variable Region of the Mouse Strain 129S1," Journal of Immunology 179(4):2419-2427, American Association of Immunologists, United States (Aug. 2007).
Ringrose, L., et al., "Quantitative Comparison of DNA Looping in Vitro and in Vivo: Chromatin Increases Effective DNA Flexibility at Short Distances," The EMBO journal 18(23):6630-6641, Wiley Blackwell, England (Dec. 1999).
Sharova, L.V., et al., "Global Gene Expression Profiling Reveals Similarities and Differences Among Mouse Pluripotent Stem Cells of Different Origins and Strains," Development Biology 307(2):446-459, Elsevier, United States (Jul. 2007).
Shen, W., et al., "A General Method to Modify BACs to Generate Large Recombinant Dna Fragments," Molecular biotechnology 31(3):181-186, Humana Press, United States (Nov. 2005).
Skarnes, W.C., et al., "A Conditional Knockout Resource for the Genome-wide Study of Mouse Gene Function," Nature 474(7351):337-342, Nature Publishing Group, England (Jun. 2011).
Smith, A.J., et al., "A Site-directed Chromosomal Translocation Induced in Embryonic Stem Cells by Cre-loxp Recombination," Nature Genetics 9(4):376-385, Nature Pub. Co., United States (Apr. 1995).
Office Action dated Apr. 12, 2017, in U.S. Appl. No. 15/158,543 Hendrikus Van Berkel. et al., filed May 18, 2016, 18 pages.
Office Action dated Feb. 15, 2018 , in U.S. Appl. No. 15/855,258 Hendrikus Van Berkel. et al.,filed Dec. 27, 2017, 19 pages.

(56) References Cited

OTHER PUBLICATIONS

Stacey, A., et al., "Use of Double-replacement Gene Targeting to Replace the Murine Alpha-lactalbumin Gene With Its Human Counterpart in Embryonic Stem Cells and Mice," Molecular and Cellular Biology 14(2):1009-1016, American Society for Microbiology, United States (Feb. 1994).
Statement of Dr. Anne Corcoran dated Jul. 8, 2016 with listing of Literature Cited and curriculum vitae.
Storb, et al., "Ig Gene Expression and Regulation in Ig Transgenic Mice," Immunoglobin Genes, 345-363 (1995).
Takahashi, K. and Yamanaka, S., "Induction of Pluripotent Stem Cells from Mouse Embryonic and Adult Fibroblast Cultures by Defined Factors," Cell 126(4):663-676, Cell Press, United States (2006).
Taki, S., et al., "Targeted Insertion of a Variable Region Gene Into the Immunoglobulin Heavy Chain Locus," Science 262(5137):1268-1271, American Association for the Advancement of Science, United States (Nov. 1993).
Technical Primer, author unknown, undated, 9 pages.
Toyooka, Y., et al., "Identification and Characterization of Subpopulations in Undifferentiated ES Cell Culture," Development 135(5):909-918, Company of Biologists Limited, England (Mar. 2008).
United States District Court Southern District of New York, *Regeneron Pharmaceuticals, Inc.*, Plaintiff v. *Merus BV.*, Defendant, 14 Civ. 1650 (KBF) Opinion & Order (Claim Construction) dated Nov. 21, 2014.
United States District Court Southern District of New York, *Regeneron Pharmaceuticals, Inc.*, Plaintiff v. *Merus BV.*, Defendant, 14 Civ. 1650 (KBF) Opinion & Order dated Nov. 2, 2015.
Valenzuela, D.M., et al., "High-throughput Engineering of the Mouse Genome Coupled With High-resolution Expression Analysis," Nature Biotechnology 21(6):652-659, Nature America Publishing, United States (May 2003).
Wallace, H.A., et al., "Manipulating the Mouse Genome to Engineer Precise Functional Syntenic Replacements With Human Sequence," Cell 128(1):197-209, Cell Press, United States (Jan. 2007).
Wu, S., et al., "A Protocol for Constructing Gene Targeting Vectors: Generating Knockout Mice for the Cadherin Family and Beyond," Nature Protocols 3(6):1056-1076, Nature Pub. Group, England (May 2008).
Yu, T., et al., "A Mouse Model of Down Syndrome Trisomic for All Human Chromosome 21 Syntenic Regions," Human Molecular Genetics 19(14):2780-2791, IRL Press at Oxford University Press, England (May 2010).
Zambrowicz, B.P., et al., "Disruption and Sequence Identification of 2,000 Genes in Mouse Embryonic Stem Cells," Nature 392(6676):608-611, Nature Publishing Group, England (Apr. 1998).
Zheng, B., et al., "Engineering a Mouse Balancer Chromosome," Nature Genetics 22(4):375-378, Nature Pub. Co., United States (Aug. 1999).
Office Action dated May 5, 2015, in U.S. Appl. No. 12/932,719 Hendrikus Van Berkel. et al., filed Mar. 4, 2011, 15 pages.
Office Action dated Mar. 11, 2014, in U.S. Appl. No. 12/932,719 Hendrikus Van Berkel. et al., filed Mar. 4, 2011, 14 pages.
Office Action dated May 2, 2012, in U.S. Appl. No. 12/932,719 Hendrikus Van Berkel. et al., filed Mar. 4, 2011, 11 pages.
Office Action dated Aug. 27, 2014, in U.S. Appl. No. 12/932,719 Hendrikus Van Berkel. et al., filed Mar. 4, 2011, 20 pages.
Office Action dated May 9, 2013, in U.S. Appl. No. 12/932,719 Hendrikus Van Berkel. et al., filed Mar. 4, 2011, 11 pages.
Office Action dated Sep. 27, 2011, in U.S. Appl. No. 12/932,719 Hendrikus Van Berkel. et al., filed Mar. 4, 2011, 7 pages.
Beaudette-Zlatanova, B.C., et al., "B Cells and Dendritic Cells from VK8 Light Chain Transgenic Mice Activate MRL-lpr/gld CD4+ T Cells," J. Immunol 177:45-52, American Association of Immunologists, United States (2006).
Paul, W.E., et al., "Structure and Function of Immunoglobulins," 3ed. 292-295, Fundamental Immunology, Raven Press, United States (1993).
Office Action dated Jan. 10, 2020, in U.S. Appl. No. 15/855,258 Hendrikus Van Berkel. et al., filed Dec. 27, 2017, 26 pages.
Office Action dated Jul. 1, 2019, in U.S. Appl. No. 15/855,258 Hendrikus Van Berkel. et al., filed Dec. 27, 2017, 14 pages.
Office Action dated Jan. 29, 2019, in U.S. Appl. No. 15/855,258 Hendrikus Van Berkel. et al., filed Dec. 27, 2017, 16 pages.
Office Action dated May 29, 2018, in U.S. Appl. No. 15/855,258 Hendrikus Van Berkel. et al., filed Dec. 27, 2017, 15 pages.
Office Action dated Feb. 4, 2019 in U.S. Appl. No. 15/158,543 Hendrikus Van Berkel. et al., filed May 18, 2016, 18 pages.
Office Action dated May 16, 2018 in U.S. Appl. No. 15/158,543 Hendrikus Van Berkel. et al., filed May 18, 2016, 18 pages.
Notice of Allowance for U.S. Appl. No. 11/490,545, dated Jun. 15, 2012, 5 pages.
Third Party Pre-Issuance Under 37 C.F.R. .sctn. in U.S. Appl. No. 15/140,321, dated Feb. 10, 2017, 19 pages.
Online Response of Regeneron Pharmaceuticals, Inc. for European Patent Application No. 12173456.0 dated Apr. 12, 2013.
Janeway's Immunobiology, Murphy, Travers, Walport eds, Seventh Edition, 2008 (pp. 144-155).
Janeway's Immunobioloby, Murphy, Travers, Walport eds, Seventh Edition, 2008 (pp. 266-267).
Tada, et al., Expression and characterization of a chimeric bispecific antibody against fibrin and against urokinase-type plasminogen activator, J. Biotech., 33:157-174, 1994.†
Staerz and Bevan, Hybrid Hybridoma Producing a Bispecific Monoclonal Antibody that can Focus Effector T-Cell Activity, PNAS USA, 83:1453-1457, 1986.†
Moldenhauer, Bispecific Antibodies from Hybrid Hybridoma, In R. E. Kontermann (ed.) Bispecific Antibodies, Berlin Heidelberg: Spinger-Verlag (2011):29-46.†
Merchant, et al., An Efficient Route to Human Bispecific IgG, Nat. Biotech., 16:677-681, 1998.†
Kroesen, et al. Bispecific Antibodies for Treatment of Cancer in Experimental Animal Models and Man, Adv. Drug Deliv., Rev. 31:105-129, 1998.†
Declaration of Dr. Joel Martin, Executed May 18, 2016, Submitted May 20, 2016, and entered into public record in European Patent No. 2314629.†
Cheong, et al., Affinity Enhancement of Bispecific Antibody Against Two Different Epitopes in the Same Antigen, Biochem. Biophys. Res. Com., 173(3):795-800, 1990.†
Carter, Bispecific Human IgG by Design, J. Immunol. Methods, 248:7-15, 2001.†

\* cited by examiner
† cited by third party

```
UBS54-VL    GAAATTGAGCTCACTCAGTCTCCACTCTCCCTGCCCGTCACCCCTGGAGAGCCGGCC
K53-VL      GAAATTGAGCTCACTCAGTCTCCACTCTCCCTGCCCGTCACCCCTGGAGAGCCGGCC
02-237-VL   GACATCGTGATGACTCAGTCTCCAGACTCCCTGGCTGTGTCTCTGGGCGAGAGGGCC
            **  *  **  *********** *  ****** ***  *  * * * ** ** ***

UBS54-VL    TCCATCTCCTGCAGGTCTAGTCAGAGCCTCCTGCATAGTAATGGATACAACTATTTGGAT
K53-VL      TCCATCTCCTGCAGGTCTAGTCAGAGCCTCCTGCATAGTAATGGATACAACTATTTGGAT
02-237-VL   TCCATCTCCTGCAGGTCTAGTCAGAGCCTCCTGCATAGTAATGGATACAACTATTTGGAT
            ************************************************************

UBS54-VL    TGGTACCTGCAGAAGCCAGGGCAGTCTCCACAGCTCCTGATCTATTTGGGTTCTAATCGG
K53-VL      TGGTACCTGCAGAAGCCAGGGCAGTCTCCACAGCTCCTGATCTATTTGGGTTCTAATCGG
02-237-VL   TGGTACCTGCAGAAGCCAGGGCAGTCTCCACAGCTCCTGATCTATTTGGGTTCTAATCGG
            ************************************************************

UBS54-VL    GCCTCCGGGGTCCCTGACAGGTTCAGTGGCAGTGGATCAGGCACAGATTTTACACTGAAA
K53-VL      GCCTCCGGGGTCCCTGACAGGTTCAGTGGCAGTGGATCAGGCACAGATTTTACACTGAAA
02-237-VL   GCCTCCGGGGTCCCTGACAGGTTCAGTGGCAGTGGATCAGGCACAGATTTTACACTGAAA
            ************************************************************

UBS54-VL    ATCAGCAGAGTGGAGGCTGAGGATGTTGGGGTTTATTACTGCATGCAAGCTCTACAAACT
K53-VL      ATCAGCAGAGTGGAGGCTGAGGATGTTGGGGTTTATTACTGCATGCAAGCTCTACAAACT
02-237-VL   ATCAGCAGAGTGGAGGCTGAGGATGTTGGGGTTTATTACTGCATGCAAGCTCTACAAACT
            ************************************************************

UBS54-VL    TTCACTTTCGGCCCTGGGACCAAGGTGGAGATCAAA
K53-VL      TTCACTTTCGGCCCTGGGACCAAGGTGGAGATCAAA
02-237-VL   TTCACTTTCGGCCCTGGGACCAAGGTGGAGATCAAA
            ************************************
```

FIG. 3A

| | |
|---|---|
| K53-VH     | CAGGTGCAGCTGGTGCAGTCTGGGGCTGAGGTGAAGAAGCCTGGGGCCTCAGTGAAGGTC |
| 02-237-VH  | CAGGTGCAGCTGGTGCAGTCTGGGGCTGAGGTGAAGAAGCCTGGGGCCTCAGTGAAGGTC |
| UBS54-VH   | CAGGTGCAGCTGGTGCAGTCTGGGGCTGAGGTGAAGAAGCCTGGTCCTCGGTGAGGGTC |
|            | ************************************** ***** **** ******* |
| K53-VH     | TCCTGCAAGGCTTCTGGTTACACCTTTACCAGCTATGTATCAGCTGGTGCGACAGGCC |
| 02-237-VH  | TCCTGCAAGGCTTCTGGTTACACCTTTACCAGCTATGTATCAGCTGGTGCGACAGGCC |
| UBS54-VH   | TCCTGCAAGGCTTCTGGAGGCACCTTCAGCAGCTATCAGCTGGTGCGACAGGCC |
|            | ***************** ***** * ******* ** * ***************** |
| K53-VH     | CCTGGACAAGGGCTTGAGTGGATGGATGGATCAGCGCTTACAATGTAACACAAACTAT |
| 02-237-VH  | CCTGGACAAGGGCTTGAGTGGATGGATGGATCAGCGCTTACAATGTAACACAAACTAT |
| UBS54-VH   | CCTGGACAAGGCTTGAGTGGATGGGATGGATCATCCCTATCTTTGTACAGCAAACTAC |
|            | *********** *********** * ****** ** * * ***** ******* |
| K53-VH     | GCACAGAAGCTCCAGGGCAGAGTCACCATGACCACAGACACATCCACGAGCACAGCCTAC |
| 02-237-VH  | GCACAGAAGCTCCAGGGCAGAGTCACCATGACCACAGACACATCCACGAGCACAGCCTAC |
| UBS54-VH   | GCACAGAAGTTCCAGGGCAGAGTCACCATGACCACAGACACGGACGAATCCACGAGCACAGCCTAC |
|            | ********* ***************************** *** ************ |
| K53-VH     | ATGGAGCTGAGGAGCCTGAGATCTGACGACACGGCCGTGTATTACTGTGCAAGGGGCATG |
| 02-237-VH  | ATGGAGCTGAGGAGCCTGAGATCTGACGACACGGCCGTGTATTACTGTGCAAGGGGCTTT |
| UBS54-VH   | ATGGAGCTGAGCAGCCTGAGATCTGAGGACACGGCTGTGTATTACTGTGCAAGAGACC-- |
|            | *********** ************** ******* *************** * |
| K53-VH     | ATGAGGGGTGTGTTTGACTACTGGGGCCAAGTACCCTGGTCACCGTCTCGACA |
| 02-237-VH  | CCGCGTACCTCGTTGACTCCTGGGGCCAGGCACCCTGGTCACCGTCTCCTCA |
| UBS54-VH   | ------CGTTTCTTCACTATTGGGGCCAAGTACCCTGGTCACCGTCTCGACA |
|            | * *** ********** ** ************* *********** |

FIG. 3B

Anti-CD22 V_H fragment (Phage B28)
        M   A   E   V   Q   L   V   E   S   G   G   G   V   V   R   P   G   G   S   L   R   L   S   C   .
    1   ATGGCCGAGGTGCAGCTGGTGGAGTCTGGGGGAGGTGTGGTACGGCCTGGAGGGTCCCTGAGACTCTCCTG
        .   A   A   S   G   F   T   F   D   D   Y   G   M   S   W   V   R   Q   A   P   G   K   G   L   E   .
   72   TGCAGCCCTCTGGATTCACCTTTGATGATTATGGCATGAGCTGGGTCCGCCAAGCTCCAGGGAAGGGGCTGG
        .   W   V   S   G   I   N   W   N   G   S   T   G   Y   A   D   S   V   K   G   R   F   T   .
  143   AGTGGGTCTCTGGTATTAATTGGAATGGTAGCACAGGTTATGCAGACTCTGTGAAGGGCCGATTCACC
        .   I   S   R   D   N   A   K   N   S   L   Y   L   Q   M   N   S   L   R   A   E   D   T   A   V   .
  214   ATCTCCAGAGACAACGCCAAGAACTCCCTGTATCTGCAAATGAACAGTCTGAGAGCCGAGGACACGGCCGT
        .   Y   Y   C   A   R   G   F   L   R   F   A   S   S   W   F   D   Y   W   G   Q   G   T   L   V   .
  285   GTATTACTGTGCAAGAGGCTTTCTTCGTTTTGCTTCCTCCTGGTTTGACTATTGGGGCCAAGGTACCCTGG
        .   T   V   S   R
  356   TCACCGTCTCGAGA Anti-CD72 V_H fragment (Phage II-2)
        M   A   Q   V   Q   L   V   Q   S   G   A   E   V   K   K   P   G   A   S   V   K   V   S   C   .
    1   ATGGCCCAGGTGCAGCTGGTGCAGTCTGGGGCTGAGGTGAAGAAGCCTGGGGCCTCAGTGAAGGTTTCCTG
        .   K   A   S   G   Y   T   F   T   S   Y   Y   M   H   W   V   R   Q   A   P   G   Q   G   L   E   .
   72   CAAGGCATCTGGATACACCTTCACCAGCTACTATATGCACTGGGTGCGACAGGCCCCTGGACAAGGGCTTG
        .   W   M   G   I   I   N   P   S   G   G   G   T   S   Y   A   Q   K   F   Q   G   R   V   T   .
  143   AGTGGATGGGAATAATCAACCCTAGTGGTGGTGGCACAAGCTACGCACAGAAGTTCCAGGGCAGAGTCACC
        .   M   T   R   D   T   S   T   S   T   V   Y   M   E   L   S   S   L   R   S   E   D   T   A   V   .
  214   ATGACCAGGGACACGTCCACGAGCACAGTCTACATGGAGCTGAGCAGCCTGAGATCTGAGGACACGGCCGT
        .   Y   Y   C   A   R   D   Y   Y   V   T   Y   D   S   W   F   D   S   W   G   Q   G   T   L   V   .
  285   GTATTACTGTGCAAGAGACTACTACGTTACGTATGATTCCTGGTTTGACTCCTGGGGCCAAGGTACCCTGG
        .   T   V   S   R
  356   TCACCGTCTCGAGA

FIG. 7A

Anti-Class II V_H fragment (Phage I-2)

```
            M   A   E   V   Q   L   V   E   S   G   G   G   L   V   Q   P   G   R   S   L   R   L   S   C   .
  1   ATGGCCGAGTGCAGCTGGTGGAGTCTGGGGGAGGCTTGGTACAGCCTGGCCAGTCCCTGAGACTCTCCTG
            .   A   A   S   G   F   T   F   D   D   Y   A   M   H   W   V   R   Q   A   P   G   K   G   L   E
 72   TGCAGCCCTCTGGATTCACCTTTGATGATTATGCCATGCACTGGGTCCGGCAAGCTCCAGGGAAGGGCCTGG
            .   W   V   S   G   I   S   W   N   S   G   S   I   G   Y   A   D   S   V   K   G   R   F   T
143   AGTGGGTCTCAGTTATTAGTTGGAATAGTGGTAGCATAGGCTATGCGGACTCTGTGAAGGGCCGATTCACC
            .   I   S   R   D   N   A   K   N   S   L   Y   L   Q   M   N   S   L   R   A   E   D   T   A   V
214   ATCTCCAGAGACAACGCCAAGAACTCCCTGTATCTGCAAATGAACAGTCTGAGAGCTGAGGACACGGCCGT
            .   Y   C   A   R   D   L   Y   L   A   H   F   D   Y   W   G   Q   G   T   L   V   T   V   S
285   GTATTACTGTGCAAGGGACCTTTATCTTGCCCATTTGACTACTGGGGCCAAGGTACCCTGGTCACCGTCT
            .   R
356   CGAGA
```

Shared V_L sequence of Phages I-2, II-2 and B28

```
            S   S   E   L   T   Q   D   P   A   V   S   V   A   L   G   Q   T   V   R   I   T   C   Q   G   .
  1   TCGTCTGAGCTGACTCAGGACCCTGCTGTCTGTGGCCTTGGGACAGACAGTCAGGATCACATGCCAAGG
            .   D   S   L   R   S   Y   Y   A   S   W   Y   Q   Q   K   P   G   Q   A   P   V   L   V   I   Y   .
 72   AGACAGCCTCAGAAGCTATTATGCAAGCTGGTACCAGCAGAAGCCAGGACAGGCCCCTGTACTTGTCATCT
            .   G   K   N   N   R   P   S   G   I   P   D   R   F   S   G   S   S   S   G   N   T   A   S
143   ATGGTAAAAACAACCGGCCCTCAGGGATCCCAGACCGATTCTCTGGCTCAGGAAGCAGCAGCTTCC
            .   L   T   I   T   G   A   Q   A   E   D   E   A   D   Y   C   N   S   R   D   S   S   G   N   .
214   TTGACCATCACTGGGGCTCAGGCGGAAGATGAGGCTGACTATTACTGTAACTCCCGGGACAGCAGTGGTAA
            .   H   V   V   F   G   G   G   T   K   L   T   V   L   G   A   A   A
285   CCATGTGGTATTCGGCGGAGGGACCAAGCTGACCGTCCTAGGTGCGGCCGCA
```

FIG. 7B

V_H sequence of K53 IgG

```
      Q   V   Q   L   V   Q   S   G   A   E   V   K   K   P   G   A   S   V   K   V
  1   CAGGTGCAGCTGGTGCAGTCTGGGGCTGAGGTGAAGAAGCCTGGGGCCTCAGTGAAGGTC

S   C   K   A   S   G   Y   T   F   T   S   Y   G   I   S   W   V   R   Q   A
 61   TCCTGCAAGGCTTCTGGTTACACCTTTACCAGCTATGGTATCAGCTGGGTGCGACAGGCC

P   G   Q   G   L   E   W   M   G   W   I   S   A   Y   N   G   N   T   N   Y
121   CCTGGACAAGGGCTTGAGTGGATGGGATGGATCAGCGCTTACAATGTAACACAAACTAT

A   Q   K   L   Q   G   R   V   T   M   T   T   D   T   S   T   S   T   A   Y
181   GCACAGAAGCTCCAGGGCAGAGTCACCATGACCACAGACACATCCACGAGCACAGCCTAC

M   E   L   R   S   L   R   S   D   D   T   A   V   Y   Y   C   A   R   G   M
241   ATGGAGCTGAGGAGCCTGAGATCTGACGACACGGCCGTGTATTACTGTGCAAGGGGCATG

M   R   G   V   F   D   Y   W   G   Q   G   T   L   V   T   V   S   T
301   ATGAGGGGTGTGTTTGACTACTGGGGCCAAGTACCCTGGTCACCGTCTCGACA
```

FIG. 12A

V_H sequence of 02-237 IgG

```
1    Q  V  Q  L  V  Q  S  G  A  E  V  K  K  P  G  A  S  V  K  V
     CAGGTGCAGCTGGTGCAGTCTGGGGCTGAGGTGAAGAAGCCTGGGGCCTCAGTGAAGGTC

61   S  C  K  A  S  G  Y  T  F  T  S  Y  G  I  S  W  V  R  Q  A
     TCCTGCAAGGCTTCTGGTTACACCTTTACCAGCTATGGTATCAGCTGGGTGCGACAGGCC

121  P  G  Q  G  L  E  W  M  G  W  I  S  A  Y  N  G  N  T  N  Y
     CCTGGACAAGGGCTTGAGTGGATGGGATGGATCAGCGCTTACAATGGTAACACAAACTAT

181  A  Q  K  L  Q  G  R  V  T  M  T  T  D  T  S  T  S  T  A  Y
     GCACAGAAGCTCCAGGGCAGAGTCACCATGACCACAGACACATCCACGAGCACAGCCTAC

241  M  E  L  R  S  L  R  S  D  D  T  A  V  Y  Y  C  A  R  G  F
     ATGGAGCTGAGGAGCCTGAGATCTGACGACACGGCCGTGTATTACTGTGCAAGGGGCTTT

301  P  R  T  S  F  D  S  W  G  Q  G  T  L  V  T  V  S  S
     CCGCGTACGTCGTTTGACTCCTGGGGCCAGGCCACCCTGGTGACCGTCTCCTCA
```

FIG. 12B

V_H sequence of UBS54 IgG

```
    Q  V  Q  L  V  Q  S  G  A  E  V  K  K  P  G  S  S  V  R  V
1   CAGGTGCAGCTGGTGCAGTCTGGGGCTGAGGTGAAGAAGCCTGGGTCCTCGGTGAGGGTC

S  C  K  A  S  G  G  T  F  S  S  Y  A  I  S  W  V  R  Q  A
61  TCCTGCAAGGCTTCTGGAGGCACCTTCAGCAGCTATGCTATCAGCTGGGTGCGACAGGCC

P  G  Q  G  L  E  W  M  G  G  I  I  P  I  F  G  T  A  N  Y
121 CCTGGACAAGGGCTTGAGTGGATGGGAGGGATCATCCCTATCTTTGGTACAGCAAACTAC

A  Q  K  F  Q  G  R  V  T  I  T  A  D  E  S  T  S  T  A  Y
181 GCACAGAAGTTCCAGGGCAGAGTCACGATTACCGCGGACGAATCCACGAGCACAGCCTAC

M  E  L  S  S  L  R  S  E  D  T  A  V  Y  Y  C  A  R  D  P
241 ATGGAGCTGAGCAGCCTGAGATCTGAGGACACGGCTGTGTATTACTGTGCAAGAGACCCG

F  L  H  Y  W  G  Q  G  T  L  V  T  V  S  T
301 TTTCTTCACTATTGGGGCCAAGGTACCCTGGTCACCGTCTCGACA
```

FIG. 12C $V_L$ sequence of K53 and UBS54 IgG

```
       E  I  E  L  T  Q  S  P  L  S  L  P  V  T  P  G  E  P  A
  1    GAAATTGAGCTCACTCAGTCTCCACTCTCCCTGCCCGTCACCCTGGAGAGCCGGCC

S  I  S  C  R  S  S  Q  S  L  L  H  S  N  G  Y  N  Y  L  D
 58    TCCATCTCCTGCAGGTCTAGTCAGAGCCTCCTGCATAGTAATGGATACAACTATTTGGAT

W  Y  L  Q  K  P  G  Q  S  P  Q  L  L  I  Y  L  G  S  N  R
118    TGGTACCTGCAGAAGCCAGGCCAGTCTCCACAGCTCCTGATCTATTTGGGTTCTAATCGG

A  S  G  V  P  D  R  F  S  G  S  G  S  G  T  D  F  T  L  K
178    GCCTCCGGGGTCCCTGACAGGTTCAGTGGCAGTGGATCAGGCACAGATTTTACACTGAAA

I  S  R  V  E  A  E  D  V  G  V  Y  Y  C  M  Q  A  L  Q  T
238    ATCAGCAGAGTGGAGGCTGAGGATGTTGGGGTTTATTACTGCATGCAAGCTCTACAAACT

F  T  F  G  P  G  T  K  V  E  I  K
298    TTCACTTTCGGCCCTGGGACCAAGGTGGAGATCAAA
```

FIG. 12D

V_L sequence of 02-237 IgG

```
1     D   I   V   M   T   Q   S   P   L   S   L   P   V   T   P   G   E   P   A
      GACATCGTGATGACTCAGTCTCCACTCTCCCTGCCCGTCACCCCTGGAGAGCCGGCC

58    S   I   S   C   R   S   S   Q   S   L   L   H   S   N   G   Y   N   Y   L   D
      TCCATCTCCTGCAGGTCTAGTCAGAGCCTCCTGCATAGTAATGATACAACTATTTGGAT

118   W   Y   L   Q   K   P   G   Q   S   P   Q   L   L   I   Y   L/G S   N   R.
      TGGTACCTGCAGAAGCCAGGCCAGTCTCCACAGCTCCTGATCTATTGGGTTCTAATCGG

178   A   S   G   V   P   D   R   F   S   G   S   G   S   G   T   D   F   T   L   K
      GCCTCCGGGGTCCCTGACAGGTTCAGTGGCAGTGGATCAGGCACAGATTTTACACTGAAA

238   I   S   R   V   E   A   E   D   V   G   V   Y   Y   C   M   Q   A   L   Q   T
      ATCAGCAGAGTGGAGGCTGAGGATGTTGGGGTTTATTACTGCATGCAAGCTCTACAAACT

298   F   T   F   G   P   G   T   K   V   E   I   K
      TTCACTTTCGGCCCTGGGACCAAGGTGGAGATCAAA
```

FIG. 12E

```
                      CDR1
K53 VH      1  QVQLVQSGAEVKKPGASVKVSCKASGYTFTSYGISWVRQAPGQGLEWMG
UBS54 VH    1  QVQLVQSGAEVKKPGSSVRVSCKASGGTFSSYAISWVRQAPGQGLEWMG
02-237      1  QVQLVQSGAEVKKPGASVKVSCKASGYTFTSYGISWVRQAPGQGLEWMG
               *********..***..********..***.*****************

CDR2
K53 VH     50  WISAYNGNTNYAQKLQGRVTMTTDTSTSTAYMELRSLRSDDTAVYYCAR
UBS54      50  GIIPIFGNANYAQKFQGRVTITADESTSTAYMELSSLRSEDTAVYYCAR
02-237     50  WISAYNGNTNYAQKLQGRVTMTTDTSTSTAYMELRSLRSDDTAVYYCAR
               .*...*.*.*****.*****.*.*.********..***.*********

CDR3
K53 VH     99  GMMRGVFDYWGQGTLVTVST
UBS54 VH   99  DPFLH---YWGQGTLVTVST
02-237     99  GFPRTSFDSWGQGTLVTVSS
               .....*.*************

FIG. 13
```

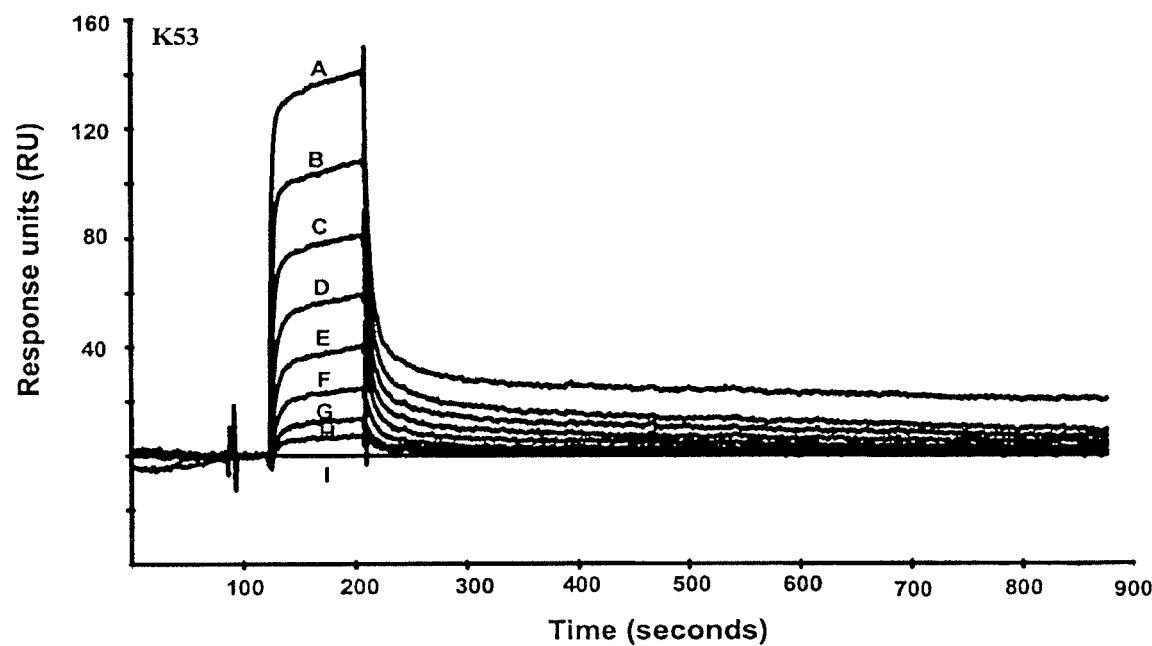
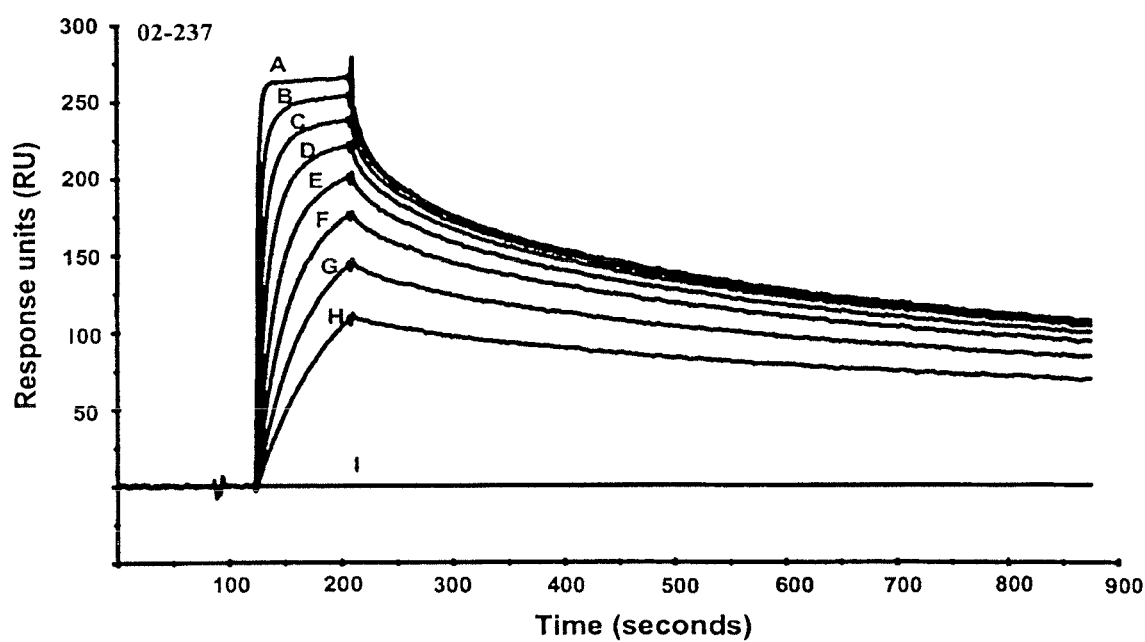
FIG. 14

A.
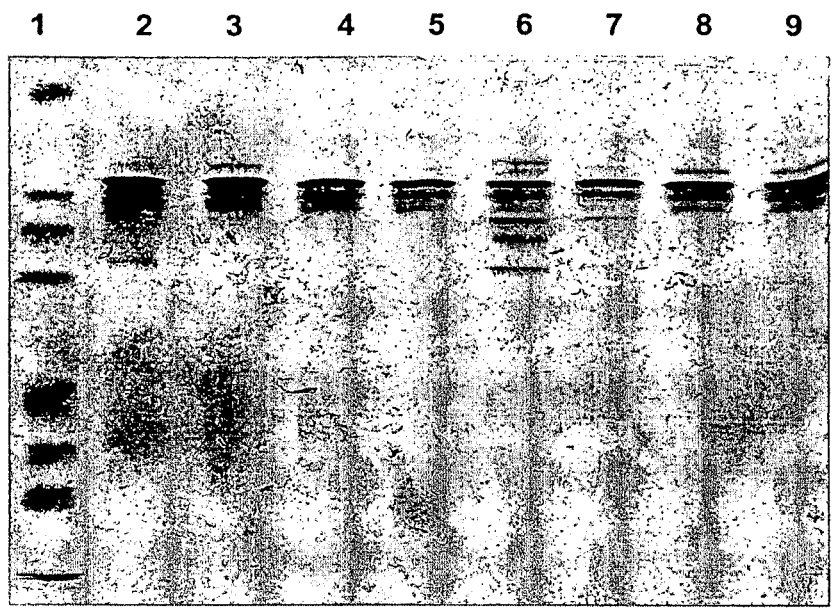
B.
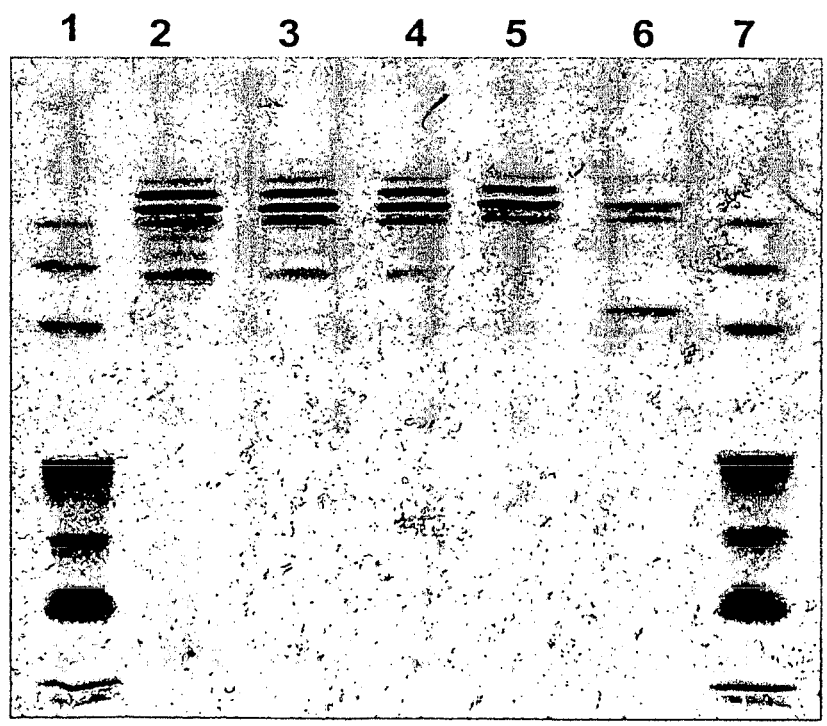
FIG. 21

RECOMBINANT PRODUCTION OF MIXTURES OF ANTIBODIES

CROSS-REFERENCE TO RELATED APPLICATIONS

This application is a continuation of U.S. patent application Ser. No. 12/932,719, filed Mar. 4, 2011, pending, which application is a continuation of U.S. patent application Ser. No. 12/221,021, filed Jul. 29, 2008, now U.S. Pat. No. 7,927,834, issued Apr. 19, 2011, which is a divisional of U.S. patent application Ser. No. 11/593,279, filed Nov. 6, 2006, now U.S. Pat. No. 7,429,486, issued Sep. 30, 2008, which is a divisional patent application of patent application Ser. No. 11/039,767, filed Jan. 18, 2005, now U.S. Pat. No. 7,262,028, issued Aug. 28, 2007, which is a continuation of PCT International Patent Application No. PCT/EP2003/007690, filed on Jul. 15, 2003, designating the United States of America, published in English as International Publication No. WO 2004/009618 A2 on Jan. 29, 2004, which itself claims the benefit of PCT International Patent Application No. PCT/EP03/50201, filed May 27, 2003, European Patent Application No. 02077953.4, filed Jul. 18, 2002, and U.S. Provisional Patent Application Ser. No. 60/397,066, filed Jul. 18, 2002, the contents of the entirety of each of which are incorporated herein by this reference.

STATEMENT ACCORDING TO 37 C.F.R. § 1.821(c) or (e) SEQUENCE LISTING SUBMITTED

Pursuant to 37 C.F.R. § 1.821(c) or (e), a file containing an electronic version of the Sequence Listing has been submitted concomitant with this application, the contents of which are hereby incorporated by reference. One file titled "0079WO00ORD.ST25.txt" that is 27 KB and created on Mar. 4, 2011 is submitted electronically.

TECHNICAL FIELD

The invention relates generally to the field of biotechnology, and more particularly, to the field of medicine and the production of antibodies, and even more particularly, to the production of mixtures of antibodies.

BACKGROUND

The essential function of the immune system is the defense against infection. The humoral immune system combats molecules recognized as non-self, such as pathogens, using immunoglobulins. These immunoglobulins, also called antibodies, are raised specifically against the infectious agent, which acts as an antigen, upon first contact (Roitt, *Essential Immunology*, Blackwell Scientific Publications, fifth edition, 1984; all references cited herein are incorporated in their entirety by reference). Antibodies are multivalent molecules comprising heavy (H) chains and light (L) chains joined with interchain disulfide bonds. Several isotypes of antibodies are known, including IgG1, IgG2, IgG3, IgG4, IgA, IgD, IgE, and IgM. An IgG contains two heavy and two light chains. Each chain contains constant (C) and variable (V) regions, which can be broken down into domains designated $C_{H1}$, $C_{H2}$, $C_{H3}$, $V_H$, and $C_L$, $V_L$ (FIG. 1). Antibody binds to antigen via the variable region domains contained in the Fab portion and, after binding, can interact with molecules and cells of the immune system through the constant domains, mostly through the Fc portion.

B-lymphocytes can produce antibodies in response to exposure to biological substances like bacteria, viruses and their toxic products. Antibodies are generally epitope-specific and bind strongly to substances carrying these epitopes. The hybridoma technique (Kohler and Milstein, 1975) makes use of the ability of B-cells to produce monoclonal antibodies to specific antigens and to subsequently produce these monoclonal antibodies by fusing B-cells from mice exposed to the antigen of interest to immortalized murine plasma cells. This technology resulted in the realization that monoclonal antibodies produced by hybridomas could be used in research, diagnostics and therapies to treat different kinds of diseases like cancer and auto-immune-related disorders.

Because antibodies that are produced in mouse hybridomas can induce strong immune responses in humans, it has been appreciated in the art that antibodies required for successful treatment of humans needed to be less immunogenic or, preferably, non-immunogenic. For this to be done, murine antibodies were first engineered by replacing the murine constant regions with human constant regions (referred to as chimeric antibodies). Subsequently, domains between the complementarity-determining regions (CDRs) in the variable domains, the so-called framework regions, were replaced by their human counterparts (referred to as humanized antibodies). The final stage in this humanization process has been the production of fully human antibodies.

In the art, bispecific antibodies, which have binding specificities for two different antigens, have also been described. These are generally used to target a therapeutic or diagnostic moiety, for instance, T-cell, a cytotoxic trigger molecule, or a chelator that binds a radionuclide, that is recognized by one variable region of the antibody to a cell that is recognized by the other variable region of the antibody, for instance, a tumor cell (for bispecific antibodies, see Segal et al., 2001).

One very useful method known in the art to obtain fully human monoclonal antibodies with desirable binding properties, employs phage display libraries. This is an in vitro, recombinant DNA-based, approach that mimics key features of the humoral immune response (for phage display methods, see, e.g., C. F. Barbas III et al., *Phage Display, A laboratory manual*, Cold Spring Harbor Laboratory Press, Cold Spring Harbor, N.Y., 2001). For the construction of phage display libraries, collections of human monoclonal antibody heavy- and light-chain variable region genes are expressed on the surface of bacteriophage particles, usually in single-chain Fv (scFv) or in Fab format. Large libraries of antibody fragment-expressing phages typically contain more than $10^9$ antibody specificities and may be assembled from the immunoglobulin V regions expressed in the B lymphocytes of immunized or non-immunized individuals.

Alternatively, phage display libraries may be constructed from immunoglobulin variable regions that have been partially assembled or rearranged in vitro to introduce additional antibody diversity in the library (semi-synthetic libraries) (De Kruif et al., 1995b). For example, in vitro-assembled variable regions contain stretches of synthetically produced, randomized or partially randomized DNA in those regions of the molecules that are important for antibody specificity.

The genetic information encoding the antibodies identified by phage display can be used for cloning the antibodies in a desired format, for instance, IgG, IgA or IgM, to produce the antibody with recombinant DNA methods (Boel et al., 2000).

An alternative method to provide fully human antibodies uses transgenic mice that comprise genetic material encoding a human immunoglobulin repertoire (Fishwild et al., 1996; Mendez et al., 1997). Such mice can be immunized with a target antigen and the resulting immune response will produce fully human antibodies. The sequences of these antibodies can be used in recombinant production methods.

Production of monoclonal antibodies is routinely performed by use of recombinant expression of the nucleic acid sequences encoding the H and L chains of antibodies in host cells (see, e.g., EP0120694; EP0314161; EP0481790; U.S. Pat. No. 4,816,567; WO 00/63403, the contents of the entirety of each which are incorporated herein by reference).

To date, many different diseases are being treated with either humanized or fully human monoclonal antibodies. Products based on monoclonal antibodies that are currently approved for use in humans include HERCEPTIN™ (trastuzumab, anti-Her2/Neu), REOPRO™ (abciximab, anti-Glycoprotein IIB/IIIA receptor), MYLOTARG™ (gemtuzumab, anti-CD33), RITUXAN™ (Rituximab, anti-CD20), SIMULECT™ (basiliximab, anti-CD25), REMICADE™ (infliximab, anti-TNF), SYNAGIS™ (palivizumab, anti-RSV), ZENAPAX™ (daclizumab, IL2-receptor), and CAMPATH™ (alemtuzumab, anti-CD52). Despite these successes, there is still room for new antibody products and for considerable improvement of existing antibody products.

The use of monoclonal antibodies in cancer treatment has shown that so-called "antigen-loss tumor variants" can arise, making the treatment with the monoclonal antibody less effective. Treatment with the very successful monoclonal antibody RITUXIMAB® (anti-CD20) has, for instance, shown that antigen-loss escape variants can occur, leading to relapse of the lymphoma (Massengale et al., 2002). In the art, the potency of monoclonal antibodies has been increased by fusing them to toxic compounds, such as radionuclides, toxins, cytokines, and the like. Each of these approaches, however, has its limitations, including technological and production problems and/or high toxicity.

Furthermore, it appears that the gain in specificity of monoclonal antibodies compared to traditional undefined polyclonal antibodies, comes at the cost of loss of efficacy. In vivo, antibody responses are polyclonal in nature, i.e., a mixture of antibodies is produced because various B-cells respond to the antigen, resulting in various specificities being present in the polyclonal antibody mixture. Polyclonal antibodies can also be used for therapeutic applications, for instance, for passive vaccination or for active immunotherapy, and currently are usually derived from pooled serum from immunized animals or from humans who recovered from the disease. The pooled serum is purified into the proteinaceous or gamma globulin fraction, so named because it contains predominantly IgG molecules.

Polyclonal antibodies that are currently used for treatment include anti-rhesus polyclonal antibodies, gamma globulin for passive immunization, anti-snake venom polyclonal (CroFab), THYMOGLOBULIN™ for allograft rejection, anti-digoxin to neutralize the heart drug digoxin, and anti-rabies polyclonal antibodies. In currently marketed therapeutic antibodies, an example of the higher efficacy of polyclonal antibodies compared to monoclonal antibodies can be found in the treatment of acute transplant rejection with anti-T-cell antibodies. The monoclonal antibodies on the market (anti-CD25 BASILIXIMAB®) are less efficacious than a rabbit polyclonal antibody against thymocytes (THYMOGLOBULIN™) (press releases dated March 12, April 29, and Aug. 26, 2002, on sangstat.com). The use of pooled human sera, however, potentially bears the risk of infections with viruses such as HIV or hepatitis, with toxins such as lipopolysaccharide, with proteinaceous infectious agents such as prions, and with unknown infectious agents. Furthermore, the supply that is available is limited and insufficient for widespread human treatments. Problems associated with the current application of polyclonal antibodies derived from animal sera in the clinic include a strong immune response of the human immune system against such foreign antibodies. Therefore, such polyclonals are not suitable for repeated treatment or for treatment of individuals that were injected previously with other serum preparations from the same animal species.

The art describes the idea of the generation of animals with a human immunoglobulin repertoire, which can subsequently be used for immunization with an antigen to obtain polyclonal antibodies against this antigen from the transgenic animals (WO 01/19394, the entirety of which is incorporated herein by reference). However, many technological hurdles still will have to be overcome before such a system is a practical reality in larger animals than mice and it will take years of development before such systems can provide the polyclonal antibodies in a safe and consistent manner in sufficient quantities. Moreover, antibodies produced from pooled sera, whether being from human or animal origin, will always comprise a high amount of unrelated and undesired specificities, as only a small percentage of the antibodies present in a given serum will be directed against the antigen used for immunization. It is, for instance, known that in normal, i.e., non-transgenic, animals, about 1% to 10% of the circulating immunoglobulin fraction is directed against the antigen used for hyper-immunization; hence, the vast majority of circulating immunoglobulins is not specific.

One approach towards expression of polyclonal antibody libraries has been described (WO 95/20401; U.S. Pat. Nos. 5,789,208 and 6,335,163, the contents of the entirety of each of which are incorporated herein by reference). A polyconal library of Fab antibody fragments is expressed using a phage display vector and selected for reactivity towards an antigen. To obtain a sub-library of intact polyconal antibodies, the selected heavy and light chain-variable region gene combinations are transferred en mass as linked pairs to a eukaryotic-expression vector that provides constant region genes. Upon transfection of this sub-library into myeloma cells, stable clones produce monoclonal antibodies that can be mixed to obtain a polyclonal antibody mixture. While in theory it would be possible to obtain polyclonal antibodies directly from a single recombinant production process using this method by culturing a mixed population of transfected cells, potential problems would occur concerning the stability of the mixed cell population and, hence, the consistency of the produced polyclonal antibody mixture. The control of a whole population of different cells in a pharmaceutically acceptable large-scale process (i.e., industrial) is a daunting task. It would seem that characteristics, such as growth rates of the cells and production rates of the antibodies, should remain stable for all of the individual clones of the non-clonal population in order to keep the ratio of antibodies in the polyclonal antibody mixture more or less constant.

BRIEF SUMMARY

Disclosed are means and methods for producing a mixture of antibodies in recombinant hosts.

In one aspect, provided is a method of producing a mixture of antibodies in a recombinant host, the method comprising expressing in a recombinant host cell a nucleic acid sequence or nucleic acid sequences encoding at least one light chain and at least three different heavy chains that are capable of pairing with at least one light chain. A further aspect is the elimination of the production of potentially non-functional light-heavy chain pairing by using pre-selected combinations of heavy and light chains. It has been recognized that phage display libraries built from a single light chain and many different heavy chains can encode antibody fragments with very distinct binding properties. This feature can be used to find different antibodies having the same light chain but different heavy chains, against the same target or different targets, wherein a target can be a whole antigen or an epitope thereof. Such different targets may, for instance, be on the same surface (e.g., cell or tissue). Such antibody fragments obtained by phage display can be cloned into vectors for the desired format, e.g., IgG, IgA or IgM, and the nucleic acid sequences encoding these formats can be used to transfect host cells. In one approach, H and L chains can be encoded by different constructs that, upon transfection into a cell wherein they are expressed, give rise to intact Ig molecules. When different H chain constructs are transfected into a cell with a single L chain construct, H and L chains will be assembled to form all possible combinations. However, in contrast to approaches where different light chains are expressed, such as for the production of bispecific antibodies, this method will result only in functional binding regions. It would be particularly useful when the host, for example, a single cell line, is capable of expressing acceptable levels of recombinant antibodies without the necessity to first amplify in the cell the nucleic acid sequences encoding the antibodies. The advantage is that cell lines with only a limited copy number of the nucleic acids are expected to be genetically more stable, because there will be less recombination between the sequences encoding the heavy chains, than in cell lines where a multitude of these copies is present. A cell line suitable for use in these methods is the human cell line PER.C6® (human retina cells that express adenovirus E1A and E1B proteins). Using this method, a mixture of antibodies with defined specificities can be produced from a single cell clone in a safe, controlled, and consistent manner.

In certain embodiments, provided is a method for producing a mixture of antibodies in a recombinant host, the method comprising expressing a nucleic acid sequence or nucleic acid sequences encoding at least one light chain and at least three different heavy chains that are capable of pairing with at least one light chain in a recombinant host cell. In certain embodiments, the recombinant host cell comprises a nucleic acid sequence encoding a common light chain that is capable of pairing with at least three different heavy chains, such that the produced antibodies comprise a common light chain. Those of skill in the art will recognize that "common" also refers to functional equivalents of the light chain of which the amino acid sequence is not identical. Many variants of the light chain exist wherein mutations (deletions, substitutions, additions) are present that do not materially influence the formation of functional binding regions.

Further provided is a composition comprising a mixture of recombinantly produced antibodies, wherein at least three different heavy chain sequences are represented in the mixture. In certain embodiments, the light chains of such mixtures have a common sequence. The mixture of antibodies can be produced by the method according to the invention. Preferably, the mixture of antibodies is more efficacious than the individual antibodies it comprises. More preferably, the mixture acts synergistically in a functional assay.

Further provided is a recombinant host cell for producing mixtures of antibodies and methods for making such host cells.

Independent clones obtained from the transfection of nucleic acid sequences encoding a light chain and more than one heavy chain may express the different antibodies in the mixture at different levels. It is another aspect to select a clone using a functional assay for the most potent mixture of antibodies. Further provides a method for identifying at least one host cell clone that produces a mixture of antibodies, wherein the mixture of antibodies has a desired effect according to a functional assay, the method comprising: (i) providing a host cell with nucleic acid sequences encoding at least one light chain and nucleic acid sequences encoding at least two different heavy chains, wherein the heavy and light chains are capable of pairing with each other; (ii) culturing at least one clone of the host cell under conditions conducive to expression of the nucleic acid sequences; (iii) screening at least one clone of the host cell for production of a mixture of antibodies having the desired effect by a functional assay; and (iv) identifying at least one clone that produces a mixture of antibodies having the desired effect. This method, as used herein, can be performed using high-throughput procedures if desired. The clones identified by the method can be used to produce antibody mixtures.

In certain embodiments, further provided are transgenic non-human animals and transgenic plants or transgenic plant cells capable of expressing mixtures of antibodies and mixtures of antibodies produced by these.

In certain embodiments, further provided are pharmaceutical compositions comprising a mixture of recombinantly produced antibodies and a suitable carrier.

In certain embodiments, further provided are mixtures of antibodies for use in the treatment or diagnosis and for the preparation of a medicament for use in the treatment or diagnosis of a disease or disorder in a human or animal subject.

In certain embodiments, further provided is a method for producing a mixture of antibodies comprising different isotypes from a single host cell clone.

In certain embodiments, further provided is a method for identifying a mixture of antibodies having a desired effect in a functional assay.

In certain embodiments, further provided is a method for producing a mixture of antibodies that are capable of binding to a target, the method comprising: i) bringing a phage library comprising antibodies into contact with material comprising a target, ii) at least one step of selecting phages binding to the target, iii) identifying at least two phages that comprise antibodies binding to the target, wherein at least two antibodies comprise a common light chain, iv) introducing a nucleic acid sequence encoding the light chain and a nucleic acid sequence or sequences encoding the heavy chains of at least two antibodies into a host cell, v) culturing a clone of the host cell under conditions conducive to expression of the nucleic acid sequences.

BRIEF DESCRIPTION OF THE FIGURES

FIGS. 3A and 3B show a sequence alignment of $V_L$ (FIG. 3A) and $V_H$ (FIG. 3B) of K53, UBS-54 and 02-237. The DNA sequence of common $V_L$ of UBS54 and K53 is SEQ ID NO:1, while the amino acid sequence is given as SEQ ID NO:2. DNA sequences of $V_L$ of 02-237, $V_H$ of UBS54, K53 and 02-237 are SEQ ID NOS:3, 5, 7 and 9, respectively, while the amino acid sequences are given in SEQ ID NOS:4, 6, 8 and 10, respectively.

FIGS. 7A and 7B show the sequence of $V_H$ and $V_L$ of phages directed against CD22 (clone B28), CD72 (clone II-2) (FIG. 7A), and HLA-DR (class II; clone I-2) (FIG. 7B). DNA sequences of $V_L$ of clones B28, II-2 and I-2 are SEQ ID NOS:11, 13 and 15, respectively, while the amino acid sequences are SEQ ID NOS:12, 14 and 16, respectively. DNA sequence of the common light chain of these clones is SEQ ID NO:17, while the amino acid sequence is SEQ ID NO:18.

FIGS. 12A-12E depict DNA and protein sequences of variable domains of heavy chains of K53 (FIG. 12A), UBS54 (FIG. 12C) and 02-237 (FIG. 12B) IgG (SEQ ID NOS:7, 9 and 5, respectively) and light chains (SEQ ID NOS:1 and 3, respectively, for K53/UBS54 (FIG. 12D) and 02-237 IgG (FIG. 12E)).

FIG. 13 shows alignment of the variable sequences of the heavy chains of K53, 02-237 and UBS54 (SEQ ID NOS:7, 9, and 5, respectively). CDR1, CDR2 and CDR3 regions are indicated in bold.

FIG. 14 is a BIACORE™ (surface plasmon resonance) analysis of K53 and 02-237. Affinity-purified human CD46 from LS174T cells was coupled (640 RU) to CM5 chips (BIACORE BR-1000-14™). Binding of 1000 (A), 500 (B), 250 (C), 125 (D), 63 (E), 31 (F), 16 (G), 8 (H) or 0 (I) nM 02-237 or K53 purified from stable PER.C6® (human retina cells that express adenovirus E1A and E1B proteins)-derived cell lines to the CD46 was monitored using a BIACORE 3000™ system at 37° C. Using this experimental set-up, a $K_d$ of $9.1 \times 10^7$ and $2.2 \times 10^8$ was found for K53 and 02-237, respectively.

Purified IgG was dissolved in a 0.1% RAPIGEST™ (Waters) in 50 mM $NH_4HCO_3$. The disulfides were reduced using 1 M DTT (1,4-dithio-DL-threitol), followed by incubation at 65° C. for 30 minutes. Then, for alkylation of all sulfhydryl groups, 1 M iodoacetamide was added, followed by incubation at room temperature for 45 minutes in the dark. Alkylation was stopped by addition of 1 M DTT. The buffer was exchanged to 25 mM $NH_4HCO_3$, pH 7.5. Finally, the antibodies were digested overnight at 37° C. by addition of a freshly prepared trypsin solution in 25 mM $NH_4HCO_3$. The peptide mixture was analyzed by LC-MS. The LC-system consisted of a Vydac reversed-phase C18 column that was eluted by applying a gradient of solvent A (5/95/1 acetonitrile, water, glacial acetic acid v/v/v) and solvent B (90/10/1 acetonitrile, water, glacial acetic acid v/v/v). The LC was on-line coupled to a Q-TOF2 mass spectrometer (Micromass), equipped with an electrospray source operated at 3 kV. Mass spectra were recorded in a positive ion mode from m/z 50 to 1500 at a cone voltage of 35 V. The instrumental resolution of >10,000 enabled unambiguous determination of the charge and, therefore, the mass of most ions up to at least +7. In this way, all peptides were identified according to their molecular weight. The amino acid sequence of the peptide was confirmed by MS/MS-experiments. MS/MS spectra were recorded in a positive ion mode from m/z 50-2000 with collision energy between 20 and 35 eVolts.

Figure 20:
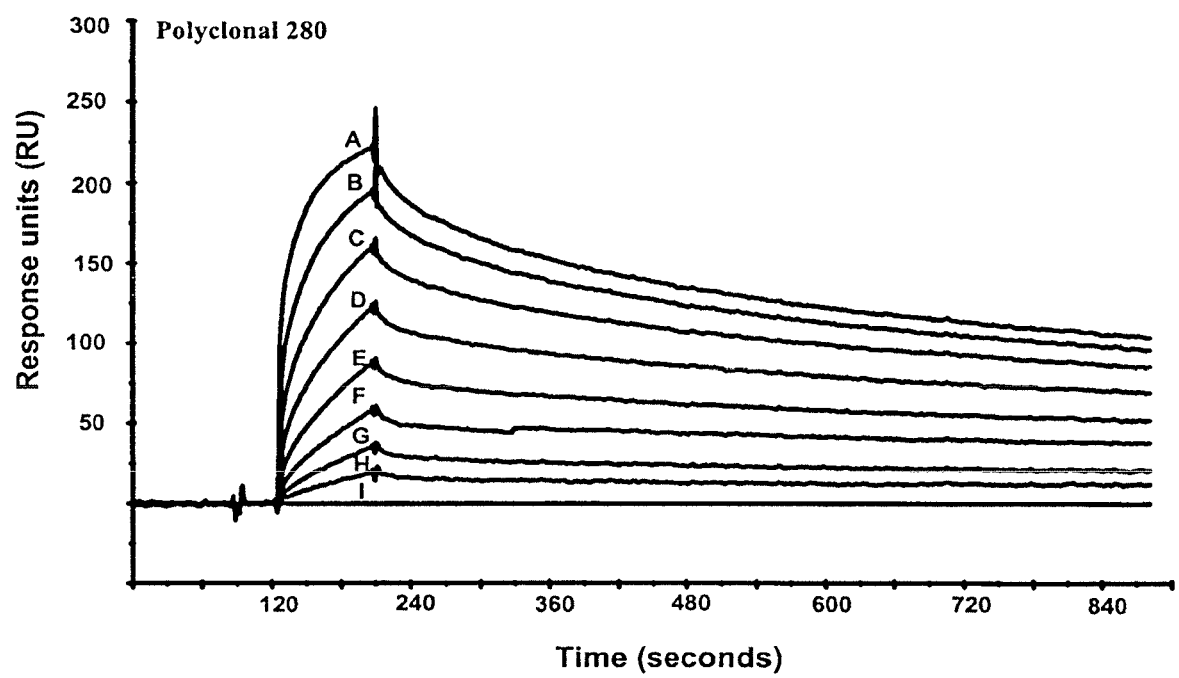

FIG. 20 is a BIACORE™ (surface plasmon resonance) analysis of polyclonal 280. Affinity-purified human CD46 from LS174T cells was coupled (640 RU) to CM5 chips (BIACORE BR-1000-14™). Binding of 1000 (A), 500 (B), 250 (C), 125 (D), 63 (E), 31 (F), 16 (G), 8 (H) or 0 (I) nM Poly1-280 to CD46 was monitored using a BIACORE 3000™ system at 37° C.

FIG. 21 is an IEF analysis of sub-clones from clones poly 1-241, poly 1-280 and poly 1-402 producing a mixture of antibodies.

Panel A contains clones poly 1-241 and poly 1-280. Lane 1 contains a pI marker (Amersham, Cat. No. 17-0471-01). Lane 2 contains isolated IgG from the parent clone poly 1-241 (as in FIG. 18). Lanes 3, 4 and 5, respectively, contain isolated IgG from three independent sub-clones derived from poly 1-241 by limiting dilution. Lane 6 contains isolated IgG from the parent clone poly 1-280 (as in FIG. 18). Lanes 7, 8 and 9, respectively, contain isolated IgG from three independent sub-clones derived from poly 1-280 by limiting dilution.

Panel B contains clone poly 1-402. Lanes 1 and 7 contain a pI marker. Lane 2 contains isolated IgG from the parent clone poly 1-402 (as in FIG. 18). Lanes 3, 4 and 5, respectively, contain isolated IgG from three independent sub-clones derived from poly 1-402 by limiting dilution. Lane 6 contains a control (a 1:1:1 mixture of 02-237, K53 and UBS54).

Figure 22:
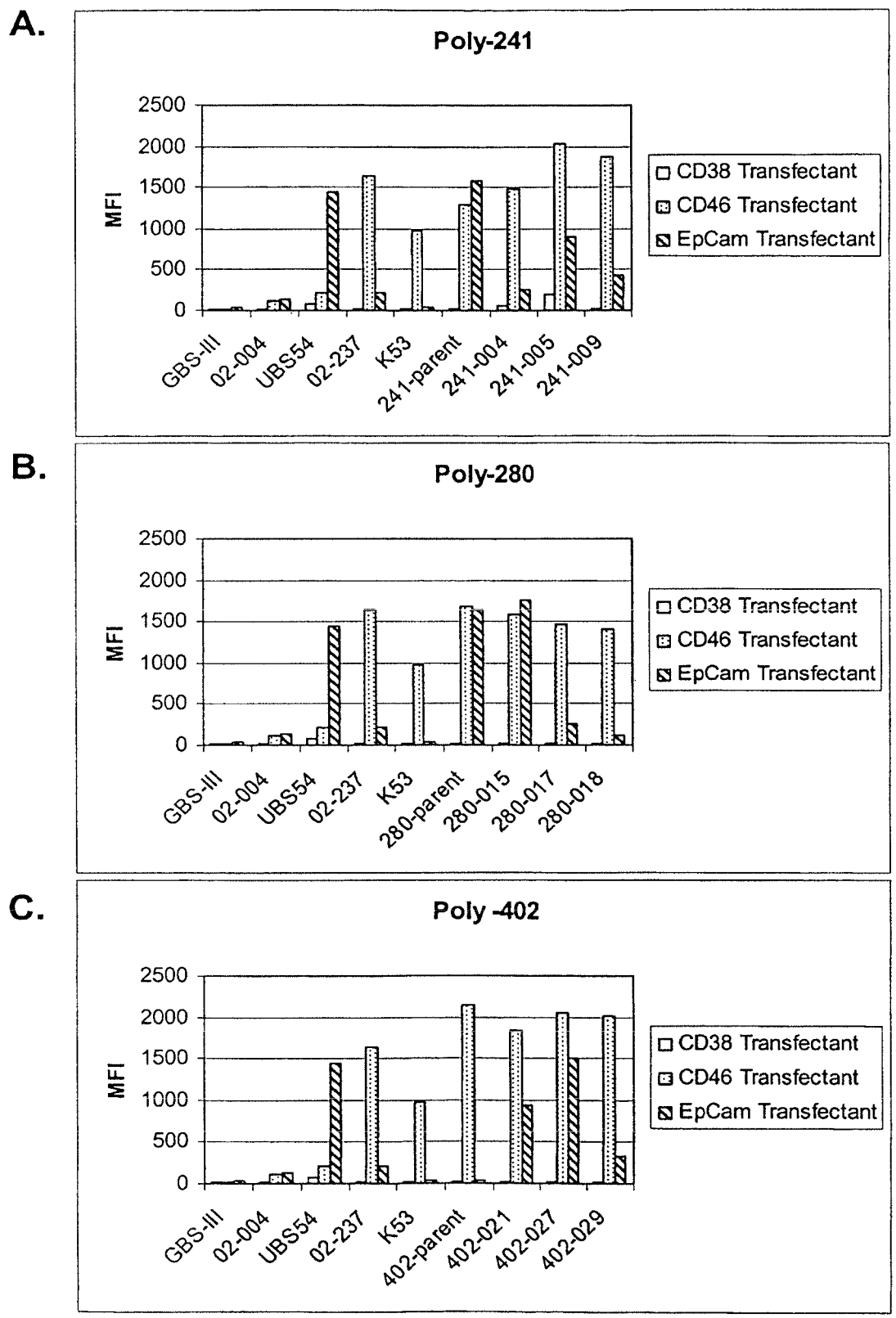

FIG. 22 is a fluorescence activated cell sorting (FACS) analysis of mixtures of antibodies produced from sub-clones of poly 1-241 (A), poly 1-280 (B) and poly 1-402 (C). Binding of the mixtures of antibodies to cells transfected with cDNA of CD46, EpCAM, or a negative control (CD38), was determined with FACS analysis. Mean fluorescent intensity (MFI) is shown for the various parent clones and three independent sub-clones of each. Control antibodies GBS-III (negative control), anti-CD72 (02-004; negative control) and the single antibodies UBS54, 02-237 and K53 are also included.

DETAILED DESCRIPTION OF THE INVENTION

Provided is a method for producing a mixture of antibodies in a recombinant host, the method comprising expressing, in a recombinant host cell, a nucleic acid sequence or nucleic acid sequences encoding at least one light chain and at least three different heavy chains that are capable of pairing with at least one light chain. In certain embodiments, the light and heavy chains form functional antigen-binding domains when paired. A functional antigen-binding domain is capable of specifically binding to an antigen.

In certain embodiments, the method for producing a mixture of antibodies further comprises the step of recovering the antibodies from the cell or the host cell culture to obtain a mixture of antibodies suitable for further use.

In certain embodiments, a method is provided for production of a mixture of antibodies, the method comprising expressing in a recombinant host cell a nucleic acid sequence encoding a common light chain and nucleic acid sequence or sequences encoding at least three different heavy chains that are capable of pairing with the common light chain, such that the antibodies that are produced comprise common light chains. In one aspect, the common light chain is identical in each light chain/heavy chain pair.

Figure 1:
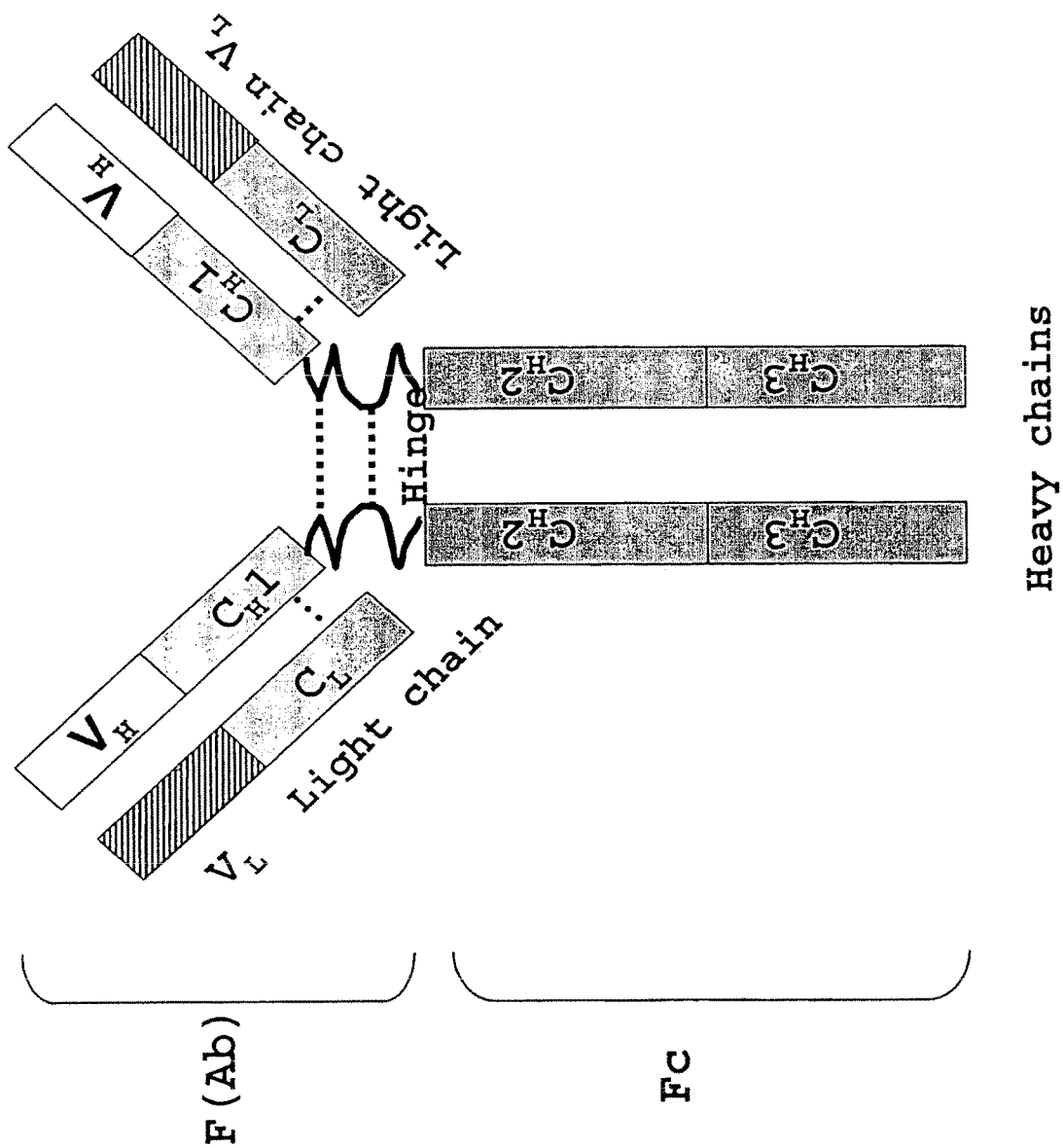
FIG. 1 is a schematic representation of an antibody. The heavy and light chains are paired via interchain disulfide bonds (dotted lines). The heavy chain can be either of the α, γ, μ, δ or ε isotype. The light chain is either λ, or κ. An antibody of IgG1 isotype is shown.

The term "antibody," as used herein, means a polypeptide containing one or more domains that bind an epitope on an antigen, where such domains are derived from, or have sequence identity with, the variable region of an antibody. The structure of an antibody is schematically represented in FIG. 1. Examples of antibodies according to the invention include full length antibodies, antibody fragments, bispecific antibodies, immunoconjugates, and the like. An antibody, as used herein, may be isotype IgG1, IgG2, IgG3, IgG4, IgA1, IgA2, IgD, IgE, IgM, and the like, or a derivative of these. Antibody fragments include Fv, Fab, Fab', F(ab')$_2$ fragments, and the like. Antibodies according to the invention can be of any origin, including murine, of more than one origin, e.g., chimeric, humanized, or fully human antibodies. Immunoconjugates comprise antigen-binding domains and a non-antibody part such as a toxin, a radiolabel, an enzyme, and the like.

Figure 2:
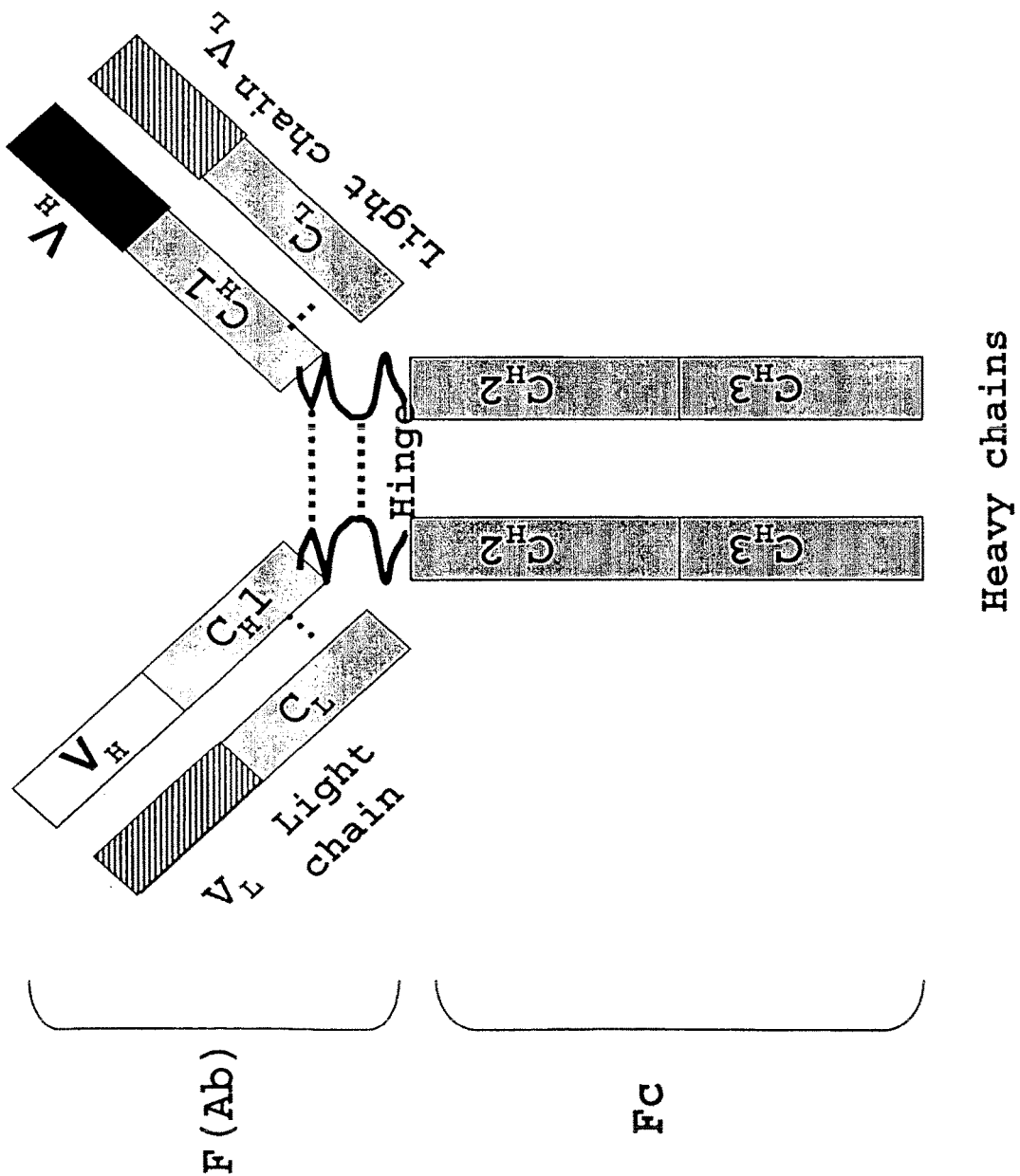
FIG. 2 is a schematic representation of a bispecific monoclonal antibody. A bispecific antibody contains two different functional F(Ab) domains, indicated by the different patterns of the $V_H$-$V_L$ regions.

An "antigen-binding domain" preferably comprises variable regions of a heavy and a light chain and is responsible for specific binding to an antigen of interest. Recombinant antibodies are prepared by expressing both a heavy and a light chain in a host cell. Similarly, by expressing two chains with their respective light chains (or a common light chain), wherein each heavy chain/light chain has its own specificity, so-called "bispecific" antibodies can be prepared. "Bispecific antibodies" comprise two non-identical heavy-light chain combinations (FIG. 2), and both antigen-binding regions of a bispecific antibody may recognize different antigens or different epitopes on an antigen. "Epitope" means a moiety of an antigen to which an antibody binds. A single antigen may have multiple epitopes.

A "common light chain," refers to light chains which may be identical or have amino acid sequence differences. Common light chains may comprise mutations which do not alter the specificity of the antibody when combined with the same heavy chain without departing from the scope of the invention. It is, for instance, possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. In an exemplary embodiment, provided is the use of a common light chain, one identical light chain, to combine with different heavy chains to form antibodies with functional antigen-binding domains. The use of one common light chain avoids the formation of heterodimers in which pairing of light and heavy chains results in antigen-binding domains that are not functional or, in other words, which are not capable of binding to the target antigen or antigens. The use of a common light chain and two heavy chains has been proposed (Merchant et al., 1998; WO 98/50431, the entirety of which are incorporated herein by reference) for a different purpose, viz., to increase the formation of functional bispecific antibodies at the expense of antibody mixture complexity. These publications teach a method for preferentially producing one defined and desired bispecific antibody, thereby minimizing the complexity of the produced mixture. Hence, Merchant specifically teaches to prevent the production of monospecific antibodies because these are undesired byproducts in the process for bispecific antibody production described in those publications. Clearly, there is no teaching in the prior art to prepare a complex mixture of antibodies from a recombinant host cell avoiding the formation of non-functional binding domains or the benefits thereof, let alone how. In the method according to the invention, at least three different heavy chains that are capable of pairing with the common light chain are expressed. In other embodiments, the host cell, as used herein, is provided with nucleic acid sequences encoding for 4, 5, 6, 7, 8, 9, 10, or more, heavy chains capable of pairing with the common light chain, to increase the complexity of the produced mixture of antibodies.

"Different heavy chains," according to the invention, may differ in the variable region and have the same constant region. In other embodiments, where it is clear from the context, they may have the same variable region and differ in the constant region, e.g., be of a different isotype. The use of a mixture of antibodies having different constant regions, such as the Fc-portion, may be advantageous if different arms of the immune system are to be mobilized in the treatment of the human or animal body. In yet other embodiments, also to be clear from the context, both the variable and the constant regions may differ.

A "mixture of antibodies," according to the invention, comprises at least two non-identical antibodies, but may comprise 3, 4, 5, 6, 7, 8, 9, 10, or more, different antibodies and may resemble a polyclonal or at least an oligoclonal antibody mixture with regard to complexity and number of functional antigen-binding molecules. The mixtures produced according to the invention usually will comprise bispecific antibodies. If desired, formation of monospecific antibodies in the mixture can be favored over the formation of bispecific antibodies.

When n heavy chains and one common light chain are expressed, as used herein, in a host cell at equal levels, the theoretical percentage of bispecific antibodies produced by the method according to the invention is $(1-1/n) \times 100\%$. The total number of different antibodies in the mixture produced by the method according to the invention is theoretically $n+\{(n^2-n)/2\}$, of which $(n^2-n/2)$ are bispecific antibodies. Distortion of the ratio of expression levels of the different heavy chains may lead to values deviating from the theoretical values. The amount of bispecific antibodies can also be decreased, compared to these theoretical values, if all heavy chains do not pair with equal efficiency. It is, for instance, possible to engineer the heavy chains, for example, by introducing specific and complementary interaction surfaces between selected heavy chains, to promote homodimer pairing over heterodimer pairing, contrary to what has been proposed by Merchant, supra. Heavy chains may also be selected so as to minimize heterodimer formation in the mixture. A special form of this embodiment involves heavy chains of two or more different isotypes (e.g., IgG1, IgG3, IgA). When heavy chains of different isotype are expressed in the same host cell in accordance with the invention and one light chain that can pair to these heavy chains, the amount of bispecific antibodies will be reduced, possibly to very low or even undetectable levels. Thus, when bispecific antibodies are less desirable, it is possible to produce a mixture of antibodies according to the invention, wherein a nucleic acid sequence encoding a common light chain and nucleic acid sequences encoding at least two different heavy chains with a different variable region capable of pairing to the common light chain are expressed in a recombinant host, and wherein the heavy chains further differ in their constant regions sufficiently to reduce or prevent pairing between the different heavy chains. The mixtures of antibodies may be produced from a clone that was derived from a single host cell, i.e., from a population of cells containing the same recombinant nucleic acid sequences.

It will be understood that the different heavy chains can be encoded on separate nucleic acid molecules, but may also be present on one nucleic acid molecule comprising different regions encoding at least three heavy chains. The nucleic acid molecules usually encode precursors of the light and/or heavy chains, which, when expressed, are secreted from the host cells, thereby becoming processed to yield the mature form. These and other aspects of expressing antibodies in a host cell are well known to those having ordinary skill in the art.

A "recombinant host cell," as used herein, is a cell comprising one or more so-called transgenes, i.e., recombinant nucleic acid sequences not naturally present in the cell. These transgenes are expressed in the host cell to produce recombinant antibodies encoded by these nucleic acid sequences when these cells are cultured under conditions conducive to expression of nucleic acid sequences. The host cell, as used herein, can be present in the form of a culture from a clone that is derived from a single host cell wherein the transgenes have been introduced. To obtain expression of nucleic acid sequences encoding antibodies, it is well known to those skilled in the art that sequences capable of driving such expression can be functionally linked to the nucleic acid sequences encoding the antibodies.

"Functionally linked" is meant to describe that the nucleic acid sequences encoding the antibody fragments or precursors thereof is linked to the sequences capable of driving expression such that these sequences can drive expression of the antibodies or precursors thereof.

Useful expression vectors are available in the art, for example, the pcDNA vector series of Invitrogen. Where the sequence encoding the polypeptide of interest is properly inserted with reference to sequences governing the transcription and translation of the encoded polypeptide, the resulting expression cassette is useful to produce the polypeptide of interest, referred to as expression. Sequences driving expression may include promoters, enhancers and the like, and combinations thereof. These should be capable of functioning in the host cell, thereby driving expression of the nucleic acid sequences that are functionally linked to them. Promoters can be constitutive or regulated and can be obtained from various sources, including viruses, prokaryotic or eukaryotic sources, or artificially designed. Expression of nucleic acids of interest may be from the natural promoter or derivative thereof or from an entirely heterologous promoter. Some well-known and much-used promoters for expression in eukaryotic cells comprise promoters derived from viruses, such as adenovirus, for instance, the E1A promoter, promoters derived from cytomegalovirus (CMV), such as the CMV immediate early (IE) promoter, promoters derived from Simian Virus 40 (SV40), and the like. Suitable promoters can also be derived from eukaryotic cells, such as methallothionein (MT) promoters, elongation factor 1α (EF-1α) promoter, an actin promoter, an immunoglobulin promoter, heat shock promoters, and the like. Any promoter or enhancer/promoter capable of driving expression of the sequence of interest in the host cell is suitable in the invention. In one embodiment, the sequence capable of driving expression comprises a region from a CMV promoter, preferably the region comprising nucleotides −735 to +95 of the CMV immediate early gene enhancer/promoter. The skilled artisan will be aware that the expression sequences used in the invention may suitably be combined with elements that can stabilize or enhance expression, such as insulators, matrix attachment regions, STAR elements (WO 03/004704, the entirety of which is incorporated herein by reference), and the like. This may enhance the stability and/or levels of expression.

Protein production in recombinant host cells has been extensively described, e.g., in *Current Protocols in Protein Science*, 1995, J. E. Coligan, B. M. Dunn, H. L. Ploegh, D. W. Speicher, P. T. Wingfield, ISBN 0-471-11184-8; Bendig, 1988, the entirety of which is incorporated herein by reference. Culturing a cell is done to enable it to metabolize, grow, divide, and/or produce recombinant proteins of interest. This can be accomplished by methods well known to persons skilled in the art and includes, but is not limited to, providing nutrients for the cell. The methods comprise growth adhering to surfaces, growth in suspension, or combinations thereof. Several culturing conditions can be optimized by methods well known in the art to optimize protein production yields. Culturing can be done, for instance, in dishes, roller bottles or in bioreactors, using batch, fed-batch, continuous systems, hollow fiber, and the like. In order to achieve large-scale (continuous) production of recombinant proteins through cell culture, it is preferred in the art to have cells capable of growing in suspension and it is preferred to have cells capable of being cultured in the absence of animal- or human-derived serum or animal- or human-derived serum components. Thus, purification is easier and safety is enhanced due to the absence of additional animal or human proteins derived from the culture medium, while the system is also very reliable as synthetic media are the best in reproducibility.

"Host cells," according to the invention, may be any host cell capable of expressing recombinant DNA molecules, including bacteria such as *Escherichia* (e.g., *E. coli*), *Enterobocter, Salmonella, Bacillus, Pseudomonas, Streptomyces*, yeasts such as *S. cerevisiae, K. lactis, P. pastoris, Candida*, or *yarrowia*, filamentous fungi such as *Neurospora, Aspergillus oryzae, Aspergillus nidulans* and *Aspergillus niger*, insect cells such as *Spodoptera frugiperda* SF-9 or SF-21 cells, mammalian cells such as Chinese hamster ovary (CHO) cells, BHK cells, mouse cells including SP2/0 cells and NS-0 myeloma cells, primate cells such as COS and Vero cells, MDCK cells, BRL 3A cells, hybridomas, tumor cells, immortalized primary cells, human cells such as W138, HepG2, HeLa, HEK293, HT1080 or embryonic retina cells such as PER.C6® (human retina cells that express adenovirus E1A and E1B proteins), and the like. Often, the expression system of choice will involve a mammalian cell expression vector and host so that the antibodies are appropriately glycosylated. A human cell line, preferably PER.C6® (human retina cells that express adenovirus E1A and E1B proteins), can advantageously be used to obtain antibodies with a completely human glycosylation pattern. The conditions for growing or multiplying cells (see, e.g., *Tissue Culture*, Academic Press, Kruse and Paterson, editors (1973), the entirety of which is incorporated herein by reference) and the conditions for expression of the recombinant product may differ somewhat and optimization of the process is usually performed to increase the product yields and/or growth of the cells with respect to each other, according to methods generally known to one of ordinary skill in the art.

In general, principles, protocols, and practical techniques for maximizing the productivity of mammalian cell cultures can be found in *Mammalian Cell Biotechnology: a Practical Approach* (M. Butler, ed., IRL Press, 1991), the entirety of which is incorporated herein by reference. Expression of antibodies in recombinant host cells has been extensively described in the art (see, e.g., EP0120694; EP0314161; EP0481790; EP0523949; U.S. Pat. No. 4,816,567; WO 00/63403, the entirety of which are incorporated herein by reference). The nucleic acid molecules encoding the light and heavy chains may be present as extrachromosomal copies and/or stably integrated into the chromosome of the host cell. With regard to stability of production, the latter is preferred.

The antibodies are expressed in the cells according to the invention and may be recovered from the cells or, preferably, from the cell culture medium, by methods generally known to persons skilled in the art. Such methods may include precipitation, centrifugation, filtration, size-exclusion chromatography, affinity chromatography, cation- and/or anion-exchange chromatography, hydrophobic interaction chromatography, and the like. For a mixture of antibodies comprising IgG molecules, protein A- or protein G-affinity chromatography can be suitably used (see, e.g., U.S. Pat. Nos. 4,801,687 and 5,151,504, the entirety of which are incorporated herein by reference).

In one embodiment, at least two antibodies from the mixture produced according to the invention comprise a heavy-light chain dimer having different specificities and/or affinities. The specificity determines which antigen or epitope thereof is bound by the antibody. The affinity is a measure for the strength of binding to a particular antigen or epitope. Specific binding is defined as binding with an affinity ($K_a$) of at least $5 \times 10^4$ liter/mole, more preferably, $5 \times 10^5$, even more preferably, $5 \times 10^6$, and still more preferably, $5 \times 10^7$, or more. Typically, monoclonal antibodies may have affinities which go up to $10^{10}$ liter per mole or even higher. The mixture of antibodies produced according to the invention may contain at least two antibodies that bind to different epitopes on the same antigen molecule and/or may contain at least two antibodies that bind to different antigen molecules present in one antigen-comprising mixture. Such an antigen-comprising mixture may be a mixture of partially or wholly purified antigens, such as toxins, membrane components and proteins, viral envelope proteins, or it may be a healthy cell, a diseased cell, a mixture of cells, a tissue or mixture of tissues, a tumor, an organ, a complete human or animal subject, a fungus or yeast, a bacteria or bacterial culture, a virus or virus stock, or combinations of these, and the like. Unlike monoclonal antibodies that are able to bind to a single antigen or epitope only, the mixture of antibodies according to the invention may, therefore, have many of the advantages of a polyclonal or oligoclonal antibody mixture.

In a preferred embodiment, the host cell according to the method of the invention is capable of high-level expression of human immunoglobulin, i.e., at least 1 picograms per cell per day, preferably, at least 10 picograms per cell per day and, even more preferably, at least 20 picograms per cell per day or more without the need for amplification of the nucleic acid molecules encoding the heavy and light chains in the host cell.

Preferably, host cells according to the invention contain in their genome between one and ten copies of each recombinant nucleic acid to be expressed. In the art, amplification of the copy number of the nucleic acid sequences encoding a protein of interest in, e.g., CHO cells can be used to increase expression levels of the recombinant protein by the cells (see, e.g., Bendig, 1988; Cockett et al., 1990; U.S. Pat. No. 4,399,216, the entirety of which are incorporated herein by reference). This is currently a widely used method. However, a significant time-consuming effort is required before a clone with a desired high copy number and high expression levels has been established and, moreover, clones harboring very high copy numbers (up to hundreds) of the expression cassette often are unstable (e.g., Kim et al., 1998, the entirety of which is incorporated herein by reference). It is, therefore, a preferred embodiment of the invention to use host cells that do not require such amplification strategies for high-level expression of the antibodies of interest. This allows fast generation of stable clones of host cells that express the mixture of antibodies according to the invention in a consistent manner. We provide evidence that host cells according to the invention can be obtained, sub-cloned and further propagated for at least around 30 cell divisions (population doublings) while expressing the mixture of antibodies according to the invention in a stable manner, in the absence of selection pressure. Therefore, in certain aspects, the methods of the invention include culturing the cells for at least 20, preferably 25, more preferably 30, population doublings and, in other aspects, the host cells according to the invention have undergone at least 20, preferably 25, more preferably 30, population doublings and are still capable of expressing a mixture of antibodies according to the invention. Also provided is a culture of cells producing a mixture of immunoglobulins from a single cell, the mixture comprising at least three different heavy chains. Also provided is a culture of cells producing at least three different monospecific immunoglobulins from a single cell. In certain exemplary aspects, the culture produces the mixture or at least three different monospecific immunoglobulins in a single cell for more than 20, preferably more than 25, more preferably, more than 30 population doublings.

Preferably, host cells according to the method are derived from human retina cells that have been immortalized or transformed with adenoviral E1 sequences. A particularly preferred host cell according to methods of the invention is PER.C6® (human retina cells that express adenovirus E1A and E1B proteins) as deposited under ECACC no. 96022940, or a derivative thereof. PER.Ce-derived clones can be generated fast, usually contain a limited number of copies (about 1-10) of the transgene, and are capable of high-level expression of recombinant antibodies (Jones et al., 2003, the entirety of which is incorporated herein by reference). Therefore, such clones are expected to maintain a stable copy number over many generations, which is an advantage in the production of biopharmaceuticals. PER.C6® (human retina cells that express adenovirus E1A and E1B proteins) cells have been extensively characterized and documented, demonstrating good process of scaling up, suspension growth and growth factor independence. Furthermore, PER.C6® (human retina cells that express adenovirus E1A and E1B proteins) can be incorporated into a suspension in a highly reproducible manner, making it particularly suitable for large-scale production. In this regard, the PER.C6® cell line (human retina cells that express adenovirus E1A and E1B proteins) has been characterized for bioreactor growth, where it can grow to very high densities. The use of PER.C6® (human retina cells that express adenovirus E1A and E1B proteins) for recombinant production of antibodies has been described in detail in publication WO 00/63403 and in (Jones et al., 2003, the entirety of which is incorporated herein by reference).

Also provided is a mixture of antibodies obtainable by a method described herein. Such mixtures of antibodies are expected to be more effective than the sole components it comprises, in analogy to polyclonal antibodies usually being more effective than monoclonal antibodies to the same target. Such mixtures can be prepared against a variety of target antigens or epitopes.

It certain embodiments, provided is a recombinant host cell comprising a nucleic acid sequence encoding a light chain and a nucleic acid sequence or nucleic acid sequences encoding at least three different heavy chains of an antibody, wherein the light chain and heavy chains are capable of pairing, preferably to form a functional binding domain. The paired heavy and light chains form functional antigen-binding regions against the target antigen or target antigens. The host cells are useful in the described methods. They can be used to produce mixtures of antibodies.

In certain embodiments, provided is a composition comprising a mixture of recombinantly produced antibodies, wherein at least three different heavy chain sequences are represented in the mixture of recombinant antibodies. Monoclonal antibodies are routinely produced by recombinant methods. Also disclosed are mixtures of antibodies useful for diagnosis or treatment in various fields. In certain embodiments, the compositions of the invention comprise mixtures of at least three different heavy chains paired to light chains in the form of antibodies. Preferably, the light chains of the antibodies in the mixtures have a common light chain. The mixtures may comprise bispecific antibodies. The mixtures may be produced from a clone that was derived from a single host cell, e.g., from a population of cells containing the same recombinant nucleic acid sequences. The mixtures can be obtained by methods according to the invention or be produced by host cells according to the invention. In other embodiments, the number of heavy chains represented in the mixture is 4, 5, 6, 7, 8, 9, 10, or more. The optimal mixture for a certain purpose may be determined empirically by methods known to one of ordinary skill in the art or by methods provided by the invention. Such compositions according to the invention may have several of the advantages of a polyclonal antibody mixture, without the disadvantages usually inherently associated with polyclonal antibody mixtures, because of the manner in which they are produced. It is furthermore expected that the mixture of antibodies is more efficacious than separate monoclonal antibodies. Therefore, the dosage and, hence, the production capacity required may be less for the mixtures of antibodies according to the invention than for monoclonal antibodies.

It has, for instance, been described that although no single monoclonal antibody to botulinum neurotoxin (BoNT/A) significantly neutralized toxin, a combination of three such monoclonal antibodies (oligoclonal antibody) neutralized 450,000 50% lethal doses of BoNT/A, a potency 90 times greater than human hyperimmune globulin (Nowakowski et al., 2002, the entirety of which is incorporated herein by reference). This result demonstrates that oligoclonal mixtures of antibodies comprising only two to three different specificities may have very high potency.

Furthermore, the chances of a mixture herein losing its activity due to target or epitope loss are reduced, when compared to a single monoclonal antibody. In particular embodiments, 2, 3, 4, 5, 6, 7, 8, 9, 10, or more of the antibodies present in the mixture according to the invention have different specificities. Different specificities may be directed to different epitopes on the same antigen and/or may be directed to different antigens present in one antigen-comprising mixture. A composition as described herein may also further comprise 2, 3, 4, 5, 6, 7, 8, 9, 10, or more antibodies having different affinities for the same epitope. Antibodies with differing affinities for the same epitope may, for instance, be generated by methods of affinity maturation known to one of ordinary skill in the art.

In a particularly preferred embodiment, the composition according to the invention has an effect that is greater than the effect of each individual monospecific antibody present in the composition. The effect can be measured in a functional assay. A "functional assay," as used herein, is an assay that can be used to determine one or more desired parameters of the antibody or the mixture of antibodies subject to the assay conditions. Suitable functional assays may be binding assays, apoptosis assays, antibody-dependent cellular cytotoxicity (ADCC) assays, complement-dependent cytotoxicity (CDC) assays, inhibition of cell growth or proliferation (cytostatic effect) assays, cell-killing (cytotoxic effect) assays, cell-signaling assays, assays for measuring inhibition of binding of pathogen to target cell, assays to measure the secretion of vascular endothelial growth factor (VEGF) or other secreted molecules, assays for bacteriostasis, bactericidal activity, neutralization of viruses, assays to measure the attraction of components of the immune system to the site where antibodies are bound, including in situ hybridization methods, labeling methods, and the like. Clearly, also in vivo assays, such as animal models, including mouse tumor models, models of auto-immune disease, virus-infected or bacteria-infected rodent or primate models, and the like, can be used for this purpose. The efficacy of a mixture of antibodies according to the invention can be compared to individual antibodies in such models by methods generally known to one of ordinary skill in the art.

In certain embodiments, provided is a method for identifying at least one host cell clone that produces a mixture of antibodies, wherein the mixture of antibodies has a desired effect according to a functional assay, the method comprising (i) providing a host cell comprising a nucleic acid sequence encoding at least one light chain and nucleic acid sequence or sequences encoding at least two different heavy chains, wherein the heavy and light chains are capable of pairing with each other; (ii) culturing at least one clone of the host cell under conditions conducive to expression of nucleic acid sequences; (iii) screening at least one clone of the host cell for production of a mixture of antibodies having the desired effect by a functional assay; and (iv) identifying at least one clone that produces a mixture of antibodies having the desired effect. Preferably, the host cell comprises a nucleic acid sequence encoding a common light chain that is capable of pairing with at least two different heavy chains, such that produced antibodies comprise common light chains, as described above. In specific embodiments, culturing in step (ii) and screening in step (iii) of the method is performed with at least two clones. The method may optionally include an assay for measuring the expression levels of the antibodies that are produced, which assay may be during or after step (ii) according to the method, or later in the procedure. Such assays are well known to one of ordinary skill in the art and include protein concentration assays, immunoglobulin-specific assays such as ELISA, DELFIA, and the like. In particular embodiments of the method according to the invention, the host cell comprises nucleic acid sequence or sequences encoding at least 3, 4, 5, 6, 7, 8, 9, 10, or more, heavy chains capable of pairing with at least one light chain. Functional assays useful for the method according to the invention may be assays for apoptosis, ADCC, CDC, cell killing, inhibition of proliferation, virus neutralization, bacterial opsonization, receptor-mediated signaling, cell signaling, bactericidal activity, and the like. Useful screening assays for anti-cancer antibodies have, for instance, been described in U.S. Pat. No. 6,180,357, the entirety of which is incorporated herein by reference. Such assays may also be used to identify a clone according to the method of the invention. It is, for instance, possible to use enzyme-linked immunosorbent assays (ELISAs) for the testing of antibody binding to their target. Using such assays, it is possible to screen for antibody mixtures that most avidly bind the target antigen (or mixture of target antigens against which the mixture of antibodies is to be tested). Another possibility that can be explored is to directly screen for cytotoxicity or cytostatic effects. It is possible that upon such a different screen, other or the same clones producing mixtures of antibodies will be chosen than with the ELISA mentioned above. The screening for cell killing or cessation of growth of cancerous cells may be suitably used according to the invention. Cell death can be measured by various endpoints, including the absence of metabolism or the denaturation of enzymes. In one possible embodiment of the invention, the assay is conducted by focusing on cytotoxic activity toward cancerous cells as an endpoint. For this assay, a live/dead assay kit, for example, the LIVE/DEAD® Viability/Cytotoxicity Assay Kit (L-3224) by Molecular Probes (Eugene, Oreg.), can suitably be used. Other methods of assessing cell viability, such as tryspan blue exclusion, $^{51}$Cr release, Calcein-AM, ALAMAR BLUE™, LDH activity, and similar methods, can also be used. The assays may also include screening of the mixture of antibodies for specificity to the desired antigen-comprising tissue. The antibodies according to the invention may have a limited tissue distribution. It is possible to include testing the mixtures of antibodies against a variety of cells, cell types, or tissues, to screen for mixtures of antibodies that preferably bind to cells, cell types or tissues of interest.

Irrespective of a functional assay as described above, also disclosed herein are ways to determine the identity of the antibodies expressed by a clone, using methods such as isoelectric focusing (IEF), mass-spectrometry (MS), and the like. In certain embodiments, therefore, provided is use of MS and/or IEF in selecting a clone that expresses a mixture of antibodies according to the invention.

When monoclonal antibodies are produced by recombinant host cells, a screening step is usually performed to assess expression levels of the individual clones that were generated. The addition of more heavy chains to produce mixtures adds a level of complexity to the production of antibodies. When host cells are transfected with nucleic acid molecules encoding the light and heavy chains that will form the mixture of antibodies desired, independent clones may arise containing the same genetic information but, nevertheless, differing in expression levels, thereby producing different ratios of the encoded antibodies, giving rise to different mixtures of antibodies from the same genetic repertoire. The method according to the invention is useful for identifying a clone that produces an optimal mixture for a certain purpose.

The culturing and/or screening according to steps (ii) and (iii), respectively, may be suitably performed using high-throughput procedures, optionally in an automated fashion. Clones can, for instance, be cultured in 96-well plates or other multi-well plates, e.g., in arrayed format, and screened for production of a desired mixture. Robotics may be suitably employed for this purpose. Methods to implement high-throughput culturing and assays are generally available and known to one of ordinary skill in the art. It will also be clear that for this method according to the invention, it is beneficial to use host cells capable of high-level expression of proteins, without the need for amplification of the nucleic acid encoding the proteins in the cell. In one embodiment, the host cell is derived from a human embryonic retinoblast cell that has been immortalized or transformed by adenoviral E1 sequences. In a preferred embodiment, the cell is derived from PER.C6® (human retina cells that express adenovirus E1A and E1B proteins). This cell line has already been shown to be amenable to high-throughput manipulations, including culturing (WO 99/64582, the entirety of which is incorporated herein by reference).

In specific embodiments of the invention, the mixture of antibodies according to the method of identifying at least one host cell according to the invention comprises at least 2, 3, 4, 5, 6, 7, 8, 9, 10, or more, antibodies having different specificities and/or affinities.

A potential advantage of the method will be that it will allow exploring many possible combinations simultaneously, the combinations inherently including the presence of bispecific antibodies in the produced mixture. Therefore, more combinations can be tested than by just mixing purified known monoclonal antibodies, both in number of combinations and in ratios of presence of different antibodies in these combinations.

The clone that has been identified by the method according to the invention can be used for producing a desired mixture of antibodies. In certain embodiments, provided is a method of producing a mixture of antibodies, the method comprising culturing a host cell clone identified by the method of identifying at least one host cell clone that produces a mixture of antibodies according to the invention, culturing being under conditions conducive to expression of the nucleic acid molecules encoding at least one light chain and at least two different heavy chains. The produced antibodies may be recovered from the host cells and/or from the host cell culture, for example, from the culture medium. The mixture of antibodies can be recovered according to a variety of techniques known to one of ordinary skill in the art.

In certain embodiments, provided is a mixture of antibodies obtainable by the method according to the invention described above. The mixtures can be used for a variety of purposes, such as in the treatment or diagnosis of disease, and may replace, or be used in addition to, monoclonal or polyclonal antibodies.

The methods according to the invention may suitably use nucleic acid molecules for encoding the antibodies, which nucleic acid molecules have been obtained by any suitable method, including in vivo, e.g., immunization, methods or in vitro, for instance, antibody display methods (A. Plückthun et al., In vitro selection and evolution of proteins, in *Adv. Prot. Chem.*, F. M. Richards et al., Eds, Academic Press, San Diego, 2001, vol. 55:367-403, the entirety of which is incorporated herein by reference), such as phage display, ribosome display or mRNA display (C. Schaffitzel et al., In vitro selection and evolution of protein-ligand interactions by ribosome display, in *Protein-Protein Interactions, A Molecular Cloning Manual*, E. Golemis, Ed., Cold Spring Harbor Laboratory Press, New York, 2001, pp. 535-567, the entirety of which is incorporated herein by reference), and yeast display (e.g., WO 99/36569, the entirety of which is incorporated herein by reference). Methods of identifying antibodies to a certain target, which target may be a known antigen or an unknown antigen present in an antigenic mixture, by phage display are known to one of ordinary skill in the art. In general, a library of phages that express an antigen-binding domain or derivative thereof on their surface, the antigen-binding domain encoded by genetic material present in the phages, is incubated with the antigen or antigen mixture of interest, after which binding of a subpopulation of the phages that display antigen-binding sites binding to the desired antigen is obtained whereas the non-binding phages are discarded. Such selection steps may be repeated one, two, or more times to obtain a population of phages that are more or less specific for the antigen of interest. Phage display methods to obtain antibodies, parts or derivatives thereof have been extensively described in C. F. Barbas III et al., *Phage Display, A laboratory manual*, Cold Spring Harbor Laboratory Press, Cold Spring Harbor, N.Y., 2001, the entirety of which is incorporated herein by reference. The library used for such screening may be generated by using the genetic information of one or more light chains, combined with genetic information encoding a plurality of heavy chains. The library described by De Kruif et al. (1995b), the entirety of which is incorporated herein by reference, comprises seven light chains, the entirety of which is incorporated herein by reference. Therefore, in a panel of phages binding to a target, which can, e.g., be obtained by methods described in De Kruif et al. (supra), and U.S. Pat. No. 6,265,150 (the entirety of which is incorporated herein by reference), not more than seven different light chains will be represented and, if the panel is large enough, several phages with the same light chain coupled to unrelated heavy chains may be found. Such phages can be used to obtain the nucleic acid molecules useful in the methods according to the invention.

In certain embodiments, provided is a method for producing a mixture of antibodies to a target, the method comprising i) bringing an antibody display library comprising antibodies or antibody fragments into contact with material comprising a target, ii) at least one step of selecting antibodies or antibody fragments binding to the target, iii)

identifying at least two antibodies or antibody fragments binding to the target, wherein at least two antibodies or antibody fragments comprise a common light chain, iv) introducing a nucleic acid sequence encoding the light chain and a nucleic acid sequence or nucleic acid sequences encoding the heavy chains of at least two antibodies into a host cell, v) culturing a clone of the host cell under conditions conducive to expression of nucleic acid sequences. The antibody display library may be a phage display library, a ribosome display library, an mRNA display library, or a yeast display library. Steps i) and ii) may optionally be repeated one or more times.

The nucleic acid sequences encoding the antibodies obtained by the phage display, ribosome display or yeast display method may be converted to encode any desired antibody format such as IgG1, IgG2, IgG3, IgG4, IgA, IgM, IgD, IgE, before introducing them into a host cell, using standard molecular cloning methods and means known to one of ordinary skill in the art (e.g., described in Boel et al., 2000, the entirety of which is incorporated herein by reference).

It will be clear to one of ordinary skill in the art that libraries in which only one light chain is represented are especially useful in light of the invention, since all antibodies that can be obtained from such a library will have a common light chain that is functional in binding target antigen with each of the heavy chains. In other words, in accordance with the methods of the invention, the formation of non-functional light chain-heavy chain dimers is avoided. Phage antibody display libraries having extensive H chain repertoires and unique or very few L chain sequences have been disclosed in the art (Nissim et al., 1994; Vaughan et al., 1996, the entirety of which are incorporated herein by reference). In general, the specificity of an antibody appears to be determined to a large extent by its heavy chain. It is even possible to screen for and identify light chains that do not contribute significantly to binding of the antibody, which light chains also could be suitably used according to the invention. It may also be possible to follow the teachings of the invention but use one heavy chain and vary the light chains. However, the use of a common light chain and different heavy chains appears preferable and the following observations support the idea that the specificity of an antibody appears to be dominated by its heavy chain sequence. In the process of receptor editing, a mechanism of B-cells to monitor if their immunoglobulin receptor encodes a potentially harmful auto-antibody, B-cells expressing an auto-antibody replace the expressed heavy chain with another heavy chain while retaining the expressed light chain. Thus, a new antibody specificity is generated that does not encode an auto-antibody. This shows that a single light chain can successfully dimerize with multiple heavy chains to form different antibody specificities (Nemazee, 2000; Casellas et al., 2001, the entirety of which are incorporated herein by reference). Series of transfected cell lines using a single heavy chain gene with different light chain genes have been reported, the antibodies produced to a large extent maintaining their specificity, regardless of the light chain (Radic et al., 1991, the entirety of which is incorporated herein by reference).

Different antibodies have been obtained from a library that has been constructed using a single light chain (Nissim et al., 1994). Several antibodies have been obtained from the library described by De Kruif et al. (1995, the entirety of which is incorporated herein by reference), which was constructed using seven light chains, that have the same light chain but different specificities (see, e.g., Example 1: antibodies binding to EpCAM and to CD46, described in WO 01/48485 and WO 02/18948, respectively, the entirety of which are incorporated herein by reference).

Besides screening a phage library against a target, it will also be possible to start with an antibody that has already proven its merits and use the light chain of this antibody in the preparation of a library of heavy chains combined with this particular light chain only, according to methods known to one of ordinary skill in the art, such as phage display. Using this strategy, a monoclonal antibody can be used to obtain a mixture of antibodies according to the invention, functionally resembling a polyclonal or oligoclonal antibody to the same target. Alternatively, a method reminiscent of the method described by Jespers et al. (1994, the entirety of which is incorporated herein by reference) to obtain a human antibody based on a functional rodent antibody can be used. The heavy chain of a known antibody of non-human origin is first cloned and paired as a template chain with a repertoire of human light chains for use in phage display, after which the phages are selected for binding to the antigen or mixture of antigens. The selected light chain is, in turn, paired with a repertoire of human heavy chains displayed on a phage and the phages are selected again to find several heavy chains that, when paired with the light chain, are able to bind to the antigen or mixture of antigens of interest. This enables creating a mixture of human antibodies against a target for which thus far only a non-human monoclonal antibody is described. It is possible that a mixture according to the invention already has beneficial functional effects when the individual antibodies do not have high affinities for the target, whereas high affinities are often required for monoclonal antibodies to be effective. This would have the advantage that affinity maturation may be required in less instances for methods and mixtures according to the invention than when an approach with monoclonal antibodies is envisaged.

The heavy and light chain coding sequences can be introduced simultaneously or consecutively into the host cell. It is also an aspect to prepare a host cell comprising a recombinant nucleic acid encoding a light chain of an antibody. Such a cell can, for instance, be obtained by transfection of the nucleic acid and, optionally, a clone can be identified that has a high expression of the light chain. An established clone may then be used to add genetic information encoding 2, 3, 4, 5, 6, 7, 8, 9, 10, or more, heavy chains of the invention by introducing the nucleic acid molecules encoding these into cells of the clone that already contains the light chain. The nucleic acid molecules encoding the heavy chains may be introduced into the host cell concomitantly. It is, of course, also possible to introduce them consecutively, for instance, by using different selection markers, which can be advantageous if not all heavy chains can be introduced simultaneously because the cells do not take up enough copies of recombinant nucleic acid molecules. Methods to introduce recombinant nucleic acid molecules into host cells are well known to one of ordinary skill in the art and include transfection, electroporation, calcium phosphate precipitation, virus infection, and the like. One of ordinary skill in the art has several possibilities to introduce more vectors with nucleic acid sequences of interest into the same host cell, see, e.g., Sambrook, Fritsch and Maniatis, *Molecular Cloning: A Laboratory Manual*, $2^{nd}$ edition, 1989; *Current Protocols in Molecular Biology*, F. M. Ausubel et al., eds, 1987; the series *Methods in Enzymology* (Academic Press, Inc.), the entirety of which are incorporated herein by reference.

Suitable dominant selection markers for introducing nucleic acids into eukaryotic host cells, as used herein, may be G418 or neomycin (geneticin), hygromycin or mycophenolic acid, puromycin, and the like, for which genes encoding resistance are available on expression vectors. Further possibilities include, for instance, the use of vectors containing DHFR genes or glutamate synthetase to select in the presence of methotrexate in a DHFR⁻ cell or the absence of glutamine in a glutamine auxotroph, respectively. The use of expression vectors with different selection markers enables subsequent transfections with heavy chain sequences of interest into the host cell, which already stably contains other heavy chains introduced previously by use of other selection markers. It is also possible to use selection markers that can be used more than once, for instance, when containing mutations, introns, or weakened promoters that render them concentration-dependent (e.g., EP0724639; WO 01/32901; U.S. Pat. No. 5,733,779, the entirety of which are incorporated herein by reference). Alternatively, a selection marker may be re-used by deleting it from the host cell after use, for example, by site-specific recombination. A selectable marker located between sequences recognized by a site-specific recombinase, for example, lox-sites or FRT-sites, is used for the generation of the first stable transfectant (for Cre-lox site-specific recombination, see, Wilson and Kola, 2001, the entirety of which is incorporated herein by reference). Subsequently, the selectable marker is excised from the host cell DNA by the matching site-specific recombinase, for example, Cre or Flp. A subsequent transfection can suitably use the same selection marker.

Different host cell clones each comprising the genetic information encoding a different light chain may be prepared. If the antibodies are identified by an antibody display method, it is thus possible to prepare several host cells, each comprising one light chain present in the antibody display library. After identifying antibodies that bind to a target using antibody display, the nucleic acid molecules encoding the heavy chains can be introduced into the host cell containing the common light chain that is capable of pairing to the heavy chains. It is, therefore, an aspect to provide a method for making a host cell for production of a mixture of antibodies, the method comprising the steps of: introducing into the host cell a nucleic acid sequence encoding a light chain and nucleic acid sequence or sequences encoding 3, 4, 5, 6, 7, 8, 9, 10, or more, different heavy chains that are capable of pairing with the light chain, wherein the nucleic acid molecules are introduced consecutively or simultaneously. It is, of course, also possible to introduce at least two of the nucleic acid molecules simultaneously, and introduce at least one other of the nucleic acid molecules consecutively.

In yet another aspect, a method is provided for making a recombinant host cell for production of a mixture of antibodies, the method comprising the step of: introducing a nucleic acid sequence or nucleic acid sequences encoding 2, 3, 4, 5, 6, 7, 8, 9, 10, or more, different heavy chains into a recombinant host cell comprising a nucleic acid sequence encoding a light chain capable of pairing with at least two of the heavy chains.

If it appears that a recombinant host cell of the invention does not express sufficient light chain to dimerize with all of the expressed at least two heavy chains, extra copies of the nucleic acid molecules encoding the light chain may be transfected into the cell.

Besides random integration after transfection, methods to integrate the transgenes in predetermined positions of the genome resulting in favorable expression levels can also be used according to the invention. Such methods may, for instance, employ site-specific integration by homologous recombination (see, e.g., WO 98/41645, the entirety of which is incorporated herein by reference) or make use of site-specific recombinases (Gorman and Bullock, 2000, the entirety of which is incorporated herein by reference).

It is yet another aspect to provide a transgenic non-human mammal or a transgenic plant comprising a nucleic acid sequence encoding a light chain and a nucleic acid sequence or nucleic acid sequences encoding at least two different heavy chains that are capable of pairing with the light chain, wherein the nucleic acid sequences encoding the light and heavy chains are under the control of a tissue-specific promoter. Promoters in plants may also be non-tissue specific and general gene-expression elements, such as the CaMV 35S promoter and nopaline synthase polyA addition site, can also be used. The light chain is a common light chain according to the invention. In specific embodiments, the transgenic animal or plant according to the invention comprises 3, 4, 5, 6, 7, 8, 9, 10, or more, heavy chain sequences. Besides cell culture as a production system for recombinant proteins, the art also discloses the use of transgenic animals, transgenic plants and, for instance, transgenic chickens to produce proteins in the eggs, and the like to produce recombinant proteins of interest (Pollock et al., 1999; Larrick and Thomas, 2001; WO 91/08216, the entirety of which are incorporated herein by reference). These usually comprise the recombinant gene or genes encoding one or more proteins of interest in operable association with a tissue-specific promoter. It has, for instance, been shown that recombinant antibodies can be produced at high levels in the milk of transgenic animals that contain the nucleic acids encoding a heavy and a light chain behind a mammary gland-specific promoter (e.g., Pollock et al., 1999; WO 95/17085, the entirety of which are incorporated herein by reference). Particularly useful in this respect are cows, sheep, goats, pigs, rabbits, mice, and the like, which can be milked to obtain antibodies. Useful promoters are the casein promoters, such as the β-casein promoter, the αS1-casein promoter, the whey acidic protein (WAP) promoter, the β-lactoglobulin promoter, the α-lactalbumin promoter, and the like. Production of biopharmaceutical proteins in the milk of transgenic mammals has been extensively described (e.g., Pollock et al., 1999, the entirety of which is incorporated herein by reference). Besides mammary gland-specific promoters, other tissue-specific promoters may be used, directing the expression to the blood, urine, saliva, and the like. The generation of transgenic animals comprising recombinant nucleic acid molecules has been extensively documented and may include micro-injection of oocytes (see, e.g., Wilmut and Clark, 1991, the entirety of which is incorporated herein by reference), nuclear transfer after transfection (e.g., Schnieke et al., 1997, the entirety of which is incorporated herein by reference), infection by recombinant viruses (e.g., U.S. Pat. No. 6,291,740, the entirety of which is incorporated herein by reference), and the like. Nuclear transfer and cloning methods for mammalian cells are known to one of ordinary skill in the art, and are, for example, described in Campbell et al., 1996; Wilmut et al., 1997; Dinnyes et al., 2002; WO 95/17500; and WO 98/39416, the entirety of which are incorporated herein by reference. It is possible to clone animals and to generate lines of animals that are genetically identical, which renders it possible for a person skilled in the art to create such a line once an individual animal producing the desired mixture of antibodies has been identified. Alternatively, classical breeding methods can be used to generate transgenic offspring. Strategies for the generation of transgenic animals for production of recombinant proteins in milk are described in Brink et al., 2000, the entirety of which is incorporated herein by reference.

Transgenic plants or plant cells producing antibodies have also been described (Hiatt et al., 1989; Peeters et al., 2001, the entirety of which are incorporated herein by reference) and useful plants for this purpose include corn, maize, tobacco, soybean, alfalfa, rice, and the like. Constitutive promoters that can, for instance, be used in plant cells are the CaMV 35S and 19S promoters and *Agrobacterium* promoters nos and ocs. Other useful promoters are light-inducible promoters such as rbcS. Tissue-specific promoters can, for instance, be seed-specific, such as promoters from zein, napin, beta-phaseolin, ubiquitin, or tuber-specific, leaf-specific (e.g., useful in tobacco), root-specific, and the like. It is also possible to transform the plastid organelle by homologous recombination to express proteins in plants.

Methods and means for expression of proteins in recombinant plants or parts thereof, or recombinant plant cell culture, are known to one of ordinary skill in the art and have been, for instance, described in Giddings et al., 2000; WO 01/64929; WO 97/42313; U.S. Pat. Nos. 5,888,789, 6,080,560 (for practical guidelines, see *Methods In Molecular Biology* vol. 49 "Plant Gene Transfer And Expression Protocols," H. Jones, 1995), the entirety of which are incorporated herein by reference. Other transgenic systems for producing recombinant proteins have also been described, including the use of transgenic birds to produce recombinant proteins in eggs (e.g., WO 97/47739, the entirety of which is incorporated herein by reference) and the use of transgenic fish (e.g., WO 98/15627, the entirety of which is incorporated herein by reference), and can be used in combination with the teachings of the invention to obtain mixtures of antibodies. It is also possible to use an in vitro transcription/translation or in vitro translation system for the expression of mixtures of antibodies according to the invention. It will be clear to one of ordinary skill in the art that the teachings of the current invention will allow producing mixtures of antibodies in systems where recombinant nucleic acids encoding the light chain and heavy chains can be introduced and expressed. Preferably, such systems are able to produce antibodies encoded by nucleic acid sequences, without the use of amplification of nucleic acid sequences in the systems. In another aspect, a cell from a transgenic non-human animal or a transgenic plant according to the invention is provided. Such cells can be used to generate the animals or plants according to the invention, using techniques known to one of ordinary skill in the art, such as nuclear transfer or other known methods of cloning whole organisms from single cells. The cells according to the invention may also be obtained by introducing the light and at least two heavy chain sequences into isolated cells of non-human animals or plants, which cells are capable of becoming part of a transgenic animal or plant. Particularly useful for such purposes are embryonic stem cells. These can contribute to the germ line and, therefore, the genetic information introduced into such cells can be passed to future generations. In addition, plant cell cultures of cotton, corn, tomato, soybean, potato, petunia, and tobacco can be utilized as hosts when transformed with the nucleic acid molecules encoding the light chain and the heavy chains, for instance, by use of the plant-transforming bacterium *A. tumefaciens* or by particle bombardment or by infecting with recombinant plant viruses.

In certain embodiments, provided is a pharmaceutical composition comprising a mixture of recombinantly produced antibodies and a suitable carrier, wherein at least two different heavy chains are represented in the mixture of recombinantly produced antibodies. Pharmaceutically acceptable carriers as used herein are exemplified, but not limited to, adjuvants, solid carriers, water, buffers, or other carriers used in the art to hold therapeutic components, or combinations thereof. In particular embodiments, 3, 4, 5, 6, 7, 8, 9, 10, or more, different heavy chains are represented in the mixture. The mixture can be obtained by mixing recombinantly produced monoclonal antibodies, but may also be obtained by methods according to the invention. The mixture may, therefore, comprise a common light chain for the antibodies. The mixture may comprise bispecific antibodies. The mixture may be produced from a clone that was derived from a single host cell, e.g., from a population of cells containing the same recombinant nucleic acid molecules. The term "recombinantly produced" as used herein refers to production by host cells that produce antibodies encoded by recombinant nucleic acids introduced in such host cells or ancestors thereof. It does not, therefore, include the classical method of producing polyclonal antibodies, whereby a subject is immunized with an antigen or antigen-comprising mixture, after which the antibodies produced by this subject are recovered from the subject, for example, from the blood.

In certain embodiments, provided is a mixture of antibodies wherein at least two heavy chains are represented for use in the treatment or diagnosis of a human or animal subject. In another aspect, provided is the use of a mixture of antibodies wherein at least two different heavy chains are represented for the preparation of a medicament for use in the treatment or diagnosis of a disease or disorder in a human or animal subject. In particular embodiments, 2, 3, 4, 5, 6, 7, 8, 9, 10, or more, heavy chains are represented in the mixture. The mixtures of antibodies may be mixtures of antibodies according to the invention or obtained by methods according to the invention. Antibodies present in the mixture may preferably comprise a common light chain. The mixtures may comprise bispecific antibodies and may be recombinantly produced from a clone that was derived from a single host cell, i.e., from a population of cells containing the same recombinant nucleic acid molecules. The targets may be used to screen an antibody display library, as described supra, to obtain 2, 3, 4, 5, 6, 7, 8, 9, 10, or more, antibodies comprising a common light chain that bind to the target and produce a mixture of these according to the teachings of the invention. Virtually any area of medicine where monoclonal antibodies can be used is amenable for the use of the mixtures according to the invention. This can, e.g., include treatment of auto-immune diseases and cancer, including solid tumors of the brain, head, neck, breast, prostate, colon, lung, and the like, as well as hematologic tumors, such as B-cell tumors. Neoplastic disorders which can be treated with the mixtures according to the invention include leukemias, lymphomas, sarcomas, carcinomas, neural cell tumors, squamous cell carcinomas, germ cell tumors, metastases, undifferentiated tumors, seminomas, melanomas, myelomas, neuroblastomas, mixed cell tumors, neoplasias caused by infectious agents, and other malignancies. Targets for the antibody mixtures may include, but are not limited to, the HER-2/Neu receptor, other growth factor receptors (such as VEGFR1 and VEGFR2 receptors), B-cell markers (such as CD19, CD20, CD22, CD37, CD72, etc.), T-cell markers (such as CD3, CD25, etc.), other leukocyte cell surface markers (such as CD33 or HLA-DR, etc.), cytokines (such as TNF), interleukins, receptors for these cytokines (such as members of the TNF receptor family), and the like. It is anticipated that the use of such mixtures of antibodies in the treatment of cancerous tissues or other complex multi-antigen-comprising cells such as microorganisms or viruses will give rise to less occurrence of epitope-loss escape variants than the use of single monoclonal antibodies. Several treatments nowadays use polyclonal mixtures of antibodies, which are derived from immunized humans or animals. These treatments may be replaced by use of the mixtures according to the invention. Use of these mixtures can also include use in graft-versus-host rejections known in the art of transplantation, e.g., by use of anti-thymocyte antibodies. It is anticipated that the mixtures of antibodies are superior to monoclonal antibodies in the treatment of complex antigens or antigen-comprising mixtures such as bacteria or viruses. Therefore, use according to the invention can also include use against strains of bacteria and fungi, e.g., in the treatment of infectious diseases due to pathogenic bacteria such as multidrug-resistant *S. aureus* and the like, fungi such as *Candida albicans* and *Aspergillus* species, yeast and the like. The mixtures according to the invention may also be used for post exposure prophylaxis against viruses, such as members of the genus *Lyssavirus*, e.g., rabies virus, or for therapeutic or prophylactic use against viruses such as Varicella-Zoster Virus, Adenoviruses, Respiratory Syncitium Virus, Human Immunodeficiency Virus, Human Metapneumovirus, influenza virus, West Nile Virus, the virus causing Severe Acute Respiratory Syndrome (SARS), and the like. Mixtures according to the inventions can also be used to protect against agents, both bacteria and viruses, and against toxic substances that are potential threats of biological warfare. Therefore, use according to the invention can also include use against strains of bacteria such as *Bacillus anthracis, Clostridium botulinum* toxin, *Clostridium perfringens* epsilon toxin *Yersinia Pestis, Francisella tulariensis, Coxiella burnetii, Brucella* species, *Staphylococcus* enterotoxin B, or against viruses such as Variola major, alpha viruses causing meningoencephalitis syndromes (EEEV, VEEV, and WEEV), viruses known to cause hemorrhagic fevers such as Ebola, Marburg and Junin virus or against viruses such as Nipah virus, Hantaviruses, Tick borne encephalitis virus and Yellow fever virus or against toxins, for example, ricin toxin from *Ricinus communis* and the like. Use of the mixtures according to the invention can also include use against unicellular or multicellular parasites. Recombinant mixtures of antibodies according to the invention may become a safe alternative to polyclonal antibodies obtained from pools of human sera for passive immunization or from sera of hyper-immunized animals. The mixtures may be more efficacious than recombinant monoclonal antibodies in various therapeutic applications, including cancer, allergy, viral diseases, chronic inflammation, and the like.

It has been described that homodimerization of tumor-reactive monoclonal antibodies markedly increases their ability to induce growth arrest or apoptosis of tumor cells (Ghetie et al., 1997, the entirety of which is incorporated herein by reference). Possibly, when antibodies against receptors or other surface antigens on target cells, such as tumor cells or infectious microorganisms, are produced according to the invention, the bispecific antibodies present in mixtures according to the invention may also cross-link different receptors or other antigens on the surface of target cells and, therefore, such mixtures may be very suitable for killing such cells. Alternatively, when bispecific antibodies are less desirable, the invention also provides methods to recombinantly produce mixtures of antibodies comprising mainly monospecific antibodies. It has been described that the efficacy of treatment with Rituximab™ (anti-CD20 monoclonal antibody) was increased when anti-CD59 antibodies were added (Herjunpaa et al., 2000, the entirety of which is incorporated herein by reference).

Therefore, it is thought that inclusion of antibodies against CD59 in a mixture comprising anti-tumor antibodies in the form of B-cell receptor-recognizing antibodies increases the sensitivity of tumor cells to complement attack. It has also been shown that a triple combination cocktail of anti-CD19, anti-CD22, and anti-CD38-saporin immunotoxins is much more effective than the individual components in the treatment of human B-cell lymphoma in an immunodeficient mouse model (Flavell et al., 1997, the entirety of which is incorporated herein by reference). Many other combinations may also be feasible and can be designed by one of ordinary skill in the art. In general, the use of antibody mixtures that are capable of recognizing multiple B-cell epitopes will likely decrease the occurrence of escape variants.

Another possible target is a transmembrane tyrosine kinase receptor, encoded by the Her-2/Neu (ErbB2) proto-oncogene (see, e.g., U.S. Pat. Nos. 5,772,997 and 5,783,186 for anti-Her2 antibodies, the entirety of which are incorporated herein by reference). Her-2 is overexpressed on 30% of highly malignant breast cancers and successful antibodies against this target marketed under the name HERCEPTIN™ (Trastuzumab) have been developed. It has been shown that targeting multiple Her-2 epitopes with a mixture of monoclonal antibodies results in improved antigrowth activity of a human breast cancer cell line in vitro and in vivo (Spiridon et al., 2002, the entirety of which is incorporated herein by reference). Her-2 may, therefore, be a good target for antibody mixtures according to the invention. Antibodies useful for this purpose can be obtained by methods described in the invention, including antibody display methods.

Human antibodies are capable of eliciting effector function via binding to immunoglobulin receptors on immune effector cells. Human IgG and, in particular, IgG1 and IgG3, fix complement to induce CDC and interact with Fcγ receptors to induce antibody-dependent cell-mediated cytotoxicity (ADCC), phagocytosis, endocytosis, induction of respiratory burst and release of inflammatory mediators and cytokines. Human IgA interacts with FcαR, also resulting in efficient activation of ADCC and phagocytosis of target cells. Hence, due to the differential distribution of FcγR and FcαR on peripheral blood cells (Huls et al., 1999, the entirety of which is incorporated herein by reference), using a mixture of antibodies directed against the target and consisting of both IgG and IgA would potentially maximize the recruitment and activation of different immune effector cells. Such a mixture of both IgG and IgA could be obtained by producing the IgG and IgA monoclonal antibody in a separate production process using two distinct production cell lines, but could also be obtained from a single cell line producing both the IgG and the IgA monoclonal antibody. This would have the advantage that only a single production process has to be developed. Thus, when different heavy chains are mentioned, heavy chains differing in their constant regions are also encompassed in the invention. The principle of using a common light chain can also be used for the production of a mixture of isotypes from a host cell. Therefore, certain embodiments of the invention provide a method for producing a mixture of antibodies comprising different isotypes from a host cell, the method comprising the step of: culturing a host cell comprising a nucleic acid sequence encoding a light chain and nucleic acid sequences encoding at least two heavy chains of different isotype that are capable of pairing with the light chain, under conditions conducive to expression of the nucleic acid sequences. According to this aspect, different heavy chains may have identical variable regions and only differ in their constant regions (i.e., be of different isotype and have the same specificity). In a particular embodiment, the isotypes comprise at least an IgG and an IgA and/or IgM, preferably IgG1 or IgG3 and IgA. Other combinations of IgG1, IgG2, IgG3 and IgG4 can also be used. In these embodiments, bispecific antibodies will not be produced because the variable regions are the same.

Figure 11:
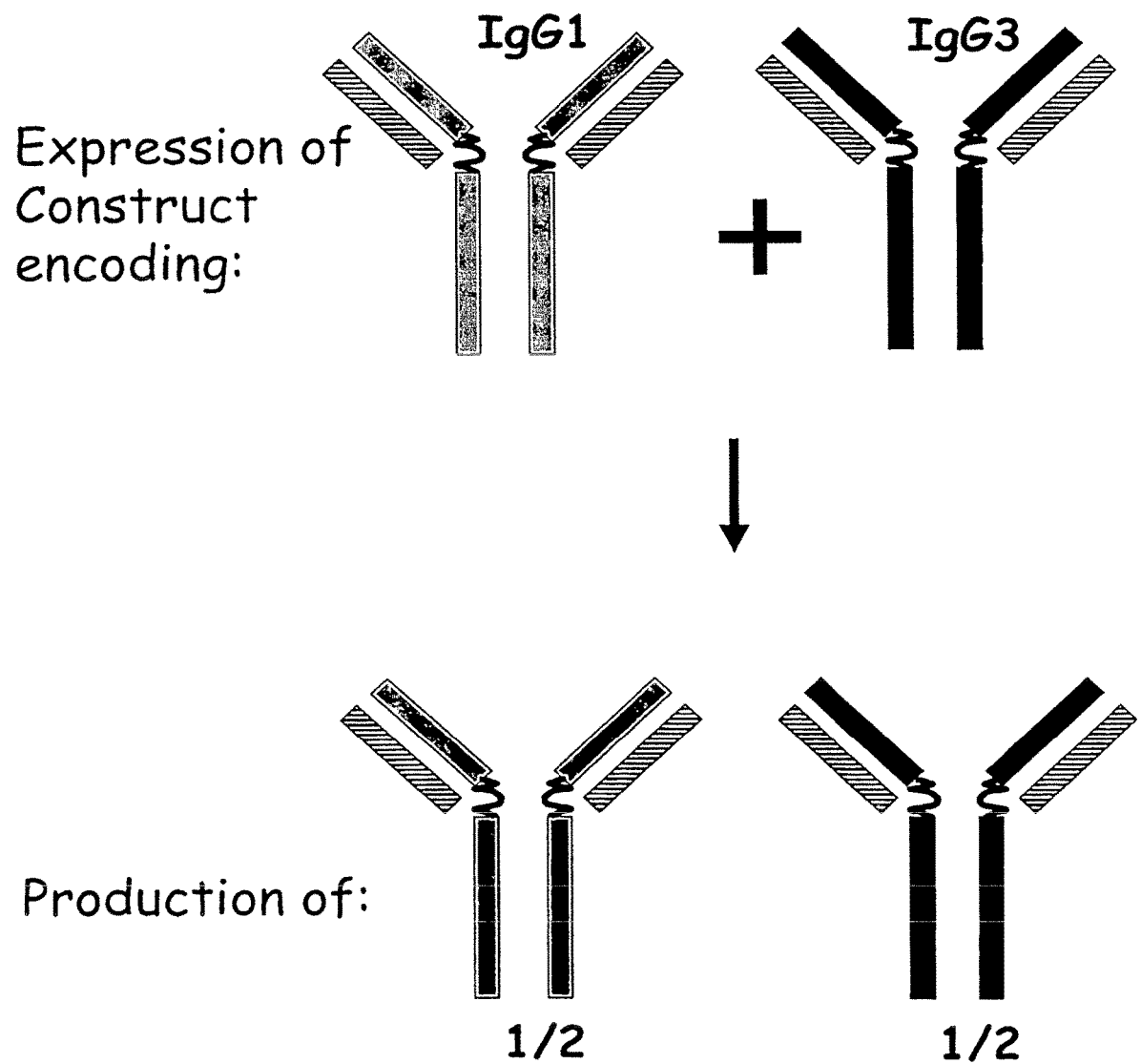
FIG. 11 depicts expression of a mixture of human IgG isotypes consisting of a common light chain but with different binding specificities in a single cell to avoid the formation of bispecific antibodies. The different binding specificities are indicated by the different colors of the $V_H$ sequences. The common light chain is indicated with the vertically striped bars. The IgG1 isotype is indicated with the grey Fc and the IgG3 isotype is indicated with the black Fc part.

In other embodiments of this aspect, not only the constant regions of the heavy chains may differ, but also the variable regions, thereby giving rise to different specificities paired with the same light chain. When bispecific antibodies are not desired for a given purpose, for example, because the mixtures of antibodies are less efficacious because of the presence of the bispecific antibodies, it is possible to use at least two heavy chains combined with the common light chain according to the invention wherein the heavy chains differ sufficient in their constant regions to reduce or prevent pairing between the different heavy chains, for example, by using heavy chains of different isotypes, such as an IgG1 and an IgG3 (see FIG. 11 for a schematic representation). It is anticipated that the heavy chains of different isotype will pair much less efficient, if at all, compared to the same heavy chains. Alternatively, it is also possible to engineer the different heavy chains in their constant region such that homodimerization is favored over heterodimerization, e.g., by introducing self-complementary interactions (see, e.g., WO 98/50431 for possibilities, such as "protuberance-into-cavity" strategies (see, WO 96/27011, the entirety of which is incorporated herein by reference)). It is, therefore, another aspect to provide a method for producing a mixture of antibodies in a recombinant host, the method including the step of: expressing in a recombinant host cell a nucleic acid sequence encoding a common light chain and nucleic acid sequences encoding at least two different heavy chains that differ in the variable region and that are capable of pairing with the common light chain, and wherein the heavy chains further differ in their constant regions sufficiently to reduce or prevent pairing between the different heavy chains. In one embodiment, the heavy chains are of different isotype. In specific embodiments, 3, 4, 5, 6, 7, 8, 9, 10, or more, different heavy chains are expressed. Mixtures of antibodies obtainable by this method are also embodied in the invention. Such mixtures will comprise mainly monospecific antibodies.

Figure 9:
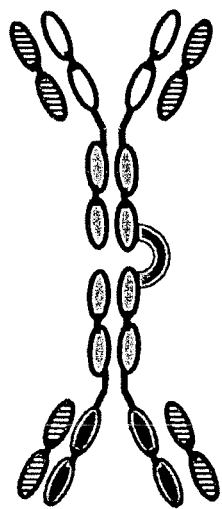
FIG. 9 shows dimeric bispecific IgA with a single light chain (indicated by horizontally striped bar). The method of the invention will produce a mixture of forms wherein different heavy chains can be paired. Only the most simple form is depicted in this schematic representation. A J-chain is shown to join the two monomers.

The teachings herein can also be used to obtain novel multispecific antibodies or mixtures thereof. Therefore, in another aspect, provided is a method for producing a mixture of antibodies comprising dimeric IgA isotype {(IgA)$_2$} antibodies in a recombinant host, wherein at least part of the dimeric IgA antibodies have different binding regions in each of the IgA sub-units, the method comprising the step of: expressing in a recombinant host cell a nucleic acid sequence encoding a common light chain and nucleic acid sequences encoding at least two different heavy chains of IgA isotype capable of pairing to the common light chain, wherein the different heavy chains differ in their variable region. Dimerization of the IgA molecules can be enhanced by co-expressing J-chain (Yoo et al., 1999, the entirety of which is incorporated herein by reference). Dimeric IgA antibodies have two specificities (see FIG. 9 for a schematic representation of one possible form produced and present in the mixture).

Figure 10:
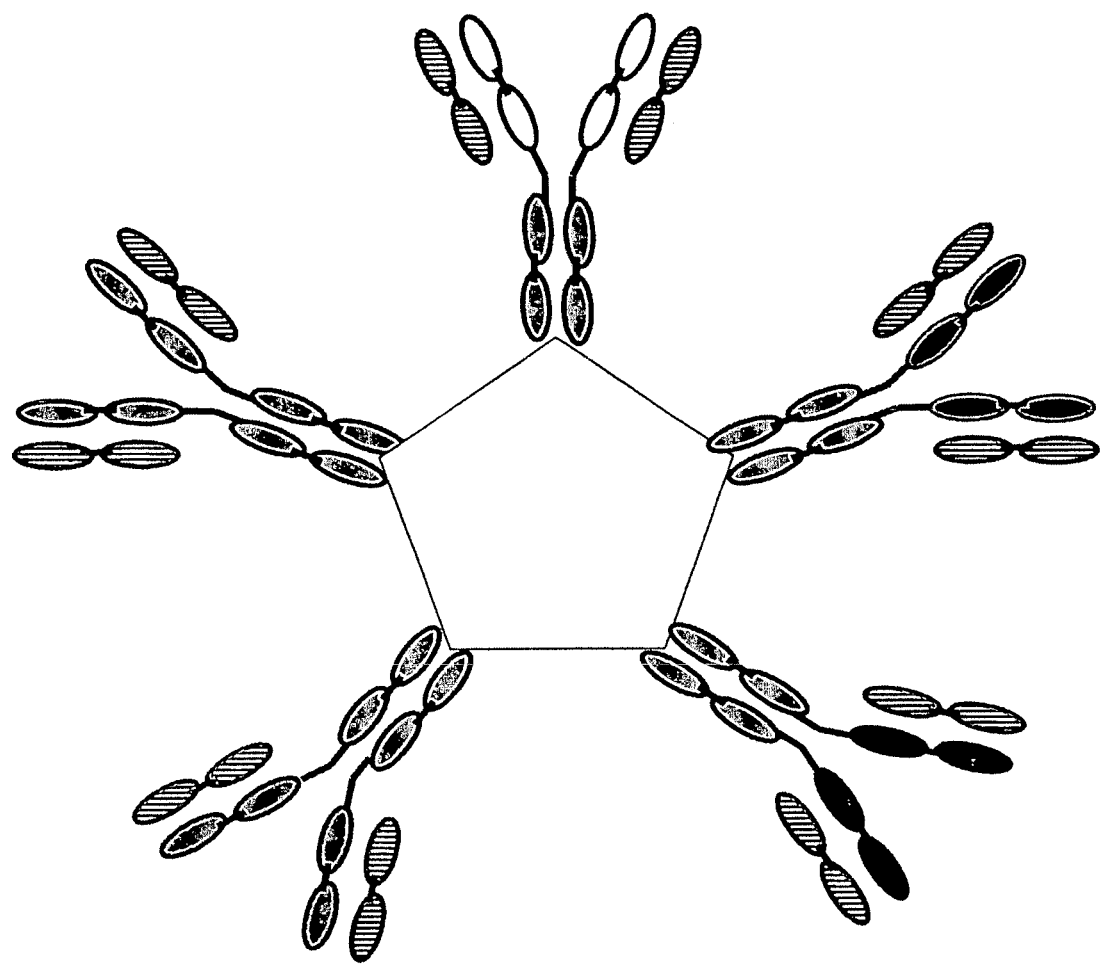
FIG. 10 is a pentameric multispecific IgM with a single light chain (indicated by horizontally striped bars). The method of the invention will produce a mixture of many different forms, wherein different heavy chains can be paired. Only the most simple form is depicted in this schematic representation when five different heavy chains are expressed with a single light chain and all five different heavy chains are incorporated in the pentamer and paired to the same heavy chain. Pentamers with less specificities can also be formed by incorporation of less than five different heavy chains. Hexamers can also be obtained, especially when the J-chain is not expressed.

In certain embodiments, provided is a method for producing a mixture of antibodies comprising an IgM antibody having at least two different specificities, the method comprising expressing in a recombinant host cell a nucleic acid sequence encoding a common light chain and nucleic acid sequences encoding at least two different heavy chains of IgM isotype, wherein the heavy chains are capable of pairing to the common light chain and form functional antigen-binding regions. Up to five specificities can be comprised in an IgM pentamer in the presence of a J-chain and up to six in an IgM hexamer in the absence of a J-chain (Yoo et al., 1999). Therefore, in specific embodiments, 3, 4, 5, or 6 IgM heavy chains are co-expressed with the common light chain according to this aspect. See FIG. 10 for a schematic representation of one of the possible forms that can be produced and present in the mixture according to this aspect, when five different heavy chains are expressed with a common light chain. Also provided is for IgA dimers, IgM pentamers or hexamers having at least two different specificities. These molecules can be produced from a clone of a single host cell according to the invention. Such molecules harboring antigen-binding regions with different specificities can bind different epitopes on the same antigen, different antigens on one cell, or different antigens on different cells, thereby cross-linking the antigens or cells.

In certain embodiments, provided is a method for identifying a mixture of antibodies having a desired effect in a functional assay, the method comprising i) adding a mixture of antibodies in a functional assay, and ii) determining the effect of the mixture in the assay, wherein the mixture of antibodies comprises antibodies having a common light chain. In a preferred embodiment, the mixture is comprised in a composition of the invention.

Also provided is a method for recombinant expression of one or more proteins in a single host cell, wherein at least four different polypeptides are expressed in the single host cell. Each polypeptide is independently expressed and may be under control of a heterologous promoter. The protein or proteins may be isolated separately or as a mixture from a culture of the host cell. Preferably, the host cell of this embodiment is a human cell and/or may be derived from a retina cell, more preferably a cell comprising adenovirus E1 sequences in its genome, most preferably a PER.C6® cell (human retina cells that express adenovirus E1A and E1B proteins).

EXAMPLES

The following examples are provided to illustrate the invention and are not to be construed in any way to limit the scope of the invention. The practice of this invention will employ, unless otherwise indicated, conventional techniques of immunology, molecular biology, microbiology, cell biology, and recombinant DNA, which are within the skill of the art. See, e.g., Sambrook, Fritsch and Maniatis, *Molecular Cloning: A Laboratory Manual*, 2$^{nd}$ edition, 1989; *Current Protocols in Molecular Biology*, F. M. Ausubel, et al., eds, 1987; the series *Methods in Enzymology* (Academic Press, Inc.); *PCR2: A Practical Approach*, M. J. MacPherson, B. D. Hams, G. R. Taylor, eds, 1995; *Antibodies: A Laboratory Manual*, Harlow and Lane, eds, 1988, the entirety of which are incorporated herein by reference.

Example 1

Figure 4:
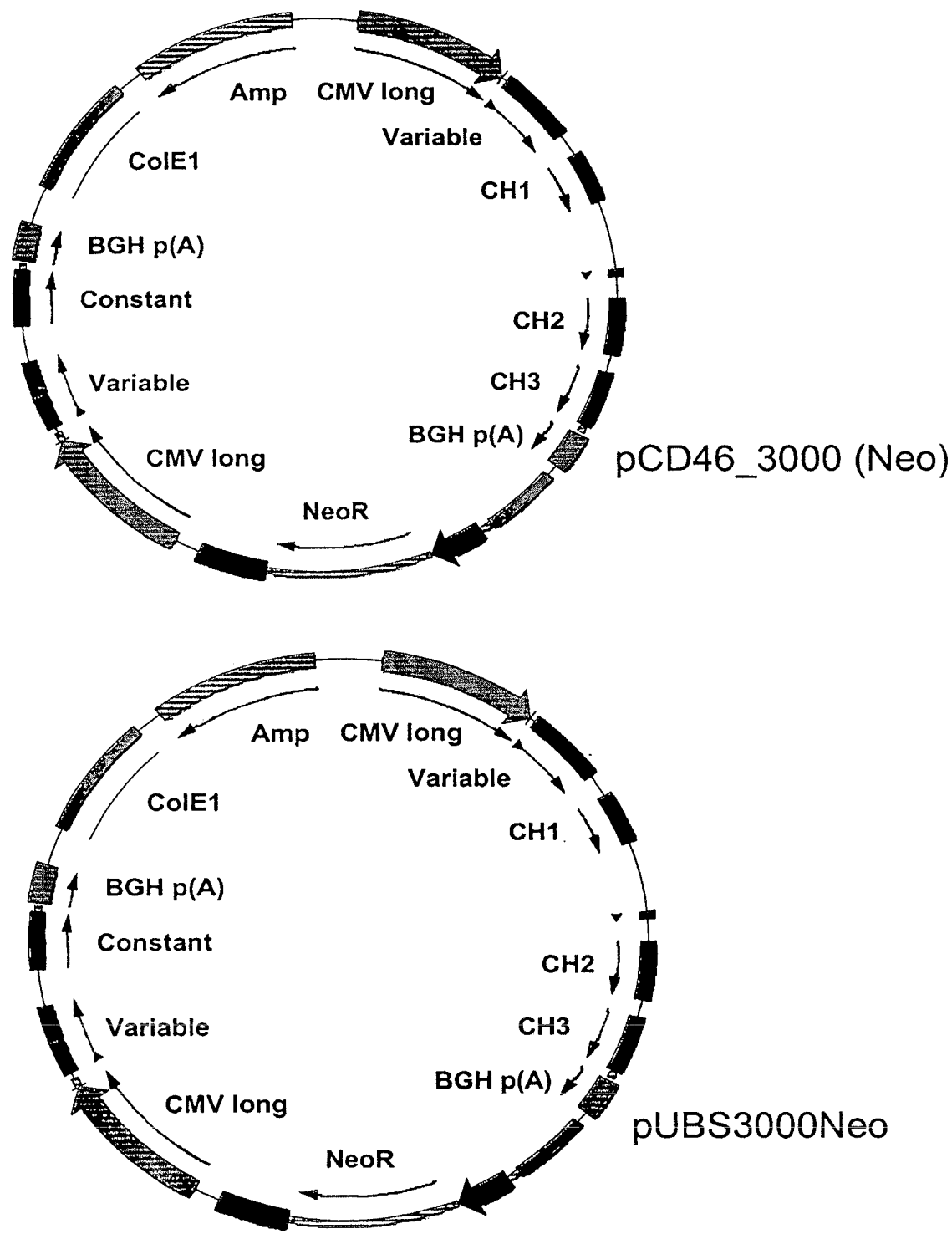
FIG. 4 is an overview of plasmids pUBS3000Neo and pCD46_3000 (Neo).

Production of a Mixture of Monoclonal Antibodies with a Common Light Chain and Two Different Heavy Chain-Variable Regions in a Single Cell Clone UBS-54 and Clone K53 were previously isolated by selections on the colorectal cell line SW40 (Huls et al., 1999) and on a heterogeneous mixture of mononuclear cells of a patient with multiple myeloma (WO 02/18948, the entirety of which is incorporated herein by reference), respectively, with a semi-synthetic library (de Kruif et al., 1995b). Further studies revealed that clone UBS-54 and K53 bound to the EP-CAM homotypic adhesion molecule (Huls et al., 1999) and the membrane cofactor protein CD46 (WO 02/18948), respectively. DNA sequencing of the clones revealed that they were unique in the Heavy chain CDRs, but that they contained an identical light chain sequence (FIG. 3). The $V_H$ and $V_L$ of clones UBS-54 and K53 were inserted into an expression vector containing the HAVT20 leader sequence and all the coding sequences for the constant domains of a human IgG1 with a Kappa light chain by a method essentially as described (Boel et al., 2000), which resulted in plasmids pUBS3000Neo and pCD46_3000(Neo) (FIG. 4). These plasmids were transiently expressed, either alone or in combination in PER.C6® cells (human retina cells that express adenovirus E1A and E1B proteins). In brief, each 80 cm$^2$ flask was transfected by incubation for four hours with 140 µl lipofectamine+10 µg DNA (either pUBS3000Neo, pCD46_3000(Neo) or 10 µg of both) in serum-free DMEM medium at 37° C. After four hours this was replaced with DMEM+10% FBS and the cells were grown overnight at 37° C. Cells were then washed with PBS and the medium was replaced with Excell 525 medium (JRH Bioscience). The cells were allowed to grow at 37° C. for six days, after which the cell culture supernatant was harvested. Human IgG-specific ELISA analysis (described in WO 00/63403, the entirety of which is incorporated herein by reference) indicated that IgG was present at approximately 10 µg/ml for all flasks containing expression plasmids. No IgG1 was present in a control flask which was not transfected with expression plasmid.

Figure 5:
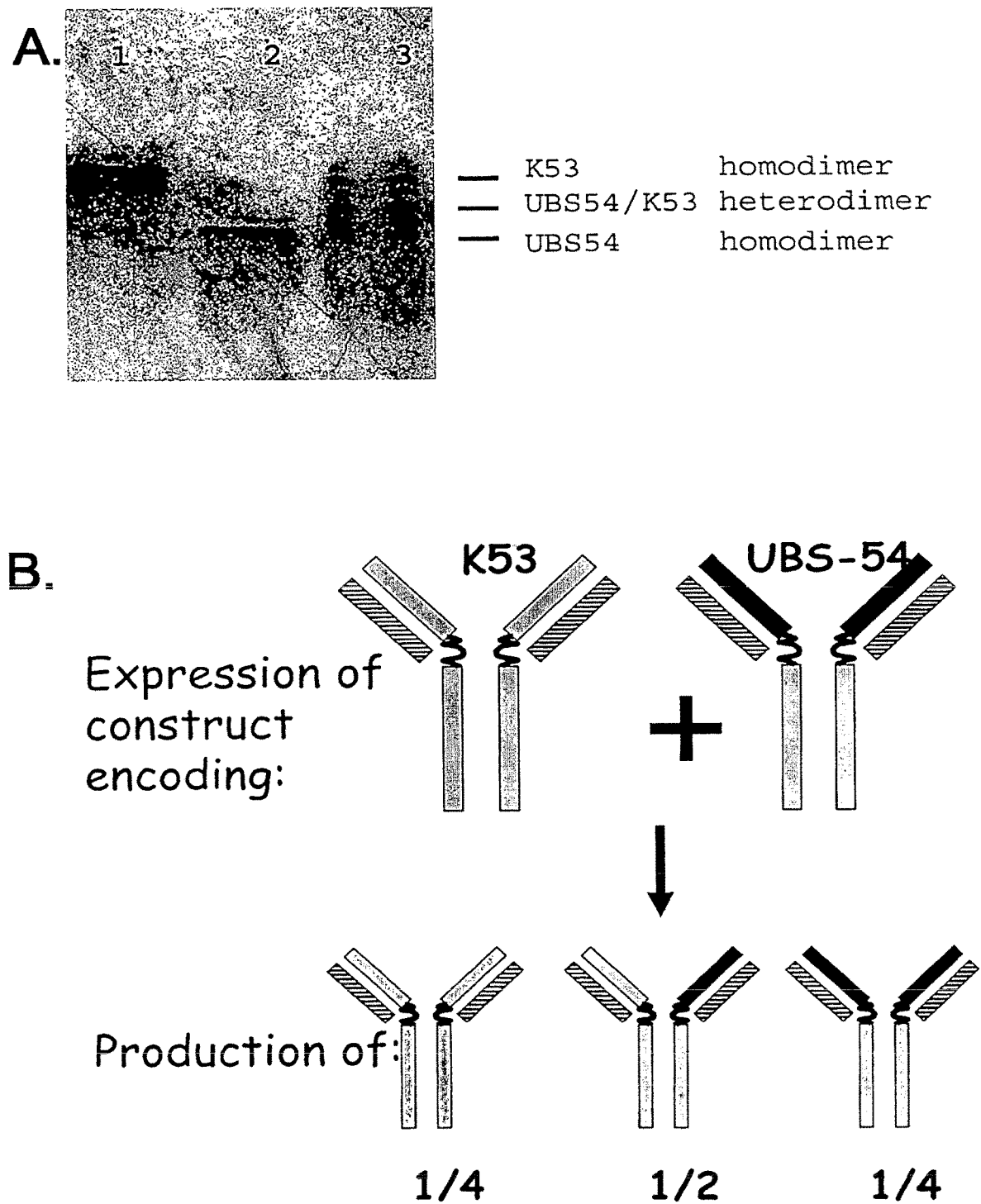
FIG. 5, Panel A, shows the isoelectric focusing (IEF) of transiently expressed pUBS3000Neo, pCD46_3000(Neo) and a combination of both. In Panel B, the upper part shows a schematic representation of the expected molecules when a single light chain and a single heavy chain are expressed in a cell, leading to monoclonal antibodies UBS-54 or K53. The lower part under the arrow shows a schematic representation of the combinations produced when both heavy chains and the common light chain are co-expressed in a host cell, with theoretical amounts when both heavy chains are expressed at equal levels and pair to each other with equal efficiency. The common light chain is indicated with the vertically striped bars.

Human IgG from each supernatant was subsequently purified using Protein A-affinity chromatography (Hightrap Protein A HP, cat. no. 1-040203) according to standard procedures, following recommendations of the manufacturer (Amersham Biosciences). After elution, samples were concentrated in a Microcon YM30 concentrator (Amicon) and buffer exchanged to 10 mM sodium phosphate, pH 6.7. Twelve µg of purified IgG was subsequently analyzed on Isoelectric-focusing gels (Serva Pre-cast IEF gels, pH range 3-10, cat. no. 42866). The samples were loaded on the pH side and after focusing, stained with colloidal blue (FIG. 5). Lane 1 shows transiently expressed K53, Lane 2 shows transiently expressed UBS-54 and Lane 3 shows the IgG sample of the cells in which both antibodies were co-transfected. Clearly, K53 and UBS-54 each have a unique pI profile and the sample from the co-transfection showed other unique isoforms, with the major isoform having a pI in between those of K53 and UBS-54. This is also anticipated on the basis of the theoretic pI when calculated with the ProtParam tool provided on the Expasy homepage (expasy.ch; Appel et al., 1994, the entirety of which is incorporated herein by reference). K53 and UBS-54 have a theoretic pI of 8.24 and 7.65, respectively, whereas an isoform representing a heterodimer of one UBS-54 heavy chain and one K53 heavy chain has a theoretical pI of 8.01. Assembly of such a heterodimer can only occur when a single cell translates both the heavy chain of K53 and the heavy chain of UBS-54 and assembles these into a full length IgG molecule together with the common light chain.

Therefore, this experiment shows that it is possible to express two unique human IgG molecules in a single cell and that a heterodimer consisting of these two unique binding specificities is also efficiently formed.

Example 2

Figure 6:
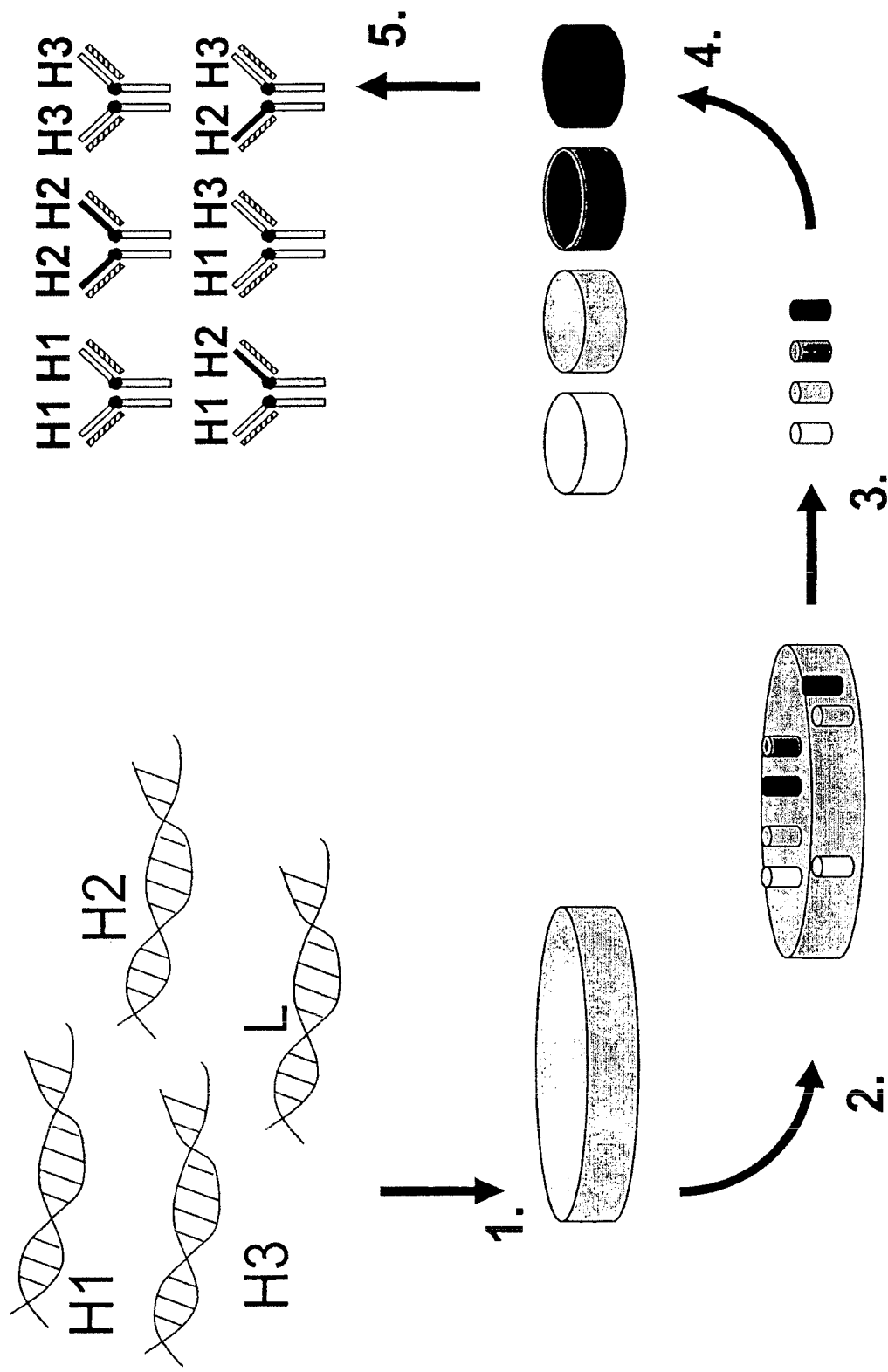
FIG. 6 is a schematic representation of a possible embodiment of the method according to the invention (see, e.g., Example 9). At (1), introduction of nucleic acid sequences encoding one light chain and three different heavy chains capable of pairing to the common light chain to give functional antibodies into host cells is shown; at (2), selection of stable clones; (3) shows clones can be screened for, for instance, expression levels, binding; at (4), clones are expanded; and at (5), production of functional mixtures of antibodies is shown. Some or all of steps 2-5 could be performed simultaneously or in a different order.

Production of a Mixture of Antibodies Against Human B-Cell Markers in a PER.C6® Cell Line (Human Retina Cells that Express Adenovirus E1A and E1B Proteins)-Derived Clone A method for producing a mixture of antibodies according to the invention, using expression in a recombinant host cell of a single light chain and three different heavy chains capable of pairing to the single light chain to form functional antibodies, is exemplified herein and is schematically shown in FIG. 6. Phages encoding antibodies capable of binding proteins present on human B-cells, i.e., CD22, CD72 and Major Histocompatibility Complex (MHC) class II (further referred to as HLA-DR) were previously isolated from a semi-synthetic phage library (de Kruif et al., 1995; van der Vuurst de Vries & Logtenberg, 1999, the entirety of which is incorporated herein by reference). DNA sequencing of the $V_H$ and $V_L$ sequences of the phages clone B28 (anti-CD22), clone I-2 (anti-HLA-DR) and clone II-2 (anti-CD72) revealed that they all contain a unique $V_H$ sequence but a common light chain sequence (Vλ3) with an identical CDR region (FIG. 7).

The $V_H$ and $V_L$ sequences of clones B28, I-1 and II-2 are cloned behind the HAVT20 leader sequences of an expression plasmid comprising a heavy chain. An example of such a plasmid is pCRU-K01 (contains kappa heavy chain sequences that can be easily interchanged for lambda heavy chain sequences if desired by a person skilled in the art), as deposited at the ECACC under number 03041601. The cloning gives rise to plasmids encoding a full length human IgG1 with binding specificities for CD22, CD72 and HLA-DR. These plasmids will further be referred to as pCRU-CD22, pCRU-CD72 and pCRU-HLA-DR, respectively.

Stable PER.C6® (human retina cells that express adenovirus E1A and E1B proteins)-derived cell lines are generated, according to methods known to one of ordinary skill in the art (see, e.g., WO 00/63403), the cell lines expressing antibodies encoded by genetic information on either pCRU-CD22, pCRU-CD72 or pCRU-HLA-DR and a cell line expressing antibodies encoded by all three plasmids. Therefore, PER.C6® cells (human retina cells that express adenovirus E1A and E1B proteins) are seeded in DMEM plus 10% FBS in tissue culture dishes (10 cm diameter) or T80 flasks with approximately 2.5×10$^6$ cells per dish and kept overnight under their normal culture conditions (10% CO$_2$ concentration and 37° C.). The next day, transfections are performed in separate dishes at 37° C. using Lipofectamine (Invitrogen Life Technologies) according to standard protocols provided by the manufacturer, with either 1-2 µg pCRU-CD22, 1-2 µg pCRU-CD72, 1-2 µg pCRU-HLA-DR or 1 µg of a mixture of pCRU-CD22, pCRU-CD72 and pCRU-HLA-DR. As a control for transfection efficiency, a few dishes are transfected with a LacZ control vector, while a few dishes will not be transfected and serve as negative controls.

After four to five hours, cells are washed twice with DMEM and given fresh medium without selection. The next day, the medium is replaced with fresh medium containing 500 µg/ml G418. Cells are refreshed every two or three days with medium containing the same concentrations of G418. About 20 to 22 days after seeding, a large number of colonies are visible and from each transfection, at least 300 are picked and grown via 96-well plates and/or 24-well plates via 6-well plates to T25 flasks. At this stage, cells are frozen (at least one, but usually four vials per sub-cultured colony) and production levels of recombinant human IgG antibody are determined in the supernatant using an ELISA specific for human IgG1 (described in WO 00/63403). Also, at this stage, G418 is removed from the culture medium and never re-applied again. For a representative number of colonies, larger volumes will be cultured to purify the recombinant human IgG1 fraction from the conditioned supernatant using Protein A affinity chromatography according to standard procedures. Purified human IgG1 from the various clones is analyzed on SDS-PAGE, Iso-electric focusing (IEF) and binding to the targets CD22, CD72 and HLA-DR using cell transfectants expressing these human antigens on their cell surface (transfectants expressing CD72 and HLA-DR have been described by van der Vuurst-de Vries and Logtenberg, 1999; a CD22 transfectant has been prepared according to similar standard procedures in PER.C6® (human retina cells that express adenovirus E1A and E1B proteins)).

Colonies obtained from the co-transfection with pCRU-CD22, pCRU-CD72 and pCRU-HLA-DR are screened by PCR on genomic DNA for the presence or absence of each of the three constructs. The identity of the PCR products is further confirmed by DNA sequencing.

Next, it is demonstrated that a clonal cell line accounts for the production of each of the three binding specificities, i.e., proving that a single cell is able to produce a mixture of more than two functional human IgGs. Therefore, a limited number of colonies, which screened positive for the production of each of the three binding specificities (both by PCR at the DNA level as well as in the specified binding assays against CD22, CD72 and HLA-DR), are subjected to single cell sorting using a fluorescence-activated cell sorter (FACS) (Becton & Dickinson FACS VANTAGE SE™ (high-performance, high-speed cell sorter)). Alternatively, colonies are seeded at 0.3 cells/well to guarantee clonal outgrowth. Clonal cell populations, hereafter designated as sub-clones, are refreshed once a week with fresh medium. Sub-clones are grown and transferred from 96-well plates via 24- and 6-well plates to T25 flasks. At this stage, sub-clones are frozen (at least one, but usually four vials per sub-clone) and production levels of recombinant human IgG1 antibody are determined in the supernatant using a human IgG1-specific ELISA. For a representative number of sub-clones, larger volumes are cultured to purify the recombinant human IgG1 fraction from the conditioned supernatant using Protein A-affinity chromatography according to standard procedures.

Purified human IgG1 from the various sub-clones is subsequently analyzed as described above for human IgG1 obtained from the parental clones, i.e., by SDS-PAGE, Iso-electric focusing (IEF) and binding to the targets CD22, CD72 and HLA-DR. Sub-clones will also be screened by PCR on genomic DNA for the presence or absence of each of the three constructs pCRU-CD22, pCRU-CD72 and pCRU-HLA-DR. The identity of the PCR products is further confirmed by DNA sequencing.

Other methods such as Southern blot and/or FISH can also be used to determine whether each of the three constructs are present in the clonal cell line.

Sub-clones that are proven to be transgenic for each of the three constructs are brought into culture for an extensive period to determine whether the presence of the transgenes is stable and whether expression of the antibody mixture remains the same, not only in terms of expression levels, but also for the ratio between the various antibody isoforms that are secreted from the cell. Therefore, the sub-clone culture is maintained for at least 25 population doubling times, either as an adherent culture or as a suspension culture. At every four to six population doublings, a specific production test is performed using the human IgG-specific ELISA and larger volumes are cultured to obtain the cell pellet and the supernatant. The cell pellet is used to assess the presence of the three constructs in the genomic DNA, either via PCR, Southern blot and/or FISH. The supernatant is used to purify the recombinant human IgG1 fraction as described supra. Purified human IgG1 obtained at the various population doublings is analyzed as described, i.e., by SDS-PAGE, Iso-electric focusing (IEF) and binding to the targets CD22, CD72 and HLA-DR using cell transfectants expressing these antigens.

Example 3

Screening of Clones Expressing Multiple Human IgGs for the Most Potent Mixture of Functional Human IgGs Functionality of the antibody mixture is analyzed in cell-based assays to determine whether the human IgG1 mixture inhibits proliferation and/or induces apoptosis of B-cell lines, such as, for example, Ramos. Other cell lines can also be used. In addition, the antibody mixtures are analyzed for their potential to induce antibody-dependent cellular toxicity and complement-dependent cytotoxicity of, for example, Ramos cells.

In each of the following experiments, the functionality of the antibody mixture recognizing the targets CD22, CD72 and HLA-DR is analyzed and can be compared to each of the individual IgG1 antibodies and to an equimolar combination of the three individual IgG1 specificities.

To assess the ability of the antibody mixtures to inhibit the proliferation of Ramos cells, these cells are incubated in 96-well plates ($0.1$-$1.0 \times 10^5$/ml) with several concentrations (5-20 μg/ml) of the antibody mixtures against CD22, CD72 and HLA-DR for 24 hours. The proliferation of the cells is measured by $^3$H-thymidine incorporation during another 16 hours of culture. Inhibition of growth is determined by plotting the percentage of $^3$H-thymidine incorporation compared to untreated cells (taken as 100% reference value).

To analyze apoptosis induction of Ramos cells, these cells are stimulated in 48-well plates ($0.2$-$1.0 \times 10^6$/ml) with several concentrations (5-20 μg/ml) of the antibody mixtures against the targets CD22, CD72 and HLA-DR for 24 or 48 hours. After the incubation period, the phosphatidyl serine exposure on apoptotic cells is analyzed (G. Koopman et al., 1994, the entirety of which is incorporated herein by reference). Therefore, the cells are harvested, washed twice with PBS and are incubated at RT for 10 minutes with 100 μl FITC-labeled annexin V (Caltag) diluted 1:25 in annexin V-binding buffer (Caltag). Prior to the analysis of the samples by flow cytometry (FACSCalibur, Becton Dickinson, San Jose, Calif.), propidium iodide (PI)(Sigma) is added to a final concentration of 5 μg/ml to distinguish necrotic cells (annexin V−/PI+) from apoptotic cells (annexin V+/PI−, early apoptotic cells; annexin V+/PI+, late apoptotic cells).

In an alternative assay, apoptosis is induced by cross-linking the antibody mixtures against CD22, CD72 and HLA-DR on the cell surface of Ramos cells with 25 μg/ml of F(ab)2 of goat-anti-human (Fc-specific) polyclonal antibodies (Jackson Immunoresearch Laboratories, West Grove, Pa.) during the incubation period.

In another alternative assay, apoptosis is induced by incubating the Ramos cells with several concentrations (5-20 µg/ml) of the antibody mixtures against CD22, CD72 and HLA-DR while co-incubating them with the chemosensitizing agents doxorubicin (Calbiochem) or dexamethasone (UMCU, Utrecht, NL).

Antibody-Dependent Cellular Cytotoxicity (ADCC) of the antibody mixtures is analyzed using peripheral blood mononuclear cells as effector cells in a standard $^{51}$Cr release assay (Huls et al., 1999). To this purpose, 1-3×10$^6$ Ramos cells are labeled with 100 µCi (Amersham, Buckinghamshire, UK) for one hour at 37° C. After three washes with medium, the Ramos target cells are plated in U bottom 96-well plates at 5×10$^3$ cells/well. Peripheral blood mononuclear cells that are obtained from healthy donors by Ficoll-Hypaque density gradients are then added to each well at effector:target ratios ranging from 80:1 to 10:1 in triplicate. The cells are incubated at 37° C. in the presence of various concentrations of the antibody mixtures (5-20 µg/ml) in a final volume of 200 µl.

After four hours of incubation, part of the supernatant is harvested and $^{51}$Cr release is measured. The percentage of specific lysis is calculated using the following formula: % specific lysis=([experimental cpm–spontaneous cpm]/ [maximal cpm–spontaneous cpm]×100%). Maximal $^{51}$Cr release is determined by adding triton X-100 to a final concentration of 1% to the target cells and spontaneous release is determined after incubation of the target cells with medium alone.

Complement-dependent cytotoxicity is determined in a similar assay. Instead of the effector cells, now 50 µl human serum is added to the target cells. Subsequently, the assay is performed in the same manner.

Alternatively, ADCC and CDC of the antibody mixtures is determined using a Europium release assay (Patel and Boyd, 1995, the entirety of which is incorporated herein by reference) or using an LDH release assay (Shields et al., 2001, the entirety of which is incorporated herein by reference).

Example 4

Use of Phage Display to Isolate Multiple Phages with an Identical $V_L$ Sequence Against a Predefined Target (her-2) and Production in a Recombinant Host Cell of a Mixture of Antibodies Capable of Binding this Target Phages displaying scFv fragments capable of binding multiple epitopes present on the same protein, for example, the epidermal growth factor receptor Her-2, can be isolated from a semi-synthetic phage library (de Kruif et al., 1995a, b). It is possible to identify several of such phages and select the ones comprising the same light chain sequence for further use according to the invention. The semi-synthetic library is formed by mixing seven sub-libraries that each contains a different light chain (de Kruif et al., 1995a, b). It is, therefore, particularly practical to use such a sub-library, containing only one light chain and many heavy chains, for screening so that multiple antibodies with an identical $V_L$ sequence are obtained and further used for expressing the antibody mixtures according to the invention.

For the selection of phages against Her-2, several fusion proteins are generated comprising different parts of the extracellular domain of Her-2 that are fused to the CH2 and CH3 domains of human IgG1. For this purpose, a pCDNA3.1zeo-expression vector (Invitrogen) has been constructed that contains in its multiple cloning region an XhoI restriction site in the hinge region in frame prior to the CH2 and CH3 domains of human IgG1. Using a Her-2 cDNA clone as a template, PCR fragments are generated using standard molecular biology techniques known to a person skilled in the art. These fragments consist of a unique 5' restriction site, a start codon followed by a eukaryotic leader sequence that is linked in frame to either the total extracellular (EC) domain of Her-2 or to a part of the EC domain of Her-2 that is followed in frame by an XhoI restriction site. These PCR fragments are subsequently cloned in frame with the CH2-CH3 IgG1 region into the pCDNA3.1zeo-expression vector. In addition to the fusion protein containing the total EC domain of Her-2, several smaller fusion proteins are generated containing non-overlapping fragments of the Her-2 EC domain. These constructs encoding the Her-2-Ig fusion proteins are used for transient transfection of 293T cells using the lipofectamine reagent (Gibco). Five days after transfection, the supernatants of the 293T cells are harvested and Her-2-Ig fusion proteins are purified using protein A-affinity chromatography according to standard procedures.

Her-2-Ig fusion proteins containing non-overlapping fragments of the Her-2 EC domain are coated for two hours at 37° C. onto the surface of MAXISORP™ (polystyrene based modified surface with a high affinity for polar groups) plastic tubes (Nunc) at a saturating concentration (0.5-5 µg/ml). The tubes are blocked for one hour in 2% fat-free milk powder dissolved in PBS (MPBS). Simultaneously, 500 µl (approximately 10$^{13}$ cfu) of a semi-synthetic phage display library (a sub-library according to the terminology used above) in which only one Vκ1 light chain is represented (prepared as described by De Kruif et al. (1995a, b) and referenced therein), is added to two volumes of 4% MPBS. In addition, human serum is added to a final concentration of 15% and blocking is allowed to proceed for 30 to 60 minutes. The Her-2-Ig-coated tubes are emptied and the blocked phage library is added. The tube is sealed and rotated slowly for one hour, followed by two hours of incubation without rotation. The tubes are emptied and washed ten times in PBS containing 0.1% TWEEN®-20, followed by washing five times in PBS. One ml glycine-HCL, 0.05 M, pH 2.2 is added, and the tube is rotated slowly for ten minutes. The eluted phages are added to 500 µl 1 M Tris-HCl pH 7.4. To this mixture, 3.5 ml of exponentially growing XL-1 blue bacterial culture is added. The tubes are incubated for 30 minutes at 37° C. without shaking. Subsequently, the bacteria are plated on 2TY agar plates containing ampicillin, tetracycline and glucose. After overnight incubation of the plates at 37° C., the colonies are scraped from the plates and used to prepare an enriched phage library, essentially as described by De Kruif et al. (1995a). Briefly, scraped bacteria are used to inoculate 2TY medium containing ampicillin, tetracycline and glucose and are grown at 37° C. to an OD$_{600\ nm}$ of ~0.3. Helper phages are added and allowed to infect the bacteria after which the medium is changed to 2TY containing ampicillin, tetracycline and kanamycin. Incubation is continued overnight at 30° C. The next day, the bacteria are removed from the 2TY medium by centrifugation, after which the phages are precipitated using polyethylene glycol 6000/NaCl. Finally, the phages are dissolved in a small volume of PBS-1% BSA, filter-sterilized and used for a next round of selection. The selection/re-infection procedure is performed twice. After the second round of selection, individual *E. coli* colonies are used to prepare monoclonal phage antibodies. Essentially, individual colonies are grown to log phase and infected with helper phages, after which phage antibody production is allowed to proceed overnight. Phage antibody containing supernatants are tested in ELISA for binding activity to Her-2-total EC-Ig coated 96-well plates.

Selected phage antibodies that are obtained in the screen described above are validated by ELISA for specificity. For this purpose, Her-2-Ig fusion proteins containing non-overlapping fragments of the Her-2 EC domain are coated to MAXISORP ELISA plates. After coating, the plates are blocked in 2% MPBS. The selected phage antibodies are incubated in an equal volume of 4% MPBS. The plates are emptied, washed once in PBS, after which the blocked phages are added. Incubation is allowed to proceed for one hour, the plates are washed in PBS 0.1% TWEEN®-20 and bound phages are detected using an anti-M13 antibody conjugated to peroxidase. The procedure is performed simultaneously using a control phage antibody directed against thyroglobulin (De Kruif et al. 1995a, b), which serves as a negative control.

In another assay, the selected phage antibodies are analyzed for their ability to bind BT474 human breast cancer cells that express Her-2. For flow cytometry analysis, phage antibodies are first blocked in an equal volume of 4% MPBS for 15 minutes at 4° C. prior to the staining of the BT474 cells. The binding of the phage antibodies to the cells is visualized using a biotinylated anti-M13 antibody (Santa Cruz Biotechnology) followed by streptavidin-phycoerythrin (Caltag).

Alternatively, phage antibodies recognizing multiple epitopes on Her-2 are selected using a method based upon competition of phage binding to Her-2 with binding of the well-characterized murine anti-Her-2 antibodies HER50, HER66 and HER70 (Spiridon et al., 2002, the entirety of which is incorporated herein by reference). To this purpose, $2 \times 10^6$ BT474 cells are incubated at 4° C. with approximately $10^{13}$ cfu (0.5 ml) of a semi-synthetic phage display library in which only one Vκ1 light chain is represented, prepared as described supra, and blocked with two volumes of medium containing 10% of FBS. The mixture is slowly rotated at 4° C. for two hours in a sealed tube.

Subsequently, non-bound phages are removed by two washes with 50 ml of cold medium containing 10% FBS. Hereafter, phages recognizing multiple epitopes on Her-2 are eluted by resuspending the BT474 cells in 1 ml of cold medium containing saturating concentrations (5-20 µg/ml) of the HER50, HER66 and HER70 murine anti-Her-2 antibodies. The cells are left on ice for 10 minutes, spun down and the supernatant containing the anti-Her-2 phage antibodies is used to reinfect XL1-Blue cells as described supra.

From the panel of Her-2-specific phage antibodies generated by the screens described above, three phage antibodies are selected that recognize three different non-overlapping epitopes on the Her-2 protein.

The $V_H$ sequences and the unique Vκ1 light chain sequence of these clones, provisionally designated Vκ1HER2-1, Vκ1HER2-2 and Vκ1HER2-3, are cloned behind the HAVT20 leader sequences of expression plasmid pCRU-K01 (ECACC deposit 03041601), or a similar expression plasmid, to obtain plasmids encoding a full-length human IgG1-κ with binding specificities for Her-2. These plasmids are provisionally designated as pCRU-Vκ1HER2-1, pCRU-Vκ1HER2-2 and pCRU-Vκ1HER2-3, respectively.

Stable PER.C6® (human retina cells that express adenovirus E1A and E1B proteins)-derived cell lines are generated, according to methods known to one of ordinary skill in the art, the cell lines expressing antibodies encoded by genetic information on either pCRU-Vκ1HER2-1, pCRU-Vκ1HER2-2 or pCRU-Vκ1HER2-3 and a cell line expressing antibodies encoded by all three plasmids. Therefore, PER.C6® cells are seeded in DMEM plus 10% FBS in tissue culture dishes (10 cm diameter) or T80 flasks with approximately $2.5 \times 10^6$ cells per dish and kept overnight under their normal culture conditions (10% $CO_2$ concentration and 37° C.). The next day, transfections are performed in separate dishes at 37° C. using Lipofectamine (Invitrogen Life Technologies) according to standard protocols provided by the manufacturer, with either 1-2 µg pCRU-Vκ1HER2-1, 1-2 µg pCRU-Vκ1HER2-2, 1-2 µg pCRU-Vκ1HER2-3 or 1 µg of a mixture of pCRU-Vκ1HER2-1, pCRU-Vκ1HER2-2 and pCRU-Vκ1HER2-3. As a control for transfection efficiency, a few dishes are transfected with a LacZ control vector, while a few dishes are not transfected and serve as negative controls.

After five hours, cells are washed twice with DMEM and re-fed with fresh medium without selection. The next day, medium is replaced with fresh medium containing 500 µg/ml G418. Cells are refreshed every two or three days with medium containing the same concentrations of G418. About 20 to 22 days after seeding, a large number of colonies are visible and from each transfection, at least 300 are picked and grown via 96-well plates and/or 24-well plates via 6-well plates to T25 flasks. At this stage, cells are frozen (at least one, but usually four vials per sub-cultured colony) and production levels of recombinant human IgG antibody are determined in the supernatant using an ELISA specific for human IgG1. Also, at this stage, G418 is removed from the culture medium and never re-applied again. For a representative number of colonies, larger volumes are cultured to purify the recombinant human IgG1 fraction from the conditioned supernatant using Protein A-affinity chromatography according to standard procedures. Purified human IgG1 from the various clones is analyzed on SDS-PAGE, Iso-electric focusing (IEF), assayed binding to Her-2-Ig fusion proteins by ELISA, and analyzed for binding to Her-2 on the surface of BT474 cells by flow cytometry.

Clones obtained from the co-transfection of pCRU-Vκ1HER2-1, pCRU-Vκ1HER2-2 and pCRU-Vκ1HER2-3 are screened by PCR on genomic DNA for the presence or absence of each of the three constructs. The identity of the PCR products is further confirmed by DNA sequencing.

Next, it is demonstrated that a clonal cell line accounts for the production of each of the three binding specificities. Therefore, a limited number of colonies, which screened positive for the production of each of the three binding specificities (both by PCR at the DNA level as well as in the specified binding assays against Her-2), are subjected to single cell sorting using a fluorescence-activated cell sorter (FACS) (Becton & Dickinson FACS VANTAGE SE™). Alternatively, colonies are seeded at 0.3 cells/well to guarantee clonal outgrowth.

Clonal cell populations, hereafter designated as sub-clones, are refreshed once a week with fresh medium. Sub-clones are grown and transferred from 96-well plates via 24- and 6-well plates to T25 flasks. At this stage, sub-clones are frozen (at least one, but usually four vials per sub-clone) and production levels of recombinant human IgG1 antibody are determined in the supernatant using a human IgG1-specific ELISA. For a representative number of sub-clones, larger volumes are cultured to purify the recombinant human IgG1 fraction from the conditioned supernatant using Protein A-affinity chromatography according to standard procedures.

Purified human IgG1 from the various sub-clones is subsequently analyzed as described above for human IgG1 obtained from the parental clones, i.e., by SDS-PAGE, Iso-electric focusing (IEF) and binding to Her-2. Sub-clones will also be screened by PCR on genomic DNA for the presence or absence of each of the three constructs pCRU-VκlHER2-1, pCRU-VκlHER2-2 and pCRU-VκlHER2-3. The identity of the PCR products is further confirmed by DNA sequencing.

Other methods such as Southern blot and/or FISH can also be used to determine whether each of the three constructs is present in the clonal cell line.

Sub-clones that are proven to be transgenic for each of the three constructs are brought into culture for an extensive period to determine whether the presence of the transgenes is stable and whether expression of the antibody mixture remains the same, not only in terms of expression levels, but also for the ratio between the various antibodies that are secreted from the cell. Therefore, the sub-clone culture is maintained for at least 25 population doubling times, either as an adherent culture or as a suspension culture. At every four to six population doublings, a specific production test is performed using the human IgG-specific ELISA and larger volumes are cultured to obtain the cell pellet and the supernatant. The cell pellet is used to assess the presence of the three constructs in the genomic DNA, either via PCR, Southern blot and/or FISH. The supernatant is used to purify the recombinant human IgG1 fraction as described supra. Purified human IgG1 obtained at the various population doublings is analyzed as described, i.e., by SDS-PAGE, Iso-electric focusing (IEF) and binding to Her-2 by ELISA and by flow cytometry using BT474 cells.

Functionality of the antibody mixture of anti-Her-2 antibodies is analyzed in cell-based assays to determine whether the human IgG1 mixture inhibits proliferation and/or induces apoptosis of BT474 cells. In addition, the antibody mixtures are analyzed for their potential to induce antibody-dependent cellular toxicity and complement-dependent cytotoxicity of BT474 cells.

In each of the experiments described below, the functionality of the antibody mixture recognizing Her-2 can be analyzed and compared to each of the individual IgG1 antibodies and to an equimolar combination of the three individual monospecific IgG1 molecules.

To assess the ability of the antibody mixtures to inhibit the proliferation of BT474 cells, these cells are allowed to adhere overnight in 96-well plates ($1.5 \times 10^5$/well) and are subsequently incubated with several concentrations (5-20 µg/ml) of the antibody mixtures against Her-2 for 72 hours. The proliferation of the cells is measured by $^3$H-thymidine incorporation during the last six hours of culture. Inhibition of growth is determined by plotting the percentage of $^3$H-thymidine incorporation compared with untreated cells (taken as 100% reference value).

To analyze apoptosis induction of BT474 cells, these cells are allowed to adhere overnight in 48-well plates ($2.5 \times 10^5$/well in 1 ml) and are subsequently incubated with several concentrations (5-20 µg/ml) of the antibody mixtures against Her-2 for four hours. Hereafter, the cells are harvested by trypsinization, washed twice with PBS and incubated at RT for ten minutes with 100 µl FITC-labeled annexin V (Caltag) diluted 1:25 in annexin V-binding buffer (Caltag). Prior to the analysis of the samples by flow cytometry (FACSCalibur, Becton Dickinson, San Jose, Calif.) propidium iodide (PI)(Sigma) is added to a final concentration of 5 µg/ml to distinguish necrotic cells (annexin $V^-$/$PI^+$) from apoptotic cells (annexin $V^-$/$PI^-$, early apoptotic cells; annexin $V^+$/$PI^+$, late apoptotic cells).

Antibody-Dependent Cellular Cytotoxicity of the antibody mixtures is analyzed using peripheral blood mononuclear cells as effector cells and BT474 cells as target cells in a standard $^{51}$Cr release assay as described supra (Huls et al., 1999). Complement-dependent cytotoxicity is determined in a similar assay. Instead of the effector cells, now 50 µl human serum is added to the target cells. Subsequently, the assay is performed as described supra.

Alternatively, ADCC and CDC of the antibody mixtures is determined using a Europium release assay (Patel and Boyd, 1995) or using an LDH release assay (Shields et al., 2001).

The functionality of the antibody mixtures against Her-2 is also tested using in vivo animal models, such as, for instance, described in Spiridon et al., 2002.

Example 5

Expression of Different Functional Human IgGs in the Milk of Transgenic Animals

The $V_H$ and $V_H$ sequences of phages against proteins present on human B-cells, i.e., CD22 (clone B28), CD72 (clone II-2) and HLA-DR (clone I-2) (FIG. 7) are cloned into expression plasmid pBC1 (as provided in the pBC1 Mouse Milk Expression System, Invitrogen Life Technologies) to obtain mammary gland- and lactation-specific expression of these human IgG molecules in transgenic animals, according to the manufacturer's instructions. These mammary gland-specific expression vectors encoding the antibody sequences for anti-CD22, anti-CD72 and anti-HLA-DR, are introduced into the murine germline according to the manufacturer's instructions. Obtained pups are screened for the presence of each of the three constructs by PCR on DNA isolated from the tail. Pups, either male or female, confirmed for being transgenic for each of the three antibodies, are weaned and matured. Female transgenic mice are fertilized at the age of 6-8 weeks and milk samples are obtained at several time points after gestation. Male transgenic mice are mated with non-transgenic females and female transgenic offspring (as determined with PCR as described above) is mated and milked as described above for the female transgenic founders. Whenever needed, female or male transgenic founders are mated for another generation to be able to obtain sufficient amounts of transgenic milk for each founder line. Transgenic milk is analyzed for the presence of human IgG with a human IgG-specific ELISA, which does not cross-react with mouse IgG or other mouse milk components. Human IgG is purified from transgenic mouse milk using Protein A-affinity chromatography according to standard procedures. Purified human IgG is analyzed on SDS-PAGE, Iso-electric focusing and binding on the targets CD22, CD72 and HLA-DR. Functionality of the antibody mixture is analyzed as described supra.

Example 6

Figure 8:
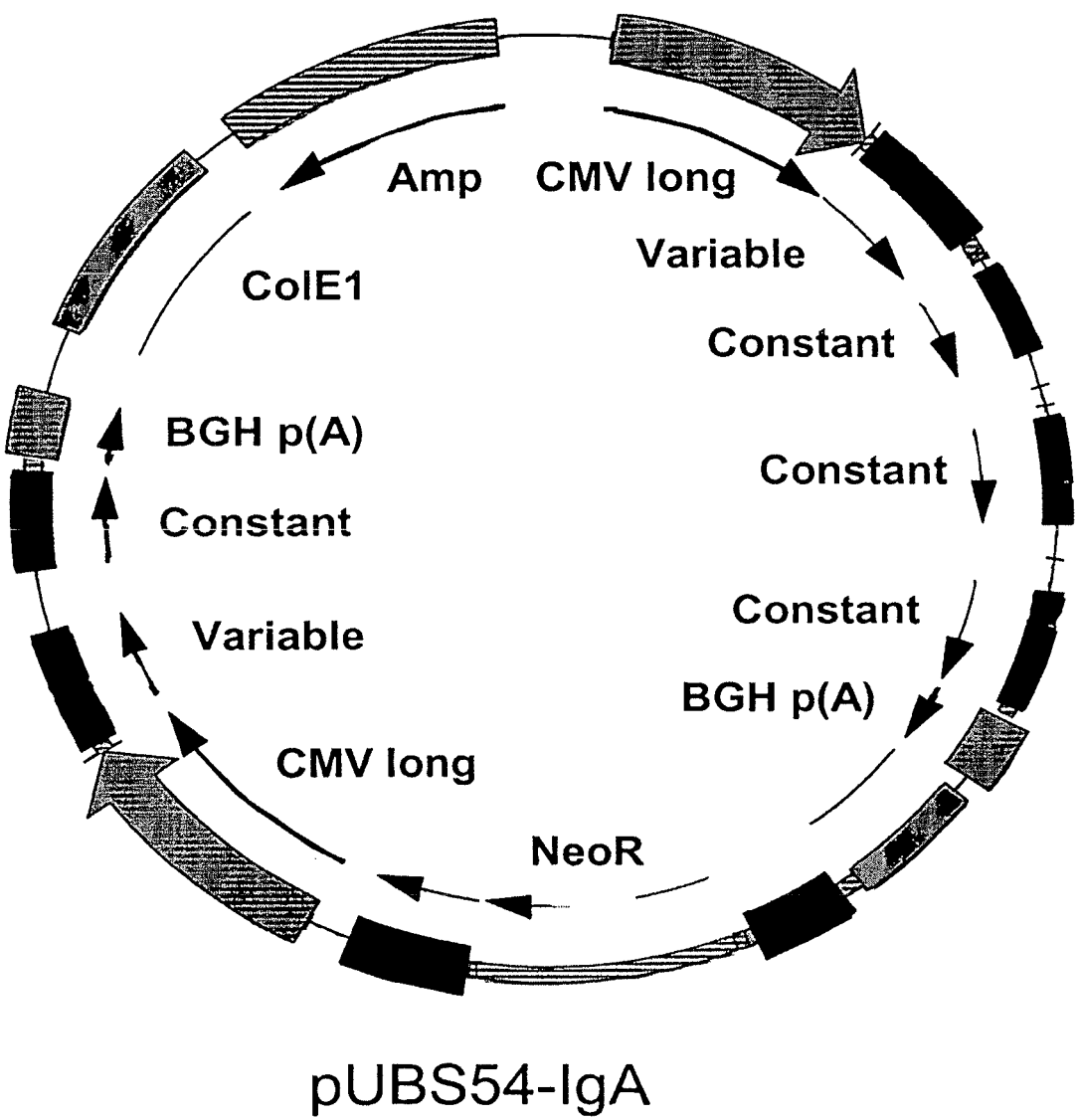
FIG. 8 is a map of pUBS54-IgA (pCRU-L01 encoding human IgA1 against EPCAM).

Production of an IgA/IgG Mixture Against a Predefined Target in a PER.C6® (Human Retina Cells that Express Adenovirus E1A and E1B Proteins)-Derived Clone The $V_H$-$V_L$ sequences of the phage UBS-54 directed against the homotypic adhesion molecule EP-CAM (Huls et al., 1999) was not only cloned into a vector encoding the constant domains of a human IgG1 with Kappa light chain (expression vector pUBS3000Neo), but also into an expression vector encoding the constant domains of a human IgA1 with Kappa light chain (expression vector pUBS54-IgA, FIG. 8). Hence, antibodies derived from pUBS3000Neo and pUBS54-IgA do bind to the same epitope on EPCAM. The only differences antibodies derived from pUBS3000Neo and pUBS54-IgA are in the sequences encoding the constant domains of the heavy chain, resulting in either an IgG1 or IgA1 isotype. The Kappa light chain sequences of these two vectors are identical.

Stable PER.C6® (human retina cells that express adenovirus E1A and E1B proteins)-derived cell lines expressing antibodies encoded by genetic information on pUBS3000Neo and pUBS54-IgA are generated by procedures well known to persons skilled in the art. Therefore, PER.C6® cells (human retina cells that express adenovirus E1A and E1B proteins) are seeded in DMEM plus 10% FBS in tissue culture dishes (10 cm diameter) or T80 flasks with approximately $2.5 \times 10^6$ cells per dish and kept overnight under their normal culture conditions (10% $CO_2$ concentration and 37° C.). The next day, transfections are performed in separate dishes at 37° C. using Lipofectamine (Invitrogen Life Technologies) according to standard protocols provided by the manufacturer, with either 1-2 µg pUBS3000Neo and pUBS54-IgA. As a control for transfection efficiency, a few dishes are transfected with a LacZ control vector, while a few dishes are not transfected and serve as negative controls.

After four to five hours, cells are washed twice with DMEM and given fresh medium without selection. The next day, medium is replaced with fresh medium containing 500 µg/ml G418. Cells are refreshed every two or three days with medium containing the same concentrations of G418. About 20 to 22 days after seeding, a large number of colonies are visible and from each transfection, at least 300 are picked and grown via 96-well plates and/or 24-well plates via 6-well plates to T25 flasks. At this stage, cells are frozen (at least one, but usually four vials per sub-cultured colony) and production levels of recombinant human IgG and human IgA antibody are determined in the supernatant using an ELISA specific for human IgG1 as well as an ELISA specific for human IgA. Also, at this stage, G418 is removed from the culture medium and never re-applied again. For a representative number of colonies, larger volumes are cultured to purify the recombinant human IgG1 and human IgA fraction from the conditioned supernatant using, for instance, a combination of Protein L- or LA-affinity chromatography, cation exchange chromatography, hydrophobic interaction chromatography and gel filtration. Purified human immunoglobulins from the various clones are analyzed on SDS-PAGE, Iso-electric focusing (IEF) and binding to the target EPCAM using cell lines having a high expression of this molecule. The clones will also be screened by PCR on genomic DNA for the presence or absence of pUBS3000Neo and pUBS54-IgA. The identity of the PCR products is further confirmed by DNA sequencing.

A limited number of clones, which are screened positive for the production of both EPCAM IgG1 and EPCAM IgA, are subjected to single cell sorting using a fluorescence-activated cell sorter (FACS) (Becton Dickinson FACS VANTAGE SE™). Alternatively, colonies are seeded at 0.3 cells/well to guarantee clonal outgrowth. Clonal cell populations, hereafter designated as sub-clones, are refreshed once a week with fresh medium. Sub-clones are grown and transferred from 96-well plates via 24- and 6-well plates to T25 flasks. At this stage, sub-clones are frozen (at least one, but usually four vials per sub-clone) and production levels of recombinant human IgG1 and IgA antibody are determined in the supernatant using a human IgG1-specific ELISA and a human IgA-specific ELISA. For a representative number of sub-clones, larger volumes are cultured to purify the recombinant human IgG1 and human IgA1 fraction from the conditioned supernatant using, for instance, a combination of Protein L- or LA-affinity chromatography, cation exchange chromatography, hydrophobic interaction chromatography and gel filtration. Purified human immunoglobulins from the various clones are analyzed on SDS-PAGE, Iso-electric focusing (IEF) and binding to the target EPCAM using cell lines having a high expression of this molecule.

Sub-clones will also be screened by PCR on genomic DNA for the presence or absence of pUBS3000Neo and pUBS54-IgA. The identity of the PCR products is further confirmed by DNA sequencing.

Other methods such as Southern blot and/or FISH may also be used to determine whether both constructs are present in the clonal cell line.

Example 7

Production of a Human IgG1/IgG3 Mixture Against Multiple Targets in a Clonal PER.C6® Cell Line (Human Retina Cells that Express Adenovirus E1A and E1B Proteins)

Phage clone UBS-54 and Clone K53 (FIG. 3) were obtained as described in Example 1. The $V_H$ and $V_L$ of clone UBS-54 was inserted into an expression vector containing the HAVT20 leader sequence and all the coding sequences for the constant domains of a human IgG1 with a Kappa light chain by a method essentially as described (Boel et al., 2000). The resulting plasmid was designated as pUBS3000Neo (FIG. 4). It will be clear that expression vectors containing heavy chain constant domains of any desired isotype can be constructed by routine methods of molecular biology, using the sequences of these regions that are all available in the art. The $V_H$ and $V_L$ sequences of Phage clone K53 are cloned into an expression vector containing the HAVT20 leader sequence and all the coding sequences for the constant domains of a heavy chain of a human IgG3 with a Kappa light chain by a method essentially as described (Boel et al., 2000). This expression vector is designated as pK53IgG3.

These plasmids are transiently expressed, either alone or in combination, in PER.C6® cells (human retina cells that express adenovirus E1A and E1B proteins). In brief, each 80 $cm^2$ flask is transfected by incubation for four hours with 140 µl lipofectamine+10 µg DNA (either pUBS3000Neo, pK53IgG3 or 10 µg of both) in serum-free DMEM medium at 37° C. After four hours, this is replaced with DMEM+10% FBS and the cells are grown overnight at 37° C. Cells are then washed with PBS and the medium is replaced with Excell 525 medium (JRH Bioscience). The cells are allowed to grow at 37° C. for six days, after which the cell culture supernatant is harvested. Human IgG-specific ELISA analysis, i.e., measuring all IgG sub-types, is done to determine the IgG concentration in transfected and non-transfected PER.C6® cells (human retina cells that express adenovirus E1A and E1B proteins). Human IgG from each supernatant is subsequently purified using Protein A-affinity chromatography (Hightrap Protein A HP, cat. no. 1-040203) according to standard procedures, following recommendations of the manufacturer (Amersham Biosciences). After elution, samples are concentrated in a Microcon YM30 concentrator (Amicon) and buffer exchanged to 10 mM sodium phosphate, pH 6.7. Samples are analyzed for binding to the targets EPCAM and CD46 using cell lines having a high expression of these molecules such as LS174T cells. Twelve µg of purified IgG, either transiently expressed UBS-54

IgG1, K53 IgG3 or IgG from the cells in which both antibodies were co-transfected, is subsequently analyzed on iso-electric-focusing gels (Serva Pre-cast IEF gels, pH range 3-10, cat. no. 42866). Samples are loaded on the low pH side and, after focusing, stained with colloidal blue. The pI values of the major isoforms for each sample are determined to illustrate whether there has been expression of UBS-54 IgG1, K53 IgG3 or bispecific heterodimers, depending on how the cells were transfected. The identification of heterodimers would indicate that single cells have translated both the IgG3 heavy chain of K53 and the IgG1 heavy chain of UBS-54 and assembled these into a full-length IgG molecule together with the common light chain.

The absence of bispecific heterodimers indicates that it is possible to translate both the IgG3 heavy chain of K53 and the IgG1 heavy chain of UBS-54 in single cells, but that these do not assemble into a full-length IgG molecule together with the common light chain, i.e., there is preferential binding of IgG1 and IgG3 heavy chains. This could, however, also be explained by the lack of co-expression of UBS-54 IgG1 and K53 IgG3. Therefore, stable clonal cell lines expressing both pUBS3000Neo and pK53IgG3 are generated by procedures as such well known to persons skilled in the art. PER.C6® cells (human retina cells that express adenovirus E1A and E1B proteins) are seeded in DMEM plus 10% FBS in tissue culture dishes (10 cm diameter) or T80 flasks with approximately $2.5 \times 10^6$ cells per dish and kept overnight under their normal culture conditions (10% $CO_2$ concentration and 37° C.). The next day, transfections are performed in separate dishes at 37° C. using Lipofectamine (Invitrogen Life Technologies) according to standard protocols provided by the manufacturer, with either 1-2 μg pUBS3000Neo, pK53IgG3 or both. As a control for transfection efficiency, a few dishes are transfected with a LacZ control vector, while a few dishes will be not transfected and serve as negative controls.

After four to five hours, cells are washed twice with DMEM and given fresh medium without selection. The next day, medium is replaced with fresh medium containing 500 μg/ml G418. Cells are refreshed every two or three days with medium containing the same concentrations of G418. About 20 to 22 days after seeding, a large number of colonies are visible and from each transfection, at least 300 are picked and grown via 96-well plates and/or 24-well plates via 6-well plates to T25 flasks. At this stage, cells are frozen (at least one, but usually four vials per sub-cultured colony) and production levels of recombinant human IgG antibody are determined in the supernatant using an ELISA specific for all sub-types of human IgG. Also, at this stage, G418 is removed from the culture medium and never re-applied again. For a representative number of colonies, larger volumes are cultured to purify the recombinant human IgG from the conditioned supernatant using Protein A-affinity chromatography (Hightrap Protein A HP, cat. no. 1-040203) according to standard procedures, following recommendations of the manufacturer (Amersham Biosciences). Purified human immunoglobulins from the various clones are analyzed on SDS-PAGE, Iso-electric focusing (IEF) and binding to the targets EPCAM and CD46 using cell lines having a high expression of these molecules such as LS174T cells. The clones are also screened by PCR on genomic DNA for the presence or absence of pUBS3000Neo and pK53IgG3. The identity of the PCR products is further confirmed by DNA sequencing.

A limited number of clones, which are screened positive for the production of both EPCAM IgG1 and K53 IgG3, are subjected to single cell sorting using a fluorescence-activated cell sorter (FACS) (Becton Dickinson FACS VANTAGE SE™) Alternatively, colonies are seeded at 0.3 cells/well to guarantee clonal outgrowth. Clonal cell populations, hereafter designated as sub-clones, are refreshed once a week with fresh medium. Sub-clones are grown and transferred from 96-well plates via 24- and 6-well plates to T25 flasks. At this stage, sub-clones are frozen (at least one, but usually four vials per sub-clone) and production levels of recombinant human IgG antibody are determined in the supernatant using a human IgG-specific ELISA. For a representative number of sub-clones, larger volumes are cultured to purify the recombinant human IgG fraction from the conditioned supernatant using Protein A-affinity chromatography (Hightrap Protein A HP, cat. no. 1-040203) according to standard procedures, following recommendations of the manufacturer (Amersham Biosciences). Purified human immunoglobulins from the various clones are analyzed on SDS-PAGE, Iso-electric focusing (IEF) and binding to the targets EPCAM and CD46 using cell lines having a high expression of these molecules, such as, for instance, LS174T cells, or transfectants expressing these molecules.

Sub-clones are also screened by PCR on genomic DNA for the presence or absence of pUBS3000Neo and pK53IgG3. The identity of the PCR products is further confirmed by DNA sequencing.

Other methods such as Southern blot and/or FISH may also be used to determine whether both constructs are present in the clonal cell line.

Once the clonal sub-clones are available and confirmed positive for the expression of both UBS-54 IgG1 and K53 IgG3, the presence of functional K53 and UBS-54 shows that it is possible to generate a mixture of functional IgGs with different isotypes with the common light chain in a single cell. Analysis of the expression of bispecific antibodies binding both EpCAM and CD46 will reveal to what extent the different heavy chains having a different sub-type will pair, which will influence the amount of bispecific antibodies produced. It is expected that no or very low levels of bispecific antibodies will be found in this case.

Example 8

Selection of Phage Carrying Single Chain Fv Fragments Specifically Recognizing Rabies Virus Glyco Protein (RVGP) Using RVGP-Ig Fusion Protein, and Expression of Mixtures of Antibodies Against the Rabies Virus This example describes the production of mixtures of antibodies against the rabies virus as another potential target. As an antigen, the Rabies Virus Glycoprotein (RVGP) is chosen, but other rabies antigens may be chosen or included as well for this purpose. Several monoclonal antibodies recognizing RVGP have already been described in the art, and polyclonal antibodies have been recognized to be useful in treatment of rabies infections as well (e.g., EP0402029; EP0445625, the entirety of which are incorporated herein by reference).

Antibody fragments are selected using antibody phage display libraries and MAbstract™ technology, essentially as described in U.S. Pat. No. 6,265,150 and in WO 98/15833, the entirety of which is incorporated herein by reference. All procedures are performed at room temperature unless stated otherwise. The sequence of RVGP is available to one of ordinary skill in the art for cloning purposes (e.g., Yelverton et al., 1983, the entirety of which is incorporated herein by reference). An RVGP-Ig fusion protein consisting of whole RVGP fused genetically to the CH2 and CH3 domains of human IgG1 is produced using vector pcDNA3.1 Zeo-CH2-CH3 expressed in PER.C6® (human retina cells that express adenovirus E1A and E1B proteins) and coated for two hours at 37° C. onto the surface of MAXISORP™ (polystyrene based modified surface with a high affinity for polar groups) plastic tubes (Nunc) at a concentration of 1.25 μg/ml. The tubes are blocked for one hour in 2% fat-free milk powder dissolved in PBS (MPBS). Simultaneously, 500 μl (approximately $10^{13}$ cfu) of a phage display library expressing single chain Fv fragments (scFvs) essentially prepared as described by De Kruif et al. (1995a, b) and references therein, is added to two volumes of 4% MPBS. In this experiment, selections are performed using fractions of the original library constructed using only one single variable light chain gene species (e.g., a "Vκ1"-library). In addition, human serum is added to a final concentration of 15% and blocking is allowed to proceed for 30 to 60 minutes. The RVGP-Ig-coated tubes are emptied and the blocked phage library is added. The tube is sealed and rotated slowly for one hour, followed by two hours of incubation without rotation. The tubes are emptied and washed ten times in PBS containing 0.1% TWEEN®-20, followed by washing five times in PBS. One ml glycine-HCL, 0.05 M, pH 2.2 is added, and the tube is rotated slowly for ten minutes. The eluted phages are added to 500 μl 1 M Tris-HCl pH 7.4. To this mixture, 3.5 ml of exponentially growing XL-1 blue bacterial culture is added. The tubes are incubated for 30 minutes at 37° C. without shaking. Then, the bacteria are plated on 2TY agar plates containing ampicillin, tetracycline and glucose. After overnight incubation of the plates at 37° C., the colonies are scraped from the plates and used to prepare an enriched phage library, essentially as described by De Kruif et al. (1995a, b). Briefly, scraped bacteria are used to inoculate 2TY medium containing ampicillin, tetracycline and glucose and grown at a temperature of 37° C. to an $OD_{600\ nm}$ of ~0.3. Helper phages are added and allowed to infect the bacteria, after which the medium is changed to 2TY containing ampicillin, tetracycline and kanamycin. Incubation is continued overnight at 30° C. The next day, the bacteria are removed from the 2TY medium by centrifugation, after which the phages are precipitated using polyethylene glycol 6000/NaCl. Finally, the phages are dissolved in a small volume of PBS-1% BSA, filter-sterilized and used for a next round of selection. The selection/re-infection procedure is performed twice.

After the second round of selection, individual *E. coli* colonies are used to prepare monoclonal phage antibodies. Essentially, individual colonies are grown to log-phase and infected with helper phages, after which phage antibody production is allowed to proceed overnight. Phage antibody-containing supernatants are tested in ELISA for binding activity to human RVGP-Ig coated 96-well plates.

Selected phage antibodies that are obtained in the screen described above are validated in ELISA for specificity. For this purpose, human RVGP-Ig is coated to Maxisorp ELISA plates. After coating, the plates are blocked in 2% MPBS. The selected phage antibodies are incubated in an equal volume of 4% MPBS. The plates are emptied, washed once in PBS, after which the blocked phages are added. Incubation is allowed to proceed for one hour, the plates are washed in PBS 0.1% TWEEN®-20 and bound phages are detected using an anti-M13 antibody conjugated to peroxidase. As a control, the procedure is performed simultaneously using a control phage antibody directed against thyroglobulin (De Kruif et al. 1995a, b), which serves as a negative control.

The phage antibodies that bind to human RVGP-Ig are subsequently tested for binding to human serum IgG to exclude the possibility that they recognized the Fc part of the fusion protein.

In another assay, the phage antibodies are analyzed for their ability to bind PER.C6® cells (human retina cells that express adenovirus E1A and E1B proteins) that express RVGP. To this purpose, PER.C6® cells (human retina cells that express adenovirus E1A and E1B proteins) are transfected with a plasmid carrying a cDNA sequence encoding RVGP or with the empty vector and stable transfectants are selected using standard techniques known to a person skilled in the art (e.g., J. E. Coligan et al. (2001), *Current Protocols In Protein Science*, volume I, John Wiley & Sons, Inc. New York, the entirety of which is incorporated herein by reference). For flow cytometry analysis, phage antibodies are first blocked in an equal volume of 4% MPBS for 15 minutes at 4° C. prior to the staining of the RVGP- and control-transfected PER.C6® cells (human retina cells that express adenovirus E1A and E1B proteins). The blocked phages are added to a mixture of unlabeled control-transfected PER.C6® cells (human retina cells that express adenovirus E1A and E1B proteins) and RGVP-transfected PER.C6® cells that have been labeled green using a lipophylic dye (PKH67, Sigma). The binding of the phage antibodies to the cells is visualized using a biotinylated anti-M13 antibody (Santa Cruz Biotechnology), followed by streptavidin-phycoerythrin (Caltag). Anti RVGP scFv selectively stains the PER.C6® RVGP transfectant while they do not bind the control transfectant.

An alternative way of screening for phages carrying single chain Fv fragments specifically recognizing human RVGP, is by use of RVGP-transfected PER.C6® cells (human retina cells that express adenovirus E1A and E1B proteins).

PER.C6® cells (human retina cells that express adenovirus E1A and E1B proteins) expressing membrane-bound RVGP are produced as described supra. Phage selection experiments are performed as described supra, using these cells as target. A fraction of the phage library comprised of scFv phage particles using only one single scFv species (500 μl, approximately $10^{13}$ cfu) is blocked with 2 ml RPMI/10% FCS/1% NHS for 15 minutes at RT. Untransfected PER.C6® cells (human retina cells that express adenovirus E1A and E1B proteins) (~$10\times10^6$ cells) are added to the PER.C6®-RVGP cells (~$1.0\times10^6$ cells). This mixture is added to the blocked light chain restricted phage library and incubated for 2.5 hours while slowly rotating at 4° C. Subsequently, the cells are washed twice and were resuspended in 500 μl RPMI/10% FCS and incubated with a murine anti-RVGP antibody (Becton Dickinson) followed by a phycoerythrin (PE)-conjugated anti-mouse-IgG antibody (Caltag) for 15 minutes on ice. The cells are washed once and transferred to a 4 ml tube. Cell sorting is performed on a FACSvantage fluorescence-activated cell sorter (Becton Dickinson) and RVGP (PE positive) cells are sorted. The sorted cells are spun down, the supernatant is saved and the bound phages are eluted from the cells by resuspending the cells in 500 μl 50 mM Glycin pH2.2 followed by incubation for five minutes at room temperature. The mixture is neutralized with 250 μl 1 M Tris-HCl pH 7.4 and added to the rescued supernatant. Collectively, these phages are used to prepare an enriched phage library as described above. The selection/re-infection procedure is performed twice. After the second round of selection, monoclonal phage antibodies are prepared and tested for binding to RVGP-PER.C6® cells and untransfected PER.C6® cells (human retina cells that express adenovirus E1A and E1B proteins) as described supra. Phages that are positive on RVGP-transfected cells are subsequently tested for binding to the RVGP-IgG fusion protein in ELISA as described supra.

The selected scFv fragments are cloned in a human IgG1 format, according to methods known in the art (e.g., Boel et al., 2000). To this purpose, the $V_L$ fragment shared by the selected scFv is PCR amplified using oligos that add appropriate restriction sites. A similar procedure is used for the $V_H$ genes. Thus, modified genes are cloned in expression pCRU-K01 (ECACC deposit 03041601), which results in expression vectors encoding a complete huIgG1 heavy chain and a complete human light chain gene having the same specificity as the original phage clone. By this method, three different heavy chains are cloned into separate expression vectors, while only one of the vectors needs to comprise the common light chain sequence. These expression vectors are provisionally designated pCRU-RVGP-1, pCU-RVGP-2, and pCRU-RVGP-3. Alternatively, these three vectors may lack DNA encoding the $V_L$ region, which can then be encoded in a fourth, separate expression vector not encoding a heavy chain. It is also possible to have $V_L$ sequences present in all three or two of the three vectors comprising the different $V_H$ sequences.

Stable PER.C6® (human retina cells that express adenovirus E1A and E1B proteins)-derived cell lines are generated, according to methods known to one of ordinary skill in the art (see, e.g., WO 00/63403), the cell lines expressing antibodies encoded by genetic information on either pCRU-RVGP-1, pCRU-RVGP-2 or pCRU-RVGP-3 and a cell line expressing antibodies encoded by all three plasmids. Therefore, PER.C6® cells are seeded in DMEM plus 10% FBS in tissue culture dishes (10 cm diameter) or T80 flasks with approximately $2.5\times10^6$ cells per dish and kept overnight under their normal culture conditions (10% $CO_2$ concentration and 37° C.). The next day, transfections are performed in separate dishes at 37° C. using Lipofectamine (Invitrogen Life Technologies) according to standard protocols provided by the manufacturer, with either 1-2 µg pCRU-RVGP-1, 1-2 µg pCRU-RVGP-2, 1-2 µg pCRU-RVGP-3 or 1 µg of a mixture of pCRU-RVGP-1, pCRU-RVGP-2 and pCRU-RVGP-3. As a control for transfection efficiency, a few dishes are transfected with a LacZ control vector, while a few dishes will not be transfected and serve as negative controls.

After four to five hours, cells are washed twice with DMEM and given fresh medium without selection. The next day, the medium is replaced with fresh medium containing 500 µg/ml G418. Cells are refreshed every two or three days with medium containing the same concentrations of G418. About 20 to 22 days after seeding, a large number of colonies are visible and from each transfection, at least 300 are picked and grown via 96-well plates and/or 24-well plates via 6-well plates to T25 flasks. At this stage, cells are frozen (at least one, but usually four vials per sub-cultured colony) and production levels of recombinant human IgG antibody are determined in the supernatant using an ELISA specific for human IgG1 (described in WO 00/63403). Also, at this stage, G418 is removed from the culture medium and never re-applied again. For a representative number of colonies, larger volumes will be cultured to purify the recombinant human IgG1 fraction from the conditioned supernatant using Protein A-affinity chromatography according to standard procedures. Purified human IgG1 from the various clones is analyzed on SDS-PAGE, Iso-electric focusing (IEF) and binding to the target RVGP using an RVGP PER.C6®-transfectant described above.

Colonies obtained from the co-transfection with pCRU-RVGP-1, pCRU-RVGP-2 and pCRU-RVGP-3 are screened by PCR on genomic DNA for the presence or absence of each of the three constructs. The identity of the PCR products is further confirmed by DNA sequencing.

A limited number of colonies, which screened positive for the production of each of the three binding specificities (both by PCR at the DNA level as well as in the specified binding assays against RVGP), are subjected to single cell sorting using a fluorescence-activated cell sorter (FACS) (Becton & Dickinson FACS VANTAGE SE™).

Alternatively, colonies are seeded at 0.3 cells/well to guarantee clonal outgrowth. Clonal cell populations, hereafter designated as sub-clones, are refreshed once a week with fresh medium. Sub-clones are grown and transferred from 96-well plates via 24- and 6-well plates to T25 flasks. At this stage, sub-clones are frozen (at least one, but usually four vials per sub-clone) and production levels of recombinant human IgG1 antibody are determined in the supernatant using a human IgG1-specific ELISA. For a representative number of sub-clones, larger volumes are cultured to purify the recombinant human IgG1 fraction from the conditioned supernatant using Protein A-affinity chromatography according to standard procedures.

Purified human IgG1 from the various sub-clones is subsequently analyzed as described above for human IgG1 obtained from the parental clones, i.e., by SDS-PAGE, Iso-electric focusing (IEF) and binding to the target RVGP.

Sub-clones are also screened by PCR on genomic DNA for the presence or absence of each of the three constructs pCRU-RVGP-1, pCRU-RVGP-2 and pCRU-RVGP-3. The identity of the PCR products is further confirmed by DNA sequencing.

Other methods such as Southern blot and/or FISH can also be used to determine whether each of the three constructs are present in the clonal cell line.

Sub-clones that are proven to be transgenic for each of the three constructs are brought into culture for an extensive period to determine whether the presence of the transgenes is stable and whether expression of the antibody mixture remains the same, not only in terms of expression levels, but also for the ratio between the various antibody isoforms that are secreted from the cell. Therefore, the sub-clone culture is maintained for at least 25 population doubling times, either as an adherent culture or as a suspension culture. At every four to six population doublings, a specific production test is performed using the human IgG-specific ELISA and larger volumes are cultured to obtain the cell pellet and the supernatant. The cell pellet is used to assess the presence of the three constructs in the genomic DNA, either via PCR, Southern blot and/or FISH. The supernatant is used to purify the recombinant human IgG1 fraction as described supra. Purified human IgG1 obtained at the various population doublings is analyzed as described, i.e., by SDS-PAGE, Iso-electric focusing (IEF) and binding to the target RVGP.

The efficacy of the antibody mixtures against rabies is tested in in vitro cell culture assays where the decrease in spread of rabies virus is measured, as well as in in vivo animal models infected by rabies. Such models are known to one of ordinary skill in the art and are, e.g., described in EP0402029.

Example 9

Production of a Mixture of Antibodies with a Common Light Chain and Three Different Heavy Chain-Variable Regions in a Single Cell A method for producing a mixture of antibodies according to the invention using expression in a recombinant host cell of a single light chain and three different heavy chains capable of pairing to the single light chain to form functional antibodies, is exemplified herein and is schematically shown in FIG. 6.

Human IgGs UBS54 and K53 against the EP-CAM homotypic adhesion molecule (Huls et al., 1999) and the membrane cofactor protein CD46 (WO 02/18948), respectively, are described in Example 1. Another clone that was identified to bind to cofactor protein CD46 was clone 02-237 (sequence of $V_H$ provided in FIG. 12, SEQ ID NO:10). DNA sequencing of this clone revealed that it contained the same light chain as UBS54 and K53 but a unique heavy chain-variable sequence (see alignment in FIG. 3). As a result, the CDR3 of the heavy chain of 02-237 differs at four positions from that of K53 (see alignment in FIG. 13). The heavy and light chain-variable sequences of phage 02-237 were cloned into the expression plasmid pCRU-K01 (pCRU-K01 is deposited at the European Collection of Cell Cultures (ECACC) under number 03041601), which contains the heavy and light chain constant domains for an IgG1 antibody.

Figure 15:
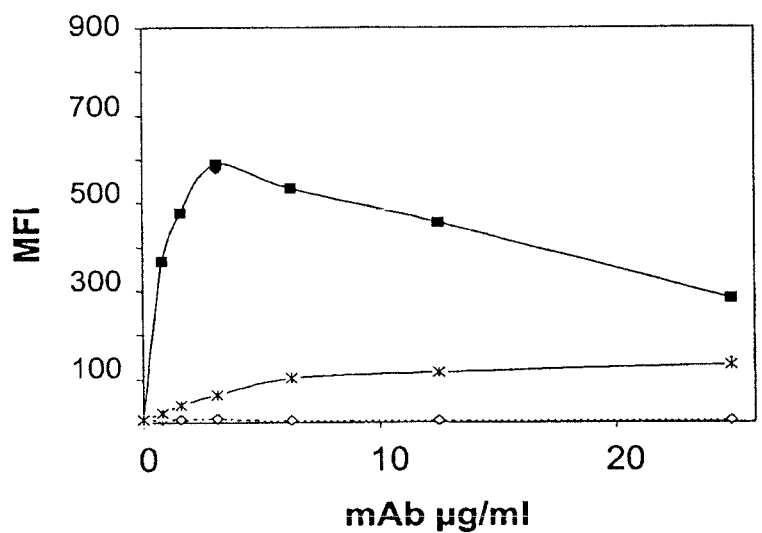
FIG. 15 shows binding of K53 and 02-237 to LS174T cells. Serial dilutions of purified 02-237 (■), K53 (*) and the negative control GBSIII (◇) conjugated to biotin were incubated with LS147T cells pre-incubated with normal human serum to block Fcγ receptor interaction. Binding (MFI, ordinate) was determined by FACS after incubation with streptavidin-conjugated phycoerythrin.

The resulting plasmid was designated pgG102-237. Due to the cloning strategy followed, the resulting N-terminus of the light chain of 02-237 as encoded by pgG102-237 differed slightly from the N-terminus of UBS54 and K53 as present by pUBS3000Neo, pCD46_3000(Neo), respectively (FIG. 3). Plasmid pgG102-237 was transiently produced in human 293(T) cells or stably in PER.C6® cells (human retina cells that express adenovirus E1A and E1B proteins). It appeared that purified 02-237 IgG had a much higher affinity for purified CD46 (FIG. 14) than K53 IgG, i.e., the affinity had increased from $9.1 \times 10^{-7}$ M to $2.2 \times 10^{-8}$ M for K53 and 02-237, respectively. Also, 02-237 bound much better to CD46 on human colon carcinoma LS174T cells than K53 (FIG. 15).

Stable PER.C6® (human retina cells that express adenovirus E1A and E1B proteins)-derived cell lines expressing a combination of the plasmids pUBS3000Neo, pCD46_3000 (Neo) and pgG102-237 encoding human IgG 02-237 were generated according to methods known as such to one of ordinary skill in the art (see, e.g., WO 00/63403). Therefore, PER.C6® cells (human retina cells that express adenovirus E1A and E1B proteins) were seeded in DMEM plus 10% FBS in tissue culture dishes (10 cm diameter) with approximately $2.5 \times 10^6$ cells per dish and kept overnight under their normal culture conditions (10% $CO_2$ concentration and 37° C.). The next day, transfections were performed in separate dishes at 37° C. using Lipofectamine (Invitrogen Life Technologies) according to standard protocols provided by the manufacturer, with 2 μg of an equimolar mixture of pUBS3000Neo, pCD46_3000(Neo) and pgG102-237. As negative control for selection, a few dishes were not transfected.

After four to five hours, cells were washed twice with DMEM and given fresh medium without selection. The next day, medium was replaced with fresh medium containing 500 μg/ml G418. Cells were refreshed every two or three days with medium containing the same concentrations of G418. About 20 to 22 days after seeding, a large number of colonies were visible and about 300 were picked and grown via 96-well plates and/or 24-well plates via 6-well plates to T25 flasks. During sub-culturing, production levels of recombinant human IgG antibody were determined in the supernatant using an ELISA specific for human IgG1 (described in WO 00/63403). About 25% of all colonies appeared to be positive in this highly specific assay. The production levels measured at this stage were comparable to the levels when a single IgG is expressed in PER.C6® cells (human retina cells that express adenovirus E1A and E1B proteins) (expression of a single IgG described in Jones et al., 2003). It is important to stress that these high expression levels were obtained without any methods for amplification of the transgene and that they occur at a low copy number of the transgene.

The 30 best producing colonies were frozen down in vials and the 19 highest producing clones were selected for purification of the IgG (Table 1). They were sub-cultured in T80 flasks and human IgG from each clone was subsequently purified using Protein A-affinity chromatography. Therefore, 15 to 25 ml of conditioned medium was loaded on a 5 ml Protein A FF Sepharose column (Amersham Biosciences). The column was washed with 4 mM phosphate buffered saline, pH 7.4 (PBS) before elution with 0.1 M citrate pH 3.0. The eluted fraction was subsequently desalted on a Sephadex G25 Fine HIPREP® Desalting column (Amersham Biotech) to PBS. The concentration of the purified IgG fraction was determined by absorbance measurement at 280 nm using a coefficient of 1.4 for a 0.1% (w/v) solution (Table 1).

Figure 16A:
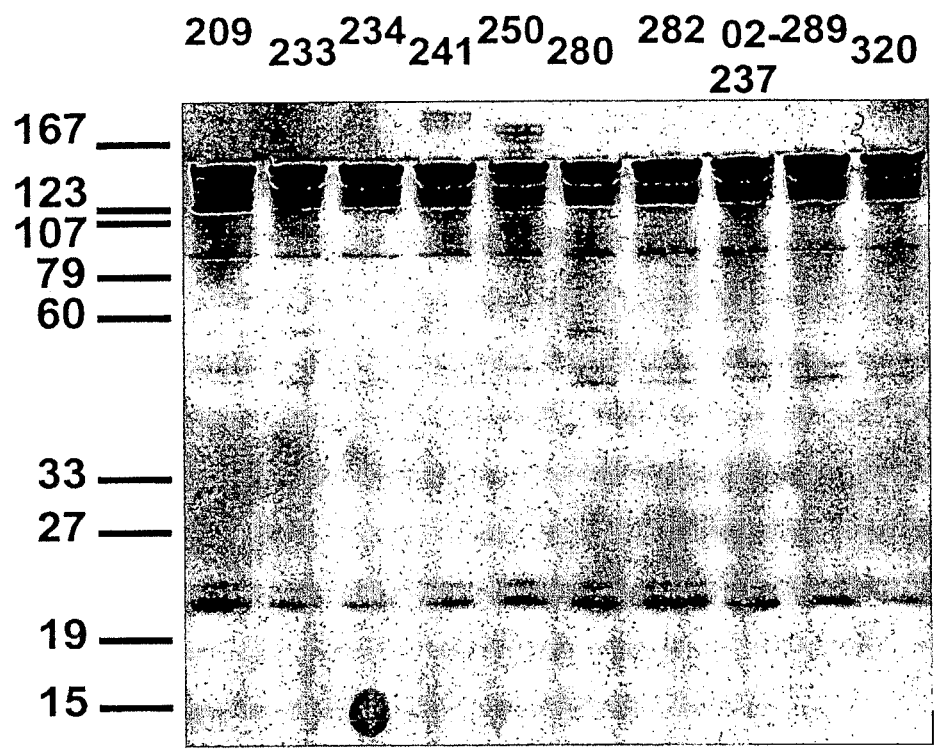
FIG. 16A is an SDS-PAGE analysis of purified IgG fractions. Three μg purified IgG was analyzed on a non-reduced 4-20% NUPAGE® gel (NOVEX) according to recommendations of the manufacturer. Proteins were visualized by staining with colloidal blue (NOVEX Cat. No LC6025) according to recommendations of the manufacturer. Clone identity is indicated on top of the SDS-PAGE. Each gel contains a control, which is either purified 02-237 or K53.
Figure 16B:
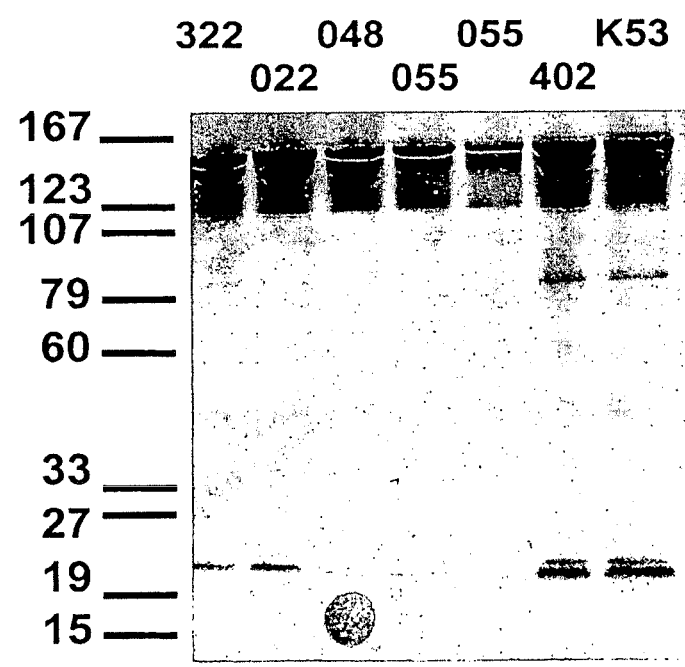
FIGS. 16B and 16C are continuations of the gel in FIG. 16A.
Figure 16C:
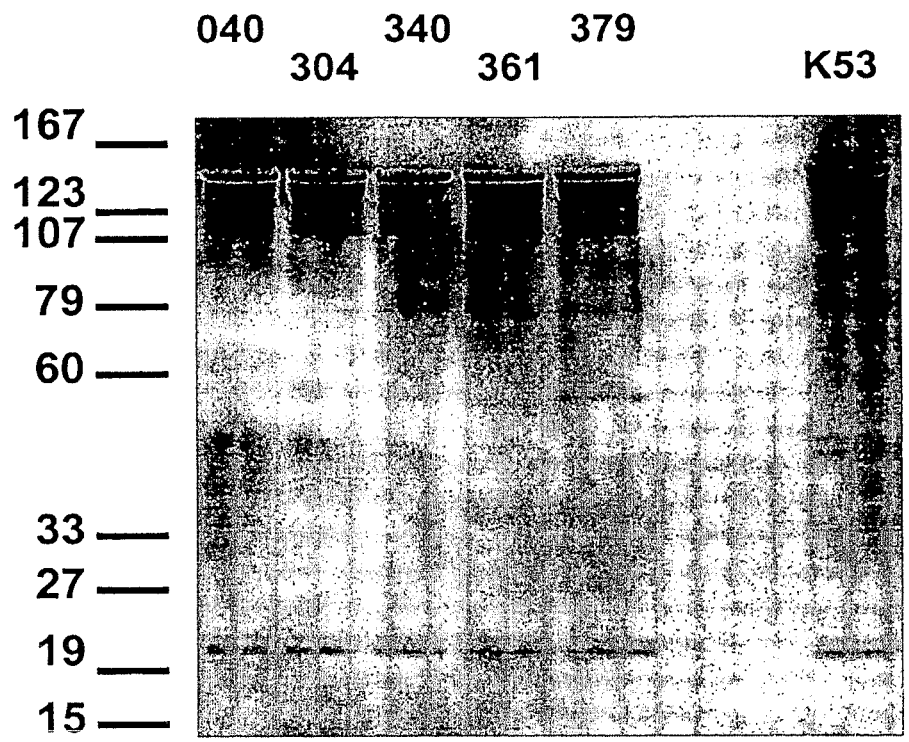
Figure 16D:
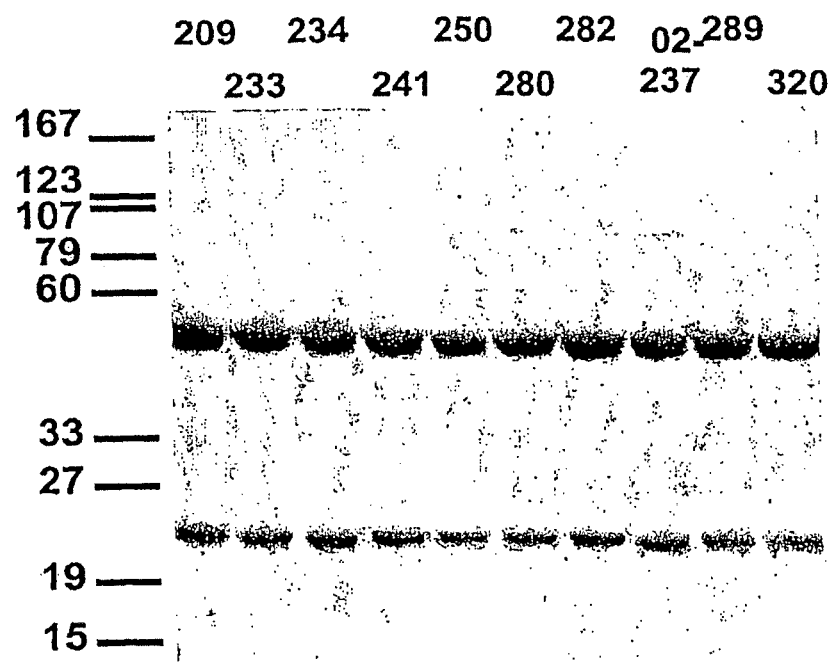
FIG. 16D is an SDS-PAGE analysis of purified IgG fractions. Three μg purified IgG was analyzed on a reduced 4-20% NUPAGE® gel according to recommendations of the manufacturer. Proteins were visualized by staining with colloidal blue (NOVEX cat. No LC6025) according to recommendations of the manufacturer. Clone identity is indicated on top of the SDS-PAGE. Each gel contains a control, which is either purified 02-237 or K53. NR, Non-reduced; R, reduced.
Figure 16E:
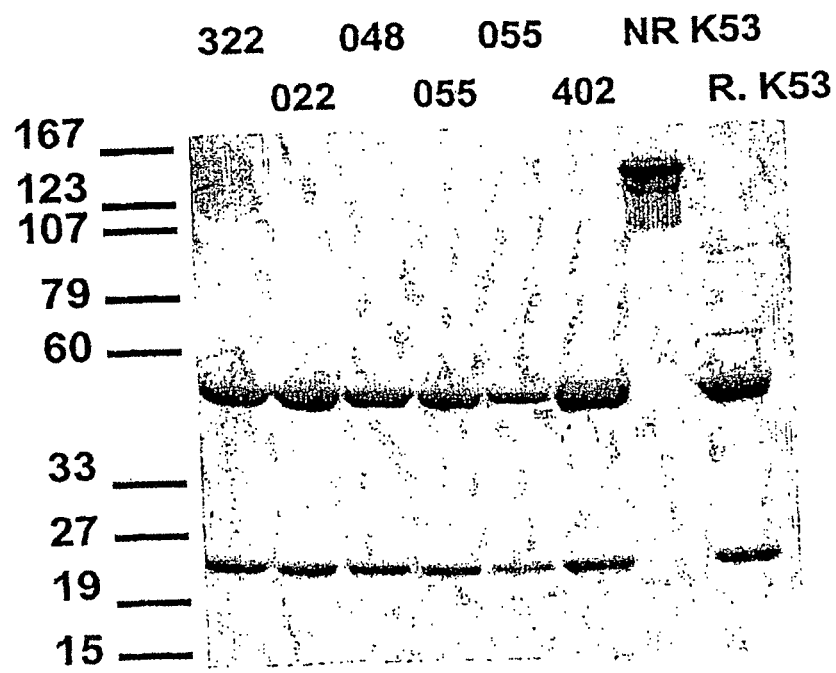
FIGS. 16E and 16F are continuations of the gel in FIG. 16D.
Figure 16F:
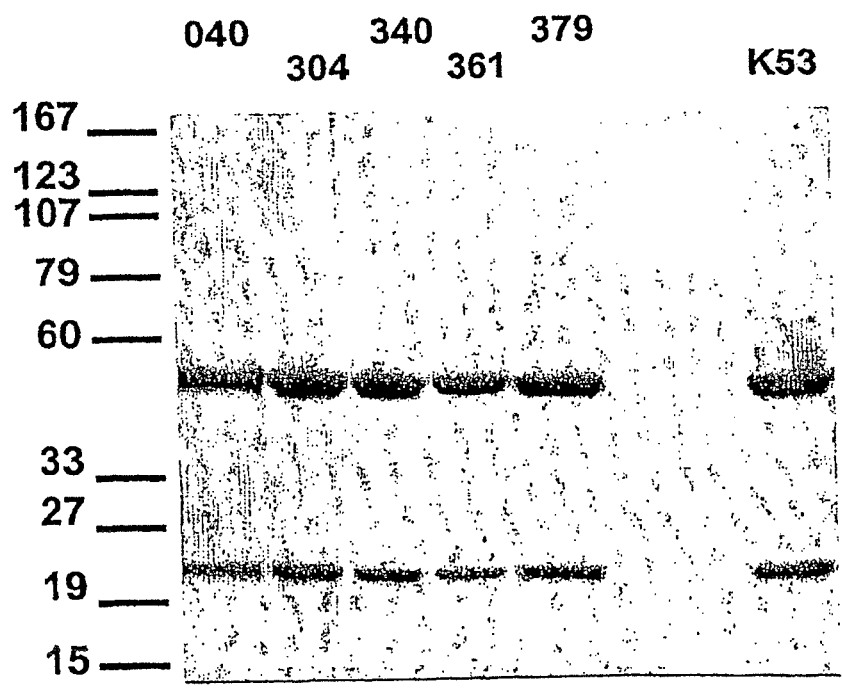
Figure 17A:
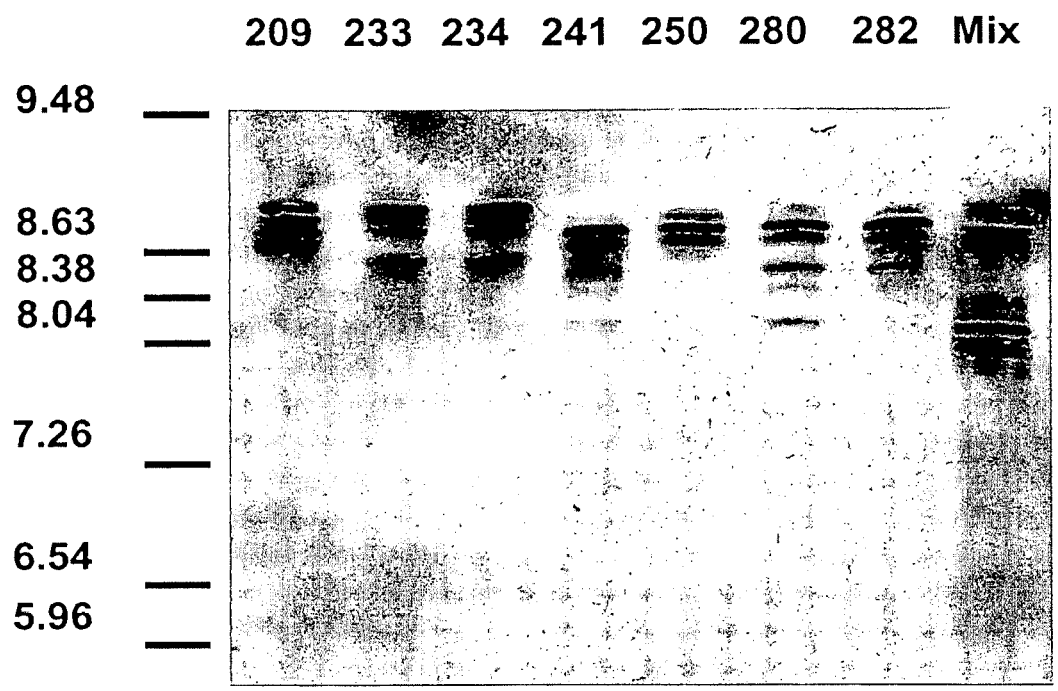
FIG. 17A shows an IEF analysis of purified IgG fractions. Ten μg purified IgG was analyzed on an Isogel 3-10 gel (BMA) according to recommendations of the manufacturer. Proteins were visualized by staining with colloidal blue according to recommendations of the manufacturer. Clone identity is indicated on top of the IEF. Each gel contains a control, consisting of a 1:1:1 mixture of 02-237, K53 and UBS54.
Figure 17B:
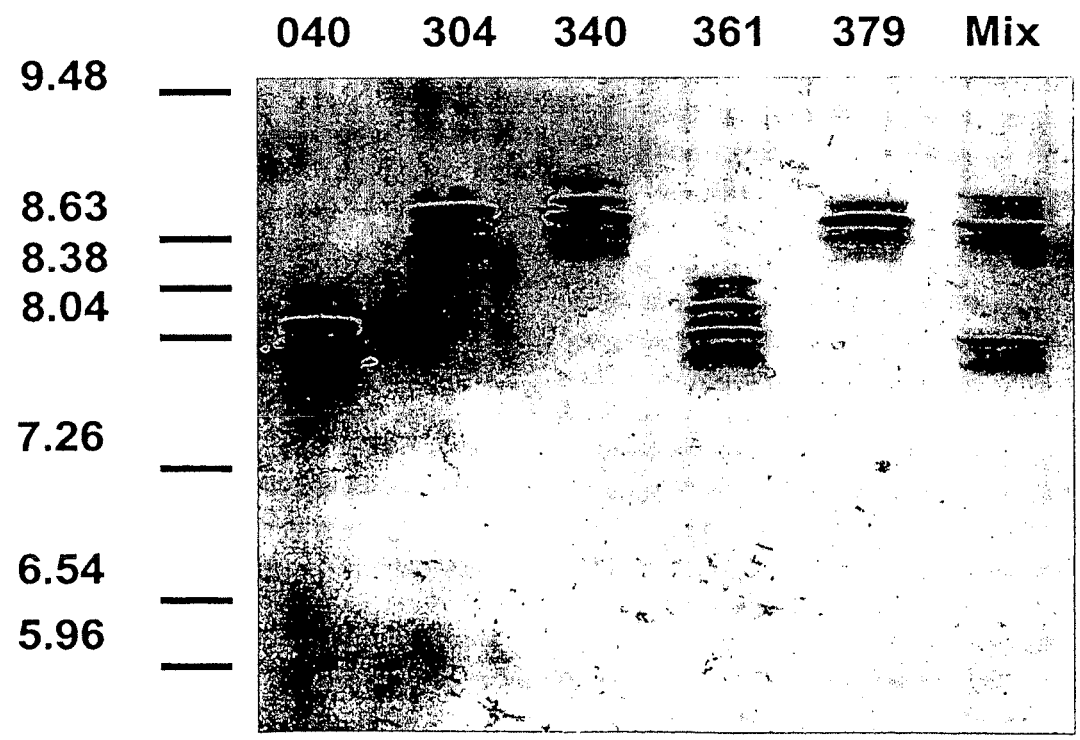
FIGS. 17B through 17D are continuations of the gel in FIG. 17A.
Figure 17C:
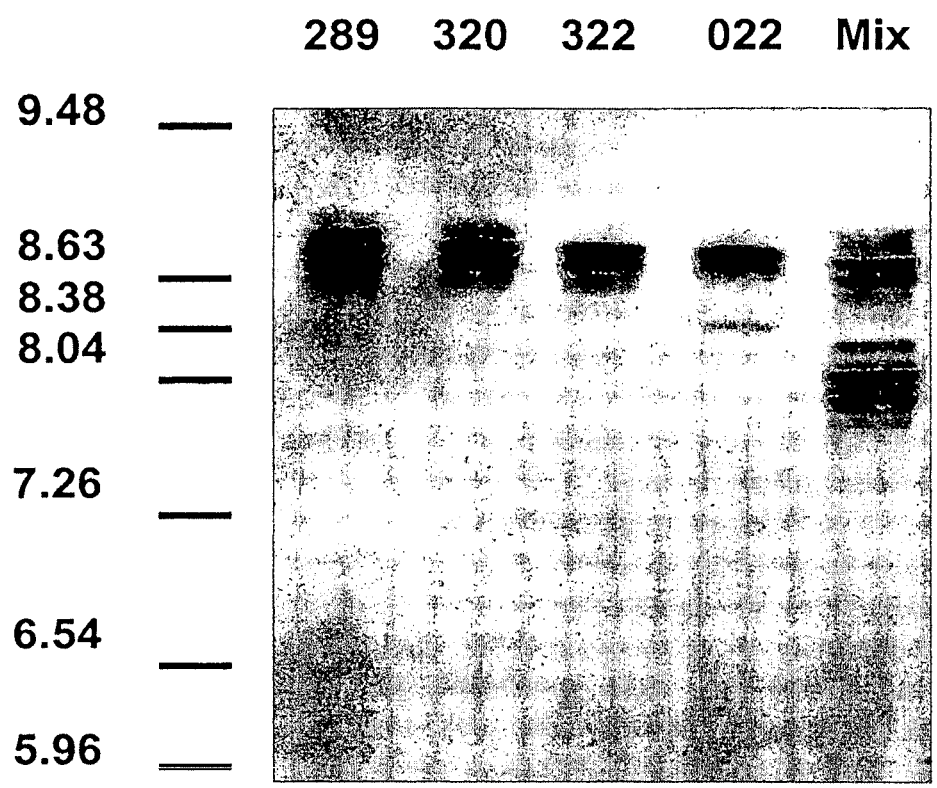
Figure 17D:
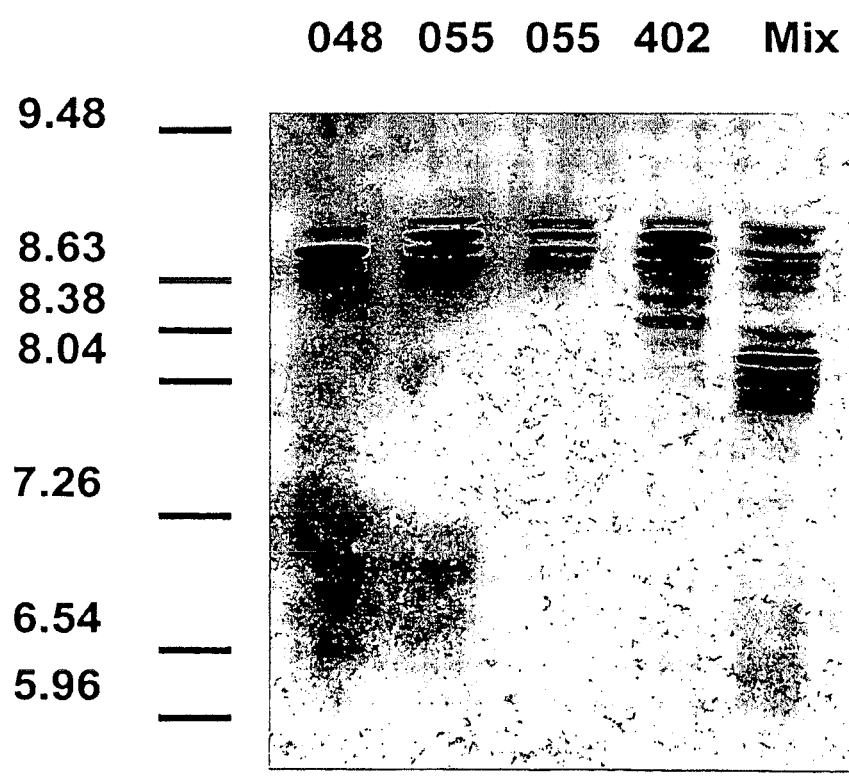

The purified IgG samples were analyzed on non-reduced and reduced SDS-PAGE and IEF. Non-reduced SDS-PAGE (FIG. 16A) showed that all IgG samples migrated comparable to the control K53 or 02-237 as an assembled, intact IgG molecule of approximately 150 kDa. On reduced SDS-PAGE (FIG. 16B), the IgG samples migrated as heavy and light chains of about 50 and 25 kDa, respectively, comparable to the heavy and light chain of the control K53 or 02-237.

Figure 18:
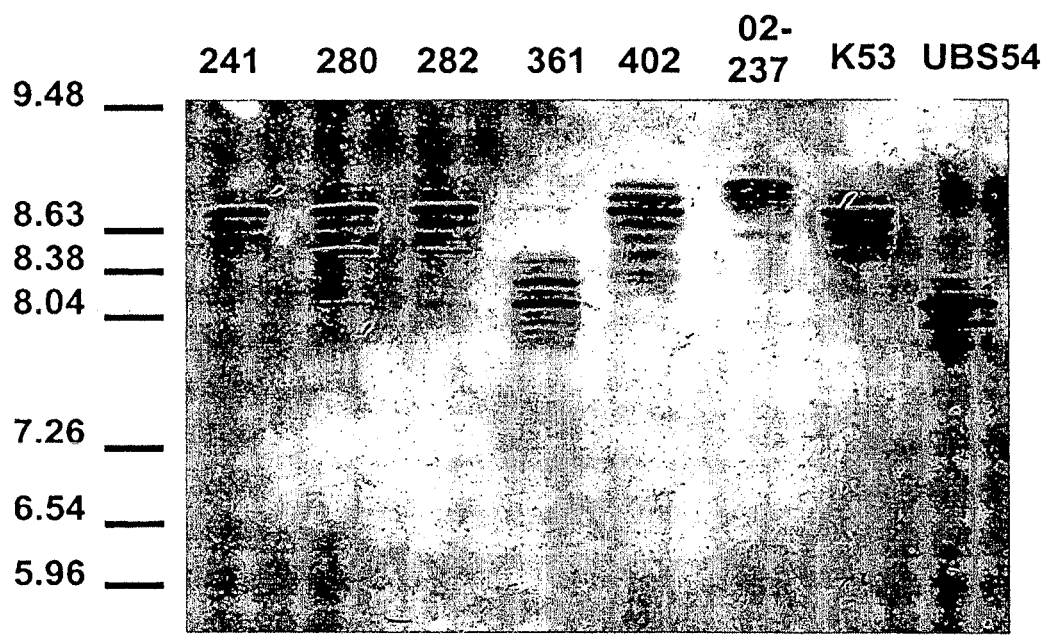
FIG. 18 is an IEF analysis of polyclonal mixtures 241, 280, 282, 361 and 402 in comparison to single K53, 02-237 and UBS54. Ten μg purified IgG was analyzed on an Isogel 3-10 gel (BMA) according to recommendations of the manufacturer. Proteins were visualized by staining with colloidal blue according to recommendations of the manufacturer. IgG identity is indicated on top of the IEF.

On IEF, the purified IgG fractions were first compared to a mixture of equal amounts of K53, UBS54 and 02-237 (FIG. 17). Clearly, some of the samples contained isoforms with a unique pI profile when compared to the mixture containing purified K53, UBS54 and 02-237. Some major unique isoforms have a pI in between the pI of K53 and 02-237 on one hand and UBS54 on the other hand. This is also anticipated on the basis of the theoretic pI when calculated with the ProtParam tool provided on the Expasy homepage (expasy.ch; Appel et al., 1994). K53, 02-237 and UBS54 have a theoretic pI of 8.24, 8.36 and 7.65, respectively, whereas an isoform representing a heterodimer of one UBS54 heavy chain and one K53 heavy chain, has a theoretical pI of 8.01. Assembly of such a heterodimer can only occur when a single cell translates both the heavy chain of K53 and the heavy chain of UBS54 and assembles these into a full-length IgG molecule together with the common light chain. Hence, these results suggest that certain clones at least express two functional antibodies. To confirm the unique identity of some of the isoforms, samples of the most interesting clones were run in parallel with K53, UBS54 and 02-237, either alone or in a mixture (FIG. 18). This furthermore showed that some clones expressed at least two antibodies (241, 282, 361). Moreover, it provided evidence that some clones express all three functional antibodies (280 and 402).

To confirm that the clones expressed IgG mixtures comprising all three heavy chains, peptide mapping (Garnick, 1992; Gelpí, 1995, the entirety of which are incorporated herein by reference) was used to analyze the polyclonal IgG fraction. We previously employed peptide mapping to recover 99% of the protein sequence of K53.

Figure 19:
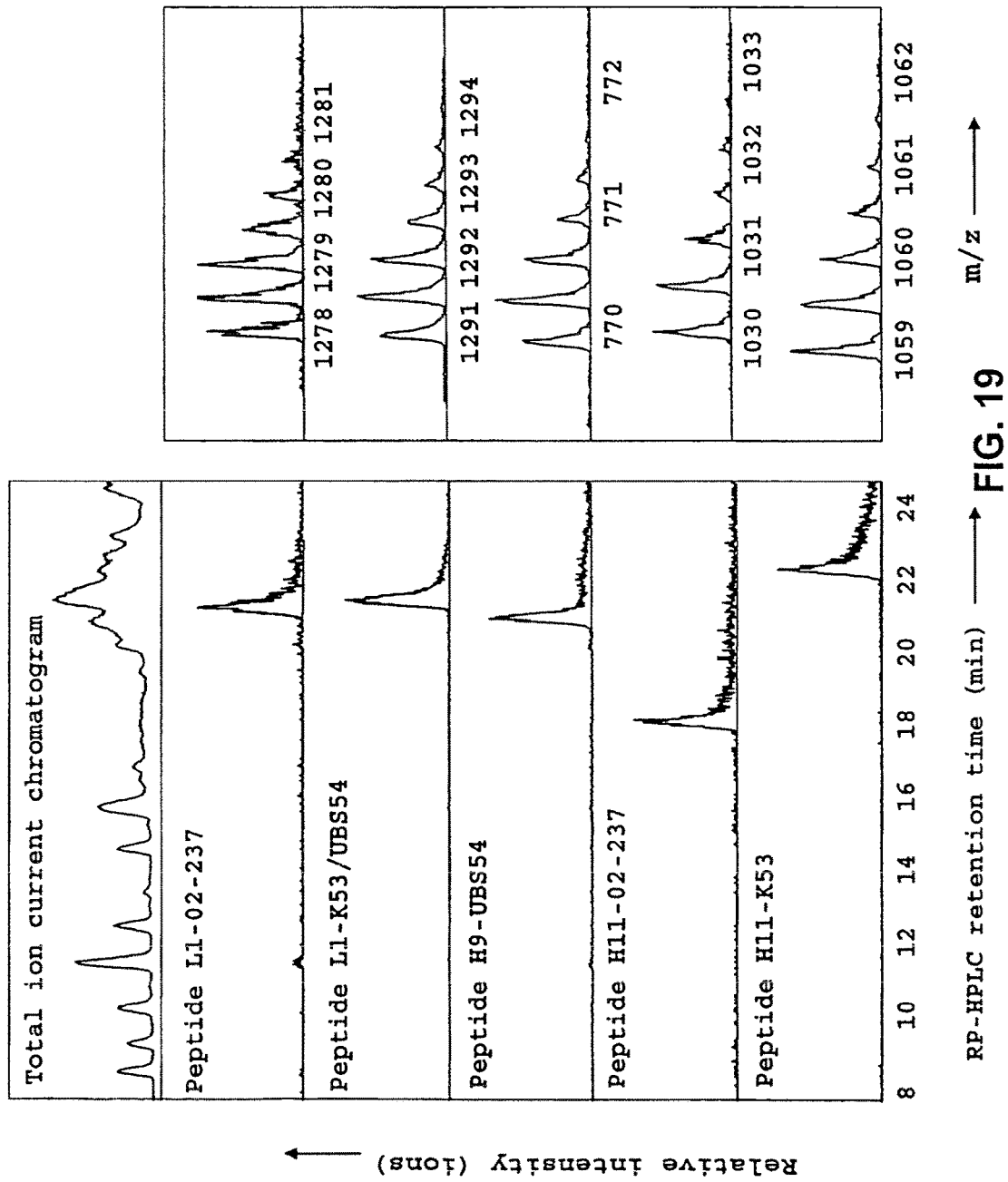
FIG. 19 contains mass chromatograms of CDR3 peptides of K53, 02-237, UBS54 and the two unique light chain peptides L1-K53/UBS54 and L1-237 in IgG fraction Poly1-280. On the right-hand side of each mass chromatogram, the isotopic pattern of the peptide is shown. The doubly charged ion at m/z 1058.98 (Mw 2115.96 Da) results from peptide H11-K53. The doubly charged ion at m/z 1029.96 (Mw 2057.92 Da) results from peptide H11-02-237. The triply charged ion at m/z 770.03 (Mw 2307.09 Da) results from peptide H9-UBS54. The doubly charged ion at m/z 1291.08 (Mw 2580.16 Da) results from peptide L1-K53/UBS54. The doubly charged ion at m/z 1278.11 (Mw 2554.22 Da) results from peptide L1-02-237.

Based on the protein sequence provided in FIG. 12, the mass of the theoretical tryptic peptides of K53, UBS54 and 02-237 was calculated (Table II and III). A few unique peptides for each IgG could be identified, for instance, the CDR3 peptides for K53, 02-237 and UBS54 with a Mw of 2116.05, 2057.99 and 2307.15 Da, respectively. Next, a tryptic digest of Poly1-280 was prepared and this was analyzed using LC-MS (FIG. 19).

Peptides with Mw of 2116, 2057 and 2308 Da, representing the unique CDR3 peptides of K53, 02-237 and UBS54, respectively, were detected. The precise amino acid sequence of these peptides (as listed in Table III) was confirmed by MS-MS analysis (Tables IV, V and VI). The presence of the two unique N-terminal light chain peptides with Mw of 2580 and 2554 Da, respectively, was also confirmed. The peptide mapping data unequivocally showed that a mixture of antibodies comprising a common light chain and three different heavy chains was expressed by PER.C6® (human retina cells that express adenovirus E1A and E1B proteins) clone Poly1-280. Also, clones 055, 241 and 402 were screened by peptide mapping. Clones 241 and 402 were confirmed positive for all three heavy chain sequences, whereas clone 055 only showed expression of the heavy chains of K53 and 02-237, and not of UBS54. This confirms the IEF screening (FIG. 18) where no UBS54-related band was seen in sample 055.

Poly1-280 was analyzed by BIACORE™ (surface plasmon resonance) for binding to CD46 (FIG. 20). The affinity of poly1-280 for CD46 was $2.1 \times 10^{-8}$ M, which shows that the IgG mixture contains CD46-binding molecules having the same affinity as 02-237 IgG alone.

Taken together, this experiment shows that it is possible to express a mixture of functional IgG molecules comprising three unique heavy chains in a single cell and that next to the homodimers, heterodimers consisting of two binding specificities are also formed. Furthermore, the frequency of clones expressing three different heavy chains suggests that it will also be possible to obtain clones expressing at least 4, 5, or more, heavy chains, using the same procedure. In the case where it would be difficult to obtain clones expressing higher numbers of heavy chains, a clone expressing at least three heavy chains according to the invention can be used to introduce more heavy chains in a separate round of transfection, for instance by using a different selection marker.

Next, it was demonstrated that a single cell is able to produce a mixture of more than two functional human IgGs. Therefore, clones 241, 280 and 402, which were screened positive for the production of each of the three IgGs, both by IEF and MS, were subjected to limiting dilution, i.e., seeded at 0.3 cells/well in 96-well plates to guarantee clonal outgrowth.

Clonal cell populations, hereafter designated as sub-clones, were refreshed once a week with fresh medium. Sub-clones were grown and transferred from 96-well plates via 24- and 6-well plates, T25, T80 and T175 flasks. At the T80 stage, sub-clones were frozen. Production levels of recombinant human IgG1 antibody were determined in the supernatant using a human IgG1-specific ELISA. For each parental clone, three sub-clones were chosen and cultured in a few T175 flasks to obtain sufficient conditioned medium for purification using Protein A-affinity chromatography as described above.

Purified human IgG1 from the sub-clones was subsequently analyzed as described above for human IgG1 obtained from the parental clone by iso-electric focusing (IEF). The result is shown in FIG. 21. Sub-clones from clone poly 1-241 each have the same pattern, but differ from the parental clone in that they appear to miss certain bands.

Sub-clones from clone poly 1-280 all appear to differ from each other and from the parental clone. Patterns obtained by IEF for sub-clones from parental clone poly 1-402 are identical for all three sub-clones and the parent clone.

From these data, it can be concluded that clone 402 is stably producing a mixture of antibodies. This demonstrates that it is feasible to produce a mixture of antibodies according to the invention from a single cell clone. The clones have undergone about 25 population doublings (cell divisions) from the transfection procedure up to the first analysis (shown in FIG. 18) under selection pressure and, from that point on, have undergone about 30 population doublings during the sub-cloning procedure in the absence of selection pressure before the material analyzed in FIG. 21 was harvested. Therefore, the production of a mixture of antibodies from a clone from a single cell can be stable over at least 30 generations.

Purified IgG1 from the parental 241, 280 and 402 clones, and sub-clones, were also analyzed for binding reactivity towards the CD46 and EpCAM antigens. To this end, cDNA of EpCAM, CD46, and control antigen CD38 were cloned into expression vectors pcDNA (Invitrogen). These vectors were transfected into CHO (dhfr–) cells using Fugene (Roche) according to the protocol supplied by the manufacturer. Cells were cultured in Iscove's medium containing 10% FBS and HT supplement (Gibco). After culturing for two days, cells were harvested by trypsinization and suspended in PBS-1% BSA (PBSB) for use in FACS analysis.

Purified IgG1 of the clones producing the mixtures of antibodies and control IgG1 samples of anti-GBSIII, an anti-CD72 antibody (02-004), as well as antibodies from anti-EpCAM clone UBS54 and anti-CD46 clones K53 and 02-237, were diluted in PBSB to a concentration of 20 µg IgG1/ml. Twenty µl of each was added to 200,000 transfected cells and incubated on ice for one hour. Thereafter, cells were washed once in ice-cold PBSB. Bound IgG was then detected using incubation with goat-anti-human IgG-biotin followed by streptavidin-PE. After a final washing step, cells were suspended in PBSB containing 1 µg/ml propidium iodide. The samples were analyzed on a FACS (FACSvantage, Becton Dickinson). Live cells were gated and Mean Fluorescent Intensities (MFI) were calculated from the FACS plots. The results are represented in FIG. 22. As expected, UBS54 bound selectively to EpCAM-transfected cells and 02-237 and K53 bound selectively to CD46 transfectants, while unrelated antibodies did not bind to these transfectants.

The results demonstrate that binding activities towards both EpCAM and CD46 were present in the purified IgG1 preps of most clones expressing a mixture of antibodies according to the invention, demonstrating that a mixture of functional antibodies was produced by sub-clones that have undergone more than 30 cell divisions and that result from a single cell. In sub-clone 280-015, binding patterns towards CD46 and EpCAM were similar as in the parent clone poly 1-280, in contrast to the other clones.

It should be stated that the quantitative aspect of this assay is not completely clear. Routine screening, for example, by a functional test, can be used to find a clone with the desired expression profile. Quantitative aspects may also be included in such screens. Such screening allows for the identification of desired clones, which express the mixture of antibodies with a given functionality in a quantitatively stable manner.

All references, including publications, patents, and patent applications, cited herein are hereby incorporated by reference to the same extent as if each reference were individually and specifically indicated to be incorporated by reference and were set forth in its entirety herein.

TABLE I

Overview of the clones used for purification of IgG.

| Clone Poly1- | Screening ELISA (µg/ml) | Purification Conc. in feed (µg/ml) | Purification Purified (mg) |
|---|---|---|---|
| 209 | 6.1 | 98 | 1.37 |
| 233 | 10.0 | 53 | 0.75 |
| 234 | 8.0 | 51 | 0.71 |
| 241 | 6.6 | 91 | 1.42 |
| 250 | 12.5 | 117 | 2.10 |
| 280 | 6.3 | 36 | 0.80 |
| 282 | 8.5 | 67 | 1.48 |
| 289 | 8.2 | 33 | 0.64 |
| 304 | 7.2 | 161 | 3.91 |
| 320 | 6.3 | 43 | 0.83 |

TABLE I-continued

Overview of the clones used for purification of IgG.

| Clone Poly1- | Screening ELISA (µg/ml) | Purification Conc. in feed (µg/ml) | Purification Purified (mg) |
|---|---|---|---|
| 322 | 15.2 | 168 | 3.27 |
| 340 | 6.0 | 109 | 2.64 |
| 361 | 10.4 | 71 | 1.73 |
| 379 | 9.5 | 78 | 1.75 |
| 402 | 39.9 | 135 | 3.14 |
| 022 | 16.2 | 83 | 1.69 |
| 040 | 7.8 | 67 | 1.43 |
| 048 | 6.5 | 43 | 0.94 |
| 055 | 11 | 55 | 1.04 |

TABLE II

Tryptic peptides of the variable domains of the light chain of K53/UBS54 and 02-237.

| Peptide | First AA[1] | Last AA | Monoisotopic Mw (Da) K53/UBS54 | Monoisotopic Mw (Da) 02-237 |
|---|---|---|---|---|
| L1 | 1 | 24 | 2580.31[2] | 2554.28[2] |
| L2 | 25 | 59 | 4039.02 | 4039.02 |
| L3 | 60 | 66 | 700.35 | 700.35 |
| L4 | 67 | 79 | 1302.61 | 1302.61 |
| L5 | 80 | 82 | 374.23 | 374.23 |
| L6 | 83 | 107 | 2810.29[2] | 2810.29[2] |
| L7 | 108 | 111 | 487.30 | 487.30 |
| L8 | 112 | 112 | 174.11 | 174.11 |

[1] AA, amino acid
[2] One Cysteine residue alkylated

TABLE III

Tryptic peptides of variable domains of heavy chains of K53, 02-237 and UBS54.

| K53 A | B | C | D | 02-237 A | B | C | D | UBS54 A | B | C | D |
|---|---|---|---|---|---|---|---|---|---|---|---|
| H1 | 1 | 12 | 1267.68 | H1 | 1 | 12 | 1267.68 | H1 | 1 | 12 | 1267.68 |
| H2 | 13 | 19 | 685.41 | H2 | 13 | 19 | 685.41 | *H2* | *13* | *19* | *729.41* |
| H3 | 20 | 23 | 492.24 | H3 | 20 | 23 | 492.24 | H3 | 20 | 23 | 492.24 |
| H4 | 24 | 38 | 1693.81 | H4 | 24 | 38 | 1693.81 | *H4* | *24* | *38* | *1587.77* |
| H5 | 39 | 63 | 2783.28 | H5 | 39 | 63 | 2783.28 | *H5* | *39* | *63* | *2646.33* |
| H6 | 64 | 67 | 472.28 | H6 | 64 | 67 | 472.28 | *H6* | *64* | *67* | *506.26* |
| H7 | 68 | 84 | 1906.87 | H7 | 68 | 84 | 1906.87 | *H7* | *68* | *87* | *2174.04* |
| H8 | 85 | 87 | 374.23 | H8 | 85 | 87 | 374.23 | — | — | — | — |
| H9 | 88 | 98 | 1319.55 | H9 | 88 | 98 | 1319.55 | H8 | 88 | 98 | 1333.56 |
| *H10* | *99* | *102* | *493.21* | *H10* | *99* | *102* | *475.25* | H9 | 99 | 119 | 2307.15 |
| *H11* | *103* | *122* | *2116.05* | *H11* | *103* | *122* | *2057.99* | — | — | — | — |

Key:
A: peptide
B: first amino acid
C: last amino acid
D: monoisotopic $M_w$ (Da)

Remarks:
1) for H1, amino acid residue 1 is a pyroglutamic acid
2) peptides H3 and H9 from K53 and 02-237, and peptides H3 and H8 of UBS54 contain one alkylated cysteine residue
3) Unique peptides that can be used to confirm the presence of the respective IgGs are indicated in bold italics

TABLE IV

MS/MS-data of CDR3 peptide (H11) of K53, obtained by collision induced dissociation of doubly charged m/z 1059.06.

| Ion | m/z |
|---|---|
| $Y''_1$ | 147.12 |
| $Y''_2$ | 248.18 |
| $Y''_3$ | 335.21 [1] |
| $Y''_4$ | 406.25 |
| $Y''_5$ | 507.30 |
| $Y''_6$ | 594.33 |
| $Y''_7$ | 693.40 |
| $Y''_8$ | 794.46 |
| $Y''_9$ | 893.54 |
| $Y''_{10}$ | 1006.63 |
| $Y''_{11}$ | 1107.67 |
| $Y''_{12}$ | 1164.68 |
| $Y''_{13}$ | 1292.81 |
| $Y''_{14}$ | 1349.77 |
| $Y''_{15}$ | 1535.85 |
| $Y''_{16}$ | 1698.95 |
| $Y''_{17}$ | 1813.95 |
| $Y''_{18}$ | 1960.97 |
| $Y''_{19}$ | n.d. [2] |
| $B_1$ | n.d. |
| $B_2$ | 157.10 |

TABLE IV-continued

MS/MS-data of CDR3 peptide (H11) of K53, obtained by collision induced dissociation of doubly charged m/z 1059.06.

| Ion | m/z |
|---|---|
| $B_3$ | 304.18 |
| $B_4$ | 419.22 |
| $B_5$ | <u>582.31</u> |
| $B_6$ | 768.38 |
| $B_7$ | 825.39 |
| $B_8$ | 953.43 |
| $B_9$ | n.d. |
| $B_{10}$ | n.d. |
| $B_{11}$ | 1224.65 |
| $B_{12}$ | 1323.68 |
| $B_{13}$ | 1424.79 |
| $B_{14}$ | 1523.86 |
| $B_{15}$ | n.d. |
| $B_{16}$ | n.d. |
| $B_{17}$ | 1782.96 |
| $B_{18}$ | n.d. |
| $B_{19}$ | n.d. |

(1) Underlined m/z-values are main peaks in the MS/MS-spectrum.
(2) n.d. is not detected.

TABLE V

MS/MS-data of CDR3 peptide (H11) of 02-237, obtained by collision induced dissociation of doubly charged m/z 1030.02.

| Ion | m/z |
|---|---|
| $Y''_1$ | 147.12 |
| $Y''_2$ | 248.18 |
| $Y''_3$ | <u>335.20</u> |
| $Y''_4$ | 406.24 |
| $Y''_5$ | 493.30 |
| $Y''_6$ | <u>580.32</u> |
| $Y''_7$ | 679.40 |
| $Y''_8$ | <u>780.44</u> |
| $Y''_9$ | <u>879.53</u> |
| $Y''_{10}$ | 992.60 |
| $Y''_{11}$ | 1093.65 |
| $Y''_{12}$ | <u>1150.67</u> |
| $Y''_{13}$ | 1278.80 |
| $Y''_{14}$ | <u>1335.80</u> |
| $Y''_{15}$ | 1521.83 |
| $Y''_{16}$ | 1608.90 |
| $Y''_{17}$ | 1724.00 |
| $Y''_{18}$ | n.d. |
| $Y''_{19}$ | n.d. |
| $B_1$ | n.d. |
| $B_2$ | 189.09 |
| $B_3$ | n.d. |
| $B_4$ | 451.22 |
| $B_5$ | n.d. |
| $B_6$ | n.d. |
| $B_7$ | n.d. |
| $B_8$ | n.d. |
| $B_9$ | n.d. |
| $B_{10}$ | n.d. |
| $B_{11}$ | n.d. |
| $B_{12}$ | n.d. |
| $B_{13}$ | n.d. |
| $B_{14}$ | n.d. |
| $B_{15}$ | n.d. |
| $B_{16}$ | n.d. |
| $B_{17}$ | n.d. |
| $B_{18}$ | n.d. |
| $B_{19}$ | n.d. |

[1] Underlined m/z-values are main peaks in the MS/MS-spectrum.
[2] n.d. is not detected.

TABLE VI

MS/MS-data of CDR3 peptide (H9) of UBS54, obtained by collision induced dissociation of triply charged m/z 770.09.

| Ion | m/z |
|---|---|
| $Y''_1$ | n.d. |
| $Y''_2$ | 248.17 |
| $Y''_3$ | <u>335.20</u> |
| $Y''_4$ | 406.25 |
| $Y''_5$ | <u>507.30</u> |
| $Y''_6$ | <u>594.33</u> |
| $Y''_7$ | <u>693.42</u> |
| $Y''_8$ | <u>794.45</u> |
| $Y''_9$ | <u>893.53</u> |
| $Y''_{10}$ | <u>1006.64</u> |
| $Y''_{11}$ | 1107.67 |
| $Y''_{12}$ | 1164.68 |
| $Y''_{13}$ | n.d. |
| $Y''_{14}$ | n.d. |
| $Y''_{15}$ | n.d. |
| $Y''_{16}$ | n.d. |
| $Y''_{17}$ | n.d. |
| $Y''_{18}$ | n.d. |
| $Y''_{19}$ | n.d. |
| $Y''_{20}$ | n.d. |
| $B_1$ | n.d. |
| $B_2$ | 213.17 |
| $B_3$ | 360.16 |
| $B_4$ | 473.27 |
| $B_5$ | 610.32 |
| $B_6$ | 773.41 |
| $B_7$ | <u>959.48</u> |
| $B_8$ | <u>1016.50</u> |
| $B_9$ | <u>1144.57</u> |
| $B_{10}$ | <u>1201.59</u> |
| $B_{11}$ | <u>1302.68</u> |
| $B_{12}$ | <u>1415.72</u> |
| $B_{13}$ | 1514.78 |
| $B_{14}$ | n.d. |
| $B_{15}$ | n.d. |
| $B_{16}$ | n.d. |
| $B_{17}$ | n.d. |
| $B_{18}$ | n.d. |
| $B_{19}$ | n.d. |
| $B_{20}$ | n.d. |

[1] Underlined m/z-values are main peaks in the MS/MS-spectrum.
[2] n.d. is not detected.

REFERENCES

Appel R. D., A. Bairoch and D. F. Hochstrasser (1994). A new generation of information retrieval tools for biologists: the example of the ExPASy WWW server. *Trends Biochem. Sci.* 19:258-260.

Bendig M. M. (1988). The production of foreign proteins in mammalian cells. *Genet. Eng.* 7:91-127.

Boel E., S. Verlaan, M. J. Poppelier, N. A. Westerdaal, J. A. Van Strijp, and T. Logtenberg (2000). Functional human monoclonal antibodies of all isotypes constructed from phage display library-derived single-chain Fv antibody fragments. *J. Immunol. Methods* 239:153-166.

Brink M. F., M. D. Bishop, and F. R. Pieper (2000). Developing efficient strategies for the generation of transgenic cattle which produce biopharmaceuticals in milk. *Theriogenology* 53:139-148.

Campbell K. H., J. McWhir, W. A. Ritchie, and I. Wilmut (1996). Sheep cloned by nuclear transfer from a cultured cell line. *Nature* 380:64-66.

Casellas R., T. A. Shih, M. Kleinewietfelt, J. Rakoniac, D. Nemazee, K. Rajewski and M. C. Nussenzweig (2001). Contribution of receptor editing to the antibody repertoire. *Science* 291:1541-1544.

Cockett M. I., C. R. Bebbington and G. T. Yarranton (1990). High level expression of tissue inhibitor of metalloproteinases in Chinese hamster ovary cells using glutamate synthetase gene amplification. *Bio/technology* 8:662-667.

De Kruif J., L. Terstappen, E. Boel and T. Logtenberg (1995a). Rapid selection of cell sub-population-specific human monoclonal antibodies from a synthetic phage antibody library. *Proc. Natl. Acad. Sci. U.S.A.* 92:3938.

De Kruif J., E. Boel, and T. Logtenberg (1995b). Selection and application of human single chain Fv antibody fragments from a semi-synthetic phage antibody display library with designed CDR3 regions. *J. Mol. Biol.* 248:97.

Dinnyes A., P. De Sousa, T. King, and I. Wilmut (2002). Somatic cell nuclear transfer: recent progress and challenges. *Cloning Stem Cells* 4:81-90.

Flavell D. J., A. Noss, K. A. Pulford, N. Ling, and S. U. Flavell (1997). Systemic therapy with 3BIT, a triple combination cocktail of anti-CD19, -CD22, and -CD38-saporin immunotoxins, is curative of human B-cell lymphoma in severe combined immunodeficient mice. *Cancer Res.* 57:4824-4829.

Fishwild D. M., S. L. O'Donnell, T. Bengoechea, D. V. Hudson, F. Harding, S. L. Bernhard, D. Jones, R. M. Kay, K. M. Higgins., S. R. Schramm, and N. Lonberg (1996). High-avidity human IgG kappa monoclonal antibodies from a novel strain of minilocus transgenic mice. *Nat. Biotechnol.* 14:845-51.

Garnick R. L. (1992). Peptide mapping for detecting variants in protein products. *Develop. Biol. Standard* 76:117-130.

Gelpí E. (1995). Biomedical and biochemical applications of liquid chromatography-mass spectrometry. *J. Chromatography A* 703:59-80.

Ghetie M.-A., E. M. Podar, A. Ilgen, B. E. Gordon, J. W. Uhr, and E. S. Vitetta (1997). Homodimerization of tumor-reactive monoclonal antibodies markedly increases their ability to induce growth arrest or apoptosis of tumor cells. *Proc. Natl. Acad. Sci. U.S.A.* 94:7509-7514.

Giddings G., G. Allison, D. Brooks, and A. Carter (2000). Transgenic plants as factories for biopharmaceuticals. *Nat. Biotechnol.* 18:1151-1155.

Gorman C. and C. Bullock (2000). Site-specific gene targeting for gene expression in eukaryotes. *Curr. Opin. Biotechnol.* 11:455-460.

Hiatt A., R. Cafferkey, and K. Bowdish (1989). Production of antibodies in transgenic plants. *Nature* 342:76-78.

Huls G. A., I. A. Heijnen, M. E. Cuomo, J. C. Koningsberger, L. Wiegman, E. Boel, A. R. van der Vuurst de Vries, S. A. Loyson, W. Helfrich, G. P. van Berge Henegouwen, M. van Meijer, J. de Kruif, and T. Logtenberg (1999). A recombinant, fully human monoclonal antibody with antitumor activity constructed from phage-displayed antibody fragments. *Nat. Biotechnol.* 17:276-281.

Jespers L. S., A. Roberts, S. M. Mahler, G. Winter, and H. R. Hoogenboom (1994). Guiding the selection of human antibodies from phage display repertoires to a single epitope of an antigen. *Biotechnology* (N Y) 12:899-903.

Jones D., N. Kroos, R. Anema, B. Van Montfort, A. Vooys, S. Van Der Kraats, E. Van Der Helm, S. Smits, J. Schouten, K. Brouwer, F. Lagerwerf, P. Van Berkel, D.-J. Opstelten, T. Logtenberg, and A. Bout (2003). High-level expression of recombinant IgG in the human cell line PER.C6®. *Biotechnol. Prog.* 19, 163-168.

Kim S. J., N. S. Kim, C. J. Ryu, H. J. Hong, and G. M. Lee (1998). Characterization of chimeric antibody producing CHO cells in the course of dihydrofolate reductase-mediated gene amplification and their stability in the absence of selective pressure. *Biotechnol. Bioeng.* 58:73-84.

Kohler G. and C. Millstein (1975). Continuous cultures of fused cells secreting antibody of predefined specificity. *Nature* 256:495-497.

Koopman G., C. P. Reutelingsperger, G. A. Kuijten, R. M. Keehnen, S. T. Pals, and M. H. van Oers (1994). Annexin V for flow cytometric detection of phosphatidylserine expression on B cells undergoing apoptosis. *Blood* 84:1415-1420.

Larrick J. W. and D. W. Thomas (2001). Producing proteins in transgenic plants and animals. *Curr. Opin. Biotechnol.* 12:411-418.

Massengale W. T., E. McBurney, and J. Gurtler (2002). CD20-negative relapse of cutaneous B-cell lymphoma after anti-CD20 monoclonal antibody therapy. *J. Am. Acad. Dermatol.* 46:441-443.

Mendez M. J., L. L. Green, J. R. Corvalan, X. C. Jia, C. E. Maynard-Currie, X. D. Yang, M. L. Gallo, D. M. Louie, D. V. Lee, K. L. Erickson, J. Luna, C. M. Roy, H. Abderrahim, F. Kirschenbaum, M. Noguchi, D. H. Smith, A. Fukushima, J. F. Hales, S. Klapholz, M. H. Finer, C. G. Davis, K. M. Zsebo, and A. Jakobovits (1997). Functional transplant of megabase human immunoglobulin loci recapitulates human antibody response in mice. *Nat. Genet.* 15:146-56.

Merchant A. M., Z. Zhu, J. Q. Yuan, A. Goddard, C. W. Adams, L. G. Presta, and P. Carter (1998). An efficient route to human bispecific IgG. *Nat. Biotech.* 16:677-681.

Nemazee D. (2000). Receptor editing in B cells. *Adv. Immunol.* 74:89-126.

Nissim A., H. R. Hoogenboom, I. M. Tomlinson, G. Flynn, C. Midgley, D. Lane, and G. Winter (1994). Antibody fragments from a "single pot" phage display library as immunological reagents. *EMBO. J.* 13:692-698.

Nowakowski A., C. Wang, D. B. Powers, P. Amersdorfer, T. J. Smith, V. A. Montgomery, R. Sheridan, R. Blake, L. A. Smith, and J. D. Marks (2002). Potent neutralization of botulinum neurotoxin by recombinant oligoclonal antibody. *Proc. Natl. Acad. Sci. U.S.A.* 99:11346-11350.

Patel A. K. and P. N. Boyd (1995). An improved assay for antibody-dependent cellular cytotoxicity based on time resolved fluorometry. *Journal of Immunological Methods* 184:29-38.

Peeters K., C. De Wilde, G. De Jaeger, G. Angenon, and A. Depicker (2001). Production of antibodies and antibody fragments in plants. *Vaccine* 19:2756-2761.

Pollock D. P., J. P. Kutzko, E. Birck-Wilson, J. L. Williams, Y. Echelard, and H. M. Meade (1999). Transgenic milk as a method for the production of recombinant antibodies. *J. Immunol. Methods* 231:147-157.

Radic M. C., M. A. Mascelli, H. Shan, and M. Weigert (1991). Ig H and L chain contributions to auto-immune specificities. *J. Immunol.* 146:176-182.

Schnieke A. E., A. J. Kind, W. A. Ritchie, K. Mycock, A. R. Scott, M. Ritchie, I. Wilmut, A. Colman, and K. H. Campbell (1997). Human factor IX transgenic sheep produced by transfer of nuclei from transfected fetal fibroblasts. *Science* 278:2130-2133.

Segal D. M., G. J. Weiner, and L. M. Weiner (2001). Introduction: bispecific antibodies. *J. Immunol. Methods* 248:1-6.

Shields R. L., A. K. Namenuk, K. Hong, Y. Gloria Meng, J. Rae, J. Biggs, D. Xie, J. Lai, A. Stadlen, B. Li, J. A. Fox, and L. G. Presta (2001). High resolution mapping of the binding site on human IgG1 for FcgRI, FcgRII, FcgRIII and FcRn and design of IgG1 variants with improved binding to the FcgR. *J. Biol. Chem.* 276:6591-6604.

Spiridon C. I., M. A. Ghetie, J. Uhr, R. Marches, J. L. Li, G. L. Shen, and E. S. Vitetta (2002). Targeting multiple her-2 epitopes with monoclonal antibodies results in improved antigrowth activity of a human breast cancer cell line in vitro and in vivo. *Clin. Cancer Res.* 8:1720-1730.

Van der Vuurst de Vries A. and T. Logtenberg (1999). Dissecting the human peripheral B-cell compartment with phage display-derived antibodies. *Immunology* 98:55-62.

Vaughan T. J., A. J. Williams, K. Pritchard, J. K. Osbourn, A. R. Pope, J. C. Earnshaw, J. McCafferty, R. A. Hodits, J. Wilton, and K. S. Johnson (1996). Human antibodies with sub-nanomolar affinities isolated from a large non-immunized phage display library. *Nat. Biotech.* 14:309-314.

Wilmut I. and A. J. Clark (1991). Basic techniques for transgenesis. *J. Reprod. Fertil. Suppl.* 43:265-275.

Wilmut I., A. E. Schnieke, J. McWhir, A. J. Kind, and K. H. Campbell (1997). Viable offspring derived from fetal and adult mammalian cells. *Nature* 385:810-813.

Wilson T. J. and I. Kola (2001). The LoxP/CRE system and genome modification. *Methods Mol. Biol.* 158:83-94.

Yelverton E., S. Norton, J. F. Obijeski, and D. V. Goeddel (1983). Rabies virus glycoprotein analogs: biosynthesis in *Escherichia coli*. *Science* 219:614-620.

Yoo E. M., M. J. Coloma, K. R. Trinh, T. Q. Nguyen, L. U. Vuong, S. L. Morrison, and K. R. Chintalacharuvu (1999). Structural requirements for polymeric immunoglobulin assembly and association with J chain. *J. Biol. Chem.* 274:33771-33777.

---

What is claimed is:

1. A method of producing a mixture of two or three non-identical antibodies in a recombinant host cell clone, the method comprising:
   expressing in the recombinant host cell clone a polynucleotide or polynucleotides encoding at least one light chain and two different heavy chains that are able to pair with the at least one light chain, wherein the at least one light chain and two different heavy chains are preselected from a display library comprising said one light chain, wherein the two or three non-identical antibodies specifically bind EP-CAM and/or CD46 and the at least one light chain comprises a sequence selected from SEQ ID NO: 2 and SEQ ID NO: 4, and the two different heavy chains comprise a sequence presented as SEQ ID NO: 6 and 8;
   wherein the two or three non-identical antibodies specifically bind EP-CAM and/or CD46 and the at least one light chain comprises a sequence selected from SEQ ID NO: 2 and SEQ ID NO: 4, and the two different heavy chains comprise the sequence of SEQ ID NO: 6 and 10;
   wherein the two or three non-identical antibodies specifically bind CD46 and the at least one light chain comprises a sequence selected from SEQ ID NO: 2 and SEQ ID NO: 4, and the two different heavy chains comprise the sequence of SEQ ID NO: 8 and 10;
   wherein the two or three non-identical antibodies specifically bind CD22, and/or CD72 and the at least one light chain comprises a sequence presented as SEQ ID NO: 18, and the two different heavy chains comprise the sequence of SEQ ID NO: 12 and 14;
   wherein the two or three non-identical antibodies specifically bind CD22, and/or HLA-DR and the at least one light chain comprises a sequence presented as SEQ ID NO: 18, and the two different heavy chains comprise the sequence of SEQ ID NO: 12 and 16; or
   wherein the two or three non-identical antibodies specifically bind CD72, and/or HLA-DR and the at least one light chain comprises a sequence presented as SEQ ID NO: 18, and the two different heavy chains comprise the sequence of SEQ ID NO: 14 and 16.

2. The method according to claim 1, wherein the recombinant host cell clone comprises a polynucleotide encoding a common light chain that is able to pair with the two different heavy chains, such that the produced antibodies comprise common light chains.

3. The method according to claim 1, wherein the mixture of two or three non-identical antibodies comprises a bispecific antibody and at least one monospecific antibody.

4. The method according to claim 1, wherein the mixture comprises a bispecific antibody and two different monospecific antibodies.

5. The method according to claim 1, further comprising: recovering antibodies separately or as a mixture from the host cell clone or a culture comprising the host cell clone.

6. The method according to claim 5, wherein the antibodies are recovered separately from the host cell clone or a culture comprising the host cell clone.

7. The method according to claim 5, wherein the antibodies are recovered as a mixture from the host cell clone or a culture comprising the host cell clone.

8. The method according to claim 1, wherein at least two antibodies comprising a heavy light chain dimer in the mixture of antibodies have different specificities and affinities for their respective antigens.

9. The method according to claim 1, wherein the method does not require amplification of said polynucleotide or polynucleotides encoding at least one light chain and two different heavy chains in the cell.

10. The method according to claim 1, wherein the mixture comprises three non-identical antibodies.

11. The method according to claim 2, wherein the common light chain is identical in each light chain/heavy chain pair of the two or three non-identical antibodies.

12. The method according to claim 2, wherein the common light chain is the only light chain present in the mixture.

13. The method according to claim 1, wherein the two different heavy chains differ in their variable region.

14. The method according to claim 1, wherein the two different heavy chains differ in both the variable region and constant region.

15. The method according to claim 2, wherein:
   the mixture comprises three non-identical antibodies;
   the common light chain is identical in each light chain/heavy chain pair of the three non-identical antibodies;
   the common light chain is the only light chain present in the mixture; and
   the two different heavy chains differ in their variable region.

16. The method of claim 1, wherein said two different heavy chains differ in their constant regions sufficiently so that the amount of bispecific antibodies is decreased as compared to the theoretical percentage of bispecific antibodies.

17. The method of claim 8, wherein the different specificities are directed to different epitopes on the same antigen.

18. The method of claim 8, wherein the different specificities are directed to different antigens present in one antigen comprising mixture.

19. The method of claim 8, wherein at least two of the antibodies have different affinities for the same epitope.

20. The method of claim 1, wherein the two different heavy chains are of IgG isotype.

* * * * *

SEQUENCE LISTING

```
<160> NUMBER OF SEQ ID NOS: 18

<210> SEQ ID NO 1
<211> LENGTH: 333
<212> TYPE: DNA
<213> ORGANISM: Artificial
<220> FEATURE:
<223> OTHER INFORMATION: VL sequence of UBS54 (anti-EpCAM) and K53
      (anti-CD46)
<220> FEATURE:
<221> NAME/KEY: CDS
<222> LOCATION: (1)..(333)

<400> SEQUENCE: 1 gaa att gag ctc act cag tct cca ctc tcc ctg ccc gtc acc cct gga        48
Glu Ile Glu Leu Thr Gln Ser Pro Leu Ser Leu Pro Val Thr Pro Gly
1               5                   10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
                20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
            35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
        50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct       288
Ser Arg Val Glu Ala Glu Asp Val Gly Val Tyr Tyr Cys Met Gln Ala
                85                  90                  95 cta caa act ttc act ttc ggc cct ggg acc aag gtg gag atc aaa           333
Leu Gln Thr Phe Thr Phe Gly Pro Gly Thr Lys Val Glu Ile Lys
                100                 105                 110

<210> SEQ ID NO 2
<211> LENGTH: 111
<212> TYPE: PRT
<213> ORGANISM: Artificial
<220> FEATURE:
<223> OTHER INFORMATION: VL sequence of UBS54 (anti-EpCAM) and K53
      (anti-CD46)

<400> SEQUENCE: 2

Glu Ile Glu Leu Thr Gln Ser Pro Leu Ser Leu Pro Val Thr Pro Gly
1               5                   10                  15
```

-continued

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Phe Thr Phe Gly Pro Gly Thr Lys Val Glu Ile Lys
            100                 105                 110

<210> SEQ ID NO 3
<211> LENGTH: 333
<212> TYPE: DNA
<213> ORGANISM: Artificial
<220> FEATURE:
<223> OTHER INFORMATION: VL sequence of 02-237 (anti-CD46)
<220> FEATURE:
<221> NAME/KEY: CDS
<222> LOCATION: (1)..(333)

<400> SEQUENCE: 3 gac atc gtg atg act cag tct cca ctc tcc ctg ccc gtc acc cct gga       48
Asp Ile Val Met Thr Gln Ser Pro Leu Ser Leu Pro Val Thr Pro Gly
1               5                   10                  15 gag ccg gcc tcc atc tcc tgc agg tct agt cag agc ctc ctg cat agt       96
Glu Pro Ala Ser Ile Ser Cys Arg Ser Ser Gln Ser Leu Leu His Ser
                20                  25                  30 aat gga tac aac tat ttg gat tgg tac ctg cag aag cca ggg cag tct      144
Asn Gly Tyr Asn Tyr Leu Asp Trp Tyr Leu Gln Lys Pro Gly Gln Ser
            35                  40                  45 cca cag ctc ctg atc tat ttg ggt tct aat cgg gcc tcc ggg gtc cct      192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc      240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct      288
Ser Arg Val Glu Ala Glu Asp Val Gly Val Tyr Tyr Cys Met Gln Ala
                85                  90                  95 cta caa act ttc act ttc ggc cct ggg acc aag gtg gag atc aaa         333
Leu Gln Thr Phe Thr Phe Gly Pro Gly Thr Lys Val Glu Ile Lys
            100                 105                 110

<210> SEQ ID NO 4
<211> LENGTH: 111
<212> TYPE: PRT
<213> ORGANISM: Artificial
<220> FEATURE:
<223> OTHER INFORMATION: VL sequence of 02-237 (anti-CD46)

<400> SEQUENCE: 4

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro

```
                  50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                     85                  90                  95

Leu Gln Thr Phe Thr Phe Gly Pro Gly Thr Lys Val Glu Ile Lys
                100                 105                 110

<210> SEQ ID NO 5
<211> LENGTH: 345
<212> TYPE: DNA
<213> ORGANISM: Artificial
<220> FEATURE:
<223> OTHER INFORMATION: VH sequence of UBS54 (anti-EpCAM)
<220> FEATURE:
<221> NAME/KEY: CDS
<222> LOCATION: (1)..(345)

<400> SEQUENCE: 5 cag gtg cag ctg gtg cag tct ggg gct gag gtg aag aag cct ggg tcc    48
Gln Val Gln Leu Val Gln Ser Gly Ala Glu Val Lys Lys Pro Gly Ser
 1               5                  10                  15 tcg gtg agg gtc tcc tgc aag gct tct gga ggc acc ttc agc agc tat    96
Ser Val Arg Val Ser Cys Lys Ala Ser Gly Gly Thr Phe Ser Ser Tyr
                20                  25                  30 gct atc agc tgg gtg cga cag gcc cct gga caa ggg ctt gag tgg atg   144
Ala Ile Ser Trp Val Arg Gln Ala Pro Gly Gln Gly Leu Glu Trp Met
             35                  40                  45 gga ggg atc atc cct atc ttt ggt aca gca aac tac gca cag aag ttc   192
Gly Gly Ile Ile Pro Ile Phe Gly Thr Ala Asn Tyr Ala Gln Lys Phe
         50                  55                  60 cag ggc aga gtc acg att acc gcg gac gaa tcc acg agc aca gcc tac   240
Gln Gly Arg Val Thr Ile Thr Ala Asp Glu Ser Thr Ser Thr Ala Tyr
 65                  70                  75                  80 atg gag ctg agc agc ctg aga tct gag gac acg gct gtg tat tac tgt   288
Met Glu Leu Ser Ser Leu Arg Ser Glu Asp Thr Ala Val Tyr Tyr Cys
                 85                  90                  95 gca aga gac ccg ttt ctt cac tat tgg ggc caa ggt acc ctg gtc acc   336
Ala Arg Asp Pro Phe Leu His Tyr Trp Gly Gln Gly Thr Leu Val Thr
            100                 105                 110 gtc tcg aca                                                        345
Val Ser Thr
        115

<210> SEQ ID NO 6
<211> LENGTH: 115
<212> TYPE: PRT
<213> ORGANISM: Artificial
<220> FEATURE:
<223> OTHER INFORMATION: VH sequence of UBS54 (anti-EpCAM)

<400> SEQUENCE: 6

Gln Val Gln Leu Val Gln Ser Gly Ala Glu Val Lys Lys Pro Gly Ser
 1               5                  10                  15

Ser Val Arg Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
```

```
                65                  70                  75                  80
Met Glu Leu Ser Ser Leu Arg Ser Glu Asp Thr Ala Val Tyr Tyr Cys
                        85                  90                  95

Ala Arg Asp Pro Phe Leu His Tyr Trp Gly Gln Gly Thr Leu Val Thr
                100                 105                 110

Val Ser Thr
        115

<210> SEQ ID NO 7
<211> LENGTH: 354
<212> TYPE: DNA
<213> ORGANISM: Artificial
<220> FEATURE:
<223> OTHER INFORMATION: VH sequence of K53 (anti-CD46)
<220> FEATURE:
<221> NAME/KEY: CDS
<222> LOCATION: (1)..(354)

<400> SEQUENCE: 7 cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc agc tat        96
Ser Val Lys Val Ser Cys Lys Ala Ser Gly Tyr Thr Phe Thr Ser Tyr
            20                  25                  30 ggt atc agc tgg gtg cga cag gcc cct gga caa ggg ctt gag tgg atg       144
Gly Ile Ser Trp Val Arg Gln Ala Pro Gly Gln Gly Leu Glu Trp Met
        35                  40                  45 gga tgg atc agc gct tac aat ggt aac aca aac tat gca cag aag ctc       192
Gly Trp Ile Ser Ala Tyr Asn Gly Asn Thr Asn Tyr Ala Gln Lys Leu
    50                  55                  60 cag ggc aga gtc acc atg acc aca gac aca tcc acg agc aca gcc tac       240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt       288
Met Glu Leu Arg Ser Leu Arg Ser Asp Asp Thr Ala Val Tyr Tyr Cys
                85                  90                  95 gca agg ggc atg atg agg ggt gtg ttt gac tac tgg ggc caa ggt acc       336
Ala Arg Gly Met Met Arg Gly Val Phe Asp Tyr Trp Gly Gln Gly Thr
            100                 105                 110 ctg gtc acc gtc tcg aca                                               354
Leu Val Thr Val Ser Thr
        115

<210> SEQ ID NO 8
<211> LENGTH: 118
<212> TYPE: PRT
<213> ORGANISM: Artificial
<220> FEATURE:
<223> OTHER INFORMATION: VH sequence of K53 (anti-CD46)

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
```

```
Met Glu Leu Arg Ser Leu Arg Ser Asp Asp Thr Ala Val Tyr Tyr Cys
                85                  90                  95

Ala Arg Gly Met Met Arg Gly Val Phe Asp Tyr Trp Gly Gln Gly Thr
            100                 105                 110

Leu Val Thr Val Ser Thr
        115

<210> SEQ ID NO 9
<211> LENGTH: 354
<212> TYPE: DNA
<213> ORGANISM: Artificial
<220> FEATURE:
<223> OTHER INFORMATION: VH sequence of 02-237 (anti-CD46)
<220> FEATURE:
<221> NAME/KEY: CDS
<222> LOCATION: (1)..(354)

<400> SEQUENCE: 9 cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc agc tat        96
Ser Val Lys Val Ser Cys Lys Ala Ser Gly Tyr Thr Phe Thr Ser Tyr
            20                  25                  30 ggt atc agc tgg gtg cga cag gcc cct gga caa ggg ctt gag tgg atg       144
Gly Ile Ser Trp Val Arg Gln Ala Pro Gly Gln Gly Leu Glu Trp Met
        35                  40                  45 gga tgg atc agc gct tac aat ggt aac aca aac tat gca cag aag ctc       192
Gly Trp Ile Ser Ala Tyr Asn Gly Asn Thr Asn Tyr Ala Gln Lys Leu
    50                  55                  60 cag ggc aga gtc acc atg acc aca gac aca tcc acg agc aca gcc tac       240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt       288
Met Glu Leu Arg Ser Leu Arg Ser Asp Asp Thr Ala Val Tyr Tyr Cys
                85                  90                  95 gca agg ggc ttt ccg cgt acg tcg ttt gac tcc tgg ggc cag ggc acc       336
Ala Arg Gly Phe Pro Arg Thr Ser Phe Asp Ser Trp Gly Gln Gly Thr
            100                 105                 110 ctg gtg acc gtc tcc tca                                                354
Leu Val Thr Val Ser Ser
        115

<210> SEQ ID NO 10
<211> LENGTH: 118
<212> TYPE: PRT
<213> ORGANISM: Artificial
<220> FEATURE:
<223> OTHER INFORMATION: VH sequence of 02-237 (anti-CD46)

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
```

```
                65                  70                  75                  80
Met Glu Leu Arg Ser Leu Arg Ser Asp Asp Thr Ala Val Tyr Tyr Cys
                        85                  90                  95

Ala Arg Gly Phe Pro Arg Thr Ser Phe Asp Ser Trp Gly Gln Gly Thr
                100                 105                 110

Leu Val Thr Val Ser Ser
        115

<210> SEQ ID NO 11
<211> LENGTH: 369
<212> TYPE: DNA
<213> ORGANISM: Artificial
<220> FEATURE:
<223> OTHER INFORMATION: VH sequence of clone B28 (anti-CD22 phage)
<220> FEATURE:
<221> NAME/KEY: CDS
<222> LOCATION: (1)..(369)

<400> SEQUENCE: 11 atg gcc gag gtg cag ctg gtg gag tct ggg gga ggt gtg gta cgg cct     48
Met Ala Glu Val Gln Leu Val Glu Ser Gly Gly Gly Val Val Arg Pro
1               5                   10                  15 gga ggg tcc ctg aga ctc tcc tgt gca gcc tct gga ttc acc ttt gat     96
Gly Gly Ser Leu Arg Leu Ser Cys Ala Ala Ser Gly Phe Thr Phe Asp
            20                  25                  30 gat tat ggc atg agc tgg gtc cgc caa gct cca ggg aag ggg ctg gag    144
Asp Tyr Gly Met Ser Trp Val Arg Gln Ala Pro Gly Lys Gly Leu Glu
        35                  40                  45 tgg gtc tct ggt att aat tgg aat ggt ggt agc aca ggt tat gca gac    192
Trp Val Ser Gly Ile Asn Trp Asn Gly Gly Ser Thr Gly Tyr Ala Asp
    50                  55                  60 tct gtg aag ggc cga ttc acc atc tcc aga gac aac gcc aag aac tcc    240
Ser Val Lys Gly Arg Phe Thr Ile Ser Arg Asp Asn Ala Lys Asn Ser
65                  70                  75                  80 ctg tat ctg caa atg aac agt ctg aga gcc gag gac acg gcc gtg tat    288
Leu Tyr Leu Gln Met Asn Ser Leu Arg Ala Glu Asp Thr Ala Val Tyr
                85                  90                  95 tac tgt gca aga ggc ttt ctt cgt ttt gct tcc tcc tgg ttt gac tat    336
Tyr Cys Ala Arg Gly Phe Leu Arg Phe Ala Ser Ser Trp Phe Asp Tyr
            100                 105                 110 tgg ggc caa ggt acc ctg gtc acc gtc tcg aga                        369
Trp Gly Gln Gly Thr Leu Val Thr Val Ser Arg
        115                 120

<210> SEQ ID NO 12
<211> LENGTH: 123
<212> TYPE: PRT
<213> ORGANISM: Artificial
<220> FEATURE:
<223> OTHER INFORMATION: VH sequence of clone B28 (anti-CD22 phage)

<400> SEQUENCE: 12

Met Ala Glu Val Gln Leu Val Glu Ser Gly Gly Gly Val Val Arg Pro
1               5                   10                  15

Gly Gly Ser Leu Arg Leu Ser Cys Ala Ala Ser Gly Phe Thr Phe Asp
            20                  25                  30

Asp Tyr Gly Met Ser Trp Val Arg Gln Ala Pro Gly Lys Gly Leu Glu
        35                  40                  45

Trp Val Ser Gly Ile Asn Trp Asn Gly Gly Ser Thr Gly Tyr Ala Asp
    50                  55                  60

Ser Val Lys Gly Arg Phe Thr Ile Ser Arg Asp Asn Ala Lys Asn Ser
```

```
                65                  70                  75                  80
Leu Tyr Leu Gln Met Asn Ser Leu Arg Ala Glu Asp Thr Ala Val Tyr
                    85                  90                  95

Tyr Cys Ala Arg Gly Phe Leu Arg Phe Ala Ser Ser Trp Phe Asp Tyr
                100                 105                 110

Trp Gly Gln Gly Thr Leu Val Thr Val Ser Arg
            115                 120

<210> SEQ ID NO 13
<211> LENGTH: 369
<212> TYPE: DNA
<213> ORGANISM: Artificial
<220> FEATURE:
<223> OTHER INFORMATION: VH sequence of clone II-2 (anti-CD72 phage)
<220> FEATURE:
<221> NAME/KEY: CDS
<222> LOCATION: (1)..(369)

<400> SEQUENCE: 13 atg gcc cag gtg cag ctg gtg cag tct ggg gct gag gtg aag aag cct      48
Met Ala Gln Val Gln Leu Val Gln Ser Gly Ala Glu Val Lys Lys Pro
1               5                   10                  15 ggg gcc tca gtg aag gtt tcc tgc aag gca tct gga tac acc ttc acc      96
Gly Ala Ser Val Lys Val Ser Cys Lys Ala Ser Gly Tyr Thr Phe Thr
            20                  25                  30 agc tac tat atg cac tgg gtg cga cag gcc cct gga caa ggg ctt gag     144
Ser Tyr Tyr Met His Trp Val Arg Gln Ala Pro Gly Gln Gly Leu Glu
        35                  40                  45 tgg atg gga ata atc aac cct agt ggt ggt ggc aca agc tac gca cag     192
Trp Met Gly Ile Ile Asn Pro Ser Gly Gly Gly Thr Ser Tyr Ala Gln
    50                  55                  60 aag ttc cag ggc aga gtc acc atg acc agg gac acg tcc acg agc aca     240
Lys Phe Gln Gly Arg Val Thr Met Thr Arg Asp Thr Ser Thr Ser Thr
65                  70                  75                  80 gtc tac atg gag ctg agc agc ctg aga tct gag gac acg gcc gtg tat     288
Val Tyr Met Glu Leu Ser Ser Leu Arg Ser Glu Asp Thr Ala Val Tyr
                85                  90                  95 tac tgt gca aga gac tac tat gtt acg tat gat tcc tgg ttt gac tcc     336
Tyr Cys Ala Arg Asp Tyr Tyr Val Thr Tyr Asp Ser Trp Phe Asp Ser
            100                 105                 110 tgg ggc caa ggt acc ctg gtc acc gtc tcg aga                         369
Trp Gly Gln Gly Thr Leu Val Thr Val Ser Arg
        115                 120

<210> SEQ ID NO 14
<211> LENGTH: 123
<212> TYPE: PRT
<213> ORGANISM: Artificial
<220> FEATURE:
<223> OTHER INFORMATION: VH sequence of clone II-2 (anti-CD72 phage)

<400> SEQUENCE: 14

Met Ala Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Ser Tyr Tyr Met His Trp Val Arg Gln Ala Pro Gly Gln Gly Leu Glu
        35                  40                  45

Trp Met Gly Ile Ile Asn Pro Ser Gly Gly Gly Thr Ser Tyr Ala Gln
    50                  55                  60

Lys Phe Gln Gly Arg Val Thr Met Thr Arg Asp Thr Ser Thr Ser Thr
```

```
                65                  70                  75                  80
Val Tyr Met Glu Leu Ser Ser Leu Arg Ser Glu Asp Thr Ala Val Tyr
                    85                  90                  95

Tyr Cys Ala Arg Asp Tyr Tyr Val Thr Tyr Asp Ser Trp Phe Asp Ser
                100                 105                 110

Trp Gly Gln Gly Thr Leu Val Thr Val Ser Arg
            115                 120

<210> SEQ ID NO 15
<211> LENGTH: 360
<212> TYPE: DNA
<213> ORGANISM: Artificial
<220> FEATURE:
<223> OTHER INFORMATION: VH sequence of clone I-2 (anti-class II phage)
<220> FEATURE:
<221> NAME/KEY: CDS
<222> LOCATION: (1)..(360)

<400> SEQUENCE: 15 atg gcc gag gtg cag ctg gtg gag tct ggg gga ggc ttg gta cag cct       48
Met Ala Glu Val Gln Leu Val Glu Ser Gly Gly Gly Leu Val Gln Pro
1               5                   10                  15 ggc agg tcc ctg aga ctc tcc tgt gca gcc tct gga ttc acc ttt gat       96
Gly Arg Ser Leu Arg Leu Ser Cys Ala Ala Ser Gly Phe Thr Phe Asp
            20                  25                  30 gat tat gcc atg cac tgg gtc cgg caa gct cca ggg aag ggc ctg gag      144
Asp Tyr Ala Met His Trp Val Arg Gln Ala Pro Gly Lys Gly Leu Glu
        35                  40                  45 tgg gtc tca ggt att agt tgg aat agt ggt agc ata ggc tat gcg gac      192
Trp Val Ser Gly Ile Ser Trp Asn Ser Gly Ser Ile Gly Tyr Ala Asp
    50                  55                  60 tct gtg aag ggc cga ttc acc atc tcc aga gac aac gcc aag aac tcc      240
Ser Val Lys Gly Arg Phe Thr Ile Ser Arg Asp Asn Ala Lys Asn Ser
65                  70                  75                  80 ctg tat ctg caa atg aac agt ctg aga gct gag gac acg gcc gtg tat      288
Leu Tyr Leu Gln Met Asn Ser Leu Arg Ala Glu Asp Thr Ala Val Tyr
                85                  90                  95 tac tgt gca agg gac ctt tat ctt gcg cat ttt gac tac tgg ggc caa      336
Tyr Cys Ala Arg Asp Leu Tyr Leu Ala His Phe Asp Tyr Trp Gly Gln
            100                 105                 110 ggt acc ctg gtc acc gtc tcg aga                                      360
Gly Thr Leu Val Thr Val Ser Arg
        115                 120

<210> SEQ ID NO 16
<211> LENGTH: 120
<212> TYPE: PRT
<213> ORGANISM: Artificial
<220> FEATURE:
<223> OTHER INFORMATION: VH sequence of clone I-2 (anti-class II phage)

<400> SEQUENCE: 16

Met Ala Glu Val Gln Leu Val Glu Ser Gly Gly Gly Leu Val Gln Pro
1               5                   10                  15

Gly Arg Ser Leu Arg Leu Ser Cys Ala Ala Ser Gly Phe Thr Phe Asp
            20                  25                  30

Asp Tyr Ala Met His Trp Val Arg Gln Ala Pro Gly Lys Gly Leu Glu
        35                  40                  45

Trp Val Ser Gly Ile Ser Trp Asn Ser Gly Ser Ile Gly Tyr Ala Asp
    50                  55                  60

Ser Val Lys Gly Arg Phe Thr Ile Ser Arg Asp Asn Ala Lys Asn Ser
```

```
                65                  70                  75                  80
Leu Tyr Leu Gln Met Asn Ser Leu Arg Ala Glu Asp Thr Ala Val Tyr
                    85                  90                  95

Tyr Cys Ala Arg Asp Leu Tyr Leu Ala His Phe Asp Tyr Trp Gly Gln
                100                 105                 110

Gly Thr Leu Val Thr Val Ser Arg
        115                 120

<210> SEQ ID NO 17
<211> LENGTH: 336
<212> TYPE: DNA
<213> ORGANISM: Artificial
<220> FEATURE:
<223> OTHER INFORMATION: common VL sequence of clones B28 (anti-CD22
      phage), II-2 (anti-CD72 phage) and I-2 (anti-class II phage)
<220> FEATURE:
<221> NAME/KEY: CDS
<222> LOCATION: (1)..(336)

<400> SEQUENCE: 17 tcg tct gag ctg act cag gac cct gct gtg tct gtg gcc ttg gga cag      48
Ser Ser Glu Leu Thr Gln Asp Pro Ala Val Ser Val Ala Leu Gly Gln
1               5                   10                  15 aca gtc agg atc aca tgc caa gga gac agc ctc aga agc tat tat gca      96
Thr Val Arg Ile Thr Cys Gln Gly Asp Ser Leu Arg Ser Tyr Tyr Ala
            20                  25                  30 agc tgg tac cag cag aag cca gga cag gcc cct gta ctt gtc atc tat     144
Ser Trp Tyr Gln Gln Lys Pro Gly Gln Ala Pro Val Leu Val Ile Tyr
        35                  40                  45 ggt aaa aac aac cgg ccc tca ggg atc cca gac cga ttc tct ggc tcc     192
Gly Lys Asn Asn Arg Pro Ser Gly Ile Pro Asp Arg Phe Ser Gly Ser
    50                  55                  60 agc tca gga aac aca gct tcc ttg acc atc act ggg gct cag gcg aa     240
Ser Ser Gly Asn Thr Ala Ser Leu Thr Ile Thr Gly Ala Gln Ala Glu
65                  70                  75                  80 gat gag gct gac tat tac tgt aac tcc cgg gac agc agt ggt aac cat     288
Asp Glu Ala Asp Tyr Tyr Cys Asn Ser Arg Asp Ser Ser Gly Asn His
                85                  90                  95 gtg gta ttc ggc gga ggg acc aag ctg acc gtc cta ggt gcg gcc gca     336
Val Val Phe Gly Gly Gly Thr Lys Leu Thr Val Leu Gly Ala Ala Ala
                100                 105                 110

<210> SEQ ID NO 18
<211> LENGTH: 112
<212> TYPE: PRT
<213> ORGANISM: Artificial
<220> FEATURE:
<223> OTHER INFORMATION: common VL sequence of clones B28 (anti-CD22
      phage), II-2 (anti-CD72 phage) and I-2 (anti-class II phage)

<400> SEQUENCE: 18

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80
```

```
                -continued

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Ala Ala Ala
            100                 105                 110
```